US009556461B2

(12) United States Patent
Osterhout et al.

(10) Patent No.: US 9,556,461 B2
(45) Date of Patent: Jan. 31, 2017

(54) MICROORGANISMS AND METHODS FOR THE BIOSYNTHESIS OF AROMATICS, 2,4-PENTADIENOATE AND 1,3-BUTADIENE

(71) Applicant: Genomatica, Inc., San Diego, CA (US)

(72) Inventors: Robin E. Osterhout, San Diego, CA (US); Anthony P. Burgard, Bellefonte, PA (US); Priti Pharkya, San Diego, CA (US); Mark J. Burk, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 14/226,631

(22) Filed: Mar. 26, 2014

(65) Prior Publication Data

US 2015/0064750 A1 Mar. 5, 2015

Related U.S. Application Data

(62) Division of application No. 13/191,375, filed on Jul. 26, 2011, now Pat. No. 8,715,957.

(60) Provisional application No. 61/381,407, filed on Sep. 9, 2010, provisional application No. 61/368,223, filed on Jul. 27, 2010, provisional application No. 61/367,792, filed on Jul. 26, 2010.

(51) Int. Cl.
| C12N 1/00 | (2006.01) |
| C12N 1/26 | (2006.01) |
| C12N 9/10 | (2006.01) |
| C12P 7/00 | (2006.01) |
| C12P 7/62 | (2006.01) |
| C12N 15/52 | (2006.01) |
| C12P 5/00 | (2006.01) |
| C12P 5/02 | (2006.01) |
| C12P 7/16 | (2006.01) |
| C12P 7/40 | (2006.01) |
| C12P 9/00 | (2006.01) |
| A61K 38/00 | (2006.01) |

(52) U.S. Cl.
CPC ............. *C12P 7/62* (2013.01); *C12N 15/52* (2013.01); *C12P 5/005* (2013.01); *C12P 5/026* (2013.01); *C12P 7/16* (2013.01); *C12P 7/40* (2013.01); *C12P 9/00* (2013.01); *Y02E 50/10* (2013.01)

(58) Field of Classification Search
None
See application file for complete search history.

(56) References Cited

U.S. PATENT DOCUMENTS

| 4,698,452 A | 10/1987 | Le Van Mao et al. |
| 4,873,392 A | 10/1989 | Le Van Mao |
| 5,008,190 A | 4/1991 | Lee et al. |
| 5,177,253 A * | 1/1993 | Drent ............... C07C 51/14 560/207 |
| 5,487,987 A | 1/1996 | Frost et al. |
| 5,686,276 A | 11/1997 | Lafend et al. |
| 5,958,745 A | 9/1999 | Gruys et al. |
| 6,133,014 A | 10/2000 | Mukouyama et al. |
| 6,187,569 B1 | 2/2001 | Bramucci et al. |
| 6,437,218 B1 | 8/2002 | Aarts et al. |
| 7,127,379 B2 | 10/2006 | Palsson et al. |
| 7,393,676 B2 | 7/2008 | Gorkarn et al. |
| 7,947,483 B2 | 5/2011 | Burgard et al. |
| 9,169,486 B2 * | 10/2015 | Burk ............... C12N 15/52 |
| 2002/0012939 A1 | 1/2002 | Palsson |
| 2002/0168654 A1 | 11/2002 | Maranas et al. |
| 2003/0059792 A1 | 3/2003 | Palsson et al. |
| 2003/0170836 A1 | 9/2003 | Bramucci et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2009/0047719 A1 | 2/2009 | Burgard et al. |
| 2010/0136595 A1 | 6/2010 | Tittiger et al. |
| 2011/0093966 A1 * | 4/2011 | He ................... C07K 14/415 800/260 |
| 2011/0300597 A1 * | 12/2011 | Burk ............... C12N 15/52 435/167 |

FOREIGN PATENT DOCUMENTS

| CN | 101329232 A | 12/2008 |
| EP | 2017344 | 1/2009 |

(Continued)

OTHER PUBLICATIONS

Aberhart and Hsu, "Stereospecific hydrogen loss in the conversion of [2H7] isobutyrate to β-hydroxyisobutyrate in Pseudomonas putida. The stereochemistry of β-hydroxyisobutyrate dehydrogenase," *J. Chem. Soc.* [*Perking 1*] 6:1404-1406 (1979).
Abiko et al., "Localization of NAD-isocitrate dehydrogenase and glutamate dehydrogenase in rice roots: candidates for providing carbon skeletons to NADH-glutamate synthase," *Plant Cell Physiol.* 46:1724-1734 (2005).
Adams and Kletzin, "Oxidoreductase-type enzymes and redox proteins involved in fermentative metabolisms of hyperthermophilic Archaea," *Adv. Protein Chem.* 48:101-180 (1996).
Agnihotri and Liu, "Enoyl-CoA Hydratase: Reaction, Mechanism, and Inhibition," *Bioorg. Med. Chem.* 11(1):9-20 (2003).

(Continued)

*Primary Examiner* — Anand Desai
*Assistant Examiner* — Samuel Liu
(74) *Attorney, Agent, or Firm* — Jones Day

(57) ABSTRACT

The invention provides non-naturally occurring microbial organisms having a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway. The invention additionally provides methods of using such organisms to produce toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene.

6 Claims, 25 Drawing Sheets

(56) References Cited

FOREIGN PATENT DOCUMENTS

| WO | WO 02/055995 | 7/2002 |
|---|---|---|
| WO | WO 03/106998 | 12/2003 |
| WO | WO 2004/056963 | 7/2004 |
| WO | WO 2007/141208 | 12/2007 |
| WO | WO 2008/080124 | 7/2008 |
| WO | WO 2008/137403 | 11/2008 |
| WO | WO 2009/014437 | 1/2009 |
| WO | WO 2009/111513 | 9/2009 |
| WO | WO 2010/001078 | 1/2010 |
| WO | WO 2011/022651 | 2/2011 |
| WO | WO 2011/052718 | 5/2011 |
| WO | WO 2011/076691 | 6/2011 |

OTHER PUBLICATIONS

Alber et al., "Malonyl-Coenzyme A reductase in the modified 3-hydroxypropionate cycle for autotrophic carbon fixation in archaeal Metallosphaera and *Sulfolobus* spp.," *J. Bacteriol.* 188(24):8551-8559 (2006).
Alber et al., "Study of an alternate glyoxylate cycle for acetate assimilation by Rhodobacter sphaeroides," *Mol. Microbiol.* 61(2):297-309 (2006).
Alhapel et al., "Molecular and functional analysis of nicotinate catabolism in Eubacterium barkeri," *Proc. Natl. Acad. Sci. U.S.A.* 103(33):12341-12346 (2006).
Altmiller and Wanger, "Purification and properties of dihydroxy acid dehydratase from soluble and mitochondrial fractions of Neurospora crassa," *Arch. Biochem. Biophys.* 138:160-170 (1970).
Anderson et al., "Evaluation of 5-enolpyruvoylshikimate-3-phosphate synthase substrate and inhibitor binding by stopped-flow and equilibrium fluorescence measurements," *Biochemistry* 27:1604-1610 (1988).
Andrei et al., "Subunit composition of the glycyl radical enzyme p-hydroxyphenylacetate decarboxylase. A small subunit, HpdC, is essential for catalytic activity," *Eur. J. Biochem.* 271(11):2225-2230 (2004).
Ansorge and Kula, "Production of Recombinant L-Leucine Dehydrogenase from Bacillus cereus in Pilot Scale Using the Runaway Replication System *E. coli*[pIET98]," *Biotechnol. Bioeng.* 68:557-562 (2000).
Aoshima and Igarashi, "A novel biotin protein required for reductive carboxylation of 2-oxoglutarate by isocitrate dehydrogenase in Hydrogenobacter thermophilus TK-6," *Mol. Microbiol.* 51(3):791-798 (2004).
Aoshima and Igarshi, "Nondecarboxylating and decarboxylating isocitrate dehydrogenases: oxalosuccinate reductase as an ancestral form of isocitrate dehydrogenase," *J. Bacteriol.* 190(6):2050-2055 (2008).
Aoshima et al., "A novel enzyme, citryl-CoA lyase, catalysing the second step of the citrate cleavage reaction in Hydrogenobacter thermophilus TK-6," *Mol. Microbiol.* 52(3):763-770 (2004).
Aoshima et al., "A novel enzyme, citryl-CoA synthetase, catalysing the first step of the citrate cleavage reaction in Hydrogenobacter thermophilus TK-6," *Mol. Microbiol.* 52(3):751-761 (2004).
Aoshima et al., "A novel oxalosuccinate-forming enzyme involved in the reductive carboxylation of 2-oxoglutarate in Hydrogenobacter thermophilus TK-6," *Mol. Microbiol.* 62(3):748-759 (2006).
Aoshima, "Novel enzyme reactions related to the tricarboxylic acid cycle: phylogenetic/functional implications and biotechnological applications," *Appl. Microbiol. Biotechnol.* 75(2):249-255 (2007).
Argyrou and Blanchard, "Kinetic and chemical mechanism of *Mycobacterium tuberculosis* 1-deoxy-D-xylulose-5-phosphate isomeroreductase," *Biochemistry* 43:4375-4384 (2004).
Arias et al., "Genetic analyses and molecular characterization of the pathways involved in the conversion of 2-phenylethylamine and 2-phenylethanol into phenylacetic acid in Pseudomonas putida U," *Environ. Microbiol.* 10(2):413-432 (2008). (Epub Dec. 27, 2007).
Arias et al., "Serine and alanine racemase activities of VanT: a protein necessary for vancomycin resistance in Enterococcus gallinarum BM4174," *Microbiology* 146 ( Pt 7):1727-1734 (2000).
Arikawa et al., "Soluble fumarate reductase isoenzymes from *Saccharomyces cerevisiae* are required for anaerobic growth," *FEMS Microbiol. Lett.* 165:111-116 (1998).
Armstrong et al., "Steroselectivity and sterospecificity of the $\alpha,\beta$-dihydroxyacid dehydratase from *Salmonella typhimurium*," *Biochim. Biophys. Acta* 498:282-293 (1977).
Arps et al., "Genetics of serine pathway enzymes in Methylobacterium extorquens AM1: phosphoenolpyruvate carboxylase and malyl Coenzyme A lyase," *J. Bacteriol.* 175:3776-3783 (1993).
Asano and Kato, "Crystalline 3-methylaspartase from a facultative anaerobe, *Escherichia coli* strain YG1002," *FEMS Microbiol. Lett.* 118(3):255-258 (1994).
Asano et al., "Alteration of substrate specificity of aspartase by directed evolution," *Biomol. Eng.* 22(1-3):95-101 (2005).
Asuncion et al., "Overexpression, purification, crystallization and data collection of 3-methylaspartase from Clostridium tetanomorphum," *Acta. Crystallogr. D. Biol. Crystallogr.* 57(Pt 5):731-733 (2001).
Asuncion, et al., "The structure of 3-methylaspartase from Clostridium tetanomorphum functions via the common enolase chemical step," *J. Biol. Chem.* 277(10):8306-8311 (2002).
Atsumi et al., "Metabolic engineering of *Escherichia coli* for 1-butanol production," *Metab. Eng.* 10(6):305-311 (2008).
Atsumi et al., "Non-fermentative pathways for synthesis of branched-chain higher alcohols as biofuels," *Nature* 451(7174):86-89 (2008).
Autor et al., "The interactions of acetoacetate decarboxylase with carbonyl compounds, hydrogen cyanide, and an organic mercurial," *J. Biol. Chem.* 245(20):5214-5222 (1970).
Bailey et al., "Identification, cloning, purification, and enzymatic characterization of *Mycobacterium tuberculosis* 1-deoxy-D-xylulose 5-phosphate synthase," *Glycobiology* 12:813-820 (2002).
Baker and van der Drift, "Purification and properties of L-erythro-3,5-diaminohexanoate dehydrogenase from Clostridium sticklandii," *Biochemistry* 13(2):292-299 (1974).
Baker et al., "Purification and properties of L-erythro-3,5-diaminohexanoate dehydrogenase from a lysine-fermenting Clostridium," *J. Biol. Chem.* 247:7724-7734 (1972).
Banerji et al., "The cloning and characterization of the arom gene of Pneumocystis carinii," *J. Gen. Microbiol.* 139:2901-2914 (1993).
Barker and Frost, "Microbial synthesis of p-hydroxybenzoic acid from glucose," *Biotechnol. Bioeng.* 76:376-390 (2001).
Barthelmebs et al., "Exression of *Escherichia coli* of Native and chimeric Phenolic Acid Decarboxylases with Modified Enzymatic Activities and Method for Screening Recombinant *E. coli* Strains Expressing These Enzymes," *Appl. Environ. Microbiol.* 67:1063-1069 (2001).
Bartsch et al., "Molecular analysis of two genes of the *Escherichia coli* gab cluster: nucleotide sequence of the glutamate succinic semialdehyde transaminase gene (gabT) and characterization of the succinic semialdehyde dehydrogenase gene (gabD)," *J. Bacteriol.* 172(12):7035-7042 (1990).
Basson et al., "*Saccharomyces cerevisiae* contains two functional genes encoding 3-hydroxy-3-methylglutaryl-coenzyme A reductase," *Proc. Natl. Acad. Sci. U. S. A.* 83(15):5563-5567 (1986).
Bekal et al., "Purification of Leuconostoc mesenteroides citrate lyase and cloning and characterization of the citCDEFG gene cluster," *J. Bacteriol.* 180(3):647-654 (1998).
Benner et al., "Stereospecificity and sterochemical infidelity of acetoacetate decarboxylase (AAD)," *J. Am. Chem. So.* 103:993-994 (1981).
Berg et al., "A 3-Hydroxypropionate/4-Hydroxybutyrate Autotrophic Carbon Dioxide Assimilation Pathway in Archaea," *Science* 318(5857) 1782-1786 (2007).
Bergquist and Gibbs, "Degenerate oligonucleotide gene shuffling," *Meth. Mol. Biol.* 352:191-204 (2007).

(56) References Cited

OTHER PUBLICATIONS

Bergquist et al., "Degenerate oligonucleotide gene shuffling (DOGS) and random drift mutagenesis (RNDM): Two complementary techniques for enzyme evolution," *Biomol. Eng.* 22:63-72 (2005).
Berkovitch et al., "A locking mechanism preventing radical damage in the absence of substrate, as revealed by the x-ray structure of lysine 5,6-aminomutase," *Proc. Natl. Acad. Sci. U.S.A.* 101:15870-15875 (2004).
Berman and Magasanik, "The pathway of myo-inositol degradation in Aerobacter aerogenes," *J. Biol. Chem.* 241(4):800-806 (1966).
Bernhard et al., "Functional and structural role of the cytochrome b subunit of the membrane-bound hydrogenase complex of Alcaligenes eutrophus H16," *Eur. J. Biochem.* 248(1):179-186 (1997).
Binieda et al., "Purification, characterization, DNA sequence and cloning of a pimeloyl-CoA synthetase from Pseudomonas mendocina 35," *Biochem. J.* 340:793-801 (1999).
Binstock and Schulz, "Fatty acid oxidation complex from *Escherichia coli*," *Methods Enzymol.* 71(Pt C):403-411 (1981).
Bisswanger, "Substrate specificity of the Pyruvate Dehydrogenase Complex from *Escherichia coli*," *J. Biol. Chem.* 256(2):815-822 (1981).
Blakley, "The catabolism of L-tyrosine by an *Arthrobacter* sp.," *Can. J. Microbiol.* 23(9):1128-1139.
Blanco et al., "The role of substrate-binding groups in the mechanism of aspartate-β-semialdehyde dehydrogenase," *Acta. Crystallogr. D. Biol. Crystallogr.* 60(Pt 8):1388-1395 (2004).
Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).
Boatright et al., "Understanding in vivo benzenoid metabolism in petunia petal tissue," *Plant Physiol.* 135(4):1993-2011 (2004). (Epub Jul. 30, 2004).
Bobik et al., "Propanediol Utilization Genes (pdu) of *Salmonella typhimurium*: Three Genes for the Propanediol Dehydratase," *J. Bacteriol.* 179(21):6633-6639 (1997).
Bochar et al., "3-hydroxy-3-methylglutaryl coenzyme A reductase of Sulfolobus solfataricus: DNA sequence, phylogeny, expression in *Escherichia coli* of the hmgA gene, and purification and kinetic characterization of the gene product," *J. Bacteriol.* 179(11):3632-3638 (1997).
Bock et al., "Purification and characterization of two extremely thermostable enzymes, phosphate acetyltransferase and acetate kinase, from the hyperthermophilic eubacterium Thermotoga maritima," *J. Bacteriol.* 181:1861-1867 (1999).
Bonnarme et al., "Itaconate biosynthesis in Aspergillus terreus," *J. Bacteriol.* 177(12):3573-3578.
Bott and Dimroth, "Klebsiella pneumoniae genes for citrate lyase and citrate lyase ligase: localization, sequencing, and expression," *Mol. Microbiol.* 14(2):347-356 (1994).
Bott, "Anaerobic citrate metabolism and its regulation in enterobacteria," *Arch. Microbiol.* 167(2/3):78-88 (1997).
Botting et al., "Substrate Specificity of the 3-Methylaspartate Ammonia-Lyase Reactin: Observation of Differential relative Reaction Rates for Substrate-Product Pairs," *Biochemistry* 27:2953-2955 (1988).
Bower et al., "Cloning, sequencing, and characterization of the Bacillus subtilis biotin biosynthetic operon," *J. Bacteriol.* 178(14):4122-4130 (1996).
Boynton et al., "Cloning, sequencing, and expression of clustered genes encoding β-hydroxybutyryl-Coenzyme A (CoA) dehydrogenase, crotonase, and butyryl-CoA dehydrogenase from Clostridium acetobutylicum ATCC 824," *J. Bacteriol.* 178(11):3015-3024 (1996).
Branlant, "Nucleotide sequence of *Escherichia coli* gap gene. Different evolutionary behavior of the NAD+-binding domain and of the catalytic domain of D-glyceraldehyde-3-phosphate dehydrogenase," *Eur. J. Biochem.* 150:61-66 (1985).
Bräsen and Schönheit, "Unusual ADP-forming acetyl-Coenzyme A synthetases from the mesophilic halophilic etuyarchaeon Haloarcula marismortui and from the hyperthermophilic crenarchaeon Pyrobaculum aerophilum," *Arch. Microbiol.* 182(4):277-287 (2004).
Bravo et al., "Reliable, sensitive, rapid and quantitative enzyme-based assay for gamma-hydroxybutyric acid (GHB)," *J. Forensic Sci.* 49:379-387 (2004).
Breitkreuz et al., "A novel γ-hydroxybutyrate dehydrogenase: Identification and expression of an Arabidopsis cDNA and potential role under oxygen deficiency," *J. Biol. Chem.* 278:41552-41556 (2003).
Brown et al., "The enzymic interconversion of acetate and acetyl-coenzyme A in *Escherichia coli*," *J. Gen. Microbiol.* 102(2):327-336 (1977).
Buck et al., "Primary structure of the succinyl-CoA synthetase of *Escherichia coli*," *Biochemistry* 24(22):6245-6252 (1985).
Buckel and Barker, "Two pathways of glutamate fermentation by anaerobic bacteria," *J. Bacteriol.* 117(3):1248-1260 (1974).
Buckel et al., "Glutaconate CoA-Transferase from Acidaminococcus fermentans," *Eur. J. Biochem.* 118:315-321 (1981).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Burgdorf et al., "The soluble NAD+-Reducing [NiFe]-hydrogenase from Ralstonia eutropha H16 consists of six subunits and can be specifically activated by NADPH," *J. Bacteriol.* 187(9):3122-3132 (2005).
Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.* 120(31):7665-7675 (1998).
Buu et al., "Functional characterization and localization of acetyl-CoA hydrolase, Achlp, in *Saccharomyces cerevisiae*," *J. Biol. Chem.* 278:17203-17209 (2003).
Cahyanto et al., "Regulation of aspartokinase, asparate semialdehyde dehydrogenase, dihydrodipicolinate synthase and dihydropdipicolinate reductase in Lactobacillus plantarum," *Microbiology* 152 (Pt 1): 105-112 (2006).
Camara et al., "Characterization of a Gene Cluster Involved in 4-Chlorocatechol Degradation by Pseudomonas reinekei MT1," *J. Bacteriol.* 191(15):4905-4915 (2009).
Campbell et al., "A complete shikimate pathway in Toxoplasma gondii: an ancient eukaryotic innovation," *Int. J. Parasitol.* 34:5-13 (2004).
Campbell et al., "A new *Escherichia coli* metabolic competency: growth on fatty acids by a novel anaerobic β-oxidation pathway," *Mol. Microbiol.* 47(3):793-805 (2003).
Carpenter et al., "Structure of dehydroquinate synthase reveals an active site capable of multistep catalysis," *Nature* 394:299-302 (1998).
Carretero-Paulet et al., "Expression and molecular analysis of the Arabidopsis DXR gene encoding1-deoxy-D-xylulose 5-phosphate reductoisomerase, the firszt committed enzyme of the 2-C-methyl-D-erythritol 4-phosphate pathway," *Plant Physiol.* 129:1581-1591 (2002).
Cary et al., "Cloning and Expression of Clostridium acetobutylicum ATCC 824 Acetoacetyl-Coenzyme A:Acetate/Butyrate:Coenzyme A-Transferase in *Escherichia coli*," *App. Environ. Microbiol.* 56(6):1576-1583 (1990).
Casas et al., "Pentadiene production from potassium sorbate by osmotolerant yeasts," *Int. J. Food Microbiol.* 94(1):93-96 (2004).
Charles et al., "The isolation and nucleotide sequence of the complex AROM locus of Aspergillus nidulans," *Nucleic Acids Res.* 14:2201-2213 (1986).
Charrier et al., "A novel class of CoA-transferase involved in short-chain fatty acid metabolism in butyrate-producing human colonic bacteria," *Microbiology* 152:179-185 (2006).

(56) References Cited

OTHER PUBLICATIONS

Chen et al., "Cloning, Sequencing, Heterologous Expression, Purification, and Characterization of Adenosylcobalamin-dependent D-Ornithine Aminomutase from Clostridium sticklandii," *J. Biol. Chem.* 276:44744-44750 (2001).
Chen et al., "The control region of the pdu/cob regulon in *Salmonella typhimurium*," *J. Bacteriol.* 176:5474-5482 (1994).
Cheng et al., "Structural basis for shikimate-binding specificity of Helicobacter pylori shikimate kinase," *J. Bacteriol.* 187:8156-8163 (2005).
Choi et al., "Enhanced production of cis,cis-muconate in a cell-recycle bioreactor," *J. Ferment. Bioeng.* 84:70-76 (1997).
Chowdhury et al., "3-Hydroxyisobutyrate dehydrogenase from Pseudomonas putida E23: purification and characterization," *Biosci. Biotechnol. Biochem.* 60(12):2043-2047 (1996).
Chowdhury et al., "Cloning and overexpression of the 3-hydroxyisobutyrate dehydrogenase gene from pseudomonas putida E23," *Biosci. Biotechnol. Biochem.* 67(2):438-441 (2003).
Clark, "Molybdenum cofactor negative mutants of *Escherichia coli* use citrate anaerobically," *FEMS Microbiol. Lett.* 55(3):245-249 (1990).
Clausen et al., "PAD1 encodes phenylarciylic acid decarboxylase which confers resistance to cinnamic acid in *Saccharomyces cerevisiae*," *Gene* 142:107-112 (1994).
Coco et al., "DNA shuffling method for generating highly recombined genes and evolved enzymes," *Nat. Biotechnol.* 19:354-359 (2001).
Coggins et al., "The arom multifunctional enzyme from Neurospora crassa," *Methods Enzymol.* 142:325-341 (1987).
Conrad et al., "D- and L-Isoleucine Metabolism and Regulation of Their Pathways in Pseudomonas Putida," *J. Bacteriol.* 118(1):103-111 (1974).
Cooper, "Glutamate-γ-aminobutyrate transaminase," *Methods Enzymol.* 113:80-82 (1985).
Coppi, "The hydrogenases of Geobacter sulfurreducens: a comparative genomic perspective," *Microbiology* 151(Pt 4):1239-1254 (2005).
Corthesy-Theulaz et al., "Cloning and Characterization of Helicobacter pylori Succinyl CoA:Acetoacetate CoA-transferase, a Novel Prokaryotic Member of the CoA-transferase Family," *J. Biol. Chem.* 272(41):25659-25667 (1997).
Cracknell et al., "A kinetic and thermodynamic understanding of O2 tolerance in [NiFe]-hydrogenases," *Proc. Natl. Acad. Sci. U. S. A.* 106(49):20681-20686 (2009). (Epub Nov. 23, 2009).
Cunningham et al., "Transcriptional regulation of the aconitase genes (acnA and acnB) of *Escherichia coli*," *Microbiology* 143(Pt 12):3795-3805 (1997).
De la Torre et al., "Identification and functional analysis of a prokaryotic-type aspartate aminotransferase: implications for plant amino acid metabolism," *Plant. J.* 46(3):414-425 (2006).
De Mendonca et al., "Functional characterization by genetic complementation of aroB-encoded dehydroquinate synthase from *Mycobacterium tuberculosis* H37Rv and its heterologous expression and purification," *J. Bacteriol.* 189:6246-6252 (2007).
Deana, "Substrate specificity of a dicarboxyl-CoA: dicarboxylic acid Coenzyme A transferase from rat liver mitochondria," *Biochem. Int.* 26(4):767-773 (1992).
DeFeyter and Pittard, "Purification and properties of shikimate kinase II from *Escherichia coli* K-12," *J. Bacteriol.* 165:331-333 (1986).
Dennis et al., "Alkane biosynthesis by decarbonylation of aldehyde catalyzed by a microsomal preparation from Botryococcus braunii," *Arch. Biochem. Biophys.* 287(2):268-275 (1991).
Di Gennaro, "Styrene lower catabolic pathway in Pseudomonas fluorescens ST: identification and characterization of genes for phenylacetic acid degradation," *Arch. Microbiol.* 188(2):117-125 (2007).
Diao et al., "Crystal structure of butyrate kinase 2 from Thermotoga maritima, a member of the ASKHA superfamily of phosphotransferases," *J. Bacteriol.* 191:2521-2529 (2009).

Diao et al., "Crystallization of the butyrate kinase 2 from Thermotoga maritima mediated by vapor diffusion of acetic acid," *Acta. Crystallogr. D. Biol. Crystallogr.* 59(Pt 6):1100-1102 (2003).
Diaz et al., "Gene cloning, heterologous overexpression and optimized refolding of the NAD-glutamate dehydrogenase from Haloferax mediterranei," *Extremophiles* 10:105-115 (2006).
Dickert et al., "The involvement of coenzyme A esters in the dehydration of (R)-phenyllactate to (E)-cinnamate by Clostridium sporogenes," *Eur. J. Biochem.* 267(12):3874-3884 (2000).
Dickinson et al., "The catabolism of amino acids to long chain and complex alcohols in *Saccharomyces cerevisiae*," *J. Biol. Chem.* 278(10):8028-8034 (2003). (Epub Dec. 23, 2002).
Dobbek et al., "Crystal structure of a carbon monoxide dehydrogenase reveals a [Ni—4Fe—5S] cluster," *Science* 293(5533):1281-1285 (2001).
Dörner and Boll, "Properties of 2-oxoglutarate:ferredoxin oxidoreductase from Thauera aromatica and its role in enzymatic reduction of the aromatic ring," *J. Bacteriol.* 184(14):3975-3983 (2002).
Doten et al., "Cloning and Genetic Organization of the pca Gene cluster from Acinetobacter calcoaceticus," *J. Bacteriol.* 169(7):3168-3174 (1987).
Drake and Daniel, "Physiology of the thermophilic acetogen Moorella thermoacetica," *Res. Microbiol.* 155(10):869-883 (2004).
Drake, "Demonstration of hydrogenase in extracts of the homoacetate-fermenting bacterium Clostridium thermoaceticum," *J. Bacteriol.* 150(2):702-709 (1982).
Draths and Frost, "Environmentally compatible synthesis of adipic acid from D-glucose," *J. Am. Chem. Soc.* 116:399-400 (1994).
Drevland et al., "Enzymology and Evolution of the Pyruvate Pathway to 2-Oxobutyrate in Methanocaldococcus jannachii," *J. Bacteriol.* 189(12):4391-4400 (2007).
Duncan et al., "The pentafunctional arom enzyme of *Saccharomyces cerevisiae* is a mosaic of monofunctional domains," *Biochem. J.* 246:375-386 (1987).
Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).
Dwiarti et al., "Purification and characterization of cis-aconitic acid decarboxylase from Aspergillus terreus TN484-M1," *J. Biosci Bioeng.* 94(1):29-33 (2002).
Eaton, "p-Cumate catabolic pathway in Pseudomonas putida F1: cloning and characterization of DNA carrying the cmt operon," *J. Bacteriol.* 178(5):1351-1362 (1996).
Egland et al., "A cluster of bacterial genes for anaerobic benzene ring biodegradation," *Proc. Natl. Acad. Sci. U.S.A.* 94:6484-6489 (1997).
Egloff and Hulla, "Conversion of Oxygen Derivatives of Hydrocarbons Into Butadiene," *Chem. Rev.* 36(1):63-141 (1945).
Eikmanns et al., "The phosphoenolpyruvate carboxylase gene of Corynebacterium glutamicum: Molecular cloning, nucleotide sequence, and expression." *Mol. Gen. Genet.* 218:330-339 (1989).
Eisen et al., "The complete genome sequence of Chlorobium tepidum TLS, a photosynthetic, anaerobic, green-sulfur bacterium," *Proc. Natl. Acad. Sci. U. S. A.* 99(14):9509-9514 (2002). (Epub Jul. 1, 2002).
Ekiel et al., "Acetate and CO2 assimilation by Methanothrix concilii," *J. Bacteriol.* 162(3):905-908 (1985).
Enomoto et al., "Cloning and sequencing of the gene encoding the soluble fumarate reductase from *Saccharomyces cerevisiae*," *DNA Res.* 3:263-267 (1996).
Escamilla-Treviño et al., "Switchgrass (*Panicum virgatum*) possesses a divergent family of cinnamoyl CoA reductases with distinct biochemical properties," *New Phytol.* 185(1):143-155 (2010). (Epub Sep. 15, 2009).
Evans et al., "A new ferredoxin-dependent carbon reduction cycle in a photosynthetic bacterium," *Proc. Natl. Acad. Sci. U. S. A.* 55(4):928-934 (1966).
Evans et al., "Specificity of substrate recognition by type II dehydroquinases as revealed by binding of polyanions," *FEBS Lett.* 530(1-3):24-30 (2002).

(56) References Cited

OTHER PUBLICATIONS

Fernandez-Canon and Penalva, "Characterization of a fungal maleylacetoacetate isomerase gene and indentification of its human homologue," *J. Biol. Chem.* 273:329-337 (1998).
Fernandez-Valverde et al., "Purification of Pseudomonas putida Acyl Coenzyme A Ligase Active with a Range of aliphatic and Aromatic substrates," *Appl. Environ. Microbiol.* 59(4):1149-1154 (1993).
Ferrández et al., "Genetic characterization and expression in heterologous hosts of the 3-(3-hydroxyphenyl)propionate catabolic pathway of *Escherichia coli* K-12," *J. Bacteriol.* 179(8):2573-2581 (1997).
Ferrandez et al., "Molecular characterization of PadA, a phenylacetaldehyde dehydrogenase from *Escherichia coli*," *FEBS Lett.* 406(1-2):23-27 (1997).
Fischer-Romero et al., "Tolumonas auensis gen. no., a toluene-producing bacterium from anoxic sediments of a freshwater lake," *International Journal of Systematic Bacteriology*, 46(1):183-188 (1996).
Flint et al., "The role and properties of the iron-sulfur cluster in *Escherichia coli* dihydroxy-acid dehydratase," *J. Biol. Chem.* 268:14732-14742 (1993).
Fonknechten et al., "A conserved gene cluster rules anaerobic oxidative degradation of L-ornithine," *J. Bacteriol.* 191(9):3162-3167 (2009).
Fontaine et al., "Molecular charcterization and transcriptional analysis of adhE2, the gene encoding the NADH-dependent aldehyde/alcohol dehydrogenase responsible for butanol production in alcohologenic cultures of Clostridium acetobutylicum ATCC 824," *J. Bacteriol.* 184:821-830 (2002).
Foor et al., "Production of L-dihydroxyphenylalanine in *Escherichia coli* with the tyrosine phenol-lyase gene cloned from Erwinia herbicola," *Appl. Environ. Microbiol.* 59(9):3070-3075 (1993).
Ford et al., "Molecular properties of the lyst1+ gene and the regulation of α-aminoadipate reductase in Schizosaccharomyces pombe," *Curr. Genet.* 28:131-137 (1995).
Fox and Roseman, "Isolation and characterization of homogeneous acetate kinase from *Salmonella typhimurium* and *Escherichia coli*," *J. Biol. Chem.* 261(29):13487-13497 (1986).
Fox et al., "Characterization of the region encoding the CO-induced hydrogenase of Rhodospirillum rubrum," *J. Bacteriol.* 178(21):6200-6208 (1996).
Frey and Magnusson, "S-Adenosylmethionine: a wolf in sheep's clothing, or a rich man's adenosylcobalamin?" *Chem. Rev.* 103(6):2129-2148 (2003).
Fujii et al., "Error-prone rolling circle amplification: the simplest random mutagenesis protocol," *Nat. Protoc.* 1:2493-2497 (2006).
Fujii et al., "One-step random mutagenesis by error-prone rolling circle amplification," *Nucleic Acids Res.* 32:e145 (2004).
Fujinaga and Meyer, "Cloning and expression in *Escherichia coli* of the gene encoding the [2Fe-2S] ferredoxin from Clostridium pasteurianum," *Biochem. Biophys. Res. Commun.* 192(3):1115-1122 (1993).
Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics* 68:144-151 (2000).
Fukuda and Wakagi, "Substrate recognition by 2-oxoacid:ferredoxin oxidoreductase from *Sulfolobus* sp. Strain 7," *Biochim. Biophys. Acta* 1597:74-80 (2002).
Fukuda et al., "Role of a highly conserved YPITP motif in 2-oxoacid:ferredoxin oxidoreductase Heterologous expression of the gene from *Sulfolobus* sp. Strain 7, and characterization of the recombinant and variant enzymes," *Eur. J. Biochem.* 268:5639-5646 (2001).
Furdui and Ragsdale, "The role of pyruvate ferredoxin oxidoreductase in pyruvate synthesis during autotrophic growth by the Wood-Ljungdahl pathway," *J. Biol. Chem.* 275(37):28494-28499 (2000).
Gallagher et al., "The crystal structure of chorismate lyase shows a new fold and a tightly retained product," *Proteins* 44:304-311 (2001).
Gangloff et al., "Molecular cloning of the Yeast Mitochondrial Aconitase Gene (ACO1) and Evidence of a Synergistic Regulation of Expression by Glucose plus Glutamate," *Mol. Cell. Biol.* 10(7):3551-3561 (1990).
Germer et al., "Overexpression, isolation, and spectroscopic characterization of the bidirectional [NiFe] hydrogenase from Synechocystis sp. PCC 6803," *J. Biol. Chem.* 284(52):36462-36472 (2009). (Epub Sep. 28, 2009).
Gescher et al., "Genes coding for a new pathway of aerobic benzoate metabolism in Azoarcus evansii," *J. Bacteriol.* 184(22):6301-6315 (2002).
Gibbs et al., "Degenerate olignucleotide gene shuffling (DOGS): a method for enhancing the frequence of recombination with family shuffling," *Gene* 271:13-20 (2001).
Gibson and McAlister-Henn, "Physical and genetic interactions of cytosolic malate dehydrogenase with other gluconeogenic enzymes," *J. Biol. Chem.* 278:25628-25636 (2003).
Giesel and Simon, "On the occurrence of enoate reductase and 2-oxo-calboxylate reductase in clostridia and some observations on the amino acid fermentation by Peptostreptococcus anaerobius," *Arch. Microbiol.* 135(1):51-57 (1983).
Gocke et al., "Branched-Chain Keto Acid Decarboxylase from Lactococcus lactis (KdcA), a Valuable Thiamine Diphosphate-Dependent Enzyme for Asymmetric C—C Bond Formation," *Adv. Synth. Catal.* 349:1425-1435 (2007).
Goda et al., "Cloning, sequencing, and expression in *Escherichia coli* of the Clostridium tetanomorphum gene encoding β-methylaspartase and characterization of the recombinant protein," *Biochemistry* 31(44):10747-10756 (1992).
Gogerty and Bobik, "Formation of isobutene from 3-hydroxy-3-methylbutyrate by diphosphomevalonate decarboxylase," *Appl. Environ. Microbiol.* 76(24):8004-8010 (2010). (Epub Oct. 22, 2010).
Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).
González and Robb, "Genetic analysis of Carboxydothermus hydrogenoformans carbon monoxide dehydrogenase genes cooF and cooS," *FEMS Microbiol. Lett.* 191(2):243-247 (2000).
Gourley et al., "The two types of 3-dehydroquinase have distinct structures but catalyze the same overall reaction," *Nat. Struct. Biol.* 6:521-525 (1999).
Grolle et al., "Isolation of the dxr gene of Zymomonas mobilis and characterization of the 1-deoxy-D-xylulose 5-phosphate reductoisomerase," *FEMS Microbiol. Lett.* 191:131-137 (2000).
Gu et al., "Crystal structure of shikimate kinase from Mycobacterium tuberculosis reveals the dynamic role of the LID domain in catalysis," *J. Mol. Biol.* 319:779-789 (2002).
Guest et al., "The fumarase genes of *Escherichia coli*: location of the fumB gene and discovery of a new gene (fumC)," *J. Gen. Microbiol.* 131(11):2971-2984 (1985).
Gulick et al., "The 1.75 A crystal structure of acetyl-CoA synthetase bound to adenosine-5'-propylphosphate and coenzyme A," *Biochemistry* 42(10):2866-2873 (2003).
Guo and Bhattacharjee, "Posttranslational activation, site-directed mutation and phylogenetic analyses of the lysine biosynthesis enzymes a-aminoadipate reductase Lys1p (AAR) and the phosphopantetheinyl transferase Lys7p (PPTase) from Schizosaccharomyces pombe," *Yeast* 21:1279-1288 (2004).
Guo and Bhattacharjee, "Site-directed mutational analysis of the novel catalytic domains of a-aminoadipate reductase (Lys2p) from candida albicans," *Mol. Gen. Gemonics* 269:271-279 (2003).
Guo et al., "Preferential hydrolysis of aberrant intermediates by the type II thioesterase in *Escherichia coli* nonribosomal enterobactin synthesis: substrate specificities and mutagenic studies on the active-site residues," *Biochemistry* 48(8):1712-1722 (2009).

(56) References Cited

OTHER PUBLICATIONS

Gutierrez et al., "A mutant D-amino acid aminotransferase with broad substrate specificity: construction by replacement of the interdoman loop Pro119-Arg120-Pro121 by Gly-Gly-Gly," *Protein Eng.* 11:53-58 (1998).
Gutierrez et al., "Modulation of activity and substrate specificity by modifying the backbone length of the distant interdomain loop of D-amino acid aminotransferase," *Eur. J. Biochem.* 267(24):7218-7223 (2000).
Ha et al., "Overexpression, crystallization and preliminary X-ray crystallographic analysis of erythronate-4-phosphate dehydrogenase from Pseudomonas aeruginosa," *Acta Crystallogr. Sect. F. Struct. Biol. Cryst. Commun.* 62(Pt 2):139-141 (2006). (Epub Jan. 27, 2006).
Hadfield et al., "Active Site Analysis of the Potential Antimicrobial Target Aspartate Semialdehyde Dehydrogenase," *Biochemistry* 40:14475-14483 (2001).
Hadfield et al., "Structure of Aspartate-β-semialdehyde Dehydrogenase from *Escherichia coli*, A Key Enzyme in the Aspartate Family of Amino Acid Biosynthesis," *J. Mol. Biol.* 289:991-1002 (1999).
Haller et al., "Discovering new enzymes and metabolic pathways: conversion of succinate to propionate by *Escherichia coli*," *Biochem.* 39(16):4622-4629 (2000).
Han et al., "Biochemical characterization and inhibitor discovery of shikimate dehydrogenase from Helicobacter pylori," *FEBS J.* 273:4682-4692 (2006).
Hanai et al., "Engineered synthetic pathway for isopropanol production in *Escherichia coli*," *Appl. Environ. Microbiol.* 73(24):7814-7818 (2007).
Hansen et al., "De novo biosynthesis of vanillin in fission yeast (*Schizosaccharomyces pombe*) and baker's yeast (*Saccharomyces cerevisiae*)," *Appl. Environ. Microbiol.* 75(9):2765-2774 (2009).
Harker and Bramley, "Expression of prokaryotic 1-deoxy-D-xylulose-5-phosphatases in *Escherichia coli* increases carotenoid and ubiquinone biosynthesis," *FEBS Lett.* 448:115-119 (1999).
Harrison and Harwood, "The pimFABCDE operon from Rhodopseudomonas palustris mediates dicarboxylic acid degradation and participates in anaerobic benzoate degradation," *Microbiology* 151:727-736 (2005).
Hartmanis, "Butyrate kinase from Clostridium acetobutylicum," *J. Biol. Chem.* 262(2):617-621 (1987).
Harwood et al., "Identification of the pcaRKF Gene cluster from Pseudomonas putida: Involvement in Chemotaxis, Biodegradation, and Transport of 4-Hydroxybenzoate," *J. Bacteriol.* 176(21):6479-6488 (1994).
Hasan and Nester, "Dehydroquinate synthase in Bacillus subtilis. An enzyme associated with chorismate synthase and flavin reductase," *J. Biol. Chem.* 253:4999-5004 (1978).
Hasegawa et al., "Transcriptional regulation of ketone body-utilizing enzyme, acetoacetyl-CoA synthetase, by C/EBPα during adipocyte differentiatiion," *Biochimica. Biophysica. Acta* 1779:414-419 (2008).
Haselbeck and McAlister-Henn, "Isolation, nucleotide sequence, and disruption of the *Saccharomyces cerevisiae* gene encoding mitochondrial NADP(H)-specific isocitrate dehydrogenase," *J. Biol. Chem.* 266(4):2339-2345 (1991).
Hashidoko et al., "Cloning of a DNA fragment carrying the 4-hydroxycinnamate decarboxylase (pofK) gene from Klebsielss oxytoca and its constitutive expression in *Escherichia coli* JM109 cells," *Biosci. Biotech. Biochem.* 58(1):217-218 (1994).
Hatakeyama et al., "Analysis of oxidation sensitivity of maleate cis-trans isomerase from Serratia marcescens," *Biosci. Biotechnol. Biochem.* 64:1477-1485 (2000).
Hatakeyama et al., "Gene Cloning and Characterization of Maleate cis-trans Isomerase from Alcaligenes faecalis," *Biochem. Biophys. Res. Comm.* 239:74-79 (1997).
Hawes et al., "Mammalian 3-hydroxyisobutyrate dehydrogenase," *Methods Enzymol.* 324:218-228 (2000).

Hayaishi et al., "Enzymatic studies on the metabolism of β-alanine," *J. Biol. Chem.* 236:781-790 (1961).
Hayden et al., "Glutamate dehydrogenase of Halobacterium salinarum: evidence that the gene sequence currently assigned to the NADP+-dependent enzyme is in fact that of the NAD+-dependent glutamate dehydrogenase," *FEMS Microbiol. Lett.* 211:37-41 (2002).
Hayes et al., "Combining computational and experimental screening for rapid optimization of protein properties," *Proc. Natl. Acad. Sci. U.S.A.* 99(25):15926-15931 (2002).
Haywood et al., "Characterization of two 3-ketothiolases possessing differing substrate specificities in the polyhydroxyalkanoate synthesizing organism Alcaligenes eutrophus," *FEMS Microbiol. Lett.* 52:91-96 (1988).
He and Wiegel. "Purification and characterization of an oxygen-sensitive reversible 4-hydroxybenzoate decarboxylase from Clostridium hydroxybenzoicum," *Eur. J Biochem.* 229:77-82 (1995).
Henriksson et al., "The 1.9 Å resolution structure of *Mycobacterium tuberculosis* 1-deoxy-D-xylulose 5-phosphate reductoisomerase, a potential drug target," *Acta. Crystallogr. D. Biol. Crystallogr.* 62(Pt 7):807-813 (2006).
Herrmann et al., "Energy Conservation via Electron-Transferring Flavoprotein in Anaerobic Bacteria," *J. Bacteriol.* 190(3):784-791 (2008).
Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).
Hibbert et al., "Directed evolution of biocatalytic processes," *Biomol. Eng.* 22:11-19 (2005).
Hijarrubia et al., "Domain Structure Characterization of the Multifunctional α-Aminoadipate Reductase from Penicillium chrysogenum by Limited Proteolysis," *J. Biol. Chem.* 278(10):8250-8256 (2003).
Hildebrandt et al., "Cloning, functional expression and biochemical characterization of a stereoselective alcohol dehydrogenase from Pseudomonas fluorescens DSM50106," *Appl. Microbiol. Biotechnol.* 59(4-5):483-487 (2002). (Epub Jun. 26, 2002).
Hillmer and Gottschalk, "Particulate Nature of Enzymes Involved in the Fermentation of Ethanol and Acetate by Clostridium Kluyveri," *FEBS Lett.* 21(3):351-354 (1972).
Hillmer and Gottschalk, "Solubilization and partial characterization of particulate dehydrogenases from Clostridium kluyveri," *Biochim Biophys. Acta.* 334:12-23 (1974).
Hirahara et al., "Cloning, nucleotide sequence, and overexpression in *Escherichia coli* of the beta-tyrosinase gene from an obligately symbiotic thermophile, Symbiobacterium thermophilum," *Appl. Microbiol. Biotechnol.* 39(3):341-346 (1993).
Hiser et al., "ERG10 from *Saccharomyces cerevisiae* encodes acetoacetyl-CoA thiolase," *J. Biol. Chem.* 269:31383-31389 (1994).
Hoffmeister et al., "Mitochondrial trans-2-enoyl-CoA reductase of wax ester fermentation from Euglena gracilis defines a new family of enzymes involved in lipid synthesis," *J. Biol. Chem.* 280(6):4329-4338 (2005).
Holden et al., "Chorismate lyase: kinetics and engineering for stability," *Biochim Biophys. Acta.* 1594(1):160-167 (2002).
Horswill and Escalante-Semerena, "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate," *Biochemistry* 40(15):4703-4713 (2001).
http://scorecard.goodguide.com/chemical-profiles/html/13butadiene.html 1,3-butadiene Scorecard (Aug. 16, 2001).
Huang et al., "Genetic characterization of the resorcinol catabolic pathway in Corynebacterium glutamicum," *Appl. Environ. Microbiol.* 72:7238-7245 (2006).
Huang et al., "Purification and characterization of a ferulic acid decarboxylase from Pseudomonas fluorescens," *J. Bacteriol.* 176:5912-5918 (1994).
Huang et al., "Identification and characterization of a second butyrate kinase from Clostridium acetobutylicum ATCC 824," *J. Mol. Microbiol. Biotechnol.* 2(1):33-38 (2000).

(56) References Cited

OTHER PUBLICATIONS

Hudson and Davidson, "Nucleotide sequence and transcription of the phenylalanine and tyrosine operons of *Escherichia coli* K12," *J. Mol. Biol.* 180(4):1023-1051 (1984).
Hughes et al.,"Evidence for isofunctional enzymes in the degradation of phenol, m- and p-toluate, and p-cresol via catechol meta-cleavage pathways in Alcaligenes eutrophus," *J. Bacteriol.* 158(1):79-83 (1984).
Hugler et al., "Autotrophic CO2 fixation via the reductive tricarboxylic acid cycle in different lineages within the phylum Aquificae: evidence for two ways of citrate cleavage," *Environ. Microbiol.* 9(1):81-92 (2007).
Hugler et al., "Evidence for autotrophic CO2 fixation via the reductive tricarboxylic acid cycle by members of the epsilon subdivision of proteobacteria," *J. Bacteriol.* 187(9):3020-3027 (2005).
Hugler et al., "Malonyl-Coenzyme A Reductase from Chloroflexus aurantiacus, a Key Enzyme of the 3-Hydroxypropionate Cycle for Autotrophic CO2 Fixation," *J. Bacteriol.* 184(9):2404-2410 (2002).
Huisman and Lalonde, "Enzyme evolution for chemical process applications," In R.N. Patel (ed.), *Biocatalysis in the pharmaceutical and biotechnology industries*, CRC Press, p. 717-742 (2007).
Hynes and Murray, "ATP-citrate lyase is required for production of cytosolic acetyl coenzyme A and development in Aspergillus nidulans," *Eukaryot. Cell.* 9(7):1039-1048 (2010). (Epub May 21, 2010).
Ikai and Yamamoto, "Identification and analysis of a gene encoding L-2,4-diaminobutyrate:2-ketoglutarate 4-aminotransferase involved in the 1,3-diaminopropane production pathway in Acinetobacter baumannii," *J. Bacteriol.* 179:5118-5125 (1997).
Ikai et al., "Two genes involved in the 1,3-diaminopropane production pathway in Haemophilus influenzae," *Biol. Pharm. Bull.* 21(2):170-173 (1998).
Ingoldsby et al., "The discovery of four distinct glutamate dehydrogenase genes in a strain of Halobacterium salinarum," *Gene* 349:237-244 (2005).
Ingram-Smith and Smith, "AMP-forming acetyl-CoA synthetases in Archaea show unexpected diversity in substrate utilization," *Archaea.* 2(2):95-107 (2007).
Ingram-Smith et al., "Characterization of the acetate binding pocket in the Methanosarcina thermophila acetate kinase," *J. Bacteriol.* 187(7):2386-2394 (2005).
Inoue et al., "Gene cloning and expression of Leifsonia alcohol dehydrogenase (LSADH) involved in asymmetric hydrogen-transfer bioreduction to produce (R)-form chiral alcohols," *Biosci. Biotechnol. Biochem.* 70(2):418-426 (2006).
Iraqui et al., "Characterisation of *Saccharomyces cerevisiae* ARO8 and ARO9 genes encoding aromatic aminotransferases I and II reveals a new aminotransferase subfamily," *Mol. Gen. Genet.* 257(2):238-248 (1998).
Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).
Ismaiel et al., "Purification and Characterization of a Primary-Secondary Alcohol Dehydrogenase from Two Strains of Clostridium beijerinckii," *J. Bacteriol.* 175(16):5097-5105 (1993).
Ismail et al., "Functional genomics by NMR spectroscopy. Phenylacetate catabolism in *Escherichia coli*," *Eur. J. Biochem.* 270(14):3047-3054 (2003).
Ismail, "Benzoyl-coenzyme A thioesterase of Azoarcus evansii: properties and function," *Arch. Microbiol.* 190(4):451-460 (2008). (Epub Jun. 10, 2008).
Itoh et al., "Continuous production of chiral 1,3-butanediol using immobilized biocatalysts in a packed bed reactor: promising biocatalysis method with an asymmetric hydrogen-transfer bioreduction," *Appl. Microbiol. Biotechnol.* 75(6):1249-1256 (2007). (Epub Apr. 19, 2007).
Iverson et al., "Structure of the *Escherichia coli* fumarate reductase respiratory complex," *Science* 284(5422):1961-1966 (1999).
Iwakura et al., "Studies on regulatory functions of malic enzymes. VI. Purification and molecular properties of NADP-linked malic enzyme from *Escherichia coli* W," *J. Biochem.* 85:1355-1365 (1979).
Izumi et al., "Structure and Mechanism of HpcG, a Hydratase in the Homoprotocatechuate Degradation Pathway of *Escherichia coli*," *J. Mol. Biol.* 370:899-911 (2007).
Jacobi et al., "The hyp operon gene products are required for the maturation of catalytically active hydrogenase isoenzymes in *Escherichia coli*," *Arch. Microbiol.* 158(6):444-451 (1992).
Jacques et al., "Characterization of yeast homoserine dehydrogenase, an antifungal target: the invariant histidine 309 is important for enzyme integrity," *Biochem. Biophys. Acta* 1544:28-41 (2001).
James and Viola, "Production and characterization of bifunctional enzymes. Domain swapping to produce new bifunctional enzymes in the aspartate pathway," *Biochemistry* 41(11) 3720-3725 (2002).
Jeng et al., "Ornithine degradation in Clostridium sticklandii; pyridoxial phosphate and Coenzyme A dependent thiolytic cleavage of 2-amino-4-ketopentanoate to alanine and acetyl Coenzyme A," *Biochemistry* 13(14):2898-2903 (1974).
Jeon et al., "Heterologous expression of the alcohol dehydrogenase (adhI) gene from Geobacillius thermoglucosidasius strain M10EXG," *J. Biotechnol.* 135:127-133 (2008).
Jogl and Tong, "Crystal structure of yeast acetyl-coenzyme A synthetase in complex with AMP," *Biochemistry* 43(6):1425-1431 (2004).
Jojima et al., "Production of isopropanol by metabolically engineered *Escherichia coli*," *Appl. Microbiol. Biotechnol.* 77:1219-1224 (2008).
Jones and Woods,"Acetone-butanol fermentation revisited," *Microbiol. Rev.* 50(4):484-524 (1986).
Jones et al., "Molecular cloning, characterization and analysis of the regulation of the ARO2 gene, encoding chorismate synthase, of *Saccharomyces cerevisiae*," *Mol. Microbiol.* 5(9):2143-2152 (1991).
Junker and Ramos, "Involvement of the cis/trans isomerase Cti in solvent resistance of Pseudomonas putida DOT-T1E," *J. Bacteriol.* 181:5693-5700 (1999).
Junker et al., "Characterization of the p-toluenesulfonate operon tsaMBCD and tsaR in Comamonas testosteroni T-2," *J. Bacteriol.* 179(3):919-927 (1997).
Kai et al., "Phosphoenolpyruvate carboxylase: three-dimensional structure and molecular mechanisms," *Arch. Biochem. Biophys.* 414:170-179 (2003).
Kamath et al., "Enzyme-catalysed non-oxidative decarboxylation of aromatic acids: I. Purification and spectroscopic properties of 2,3 dihydroxybenzoic acid decarboxylase from Aspergillus niger," *Biochem. Biophys. Res. Commun.* 145(1):586-595 (1987).
Kanao et al., "Characterization of isocitrate dehydrogenase from the green sulfur bacterium Chlorbium limicola. A carbon dioxide-fixing enzyme in the reductive tricarboxylic acid cycle," *Eur. J. Biochem.* 269(7):1926-1931 (2002).
Kanao et al., "Kinetic and biochemical analyses on the reaction mechanism of a bacterial ATP-citrate lyase," *Eur. J. Biochem.* 269(14):3409-3416 (2002).
Kasberg et al., "Cloning, characterization, and sequence analysis of the clcE gene encoding the maleylacetate reductase of *Pseufomonas* sp. Strain B13," *J. Bacteriol.* 179:3801-3803 (1997).
Kaschabek and Reineke, "Degradation of chloroaromatics: purification and characterization of maleylacetate reductase from *Pseudomonas* sp. Strain B13," *J. Bacteriol.* 175:6075-6081 (1993).
Kaschabek and Reineke, "Maleylacetate reductase of *Pseufomonas* sp. Strain B13: specificity of substrate conversion and halide elimination," *J. Bacteriol.* 177:320-325 (1995).
Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).
Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).

(56) References Cited

OTHER PUBLICATIONS

Kawasaki et al., "Enzymatic synthesis of L-tryptophan by Enterobacter aerogenes tryptophanase highly expressed in *Escherichia coli*, and some properties of the purified enzyme," *Biosci. Biotechnol. Biochem.* 59(10):1938-1943 (1995).
Kazahaya et al, "Aerobic Dissimilation of Glucose by Heterolactic Bacteria III. Aldehyde dehydrogenase and alcohol dehydrogenase of luconostoc mesenteroids" *J. Gen. Appl. Microbiol.* 18(1):43-55 (1972).
Kellum and Drake, "Effects of cultivation gas phase on hydrogenase of the acetogen Clostridium thermoaceticum," *J. Bacteriol.* 160(1):466-469 (1984).
Keng and Viola, "Specificity of Aspartokinase III from *Escherichia coli* and Examination of Important Catalytic Residues," *Arch. Biochem. Biophys.* 335(1):73-81 (1996).
Kenklies et al., "Proline biosynthesis from L-ornithine in Clostridium sticklandii purification of Δ1-pyrroline-5-carboxylate reductase, and sequence and expression of encoding gene, proC," *Microbiology* 145(Pt 4):819-826 (1999).
Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).
Khan et al., "Molecular Properties and Enhancement of Thermostability by Random Mutagenesis of Glutamate Dehydrogenase from Bacillus subtilis," *Biosci. Biotechnol. Biochem.* 69(10):1861-1870 (2005).
Kikuchi et al., "Mutational analysis of the feedback sites of phenylalanine-sensitive 3-deoxy-D-arabino-heptulosonate-7-phosphate synthase of *Escherichia coli,*" *Appl. Environ. Microbiol.* 63(2):761-762 (1997).
Kim and Lee, "Catalytic promiscuity in dihydroxy-acid dehydratase from the thermoacidophilic archaeon Sulfolobus solfataricus," *J. Biochem.* 139(3):591-596 (2006).
Kim and Tabita, "Both subunits of ATP-citrate lyase from Chlorobium tepidum contribute to catalytic activity," *J. Bacteriol.* 188(18):6544-6552 (2006).
Kim et al, "Effect of Overexpression of Actinobacillus succinogenes Phosphoenolpyruvate Carboxykinase on Succinate Production in *Escherichia coli,*" *Appl. Env. Microbiol.* 70(2) 1238-1241 (2004).
Kim et al., "Construction of an *Escherichia coli* K-12 Mutant for Homoethanologenic Fermentation of Glucose or Xylose without Foreign Genes," *Appl. Environ. Microbiol.* 73(6):1766-1771 (2007).
Kim et al., "Dihydrolipoamide dehydrogenase mutation alters the NADH sensitivity of pyruvate dehydrogenase complex of *Escherichia coli* K-12," *J. Bacteriol.* 190:3851-3858 (2008).
Kinderlerler and Hatton, "Fungal metabolites of sorbic acid," *Food Addit. Contam.* 7(5):657-669 (1990).
Kinghorn et al., "The cloning and analysis of the aroD gene of *E. coli* K-12," *Gene* 14(1-2):73-80 (1981).
Kinoshita, "Purification of two alcohol dehydrogenases from Zymomonas mobilis and their properties," *Appl. Microbiol. Biotechnol.* 22:249-254 (1985).
Kito et al., "Purification and Regulatory Properties of the Biosynthetic L-Glycerol 3-Phosphate Dehydrogenase from *Escherichia coli,*" *J. Biol. Chem.* 244(12):3316-3323 (1969).
Kitzing et al., "Spectroscopic and kinetic characterization of the bifunctional chorismate synthase from Neurospora crassa: evidence for a common binding site for 5-enolpyruvylshikimate 3-phosphate and NADPH," *J. Biol. Chem.* 276(46):42658-42666 (2001).
Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).
Klyosov, "Kinetics and specificity of human liver aldehyde dehydrogenases toward aliphatic, aromatic, and fused polycyclic aldehydes," *Biochemistry* 35(14):4457-4467 (1996).
Knappe and Sawers, "A radical-chemical route to acetyl-CoA: the anaerobically induced pyruvate formate-lyase system of *Escherichia coli,*" *FEMS. Microbiol. Rev.* 75:383-398 (1990).
Kobayashi et al., "Physicochemical, catalytic, and immunochemical properties of fumarases crystallized separately from mitochondrial and cytosolic fractions of rat liver," *J. Biochem.* 89(6):1923-1931 (1981).
Koch and Fuchs, "Enzymatic reduction of benzoyl-CoA to alicyclic compounds, a key reaction in anaerobic aromatic metabolism," *Eur. J. Biochem.* 205:195-202 (1992).
Kogan et al., "Crystallization and preliminary X-ray analysis of the apo form of *Escherichia coli* tryptophanase," *Acta. Crystallogr. D. Biol. Crystallogr.* 60(Pt 11):2073-2075 (2004). (Epub Oct. 20, 2004).
Koland and Gennis, "Proximity of Reactive Cysteine Residue and Flavin in *Escherichia coli* Pyruvate Oxidase as Estimated by Flourescence Energy Transfer," *Biochemistry* 21:4438-4442 (1982).
Kollmann-Koch et al.,"Nicotinic acid metabolism. Dimethylmaleate hydratase," *Hoppe Seylers Z Physiol Chem.* 365(8):847-857 (1984).
Koo et al., "Cloning and characterization of the bifunctional alcohol/acetaldehyde dehydrogenase gene (adhE) in Leuconostoc mesenteroides isolated from kimchi," *Biotechnol. Lett.* 27(7):505-510 (2005).
Korbert et al., "Crystallization of the NADP+-dependent Glutamate Dehydrogenase from *Escherichia coli,*" *J. Mol. Biol.* 234:1270-1273 (1993).
Korolev et al., "Autotracing of *Escherichia coli* acetate CoA-transferase a-subunit structure using 3.4 Å MAD and 1.9 Å native data," *Acta. Crystallogr. D. Biol. Crystallogr.* 58(Pt 12):2116-2121 (2002).
Kort et al., "Glutamate dehydrogenase from the hyperthermophilic bacterium Thermotoga maritima: molecular characterization and phylogenetic implications," *Extremophiles* 1:52-60 (1997).
Kosaka et al., "Characterization of the sol operon in butanol-hyperproducing Clostridium saccharoperbutylacetonicum strain N1-4 and its degeneration mechanism," *Biosci. Biotechnol. Biochem.* 71:58-68 (2007).
Koshiba et al., "Purification and Properties of Flavin- and Molybdenum-Containing Aldehyde Oxidase from Coleoptiles of Maize," *Plant Physiol.* 110(3):781-789 (1996).
Kosjek et al., "Purification and characterization of a chemotolerant alcohol dehydrogenase applicable to coupled redox reactions," *Biotechnol. Bioeng.* 86(1):55-62 (2004).
Kowalchuk et al., "Contrasting patterns of evolutionary divergence within the Acinetobacter calcoaceticus pca operon," *Gene* 146:23-30 (1994).
Kreimeyer et al., "Identification of the Last Unknown Genes in the Fermentation Pathway of Lysine," *J. Biol. Chem.* 282(10):7191-7197 (2007).
Krell et al., "Biochemical and X-ray crystallographic studies on shikimate kinase: The important structural role of the P-loop lysine," *Protein Sci.* 10(6):1137-1149 (2001).
Kuettner et al., "Active-site mobility revealed by the crystal structure of arylmalonate decarboxylase from Bordetella bronchiseptica," *J. Mol. Biol.* 377(2):386-394 (2008). (Epub Jan. 5, 2008).
Kumari et al., "Cloning, Characterization, and Functional Expression of acs, the Gene Which Encodes Acetyl Coenzyme A Synthetase in *Escherichia coli,*" *J. Bacteriol.* 177(10): 2878-2886 (1995).
Kurihara et al., "A Novel Putrescine Utilization Pathway Involves γ-Glutamylated Intermediates of *Escherichia coli* K-12," *J. Biol. Chem.* 280(6):4602-4608 (2005).
Kuzma et al., "Bacteria Produce the Volatile Hydrocarbon Isoprene," Current Microbiology, 30:97-103 (1995).
Kuznetsova et al., "Enzyme genomics: Application of general enzymatic screens to discover new enzymes," *FEMS Microbiol. Rev.* 29(2):263-279 (2005).
Kwok and Hanson, "GFP-labelled Rubisco and aspartate aminotransferase are present in plastid stromules and traffic between plastids," *J. Exp. Bot.* 55(397):595-604 (2004).
Kwon et al., "Influence of gluconegoenic phosphoenolpyruvate carbosykinase (PCK) expression on succinic acid fermentation in *Escherichi coli* under high bicarbonate condition," *J. Microbiol. Biotechnol.* 16(9):1448-1452 (2006).

(56) References Cited

OTHER PUBLICATIONS

Laivenieks et al., "Cloning sequencing, and overexpression of the Anaerobiospirillum succiniproducens phosphoenolpyruvate carboxykinase (pckA) gene," *Appl. Environ. Microbiol.* 63:2273-2280 (1997).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.* 395(1):147-155 (2006).
Lamed and Zeikus, "Novel NADP-linked alcohol-aldehyde/ketone oxidoreductase in thermophilic ethanologenic bacteria," *Biochem. J.* 195:183-190 (1981).
Lau et al., "Sequence and expression of the todGIH genes involved in the last three steps of toluene degradation by Pseudomonas putida F1," *Gene* 146(1):7-13 (1994).
Lauvergeat et al., "Two cinnamoyl-CoA reductase (CCR) genes from Arabidopsis thaliana are differentially expressed during development and in response to infection with pathogenic bacteria," *Phytochemistry* 57(7):1187-1195 (2001).
Learned et al., "3-Hydroxy-3-methylglutaryl-coenzyme A reductase from Arabidopsis thaliana is structurally distinct from the yeast and animal enzymes," *Proc. Natl. Acad. Sci. U. S. A.* 86(8):2779-2783 (1989).
Lebbink et al., "Engineering activity and stability of Thermotoga maritima glutamate dehydrogenase I. Introduction of a six-residue ion-pair network in the hinge region," *J. Mol. Biol.* 280:287-296 (1998).
Lebbink et al., "Engineering Activity and Stability of Thermotoga maritima glutamate Dehydrogenase. II: construction of a 16-Residue Ion-pair Network at the Subunit Interface," *J. Mol. Biol.* 289:357-369 (1999).
Lee et al., "A new approach to directed gene evolution by recombined extension on truncated templates (RETT)," *J. Molec. Catalysis* 26:119-129 (2003).
Lee et al., "Cloning and Characterization of Mannheimia succiniciproducens MBEL55E Phosphoenolpyruvate Carboxykinase (pckA) Gene," *Biotechnol. Bioprocess Eng.* 7:95-99 (2002).
Lee et al., "Cloning and characterization of the dxs gene, encoding 1-deoxy-D-xylulose 5-phosphate synthase from Agrobacterium tumefaciens, and its overexpression in Agrobacterium tumefaciens," *J. Biotechnol.* 128(3):555-566 (2007).
Lee et al., "Crystal structure of the type II 3-dehydroquinase from Helicobacter pylori," *Proteins* 51(4):616-617 (2003).
Lee-Peng et al., "Transaminase B from *Escherichia coli*: quaternary structure, amino-terminal sequence, substrate specificity, and absence of a separate valine-alpha-ketoglutarate activity," *J. Bacteriol.* 139(2):339-345 (1979).
Leutwein and Heider, "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).
Lian et al., "Stereochemical and Isotopic Labeling Studies of 4-Oxalocrotonate Decarboxylase and Vinylpyruvate hydratase: Analysis and Mechanistic Implications," *J. Am. Chem Soc.* 116:10403-10411 (1994).
Lilley et al., "The 92-min region of the *Escherichia coli* chromosome: location and cloning of the ubiA and alr genes," *Gene* 129(1):9-16 (1993).
Lin et al., "Fed-batch culture of a metabolically engineered *Escherichia coli* strain designed for high-level succinate production and yield under aerobic conditions," *Biotechnol. Bioeng.* 90:775-779 (2005).
Lindahl et al., "Rat liver aldehyde dehydrogenase. II. Isolation and characterization of four inducible isozymes," *J. Biol. Chem.* 259(19):11991-11996 (1984).
Liu et al., "Crystal structures of unbound and aminooxyacetate-bound *Escherichia coli* γ-aminobutyrate aminotransferase," *Biochemistry* 43(34):10896-10905 (2004).

Løbner-Olesen and Marinus, "Identification of the Gene (aroK) Encoding Shikimic Acid Kinase I of *Escherichia coli*," *J. Bacteriol.* 174(2):525-529 (1992).
Locher et al., "4-Toluene Sulfonate Methyl-Monooxygenase from Comamonas testosteroni T-2: Purification and Some Properties of the Oxygenase Component," *J. Bacteriol.* 173(12):3741-3748 (1991).
Lokanath et al., "Crystal structure of novel NADP-dependent 3-hydroxyisobutyrate dehydrogenase from Thermus thermophilus HB8," *J. Mol. Biol.* 352(4):905-917 (2005).
Long et al., "Involvement of snapdragon benzaldehyde dehydrogenase in benzoic acid biosynthesis," *Plant J.* 59(2):256-265 (2009). (Epub Mar. 9, 2009).
Lopez-Barragan et al., "The bzd gene cluster, coding for anaerobic benzoate catabolism, in *Azoarcus* sp. Strain CIB," *J. Bacteriol.* 186(17):5762-5774 (2004).
Louie and Chan, "Cloning and characterization of the gamma-glutamyl phosphate reductase gene of Campylobacter jejuni," *Mol. Gen. Genet.* 240:29-35 (1993).
Louis et al., "Characterization of genes for the biosynthesis of the compatible solute ectoine from Marinococcus halophilus and osmoregulated expression in *Escherichia coli*," *Microbiology* 143 (Pt 4):1141-1149 (1997).
Louis et al., "Restricted distribution of the butyrate kinase pathway among butyrate-producing bacteria from the human colon," *J. Bacteriol.* 186:2099-2106 (2004).
Low et al., "Mimicking somatic hypermutation: Affinity maturation of antibodies displayed on baceriophage using a bacterial mutator strain," *J. Mol. Biol.* 260(3):359-368 (1996).
Lukey et al, "How *Escherichia coli* is equipped to oxidize hydrogen under different redox conditions," *J. Biol. Chem.* 285(6):3928-3938 (2010). (Epub Nov. 16, 2009).
Lupa et al., "Distribution of genes encoding the microbial non-oxidative reversible hydroxyarylic acid decarboxylases/phenol carboxylases," *Genomics* 86:342-351 (2005).
Lupa et al., "Properties of the reversible nonoxidative vanillate/4-hydroxybenzoate decarboxylase from Bacillus subtilis," *Can. J. Microbiol.* 54:75-81 (2008).
Lutz et al., "Creating multiple-crossover DNA libraries independent of sequence identity," *Proc. Natl. Acad. Sci. U.S.A.* 98:11248-11253 (2001).
Lutz et al., "Rapid generation of incremental truncation libraries for protein enginering using α-phosphothioate nucleotides," *Nucleic Acids Res.* 29:E16 (2001).
Ma et al., "Induced rebuilding of aspartase conformation," *Ann. NY Acad. Sci.* 672:60-65 (1992).
Ma, "Characterization of a cinnamoyl-CoA reductase that is associated with stem development in wheat," *J. Exp. Bot.* 58(8):2011-2021 (2007). (Epub Apr. 23, 2007).
Macheroux et al., "A unique reaction in a common pathway: mechanism and function of chorismate synthase in the shikimate pathway," Planta 207(3):325-334 (1999).
Macis et al., "Properties and sequence of the Coenzyme B12-dependent glycerol dehydratase of Clostridium pasteruianum," *FEMS Microbiol. Lett.* 164:21-28 (1998).
Mack and Buckel, "Conversion of glutaconate CoA-transferase from Acidaminococcus fermentans into an acyl-CoA hydrolase by site-directed mutagenesis," *FEBS Lett.* 405(2):209-212 (1997).
Mack et al., "Location of the two genes encoding glutaconate Coenzyme A-transferase at the beginning of the hydroxyglutarate operon in Acidaminococcus fermentans," *Eur. J. Biochem.* 226:41-51 (1994).
Maclean and Ali, "The Structure of Chorismate Synthase Reveals a Novel Flavin Binding Site Fundamental to a Unique Chemical Reaction," *Structure* 11(12):1499-1511 (2003).
Maeda et al., "*Escherichia coli* hydrogenase 3 is a reversible enzyme possessing hydrogen uptake and synthesis activities," *Appl. Microbiol. Biotechnol.* 76(5):1035-1042 (2007). (Epub Aug. 1, 2007).
Mahan and Csonka, "Genetic analysis of the proBA genes of *Salmonella typhimurium*: physical and genetic analyses of the cloned proB+A+ genes of *Escherichia coli* and of a mutant allele that confers proline overproduction and enhanced osmotolerance," *J. Bacteriol.* 156:1249-1262 (1983).

(56) References Cited

OTHER PUBLICATIONS

Manjasetty et al., "Crystallization and preliminary X-ray analysis of dmpFG-encoded 4-hydroxy-2-ketovalerate aldolase-aldehyde dehydrogenase (acylating) from *Pseudomonas* sp strain CF600," *Acta. Crystallogr. D. Biol. Crystallogr.* 57(Pt 4):582-585 (2001).

Manning and Pollitt, "Tracer studies of the interconversion of R- and S-methylmalonic semialdehydes in man," *Biochem. J.* 231(2):481-484 (1985).

Marks et al., "Molecular cloning and characterization of (R)-3-hydroxybutyrate dehydrogenase from human heart," *J. Biol. Chem.* 267(22):15459-15463 (1992).

Marolewski et al., "Cloning and characterization of a new purine biosynthetic enzyme: a non-folate glycinamide ribonucleotide transformylase from *E. coli*," *Biochemistry* 33(9):2531-2537 (1994).

Martin et al., "Engineering a mevalonate pathway in *Escherichia coli* for production of terpenoids," *Nat. Biotechnol.* 21:796-802 (2003).

Martínez-Blanco, et al, "Purification and biochemical characterization of phenylacetyl-CoA ligase from Pseudomonas putida. A specific enzyme for the catabolism of phenylacetic acid," *J. Biol. Chem.* 265(12):7084-7090 (1990).

Martinez-Carrion and Jenkins, "D-Alanine-D-glutamate transminase. I. Purification and characterization," *J. Biol. Chem.* 240(9):3538-3546 (1965).

Martins et al., "Crystal structure of 4-hydroxybutyryl-CoA dehydratase: radical catalysis involving a [4Fe—4S] cluster and flavin," *Proc. Natl. Acad. Sci. U.S.A.* 101(44):15645-15649 (2004).

Matiasek et al., "Volatile ketone formation in bacteria: release of 3-oxopentanoate by soil pseudomonads during growth on heptanoate," *Curr. Microbiol.* 42:276-281 (2001).

Matsui et al., "Purification, characterization, and gene cloning of 4-hydroxybenzoate decarboxylase of Enterobacter cloacae P240," *Arch. Microbiol.* 186(1):21-29 (2006). (Epub Jun. 7, 2006).

Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).

McAlister-Henn and Thompson, "Isolation and expression of the gene encoding yeast mitochondrial malate dehydrogenase," *J. Bacteriol.* 169:5157-5166 (1987).

McPherson and Wootton, "Complete nucleotide sequence of the *Escherichia coli* gdhA gene," *Nucleic Acids Res.* 11:5257-5266 (1983).

Mehdi et al., "Dehydroquinate synthase from *Escherichia coli*, and its substrate 3-deoxy-D-arabino-heptulosonic acid 7-phosphate," *Methods Enzymol.* 142:306-314 (1987).

Meijer et al., "Gene deletion of cytosolic ATP: citrate lyase leads to altered organic acid production in Aspergillus niger," *J. Ind. Microbiol. Biotechnol.* 36(10):1275-1280 (2009). (Epub Jun. 25, 2009).

Melchiorsen et al., "The level of pyruvate-formate lyase controls the shift from homolactic to mixed-acid product formation in Lactococcus lactis," *Appl. Microbiol. Biotechnol.* 58:338-344 (2002).

Menon and Ragsdale, "Mechanism of the Clostridium thermoaceticum pyruvate:ferredoxin oxidoreductase: evidence for the common catalytic intermediacy of the hydroxyethylthiamine pyropyrophosphate radical," *Biochemistry* 36(28):8484-8494 (1997).

Metz et al., "Purification of a jojoba embryo fatty acyl-Coenzyme A reductase and expression of its cDNA in high erucic acid rapeseed," *Plant Phys.* 122:635-644 (2000).

Michel et al., "Structures of Shikimate Dehydrogenase AroE and its Paralog YdiB. A Common Structural Framework for Different Activities," *J. Biol. Chem.* 278(21):19463-19472 (2003).

Milić et al., "Insights into the catalytic mechanism of tyrosine phenol-lyase from X-ray structures of quinonoid intermediates," *J. Biol. Chem.* 283(43):29206-29214 (2008). (Epub Aug. 20, 2008).

Minard and McAlister-Henn, "Isolation, nucleotide sequence analysis, and disruption of the MDH2 gene from *Saccharomyces cerevisiae*: evidence for three isozymes of yeast malate dehydrogenase," *Mol. Cell. Biol.* 11:370-380 (1991).

Miyazaki et al., "α-Aminoadipate aminotransferase from an extremely thermophilic bacterium, Thermus thermophilus," *Microbiology* 150:2327-2334 (2004).

Mizobata et al., "Purification and characterization of a thermostable class II fumarase from Thermus thermophilus," *Arch. Biochem. Biophys.* 355(1):49-55 (1998).

Moore et al., "Efficient independent activity of a monomeric, monofunctional dehydroquinate synthase derived from the N-terminus of the pentafunctional AROM protein of Aspergillus nidulans," *Biochem. J.* 301 ( Pt 1):297-304 (1994).

Moore et al., "Expression and Purification of Aspartate β-Semialdehyde Dehydrogenase from Infectious Microorganisms," *Protein Expr. Purif.* 25:189-194 (2002).

Moore et al., "Plant-like biosynthetic pathways in bacteria: from benzoic acid to chalcone," *J. Nat. Prod.* 65(12):1956-1962 (2002).

Mori et al., "Characterization, Sequencing, and Expression of the Genes Encoding a Reactivating Factor for Glycerol-inactivated Adenosylcobalamin-dependent Diol Dehydratase," *J. Biol. Chem.* 272(51):32034-32041 (1997).

Morris and Jinks-Robertson, "Nucleotide sequence of the LYS2 gene of *Saccharomyces cerevisiae*: homology to Bacillus brevis tyrocidine synthetase 1," *Gene* 98:141-145 (1991).

Mukhopadhyay and Purwantini, "Pyruvate carboxylase from *Mycobacterium smegmatis*: stabilization, rapid purification, moleculare and biochemical characterization and regulation of the cellular level," *Biochim. Biophys. Acta* 1475(3):191-206 (2000).

Muller et al., "Nucleotide exchange and excisiion technology (NExT) DNA shuffling; a robust method for DNA fragmentation and directed evolution," *Nucleic Acids Res.* 33:e117 (2005).

Muratsubaki and Enomoto, "One of the fumarate reductase isoenzymes from *Saccharomyces cerevisiae* is encoded by the OSM1 gene," *Arch. Biochem. Biophys.* 352:175-181 (1998).

Musfeldt and Schönheit, "Novel type of ADP-forming acetyl Coenzyme A synthetase in hyperthermophilic archaea: heterologous expression and characterization of isoenzymes from the sulfate reducer Archaeoglobus fulgidus and the methanogen Methanococcus jannaschii," *J. Bacteriol.* 184(3):636-644 (2002).

Nagasawa et al., "Syntheses of L-tyrosine-related amino acids by tyrosine phenol-lyase of Citrobacter intermedius," *Eur. J. Biochem.* 117(1):33-40 (1981).

Naggert et al., "Cloning, sequencing, and characterization of *Escherichia coli* thioesterase II," *J. Biol. Chem.* 266(17):11044-11050 (1991).

Nakahigashi and Inokuchi, "Nucleotide sequence of the fadA and fadB genes from *Escherichia coli*," *Nucleic Acids Res.* 18(16):4937 (1990).

Nakano et al., "Characterization of Anaerobic Fermentative Growth of Bacillus subtilis: Identification of Fermentation End Products and Genes Required for Growth," *J. Bacteriol.* 179(21):6749-6755 (1997).

Nakazawa et al., "Phthalate and 4-hydroxyphthalate metabolism in Pseudomonas testosteroni: purification and properties of 4,5-dihydroxyphthalate decarboxylase," *Appl. Environ. Microbiol.* 36(2):264-269 (1978).

Ness et al., "Synthetic shuffling expands functional protein diversity by allowing amino acids to recombine independently," *Nat. Biotechnol.* 20:1251-1255 (2002).

Neuser et al., "Purification, characterisation and cDNA sequencing of pyruvate decarboxylase from Zygosaccharomyces bisporus," *Biol. Chem.* 381(4):349-353 (2000).

Nilekam and SivaRaman, "Purification and properties of citrate lyase from *Escherichia coli*," *Biochemistry* 22(20):4657-4663 (1983).

Nimmo, "Kinetic mechanism of *Escherichia coli* isocitrate dehydrogenase and its inhibition by glyoxylate and oxaloacetate," *Biochem. J.* 234(2):317-323 (1986).

Nishizawa et al., "Gene expression and characterization of two 2-oxoacid:ferredoxin oxidoreductases from Aeropyrum pernix K1," *FEBS Lett.* 579:2319-2322 (2005).

Niu et al., "Benzene-free synthesis of adipic acid," *Biotechnol. Prog.* 18:201-211 (2002).

(56) References Cited

OTHER PUBLICATIONS

Nogales et al., "Characterization of the last step of the aerobic phenylacetic acid degradation pathway," *Microbiology* 153(Pt 2):357-365 (2007).
Nowrousian et al., "The fungal acl1 and acl2 genes encode two polypeptides with homology to the N- and C-terminal parts of the animal ATP citrate lyase polypeptide," *Curr. Genet.* 37(3):189-193 (2000).
O'Brien and Gennis, "Studies of the Thiamin Pyrophosphate Binding Site of *Escherichia coli* Pyruvate Oxidase," *J. Biol. Chem.* 255(8):3302-3307 (1980).
O'Brien et al., "Regulation by Lipids of Cofactor Binding to a Peripheral Membrane Enzyme: Binding of Thiamin Pyrophosphate to Pyruvate Oxidase," *Biochemistry* 16(14):3105-3109 (1977).
O'Brien et al., "Insight into the Mechanism of the B12-Independent Glycerol Dehydratase from Clostridium butyricum: Preliminary Biochemical and Structural Characterization," *Biochemistry* 43:4635-4645 (2004).
Ohgami et al., "Expression of acetoacetyl-CoA synthetase, a novel cytosolic ketone body-utilizing enzyme, in human brain," *Biochem. Pharmacol.* 65:989-994 (2003).
Okazaki et al., "Cloning and nucleotide sequencing of phenylalanine dehydrogenase gene of Bacillus sphaericus," *Gene* 63(2):337-341 (1988).
Okuno et al., "2-Aminoadipate-2-oxoglutarate aminotransferase isoenzymes in human liver: a plausible physiological role in lysine and tryptophan metabolism." *Enzyme Protein* 47:136-148 (1993).
Oliveira et al., "Cloning and overexpression in soluble form of functional shikimate kinase and 5-enolpyruvylshikimate 3-phosphate synthase enzymes from *Mycobacterium tuberculosis*," *Protein Expr. Purif.* 22(3):430-435 (2001).
Olivera et al., "Molecular characterization of the phenylacetic acid catabolic pathway in Pseudomonas putida U: the phenylacetyl-CoA catabolon," *Proc. Natl. Acad. Sci. U.S.A.* 95(11):6419-6424 (1998).
O'Reilly and Devine, "Sequence and analysis of the citrulline biosynthetic operon argC-F from Bacillus subtilis," *Microbiology* 140:1023-1025 (1994).
Ostermeier et al., "A Combinatorial approach to hybrid enzymes independent of DNA homology," *Nat. Biotechnol.* 17:1205-1209 (1999).
Ostermeier et al., "Combinatorial protein engineering by incremental truncation," *Proc. Natl. Acad. Sci. U.S.A.* 96:3562-3567 (1999).
Otten and Quax, "Directed evolution:selecting today's biocatalysts," *Biomol. Eng.* 22:1-9 (2005).
Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).
Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).
Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).
Parkin et al., "Rapid and efficient electrocatalytic CO2/CO interconversions by Calboxydothermus hydrogenoformans CO dehydrogenase I on an electrode," *J. Am. Chem. Soc.* 129(34):10328-10329 (2007).
Parsot et al., "Nucleotide sequence of *Escherichia coli* argB and argC genes: comparison of N-acetylglutamate kinase and N-acetylglutamate-γ-semialdehyde dehydrogenase with homologous and analogous enzymes," *Gene* 68:275-283 (1988).
Pauwels et al., "The N-acetylglutamate synthase/N-acetylgltamate kinase metabolon of *Saccharomyces cerevisiae* allows co-ordinated feedback regulation of the first two steps in arginine biosynthesis," *Eur. J. Biochem.* 270:1014-1024 (2003).
Peisach et al., "Crystallographic study of steps along the reaction pathway of D-amino acid aminotransferase," *Biochemistry* 37(14)4958-4967 (1998).

Pennacchio et al., "Purification and characterization of a novel recombinant highly enantioselective short-chain NAD(H)-dependent alcohol dehydrogenase from Thermus thermophilus," *Appl. Environ. Microbiol.* 74(13):3949-3958 (2008). (Epub May 2, 2008).
Peoples and Sinskey, "Fine structural analysis of the Zoogloea ramigera phbA-phbB locus encoding β-ketothiolase and acetoacetyl-CoA reductase: nucleotide sequence of phbB," *Mol. Microbiol.* 3:349-357 (1989).
Peretz and Burstein, "Amino acid sequence of alcohol dehydrogenase from the thermophilic bacterium Thermoanaerobium brockii," *Biochemistry* 28(16):6549-6555 (1989).
Perez et al., "*Escherichia coli* YqhD exhibits aldehyde reductase activity and protects from the harmful effect of lipid peroxidation-derived aldehydes," *J. Biol. Chem.* 283(12):7346-7353 (2008).
Philipp et al., "Anaerobic degradation of protocatechuate (3,4-dihydroxybenzoate) by Thauera aromatica strain AR-1," *FEMS Microbiol. Lett.* 212(1):139-143 (2002).
Phillips et al., "Structure and mechanism of tryptophan indole-lyase and tyrosine phenol-lyase," Biochim. *Biophys. Acta.* 1647(1-2):167-172 (2003).
Pieper et al., "Engineering bacteria for bioremediation," Current Opinion in Biotechnology, 11(3):262-270 (2000).
Pierce et al., "Gene cloning and characterization of a second alanine racemase from Bacillus subtilis encoded by yncD," *FEMS Microbiol. Lett.* Jun. 2008;283(1):69-74 (2008). (Epub Apr. 8, 2008).
Pieulle et al., "Isolation and analysis of the gene encoding the pyruvate-ferredoxin oxidoreductase of Desulfovibrio africanus, production of the recombinant enzyme in *Escherichia coli*, and effect of carboxy-terminal deletions on its stability," *J. Bacteriol.* 179(18):5684-5692 (1997).
Pinches and Apps, "Production in food of 1,3-pentadiene and styrene by *Trichoderma* species," *Int. J. Food Microbiol.* 116(1):182-185 (2007). (Epub Dec. 28, 2006).
Ploux et al., "Investigation of the first step of biotin biosynthesis in Bacillus sphericus," *Biochem. J.* 287:685-690 (1992).
Ploux et al., "The NADPH-linked acetoacetyl-CoA reductase from Zoogloea ramigera, Characterization and mechanistic studies of the cloned enzyme over-produced in *Escherichia coli*," *Eur. J. Biochem.* 174:177-182 (1988).
Plumridge et al., "The decarboxylation of the weak-acid preservative, sorbic acid, is encoded by linked genes in *Aspergillus* spp.," *Fungal. Genet. Biol.* Aug. 2010;47(8):683-692 (2010). (Epub May 7, 2010).
Pohl et al., "Remarkably broad Sutstrate Tolerance of Malonyl-CoA Synthetase, an Enzyme Capable of Intracellular Synthesis of Polyketide Precursors," *J. Am. Chem. Soc.* 123:5822-5823 (2001).
Pollard et al., "Purification, characterisation and reaction mechanisms of monofunctional 2-hydroxypentadienoic acid hydratase from *Escherichia coli*," *Eur. J. Biochem.* FEBS 251:98-106 (1998).
Pollard et al., "Substrate Selectivity and biochemical Properties of 4-Hydroxy-2-Keto-Pentanoic Acid Aldolase from *Escherichia coli*," *Appl. Environ. Microbiol.* 64(10):4093-4094 (1998).
Powell et al., "The purification and properties of the aspartate aminotransferase and aromatic-amino-acid aminotransferase from *Escherichia coli*," *Eur. J. Biochem.* 87(2):391-400 (1978).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).
Priefert and Steinbuchel, "Identification and molecular characterization of the acetyl coenzyme A synthetase gene (acoE) of Alcaligenes eutrophus," *J. Bacteriol.* 174(20):6590-6599 (1992).
Priestman et al., "5-Enolpyruvylshikimate-3-phosphate synthase from *Staphylococcus aureus* is insensitive to glyphosate," *FEBS Lett.* 579(3):728-732 (2005).
Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).

(56) References Cited

OTHER PUBLICATIONS

Pritchard et al., "A general model of error-prone PCR," *J. Theor. Biol.* 234:497-509 (2005).
Pucci et al., "*Staphylococcus haemolyticus* contains two D-glutamic acid biosynthetic activities, a glutamate racemase and a D-amino acid transminase," *J. Bacteriol.* 177(2):336-342 (1995).
Purnell et al., "Modulation of higher-plant NAD(H)-dependent glutamate dehydrogenase activity in transgenic tobacco via alteration of β subunit levels," *Planta* 222:167-180 (2005).
Qi et al., "Functional expression of prokaryotic and eukaryotic genes in *Escherichia coli* for conversion of glucose to p-hydroxystyrene," *Metab. Eng.* 9:268-276 (2007).
Qi et al., "Saturation-mutagenesis in two positions distant from active site of a Klebsiella pneumoniae glycerol dehydratase identifies some highly active mutants," *J. Biotechnol.* 144(1):43-50 (2009).
Rabus et al., "Genes involved in the anaerobic degradation of ethylbenzene in a denitrifying bacterium, strain EbN1," *Arch. Microbiol.* 178(6):506-516 (2002). (Epub Oct. 3, 2002).
Rado and Hoch, "Phosphotransacetylase from Bacillus subtilis: purification and physiological studies," *Biochim Biophys. Acta* 321:114-125 (1973).
Ragsdale, "Enzymology of the wood-Ljungdahl pathway of acetogenesis," *Ann. NY Acad Sci.* 1125:129-136 (2008).
Ragsdale, "Pyruvate ferredoxin oxidoreductase and its radical intermediate," *Chem. Rev.* 103(6):2333-2346 (2003).
Rajagopal, "Metabolism of indole-3-acetaldehyde. III. Some characteristics of the aldehyde oxidase of Avena coleoptiles," *Physiol. Plant* 24:272-281 (1971).
Rajpal et al., "A general method for greatly improving the affinity of antibodies by using combinatorial libraries," *Proc. Natl. Acad. Sci. U.S.A.* 102:8466-8471 (2005).
Rákhely et al., "Cyanobacterial-type, heteropentameric, NAD+-reducing NiFe hydrogenase in the purple sulfur photosynthetic bacterium Thiocapsa roseopersicina," *Appl. Environ. Microbiol.* 70(2):722-728 (2004).
Ramos-Vera et al., "Autotrophic carbon dioxide assimilation in Thermoproteales revisited," *J. Bacteriol.* 191(13):4286-4297 (2009). (Epub May 1, 2009).
Ran and Frost, "Directed evolution of 2-keto-3-deoxy-6-phosphogalactonate aldolase to replace 3-deoxy-D-arabino-heptulosonic acid 7-phosphate synthase," *J. Am. Chem. Soc.* 129(19):6130-6139 (2007).
Rangarajan et al., "Structure of [NiFe] hydrogenase maturation protein HypE from *Escherichia coli* and its interaction with HypF," *J. Bacteriol.* 190(4):1447-1458 (2008).
Ravagnani et al., "SpoOA directly controls the switch from acid to solvent production in solvent-forming clostridia," *Mol. Microbiol.* 37(5):1172-1185 (2000).
Raynaud et al., "Molecular characterization of the 1,3-propanediol (1,3-PD) operon of clostridium butyricum," *Proc. Natl. Acad. Sci. U.S.A.* 100:5010-5015 (2003).
Recasens et al., "Cystein Sulfinate Aminotransferase and Aspartate Aminotransferase Isoenzymes of Rat Brain. Purification, Characterization, and Further Evidence of Identity," *Biochemistry* 19:4583-4589 (1980).
Reetz and Carballeira, "Iterative saturation mutagenesis (ISM) for rapid directed evolution of functional enzymes," *Nat. Protoc.* 2:891-903 (2007).
Reetz et al., "Iterative saturation mutagenesis on the basis of B factors as a strategy for incresing protein thermostability," *Angew. Chem. Int. Ed.* 45:7745-7751 (2006).
Regev-Rudzki et al., "Yeast Aconitase in Two Locations and Two Metabolic Pathways: Seeing Small Amounts is Believing," *Mol. Biol. Cell* 16:4163-4171 (2005).
Reidhaar-Olson and Sauer, "Combinatorial cassette mutagenesis as a probe of the informational content of protein sequences," *Science* 241:53-57 (1988).
Reidhaar-Olson et al., "Random mutagenesis of protein sequences using oligonucleotide cassettes," *Methods Enzymol.* 208:564-586 (1991).
Reiser and Somerville, "Isolation of mutants of Acinetobacter calcoaceticus deficient in wax ester synthesis and complementation of one mutation with a gene encoding a fatty acyl Coenzyme A reductase," *J. Bacteriol.* 179(9):2969-2975 (1997).
Riviere et al., "Acetyl:succinate CoA-transferase in procyclic Trypanosoma brucei. Gene identification and role in carbohydrate metabolism." *J. Biol. Chem.* 279:45337-45346 (2004).
Roberts et al, "The Role of Enoyl-CoA Hydratase in the Metabolism of Isoleucine by Pseudomonas putida," *Arch. Microbiol.* 117:99-108 (1978).
Robinson et al., "Studies on Rat Brain Acyl-Coenzyme A Hydrolase (Short Chain)," *Biochem. Biophys. Res. Commun.* 71(4):959-965 (1976).
Rodich et al., "Isoprenoid biosynthesis in plants—2C-methyl-D-erythritol-4-phosphate synthase (IspC protein) of Arabidopsis thaliana," *FEBS J.* 273(19):4446-4458 (2006).
Rodriguez et al., "Characterization of the p-Coumaric Acid Decarboxylase from Lactobacillus plantarium CECT 748T," *J. Agric. Food Chem.* 56:3068-3072 (2008).
Rohdich et al., "Enoate reductases of Clostridia. Cloning, sequencing, and expression," *J. Biol. Chem.* 276(8):5779-5787 (2001).
Roper et al., "Sequence of the hpcC and hpcG genes of the meta-fission homoprotocatechuic acid pathway of *Escherichia coli* C: nearly 40% amino-acid identity with the analogues enzymes of the catechol pathway," *Gene* 156:47-51 (1995).
Rozell and Benner, "Stereochemical Imperative in Enzymic Decarboxylations. Stereochemical Course of Decarboxylation Catalyzed by Acetoacetate Decarboxylase," *J. Am. Chem. Soc.* 106:4937-4941 (1984).
Samanta and Harwood, "Use of Rhodopseudomonas palustris genome sequence to identify a single amino acid that contributes to the activity of Coenzyme A ligase with chlorinated substrates," *Mol. Microbiol.* 55(4):1151-1159 (2005).
Sariaslani, "Development of a Combined biological and Chemical Process for Production of Industrial aromatics from Renewable Resources," *Annu. Rev. Microbiol.* 61:51-69 (2007).
Sass et al., "Folding of fumarase during mitochondrial import determines its dual targeting in yeast," *J. Biol. Chem.* 278(46):45109-45116 (2003).
Sato et al., "Dehydration of 1,4-butanediol into 3-buten-1-ol catalyzed by ceria," *Catal. Commun.* 5(8):397-400 (2004).
Sato et al., "Poly[(R)-3-hydroxybutyrate] formation in *Escherichia coli* from glucose through an enoyl-CoA hydratase-mediated pathway," *J. Biosci. Bioeng.* 103(1):38-44 (2007).
Sauvageot et al., "Characterisation of the diol dehydratase pdu operon of Lactobacillus collinoides," *FEMS Microbiol. Lett.* 209:69-74 (2002).
Sawers and Boxer, "Purification and properties of membrane-bound hydrogenase isoenzyme 1 from anaerobically grown *Escherichia coli* K12," *Eur. J. Biochem.* 156(2):265-275 (1986).
Sawers et al., "Characterization and physiological roles of membrane-bound hydrogenase isoenzymes from *Salmonella typhimurium,*" *J. Bacteriol.* 168(1):398-404 (1986).
Sawers et al., "Differential expression of hydrogenase isoenzymes in *Escherichia coli* K-12: evidence for a third isoenzyme," *J. Bacteriol.* 164(3):1324-1331 (1985).
Sawers, "The hydrogenases and formate dehydrogenases of *Escherichia coli,*" *Antonie Van Leeuwenhoek* 66(1-3):57-88 (1994).
Schink and Schlegel, "The membrane-bound hydrogenase of Alcaligenes eutrophus. I. Solubilization, purification, and biochemical properties," *Biochim Biophys. Acta.* 567(2):315-324 (1979).
Schlieben et al., "Atomic resolution structures of R-specific alcohol dehydrogenase from Lactobacillus brevis provide the structural bases of its substrate and cosubstrate specificity," *J. Mol. Biol.* 349(4):801-813 (2005).
Schneider and Schlegel, "Purification and properties of soluble hydrogenase from Alcaligenes eutrophus H 16," *Biochim Biophys. Acta.* 452(1):66-80 (1976).

(56) References Cited

OTHER PUBLICATIONS

Schneider et al., "Anaerobic metabolism of L-phenylalanine via benzoyl-CoA in the denitrifying bacterium Thauera aromatic," Archives of Microbiology, 168(4): 310-320 (1997).
Schneider et al., "Biosynthesis of the prosthetic group of citrate lyase," *Biochemistry* 39(31):9438-9450 (2000).
Schneider-Belhaddad et al., "Solubilization, partial purification, and characterization of a fatty aldehyde decarbonylase from a higher plant, Pisum sativum," *Arch. Biochem. Biophys.* 377(2):341-349 (2000).
Schoenlein et al., "Divergent transcription of pdxB and homology between the pdxB and serA gene products in *Escherichia coli* K-12," *J. Bacteriol.* 171(11):6084-6092 (1989).
Schofield et al., "Substrate ambiguity and crystal structure of Pyrococcus furiosus 3-deoxy-D-arabino-heptulosonate-7-phosphate synthase an ancestral 3-deoxyald-2-ulosonate-phosphate synthase?" *Biochemistry* 44(36):11950-11962 (2005).
Schühle et al., "Benzoate-coenzyme A ligase from Thauera aromatica: an enzyme acting in anaerobic and aerobic pathways," *J. Bacteriol.* 185(16):4920-4929 (2003).
Schulz et al., "Stereospecific production of the herbicide phosphinothricin (glufosinate) by transamination: isolation and characterization of a phosphinothricin-specific transaminase from *Escherichia coli*," *Appl. Environ. Microbiol.* 56(1):1-6 (1990).
Schweiger and Buckel, "On the dehydration of (R)-lactate in the fermentation of alanine to propionat by Clostridium propionicum" *FEBS Lett.* 171:79-84 (1984).
Seedorf et al., "The genome of Clostridium kluyveri, a strict anaerobe with unique metabolic features," *Proc. Natl. Acad. Sci. U.S.A.* 105(6):2128-2133 (2008).
Seibert et al., "Characterization of a gene cluster encoding the maleylacetate reductase from Ralstonia eutropha 335T, and enzyme recruited for growth with 4-fluorobenzoate," *Microbiology* 150:463-472 (2004).
Seibert et al., "Characterization of the maleylacteate reductase MacA of Rhodococcus opacus 1CP and evidence for the presence of an isofunctional enzyme," *J. Bacteriol.* 180:3503-3508 (1998).
Seibert et al., "Purification and characterization of maleylacetate reductase from Alcaligenes eutrophys JMP134(pJP4)," *J. Bacteriol.* 175:6745-6754 (1993).
Sekimoto et al., "Cloning and molecular characterization of plant aldehyde oxidase," *J. Biol. Chem.* 272(24):15280-15285 (1997).
Selifonova et al., "Rapid evolution of novel traits in microorganisms," *Appl. Environ. Microbiol.* 67:3645-3649 (2001).
Selmer et al., "p-Hydroxyphenylacetate decarboxylase from Clostridium difficile. A novel glycyl radical enzyme catalyzing the formation of p-cresol," European Journal of Biochemistry, 268(5):1363-1372 (2001).
Selmer et al., "Propionate CoA-transferase from Clostridium propionicum. Cloning of gene identification of glutamate 324 at the active site," *Eur. J. Biochem.* 269:372-380 (2002).
Seltzer, "Purification and properties of maleylacetone cis-trans isomerase from Vibrio 01," *J. Biol. Chem.* 248:215-222 (1973).
Sen et al., "Developments in directed evolution for improving enzyme functins," *Appl. Biochem. Biotechnol.* 143:212-223 (2007).
Seravalli et al., "Evidence that NiNi acetyl-CoA synthase is active and that the CuNi enzyme is not," *Biochemistry* 43(13):3944-3955 (2004).
Servos et al., "Molecular cloning and characterization of the aroD gene encoding 3-dehydroquinase from *Salmonella typhi*," *J. Gen. Microbiol.* 137(1):147-152 (1991).
Seyfried et al., "Cloning, Sequencing, and Overexpression of the Genes Encoding Coenzyme B12-Dependent Glycerol Dehydratase of Citrobacter freundii," *J. Bacteriol.* 178(19):5793-5796 (1996).
Shafiani et al., "Cloning and characterization of aspartate-β-semialdehyde dehydrogenase from *Mycobacterium tuberculosis* H37 Rv," *J. Appl. Microbiol.* 98:832-838 (2005).

Shames et al., "Interaction of Aspartate and Aspartate-derived Antimetabolites with the Enzymes of the Threonine Biosynthetic Pathway of *Escherichia coli*," *J. Biol. Chem.* 258(24):15331-15339 (1984).
Shao et al., "Random-priming in vitro recombination: an effective tool for directed evolution," *Nucleic Acids Res.* 26:681-683 (1998).
Sheflyan et al., "Enzymatic Synthesis of 3-Deoxy-d-manno-octulosonate 8-phosphate, 3,5-Dideoxy-d-manno-octulosonate 8-phosphate and 3-Deoxy-d-altro-octulosonate 8-phosphate by 3-Deoxy-d-arabino-heptulosonate 7-phosphate Synthase," *J. Am. Chem. Soc.* 120:11027-11032 (1998).
Shi et al., "The Structure of I-Aspartate Ammonia-Lyase from *Escherichia coli*," *Biochemistry* 36:9136-9144 (1997).
Shimomura et al., "3-hydroxyisobutyryl-CoA hydrolase," *Methods Enzymol.* 324:229-240 (2000).
Shimomura et al., "Purification and partial characterization of 3-hydroxyisobutyryl-Coenzyme A hydrolase of rat liver," *J. Biol. Chem.* 269(19):14248-14253 (1994).
Shimoyama et al., "MmcBC in Pelotomaculum thermopropionicum represents a novel group of prokaryotic fumarases," *FEMS Microbiol Lett.* 270(2):207-213 (2007).
Shingler et al., "Nucleotide sequence and functional analysis of the complete phenol/3,4-dimethylphenol catabolic pathway of *Pseudomonas* sp. strain CF600," *J. Bacteriol.* 174(3):711-724 (1992).
Sibilli et al., "Two regions of the bifunctional protein aspartokinase I-homoserine dehydrogenase I are connected by a short hinge," *J. Biol. Chem.* 256 (20):10228-10230 (1981).
Sieber et al., "Libraries of hybrid proteins from distantly related sequences," *Nat. Biotechnol.* 19:456-460 (2001).
Siebers et al., "Reconstruction of the central carbohydrate metabolism of Thermoproteus tenax by use of genomic and biochemical data," *J. Bacteriol.* 186(7):2179-2194 (2004).
Siebert et al., "Ubiquinone biosynthesis. Cloning of the genes coding for chorismate pyruvate-lyase and 4-hydroxybenzoate octaprenyl transferase from *Escherichia coli*," *FEBS Lett.* 307(3):347-350 (1992).
Siegert et al., "Exchanging the substrate specificities of pyruvate decarboxylase from Zymomonas mobilis and benzoylformate decarboxylase from Pseudomonas putida," *Protein. Eng. Des. Sel.* 18:345-357 (2005).
Sjöström et al., "Purification and characterisation of a plasminogen-binding protein from Haemophilus influenzae. Sequence determination reveals identity with aspartase," *Biochim. Biophys. Acta.* 1324(2):182-190 (1997).
Skarstedt and Silverstein, "*Escherichia coli* acetate kinase mechanism studied by net initial rate, equilibrium, and independent isotopic exchange kinetics," *J. Biol. Chem.* 251:6775-6783 (1976).
Slater et al., "Multiple β-ketothiolases mediate poly(β-hydroxyalkanoate) copolymer synthesis in Ralstonia eutropha," *J. Bacteriol.* 180(8):1979-1987 (1998).
Smith et al., "Purification and characteristics of a γ-glutamyl kinase involved in *Escherichia coli* proline biosynthesis," *J. Bacteriol.* 157:545-551 (1984).
Smith et al., "Structural analysis of ligand binding and catalysis in chorismate lyase," *Arch. Biochem. Biophys.* 445(1):72-80 (2006).
Smith et al., "Fumarate metabolism and the microaerophily of *Campylobacter* species," *Int. J. Biochem. Cell Biol.* 31(9):961-975 (1999).
Söhling and Gottschalk, "Molecular analysis of the anaerobic succinate degradation pathway in Clostridium kluyveri," *J. Bacteriol.* 178:871-880 (1996).
Söhling and Gottschalk, "Purification and characterization of a Coenzyme-A-dependent succinate-semialdehyde dehydrogenase from Clostridium kluyveri," *Eur. J. Biochem.* 212:121-127 (1993).
Song et al., "Structure-activity analysis of base and enzyme-catalyzed 4-hydroxybenzoyl coenzyme A hydrolysis," *Bioorg. Chem.* 35(1):1-10 (2007). (Epub Sep. 7, 2006).
Song et al., "Structure, function, and mechanism of the phenylacetate pathway hot dog-fold thioesterase PaaI," *J. Biol. Chem.* 281(16):11028-11038 (2006).

(56) References Cited

OTHER PUBLICATIONS

Spaepen et al., "Characterization of phenylpyruvate decarboxylase, involved in auxin production of Azospirillum brasilense," *J. Bacteriol.* 189(21):7626-7633 (2007). (Epub Aug. 31, 2007).
Sramek and Frerman, "Purification and properties of *Escherichia coli* Coenzyme A-transferase," *Arch. Biochem. Biophys.* 171(1):14-26 (1975).
St. Maurice et al., "Flavodoxin:quinone reductase (FqrB): a redox partner of pyruvate:ferredoxin oxidoreductase that reversibly couples pyruvate oxidation to NADPH production in Helicobacter pylori and Campylobacter jejuni," *J. Bacteriol.* 189:4764-4773 (2007).
Stadthagen et al., "p-Hydroxybenzoic acid synthesis in *Mycobacterium tuberculosis,*" *J. Biol. Chem.* 280(49):40699-40706 (2005).
Stadtman, "Phosphotransacetylase from Clostridium kluyveri," *Methods Enzymol.* 1:596-599 (1955).
Stanley et al., "Expression and stereochemical and isotope effect studies of active 4-oxalocrotonate decarboxylase," *Biochemistry* 39(12):3514 (2000).
Starai et al., "Acetate excretion during growth of *Salmonella enerica* on ethanolamine requires phosphotransacetylase (EutD) activity, and acetate recapture requires acetyl-CoA synthetase (Acs) and phosphotransacetylase (Pta) activities," *Microbiology* 151:3793-3801 (2005).
Starai et al., "Residue Leu-641 of Acetyl-CoA synthetase is critical for the acetylation of residue Lys-609 by the Protein acetyltransferase enzyme of *Salmonella enterica,*" *J. Biol. Chem.* 280(28):26200-26205 (2005).
Starnes et al., "Threonine-sensitive aspartokinase-homoserine dehydrogenase complex, amino acid composition, molecular weight, and subunit composition of the complex," *Biochemistry* 11:677-687 (1973).
Steffan and McAlister-Henn, "Isolation and characterization of the yeast gene encoding the MDH3 isozyme of malate dehydrogenase," *J. Biol. Chem.* 267:24708-24715 (1992).
Steinbüchel and Schlegel, "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).
Stemmer, "DNA shuffling by random fragmentation and reassembly: in vitro recombination for molecular evolution," *Proc. Natl. Acad. Sci. U.S.A.* 91:10747-10751 (1994).
Stemmer, "Rapid evolution of a protein in vitro by DNA shuffling," *Nature* 370:389-391 (1994).
Stols and Donnelly, "Production of succinic acid through overexpression of NAD(+)-dependent malic enzyme in an *Escherichia coli* mutant," *Appl. Environ. Microbiol.* 63(7):2695-2701 (1997).
Stols et al., "Expression of Ascaris suum malic enzyme in a mutant *Escherichia coli* allows production of succinic acid from glucose," *Appl. Biochem. Biotechnol.* 63-65: 153-158 (1997).
Stols et al., "New vectors for co-expression of proteins: Structure of Bacillus subtilis ScoAB obtained by High-throughput protocols," *Protein Expr. Purif.* 53:396-403 (2007).
Stoyan et al., "Cloning, sequencing and overexpression of the leucine dehydrogenase gene from Bacillus cereus," *J. Biotechnol.* 54:77-80 (1997).
Strauss and Fuchs, "Enzymes of a novel autotrophic CO2 fixation pathway in the phototrophic bacterium Chloroflexus aurantiacus, the 3-hydroxypropionate cycle," *Eur. J. Biochem.* 215:633-643 (1993).
Strych et al., "Characterization of the alanine racemases from two mycobacteria," *FEMS Microbiol. Lett.* 196(2):93-98 (2001).
Suda et al., "Purification and properties of α-ketoadipate reductase, a newly discovered enzyme from human placenta," *Arch. Biochem. Biophys.* 176(2):610-620 (1976).
Suda et al., "Subcellular localization and tissue distribution of α-ketoadipate reduction and oxidation in the rat," *Biochem. Biophys. Res. Commun.* 77(2):586-591 (1977).

Sulzenbacher et al., "Crystal structure of *E.coli* alcohol dehydrogenase YqhD: evidence of a covalently modified NADP Coenzyme," *J. Mol. Biol.* 342(2):489-502 (2004).
Suzuki et al., "GriC and GriD Constitute a carboxylic acid reductase involved in grixazone biosynthesis in streptomyces griseus," *J. Antibiot.* 60(6):380-387 (2007).
Suzuki et al., "Purification and properties of thermostable tryptophanase from an obligately symbiotic thermophile, Symbiobacterium thermophilum," *Agric. Biol. Chem.* 55(12):3059-3066 (1991).
Suzuki, "Phospotransacetylase of *Escherichia coli* B., activation by pyruvate and inhibition by NADH and certain nucleotides," *Biochem. Biophys. Acta* 191:559-569 (1969).
Svetlitchnyi et al., "Two membrane-associated NiFeS-carbon monoxide dehydrogenases from the anaerobic carbon-monoxide-utilizing eubacterium Carboxydothermus hydrogenoformans," *J. Bacteriol.* 183(17):5134-5144 (2001).
Takada et al., "Thermostable phenylalanine dehydrogenase of Thermoactinomyces intermedius: cloning, expression, and sequencing of its gene," *J. Biochem.* 109(3):371-376 (1991).
Takagi et al., "Isolation of a versatile Serratia marcescens mutant as a host and molecular cloning of the aspartase gene," *J. Bacteriol.* 161:1-6 (1985).
Takahashi and Yamada, "Metabolic pathways for cytoxic and end product formation from glutamate- and aspartate-containing peptides by Porphyromonas gingivalis," *J. Bacteriol.* 182:4704-4710 (2000).
Takahashi et al., "A 1-deoxy-D-xylulose 5-phosphate reductoisomerase catalyzing the formation of 2-C-methyl-D-erythritol 4-phosphate in an alternative nonmevalonate pathway for terpenoid biosynthesis," *Proc. Natl. Acad. Sci. U. S. A.* 95(17):9879-9884 (1998).
Takahashi-Abbe et al., "Biochemical and functional properties of a pyruvate formate-lyase (PFL)-activating system in *Streptococcus mutans,*" *Oral Microbiol. Immunol.* 18:293-297 (2003).
Takeo, "Existence and Properties of Two Malic Enzymes in *Escherichia coli* Especially of NAD-linked Enzyme," *J. Biochem.* 66:379-387 (1969).
Tang et al., "Identification of a novel pyridoxal 5'-phosphaste binding site in adenosylcobalamin-dependent lysine 5,6-aminomutase from Porphyromonas gingivalis," *Biochemistry* 41(27):8767-8776 (2002).
Tang et al., "Microbial conversion of glycerol to 1,3-propanediol by an engineered strain of *Escherichia coli,*" *Appl. Environ. Microbiol.* 75(6):1628-1634 (2009).
Tani et al., "Thermostable NADP+-dependent medium-chain alcohol dehydrogenase from *Acinetobacter* sp. strain M-1: purification and characterization and gene expression in *Escherichia coli,*" *Appl. Environ. Microbiol.* 66(12):5231-5235 (2000).
Tanizawa et al., "The primary structure of thermostable D-amino acid aminotransferase from a thermophilic *Bacillus* species and its correlation with L-amino acid aminotransferases," *J. Biol. Chem.* 264(5):2450-2454 (1989).
Tao et al., "Rapid synthesis of auxin via a new tryptophan-dependent pathway is required for shade avoidance in plants," *Cell* 133(1):164-176 (2008).
Taylor and Fotheringham, "Nucleotide sequence of the Bacillus licheniformis ATCC 10716 dat gene and comparison of the predicted amino acid sequence with thos of other bacterial species," *Biochim. Biophys. Acta* 1350(1):38-40 (1997).
Thauer, "Microbiology. A Fifth Pathway of Carbon Fixation," *Science* 318:1732-1733 (2007).
Tobey et al., "The nucleotide sequence of the serA gene of *Escherichia coli* and the amino acid sequence of the encoded protein, D-3-phosphoglycerate dehydrogenase," *J. Biol. Chem.* 261(26):12179-12183 (1986).
Tobimatsu et al., "Molecular cloning, Sequencing and Expression of the Genes Encoding Adenosylcobalamin-dependent Diol Dehydrase of Klebsiella oxytoca," *J. Biol. Chem.* 270(13):7142-7148 (1995).
Toraya et al., "Substrate Specificity of Coenzyme B12-Dependent Diol Dehydrase: Glycerol as Both a Good Substrate and a Potent Inactivator," *Biochem. Biophys. Res. Commun.* 69:475-480 (1976).

(56) References Cited

OTHER PUBLICATIONS

Toth et al., "The ald Gene, Encoding a Coenzyme A-Acylating Aldehyde Dehydrogenase, Distinguishes Clostridium beijerinckii and Two Other Solvent-Producing Clostridia from Clostridium acetobutylicum," *App. Environ. Microbiol.* 65(11):4973-4980 (1999).
Tseng et al., "Oxygen- and growth rate-dependent regulation of *Escherichia coli* fumarase (FumA, FumB, and BumC) activity," *J. Bacteriol.* 183(2):461-467 (2001).
Twarog and Wolfe, "Role of butyryl phosphate in the energy metabolism of Clostridium tetanomorphum," *J. Bacteriol.* 86:112-117 (1963).
Uchiyama et al., "Identification of the 4-Hydroxycinnamate Decarboxylase (PAD) Gene of Klebsiella oxytoca," *Biosci. Biotechnol. Biochem.* 72: 116-123 (2008).
Valdes-Hevia and Gancedo, "Isolation and characterization of the gene encoding phosphoenolpyruvate carboxykinase from *Saccharomyces cerevisiae*," *FEBS Lett.* 258:313-316 (1989).
Vamecq et al., "The microsomal dicarboxylyl-CoA synthetase," *Biochem. J.* 230(3):683-693 (1985).
Van der Voorhorst et al., "Genetic and biochemcial characterization of a short-chain alcohol dehydrogenase from the hyperthermophilic archaeon Pyrococcus furiosus," *Eur. J. Biochem.* 268:3062-3068 (2001).
Van Grinsven et al., "Acetate:succinate CoA-transferase in the hydrogenosomes of Trichomonas vaginalis: identification and characterization," *J. Biol. Chem.* 283:1411-1418 (2008).
Vandenende et al., "Functional characterization of an aminotransferase required for pyoverdine siderophore biosynthesis in Pseudomonas aeruginosa PAO1," *J. Bacteriol.* 186(17):5596-5602 (2004).
Vanderwinkel et al., "Growth of *Escherichia coli* on fatty acids: requirement for Coenzyme A transferase activity," *Biochem. Biophys. Res. Commun.* 33(6):902-908 (1968).
Vazquez et al., "Phosphtransbutyrylase expression in Bacillus megaterium," *Curr. Microbiol.* 42:345-349 (2001).
Venkitasubramanian et al. in *Biocatalysis in the Pharmaceutical and Biotechnology Industires*, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).
Vey et al., "Structural basis for glycyl radical formation by pyruvate formate-lyase activating enzyme," *Proc. Natl. Acad. Sci. U.S.A.* 105:16137-16141 (2008).
Viola, "L-Aspartase: New Tricks From an Old Enzyme," *Adv. Enzymol. Relat. Areas. Mol. Biol.* 74:295-341 (2000).
Volkov et al., "Random chimeragenesis by heteroduplex recombination," *Methods Enzymol.* 328:456-463 (2000).
Volkov et al., "Recombination and chimeragenesis by in vitro heteroduplex formation and in vivo repair," *Nucleic Acids Res.* 27:e18 (1999).
Wakil et al., "Studies on the fatty acid oxidizing system of animal tissues. VI. β-Hydroxyacyl Coenzyme A dehydrogenase," *J. Biol. Chem.* 207(2):631-638 (1954).
Walker et al., "Yeast pyruvate carboxylase: identification of two genes encoding isoenzymes," *Biochem. Biophys. Res. Commun.* 176:1210-1217 (1991).
Walter et al., "Molecular characterization of two Clostridium acetobutylicum ATCC 824 butanol dehydrogenase isozyme genes," *J. Bacteriol.* 174(22):7149-7158 (1992).
Walter et al., "Sequence and arrangement of two genes of the butyrate-synthesis pathway of Clostridium acetobutylicum ATCC 824," *Gene* 134(1):107-111 (1993).
Wang and Seah, "Determination of the metal ion dependence and substrate specificty of a hydratase involve din the degradation pathway of biphenyl/chlorobiphenyl," *FEBS J.* 272: 966-974 (2005).

Wang et al, "Molecular cloning and functional identification of a novel phenylacetyl-CoA ligase gene from Penicillium chrysogenum," *Biochem. Biopyhs. Res. Commun.* 360(2):453-458 (2007).
Wang et al., "Identification of a type III thioesterase reveals the function of an operon crucial for Mtb virulence," *Chem. Biol.* 14(5):543-551 (2007).
Warburg et al., "Cloning the Bacillus subtilis 168 aroC gene encoding dehydroquinase," *Gene* 32(1-2):57-66 (1984).
Weaver and Herrmann, "Cloning of an aroF allele encoding a tyrosine-insensitive 3-deoxy-D-arabino-heptulosonate 7-phosphate synthase," *J. Bacteriol.* 172(11):6581-6584 (1990).
Weaver, "Structure of free fumarase C from *Escherichia coli*," *Acta. Crystallogr. D. Biol. Crystallogr.* 61(Pt 10):1395-1401 (2005).
Webby et al., "Characterization of a recombinant type II 3-deoxy-D-arabino-heptulosonate-7-phosphate synthase from Helicobacter pylori," *Biochem. J.* 390(Pt 1):223-230 (2005).
Weidner and Sawers, "Molecular characterization of the Genes Encoding Pyruvate Formate-Lyase and Its Activating enzyme of clostridium pasteruianum," *J. Bacteriol.* 178(8):2440-2444 (1996).
Weiss et al., "Kinetics and mechanism of benzoylformate decarboxylase using 13C and solvent deuterium isotope effects on benzoylformate and benzoylformate analogues," *Biochemistry* 27(6):2197-1205 (1988).
Werther et al., "Amino acids allosterically regulate the thiamine diphosphate-dependent α-keto acid decarboxylase from *Mycobacterium tuberculosis*," *J. Biol. Chem.* 283(9):5344-5354 (2008). (Epub Dec. 17, 2007).
Westin et al., "The identification of a succinyl-CoA thioesterase suggests a novel pathway for succinate production in peroxisomes," *J. Biol. Chem.* 280(46):38125-38132 (2005).
Whalen and Berg, "Analysis of an avtA::Mu d1(Ap lac) Mutant: Metabolic Role of Transaminase C," *J. Bacteriol.* 150(2):739-746 (1982).
Whalen and Berg, "Gratuitous repression of avtA in *Escherichia coli* and *Salmonella typhimurium*," *J. Bacteriol.* 158(2):571-574 (1984).
White et al., "The overexpression, purification and complete amino acid sequence of chorismate synthase from *Escherichia coli* K12 and its comparison with the enzyme from Neurospora crassa," *Biochem. J.* 251(2):313-322 (1988).
Wiesenborn et al., "Coenzyme A Transferase from clostridium acetobutylicum ATCC 824 and Its Role in the Uptake of Acids," *Appl. Environ. Microbiol.* 55(2):323-329 (1989).
Wiesenborn et al., "Phosphotransbutyrylase from clostridium acetobutylicum ATCC 824 and its role in acidogenesis," *Appl. Environ. Microbiol.* 55:317-322 (1989).
Wild et al., "Identification of the dadX gene coding for the predominant isozyme of alanine racemase in *Escherichia coli* K12," *Mol. Gen. Genet.* 198(2):315-322 (1985).
Wilkie and Warren, "Recombinant expression, purification, and characterization of three isoenzymes of aspartate aminotransferase from Arabidopsis thaliana," *Protein Expr. Purif.* 12:381-389 (1998).
Williamson et al., "Stereospecific deuteration of 2-deoxyerythrose 4-phosphate using 3-deoxy-D-arabino-heptulosonate 7-phosphate synthase," *Bioorg. Med. Chem. Lett.* 15(9):2339-2342 (2005).
Willke and Vorlop, "Biotechnological production of itaconic acid," *Appl. Microbiol. Biotechnol.* 56(3-4):289-295 (2001).
Winzer et al., "Acetate kinase from Clostridium acetobutylicum: a highly specific enzyme that is actively transcribed during acidogenesis and solventogenesis," *Microbiology* 143 (Pt 10):3279-3286 (1997).
Winzer et al., "Differential regulation of two thiolase genes from Clostridium acetobutylicum DSM 792," *J. Mol. Microbiol. Biotechnol.* 2(4):531-541 (2000).
Wolff and Kenealy, "Purification and characterization of the oxygen-sensitive 4-hydroxybutanoate dehydrogenase from Clostridium kluyveri," *Protein Expr. Purif.* 6:206-212 (1995).
Wong et al., "Sequence saturation mutagenesis (SeSaM): a novel method for directed evolution," *Nucleic Acids Res.* 32:e26 (2004).
Wong et al., "Sequence saturation mutagenesis with tunable mutation frequencies," *Anal Biochem* 341:187-189 (2005).

(56) References Cited

OTHER PUBLICATIONS

Wong et al., "Transversion-enriched sequence saturation mutagenesis (SeSaM-Tv+): a random mutagenesis method with consecutive nucleotide exchanges that complements the bias of error-prone PCR," *Biotechnol. J.* 3:74-82 (2008).
Wood et al., "A challenge for 21st century molecular biology and biochemistry: what are the causes of obligate autotrophy and methanotrophy?," *FEMS Microbiol Rev.* 28(3):335-52 (2004).
Woods et al., "Two biochemically distinct classes of fumarase in *Escherichia coli*," *Biochim. Biophys. Acta* 954(1):14-26 (1988).
Wu et al., "Microbial synthesis of cis-cis-muconic acid by *Sphingobacterium* sp. GcG generated from effluent of a styrene monomer (SM) production plant," *Enzyme Microbial. Tech.* 35:598-604 (2004).
Wu et al., "Life in hot carbon monoxide: the complete genome sequence of Carboxydothermus hydrogenoformans Z-2901," *PLoS Genet.* 1(5):e65 (2005).
Xiang et al., "Characterization of benzoyl coenzyme A biosynthesis genes in the enterocin-producing bacterium Streptomyces maritimus," *J. Bacteriol.* 185(2):399-404 (2003).
Xiang et al., "Crystal structure of 1-deoxy-D-xylulose 5-phosphate synthase, a crucial enzyme for isoprenoids biosynthesis," *J. Biol. Chem.* 282(4):2676-2682 (2007). (Epub Nov. 29, 2006).
Yabutani et al., "Analysis of β-ketothiolase and acetoacetyl-CoA reductase genes of a methylotrophic bacterium, Paracoccus denitrificans, and their expression in *Escherichia coli*," *FEMS Microbiol. Lett.* 133:85-90 (1995).
Yagi et al., "Aspartate: 2-oxoglutarate aminotransferase from bakers' yeast: crystallization and characterization," *J. Biochem.* 92(1):35-43 (1982).
Yagi et al., "Crystallization and properties of aspartate aminotransferase from *Escherichia coli* B," *FEBS Lett.* 100(1):81-84 (1979).
Yagi et al., "Glutamate-aspartate transaminase from microorganisms," *Methods Enzymol.* 113:83-89 (1985).
Yakandawala et al., "Metabolic engineering of *Escherichia coli* to enhance phenylalanine production," *Appl. Microbiol. Biotechnol.* 78(2):283-291 (2008). (Epub Dec. 15, 2007).
Yakunin and Hallenbeck, "Purification and characterization of pyruvate oxidoreductase from the photosynthetic bacterium Rhodobacter capsulatus," *Biochim Biophys. Acta.* 1409(1):39-49 (1998).
Yamada et al., "Nucleotide sequencing of phenylalanine dehydrogenase gene from Bacillus badius IAM 11059," *Biosci. Biotechnol. Biochem.* 59:1994-1995 (1995).
Yamamoto et al., "Carboxylation reaction catalyzed by 2-oxoglutarate:ferredoxin oxidoreductases from Hydrogenobacter thermophilus," *Extremophiles* 14:79-85 (2010).
Yang et al., "Aspartate Dehydrogenase, a Novel Enzyme Identified from Structural and Functional Studies of TM1643," *J. Biol. Chem.* 278(10):8804-8808 (2003).
Yang et al., "Nucleotide sequence of the promoter and fadB gene of the fadBA operon and primary structure of the multifunctional fatty acid oxidation protein from *Escherichia coli*," *Biochemistry* 30(27):6788-6795 (1991).
Yang, "Location of the fadBA operon on the physical map of *Escherichia coli*," *J. Bacteriol.* 173(23):7405-7406 (1991).
Yatake et al., "Screening, cloning, expression, and purification of an acidic arylmalonate decarboxylase from Enterobacter cloacae KU1313," *Appl. Microbiol. Biotechnol.* 78(5):793-799 (2008). (Epub Feb. 19, 2008).

Ye et al., "The crystal structure of shikimate dehydrogenase (AroE) reveals a unique NADPH binding mode," *J. Bacteriol.* 185(14):4144-4151 (2003).
Yeung et al., "Physical, kinetic and spectrophotometric studies of a NAD(P)-dependent benzaldehyde dehydrogenase from Pseudomonas putida ATCC 12633," *Biochim Biophys. Acta.* 1784(9):1248-1255 (2008). (Epub May 2, 2008).
Yi et al., "Altered glucose transport and shikimate pathway product yields in *E. coli*," *Biotechnol. Prog.* 19(5):1450-1459 (2003).
Yi et al., "Cloning, expression, and functional characterization of the Dunaliella salina 5-enolpyruvylshikimate-3-phosphate synthase gene in *Escherichia coli*," *J. Microbiol.* 45(2):153-157 (2007).
Ylianttila et al., "Crystal Structure of Yeasat Peroxisomal Multifunctional Enzyme: Structural Basis for Substrate Specificity of (3R)-hydroxyacyl-CoA Dehydrogenase Units," *J. Mol. Biol.* 258:1286-1295 (2006).
Ylianttila et al., "Site-directed mutagenesis to enable and improve crystallizability of candida tropicalis (3R)-hydroxyacyl-CoA dehydrogenase," *Biochem. Biophys. Res. Commun.* 324:25-30 (2004).
Yoshida et al., "Identification of a functional 2-keto-myo-inositol dehydratase gene of Sinorhizobium fredii USDA191 required for myo-inositol utilization," *Biosci. Biotechnol. Biochem.* 70(12):2957-2964 (2006). (Epub Dec. 7, 2006).
Yoshida et al., "The fifth gene of the iol operon of Bacillus subtilis, iolE, encodes 2-keto-myo-inositol dehydratase," *Microbiology* 150(Pt 3):571-580 (2004).
Youngleson et al., "Homology between hydroxybutyryl and hydroxyacyl Coenzyme A dehydrogenase enzymes from Clostridium acetobutylicum fermentation and vertebrate fatty acid β-oxidation pathways," *J. Bacteriol.* 171(12):6800-6807 (1989).
Yu et al., "4-Hydroxyphenylacetate decarboxylases: properties of a novel subclass of glycyl radical enzyme systems," *Biochemistry* 45(31):9584-9592 (2006).
Yun et al., "The genes for anabolic 2-oxoglutarate: ferredoxin oxidoreductse from hydrogenobacter thermophilus TK-6," *Biochem. Biophys. Res. Commun.* 282(2):589-594 (2001).
Zeiher and Randall, "Identification and characterization of Mitochondrial Acetyl-Coenzyme A Hydrolase from *Pisum sativum* L. Seedlings," *Plant. Physiol.* 94:20-27 (1990).
Zhang et al., "Expression, purification and properties of shikimate dehydrogenase from *Mycobacterium tuberculosis*," *J. Biochem. Mol. Biol.* 38(5):624-631 (2005).
Zhang et al., "Identification of the ubiD gene on the Escherichia coli chromosome," *J. Bacteriol.* 182(21):6243-6246 (2000).
Zhao et al., "Cloning and characterization of the genes for biosynthesis of the compatible solute ectoine in the moderately halophilic bacterium Halobacillus dabanensis D-8(T)," *Curr. Microbiol.* Sep. 2006;53(3):183-188 (2006). (Epub Jul. 27, 2006).
Zhao et al., "Molecular evolution by staggered extension process (StEP) in vitro recombination," *Nat. Biotechnol.* 16:258-261 (1998).
Zhou et al., "Engineering a native homoethanol pathway in *Escherichia coli* B for ethanol production," *Biotechnol. Lett.* 30:335-342 (2008).
Lofroth et al., "Characterization of Environmental Tobacco Smoke," *Environ. Sci. Technol.*, 23:610-614 (1989).
Lu et al., "Analysis of Cigarette Smoke Condensates by Comprehensive Two-Dimensional Gas Chromatography/Time-of-Flight Mass Spectometry I Acidic Fraction," *Anal Chem.*, 75:4441-4451(2003).

\* cited by examiner

MICROORGANISMS AND METHODS FOR THE BIOSYNTHESIS OF AROMATICS, 2,4-PENTADIENOATE AND 1,3-BUTADIENE

STATEMENT OF RELATED APPLICATIONS

This application is a division of U.S. Ser. No. 13/191,375 filed Jul. 26, 2011, which claims the benefit of priority under 35 U.S.C §119(e) to U.S. Provisional Application 61/367,792, filed Jul. 26, 2010 and U.S. Provisional Application 61/368,223, filed Jul. 27, 2010, and U.S. Provisional Application 61/381,407, filed Sep. 9, 2010, each of which is incorporated herein by reference in its entirety.

BACKGROUND OF THE INVENTION

The present invention relates generally to biosynthetic processes, and more specifically to organisms having toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic capability.

Toluene is a common solvent that has replaced benzene due to benzene's greater carcinogenicity and is an industrial feedstock and used in the manufacture of trinitrotoluene ("TNT"), polyurethane foam, benzaldehyde and benzoic acid. Toluene is a byproduct in the manufacture of gasoline and exists in small concentrations in crude oil.

Benzene is often used as an intermediate to make other chemicals. Its most widely-produced derivatives include styrene, which is used to make polymers and plastics, phenol for resins and adhesives, via cumene, and cyclohexane, which is used in the manufacture of Nylon. Benzene is also used to make some types of rubbers, lubricants, dyes, detergents, drugs, explosives, napalm and pesticides. Benzene production in the petroleum industry is made by various energy intensive processes including, catalytic reforming, toluene hydrodealkylation, toluene disproportionation, and steam cracking.

Styrene is the precursor to polystyrene and numerous copolymers. Styrene based products include, acrylonitrile 1,3-butadiene styrene (ABS), styrene-1,3-butadiene (SBR) rubber, styrene-1,3-butadiene latex, SIS (styrene-isoprene-styrene), S-EB-S (styrene-ethylene/butylene-styrene), styrene-divinylbenzene (S-DVB), and unsaturated polyesters. These materials are used in rubber, plastic, insulation, fiberglass, pipes, automobile and boat parts, food containers, and carpet backing.

Styrene is most commonly produced by the catalytic dehydrogenation of ethylbenzene. Ethylbenzene is mixed in the gas phase with 10-15 times its volume in high-temperature steam, and passed over a solid catalyst bed. Most ethylbenzene dehydrogenation catalysts are based on iron (III) oxide, promoted by several percent potassium oxide or potassium carbonate. Steam serves several roles in this reaction. It is the source of heat for powering the endothermic reaction, and it removes coke that tends to form on the iron oxide catalyst through the water gas shift reaction. The potassium promoter enhances this decoking reaction. The steam also dilutes the reactant and products, shifting the position of chemical equilibrium towards products. A typical styrene plant consists of two or three reactors in series, which operate under vacuum to enhance the conversion and selectivity. Typical per-pass conversions are ca. 65% for two reactors and 70-75% for three reactors.

Over 25 billion pounds of 1,3-butadiene (or just butadiene or BD) are produced annually and is applied in the manufacture of polymers such as synthetic rubbers and ABS resins, and chemicals such as hexamethylenediamine and 1,4-butanediol. 1,3-butadiene is typically produced as a by-product of the steam cracking process for conversion of petroleum feedstocks such as naphtha, liquefied petroleum gas, ethane or natural gas to ethylene and other olefins. The ability to manufacture 1,3-butadiene from alternative and/or renewable feedstocks would represent a major advance in the quest for more sustainable chemical production processes One possible way to produce 1,3-butadiene renewably involves fermentation of sugars or other feedstocks to produce diols, such as 1,4-butanediol or 1,3-butanediol, which are separated, purified, and then dehydrated to 1,3-butadiene in a second step involving metal-based catalysis. Direct fermentative production of 1,3-butadiene from renewable feedstocks would obviate the need for dehydration steps and 1,3-butadiene gas (bp −4.4° C.) would be continuously emitted from the fermenter and readily condensed and collected. Developing a fermentative production process would eliminate the need for fossil-based 1,3-butadiene and would allow substantial savings in cost, energy, and harmful waste and emissions relative to petrochemically-derived 1,3-butadiene.

2,4-Pentadienoate is a useful substituted butadiene derivative in its own right and a valuable intermediate en route to other substituted 1,3-butadiene derivatives, including, for example, 1-carbamoyl-1,3-butadienes which are accessible via Curtius rearrangement. The resultant N-protected-1,3-butadiene derivatives can be used in Diels alder reactions for the preparation of substituted anilines. 2,4-Pentadienoate can be used in the preparation of various polymers and co-polymers.

Terephthalate (also known as terephthalic acid and PTA) is the immediate precursor of polyethylene terephthalate (PET), used to make clothing, resins, plastic bottles and even as a poultry feed additive. Nearly all PTA is produced from para-xylene by oxidation in air in a process known as the Mid Century Process. This oxidation is conducted at high temperature in an acetic acid solvent with a catalyst composed of cobalt and/or manganese salts. Para-xylene is derived from petrochemical sources and is formed by high severity catalytic reforming of naphtha. Xylene is also obtained from the pyrolysis gasoline stream in a naphtha steam cracker and by toluene disproportion.

Cost-effective methods for generating renewable PTA have not yet been developed to date. PTA, toluene and other aromatic precursors are naturally degraded by some bacteria. However, these degradation pathways typically involve monooxygenases that operate irreversibly in the degradative direction. Hence, biosynthetic pathways for PTA are severely limited by the properties of known enzymes to date.

A promising precursor for PTA is p-toluate, also known as p-methylbenzoate. P-Toluate is an intermediate in some industrial processes for the oxidation of p-xylene to PTA. It is also an intermediate for polymer stabilizers, pesticides, light sensitive compounds, animal feed supplements and other organic chemicals. Only slightly soluble in aqueous solution, p-toluate is a solid at physiological temperatures, with a melting point of 275° C. Microbiol catalysts for synthesizing this compound from sugar feedstocks have not been described to date.

Thus, there exists a need for alternative methods for effectively producing commercial quantities of compounds such as styrene, 2,4-pentadienoate, 1,3-butadiene, p-toluate, terephthalate, benzene and toluene. The present invention satisfies this need and provides related advantages as well.

SUMMARY OF THE INVENTION

The invention provides non-naturally occurring microbial organisms having a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway. The invention additionally provides methods of using such organisms to produce toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene.

The invention also provides non-naturally occurring microbial organisms having a (2-hydroxy-3-methyl-4-oxobutoxy)phosphonate (2H3M4OP) pathway, a p-toluate pathway, a terephthalate pathway, a (2-hydroxy-4-oxobutoxy)phosphonate (2H4OP) pathway, and/or a benzoate pathway. The invention additionally provides methods of using such organisms to produce (2-hydroxy-3-methyl-4-oxobutoxy)phosphonate, p-toluate, terephthalate, (2-hydroxy-4-oxobutoxy)phosphonate, or benzoate.

2,4-diaminopentanoate 4-aminotransferase and/or 4-dehydrogenase. AKP is 2-amino-4-oxopentanoate.

Figure 14:
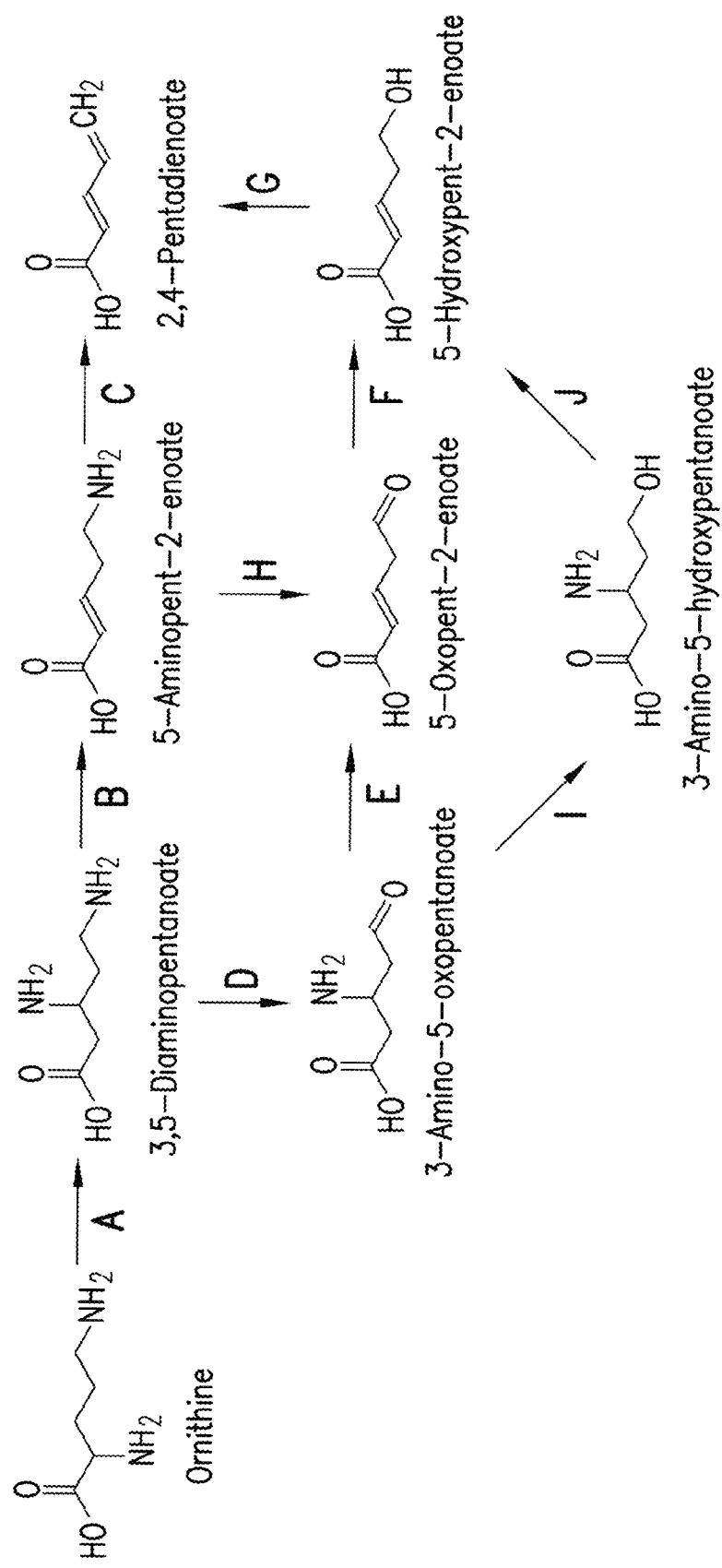

FIG. 14 shows additional pathways from ornithine to 2,4-pentadienoate. Enzymes are A. ornithine 2,3-aminomutase, B. 3,5-diaminopentanoate deaminase, C. 5-aminopent-2-enoate deaminase, D. 3,5-diaminopentanoate aminotransferase and/or dehydrogenase, E. 3-amino-5-oxopentanoate deaminase, F. 5-oxopent-2-enoate reductase, G. 5-hydroxypent-2-enoate dehydratase, H. 5-aminopent-2-enoate aminotransferase and/or dehydrogenase, I. 3-amino-5-oxopentanoate reductase, J. 3-amino-5-hydroxypentanoate deaminase.

Figure 15:
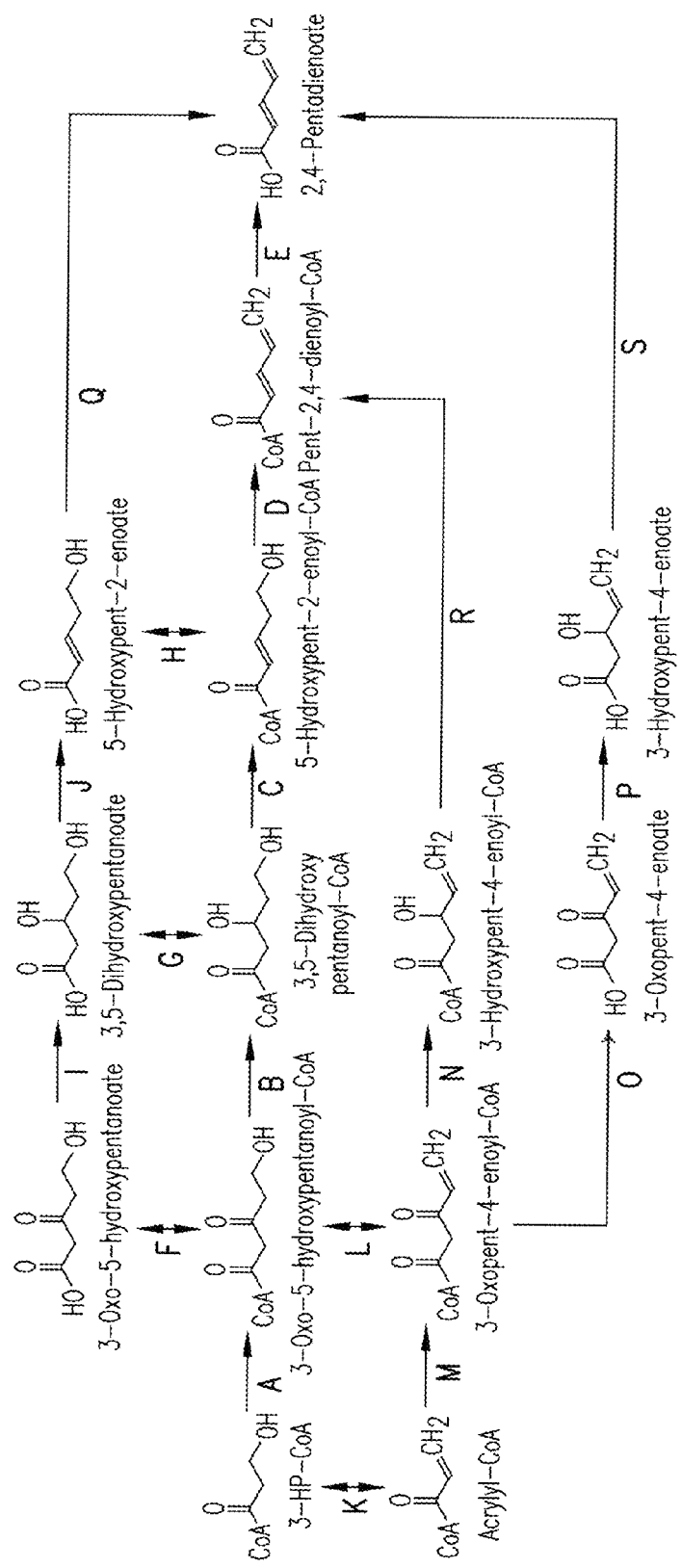

FIG. 15 shows pathways from 3-hydroxypropanoyl-CoA and/or acrylyl-CoA to 2,4-pentadienoate. Enzymes are A. 3-hydroxypropanoyl-CoA acetyltransferase, B. 3-oxo-5-hydroxypentanoyl-CoA reductase, C. 3,5-dihydroxypentanoyl-CoA dehydratase, D. 5-hydroxypent-2-enoyl-CoA dehydratase, E. pent-2,4-dienoyl-CoA synthetase, transferase and/or hydrolase, F. 3-oxo-5-hydroxypentanoyl-CoA synthetase, transferase and/or hydrolase, G. 3,5-dihydroxypentanoyl-CoA synthetase, transferase and/or hydrolase, H. 5-hydroxypent-2-enoyl-CoA synthetase, transferase and/or hydrolase, I. 3-oxo-5-hydroxypentanoate reductase, J. 3,5-dihydroxypentanoate dehydratase, K. 3-hydroxypropanoyl-CoA dehydratase, L. 3-oxo-5-hydroxypentanoyl-CoA dehydratase, M. acrylyl-CoA acetyltransferase, N. 3-oxopent-4-enoyl-CoA reductase, O. 3-oxopent-4-enoyl-CoA synthetase, transferase and/or hydrolase, P. 3-oxopent-4-enoate reductase, Q. 5-hydroxypent-2-enoate dehydratase, R. 3-hydroxypent-4-enoyl-CoA dehydratase, S. 3-hydroxypent-4-enoate dehydratase. 3-HP-CoA is 3-hydroxypropanoyl-CoA.

Figure 16:
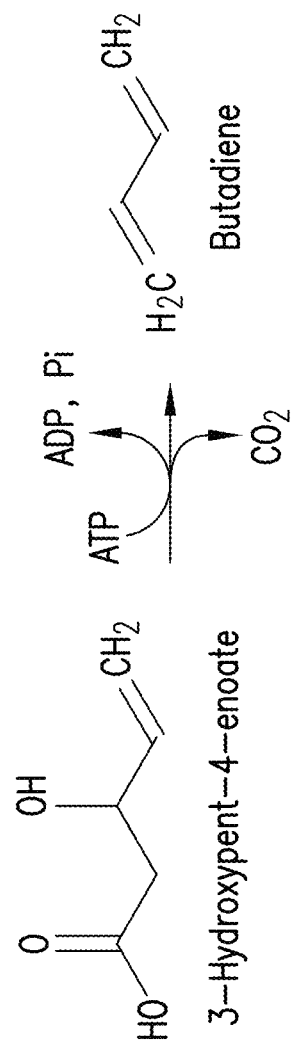

FIG. 16 shows the formation of butadiene from 3-hydroxypent-4-enoate (3HP4) by 3-hydroxypent-4-enoate decarboxylase.

Figure 17:
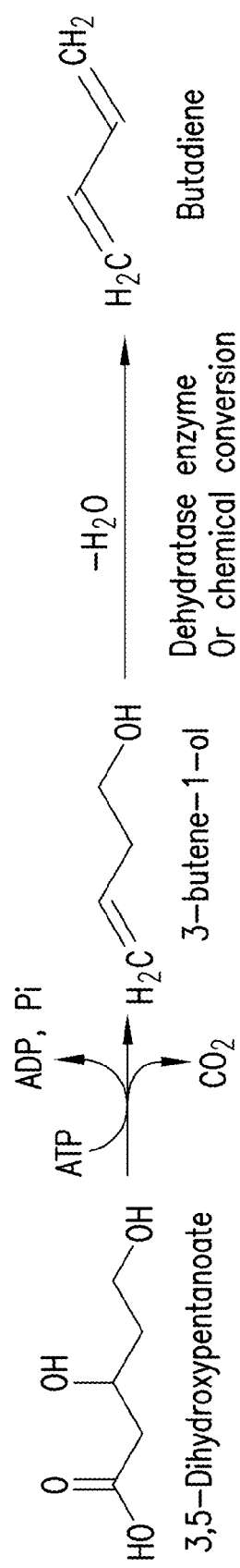

FIG. 17 shows the formation of butadiene from 3,5-dihydroxypentanoate by 3,5-dihydroxypentanoate decarboxylase and 3-butene-1-ol dehydratase. Dehydration of 3-butene-1-ol to butadiene can also occur via chemical catalysis.

Figure 18:
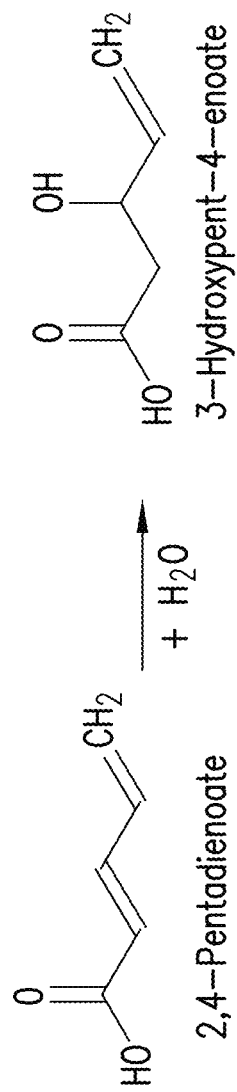

FIG. 18 shows the formation of the 3-hydroxypent-4-enoate (3HP4) intermediate from 2,4-pentadienoate via 2,4-pentadienoate hydratase.

Figure 19:
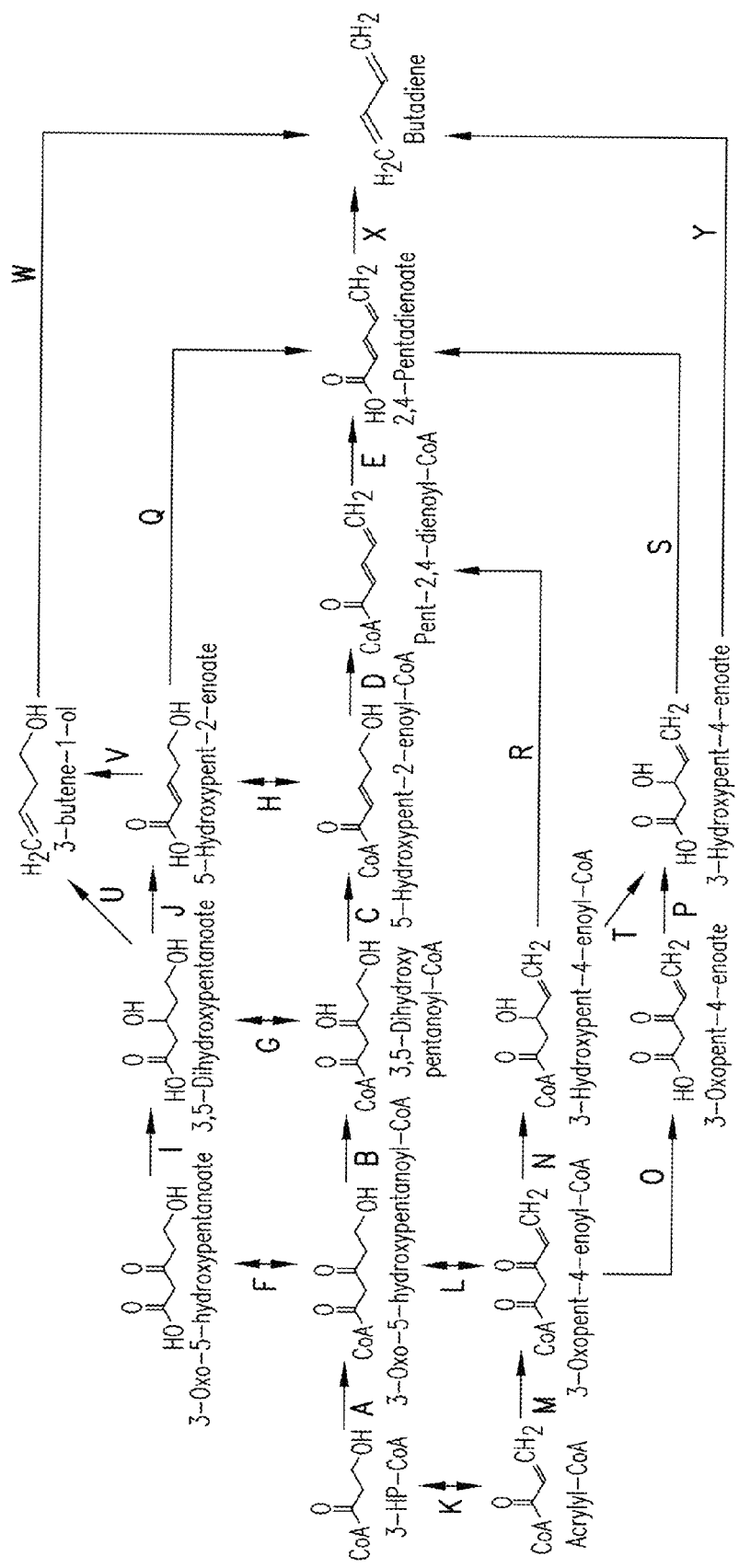

FIG. 19 shows pathways to butadiene, 3-hydroxypent-4-enoate (3HP4), 2,4-pentadienoate and 3-butene-1-ol from 3-HP-CoA and/or acrylyl-CoA. Enzymes are A. 3-hydroxypropanoyl-CoA acetyltransferase, B. 3-oxo-5-hydroxypentanoyl-CoA reductase, C. 3,5-dihydroxypentanoyl-CoA dehydratase, D. 5-hydroxypent-2-enoyl-CoA dehydratase, E. pent-2,4-dienoyl-CoA synthetase, transferase and/or hydrolase, F. 3-oxo-5-hydroxypentanoyl-CoA synthetase, transferase and/or hydrolase, G. 3,5-dihydroxypentanoyl-CoA synthetase, transferase and/or hydrolase, H. 5-hydroxypent-2-enoyl-CoA synthetase, transferase and/or hydrolase, I. 3-oxo-5-hydroxypentanoate reductase, J. 3,5-dihydroxypentanoate dehydratase, K. 3-hydroxypropanoyl-CoA dehydratase, L. 3-oxo-5-hydroxypentanoyl-CoA dehydratase, M. acrylyl-CoA acetyltransferase, N. 3-oxopent-4-enoyl-CoA reductase, O. 3-oxopent-4-enoyl-CoA synthetase, transferase and/or hydrolase, P. 3-oxopent-4-enoate reductase, Q. 5-hydroxypent-2-enoate dehydratase, R. 3-hydroxypent-4-enoyl-CoA dehydratase, S. 3-hydroxypent-4-enoate dehydratase, T. 3-hydroxypent-4-enoyl-CoA transferase, synthetase or hydrolase, U. 3,5-dihydroxypentanoate decarboxylase, V. 5-hydroxypent-2-enoate decarboxylase, W. 3-butene-1-ol dehydratase (or chemical conversion), X. 2,4-pentadiene decarboxylase, Y. 3-hydroxypent-4-enoate decarboxylase. 3-HP-CoA is 3-hydroxypropanoyl-CoA.

Figure 20:
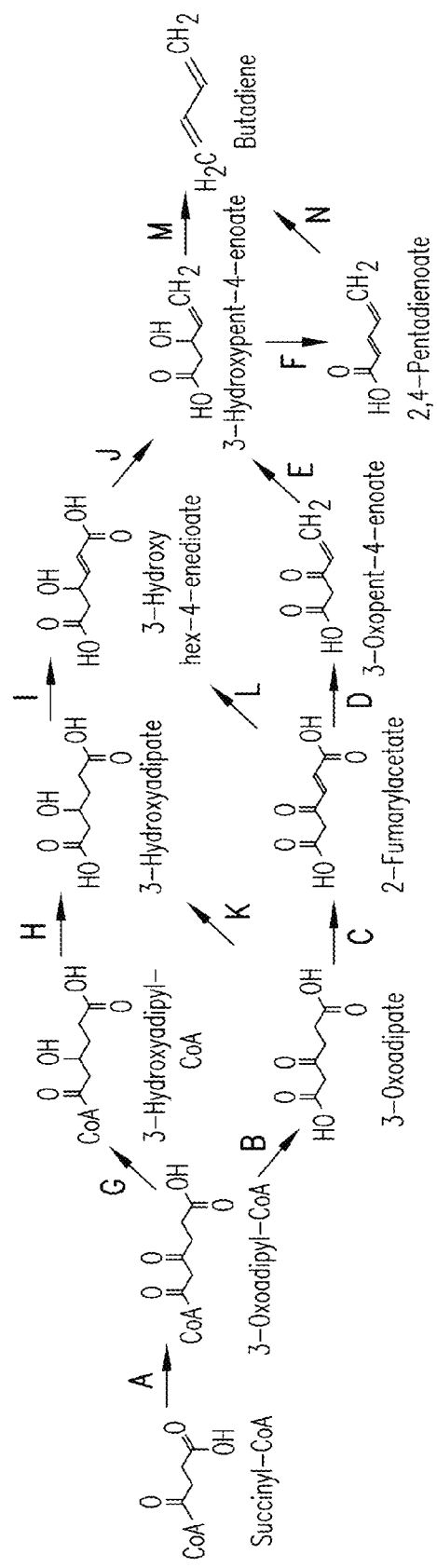

FIG. 20 shows pathways to 3-hydroxypent-4-enoate (3HP4), 2,4-pentadienoate and butadiene from succinyl-CoA. Enzymes are A. succinyl-CoA:acetyl-CoA acyltransferase, B. 3-oxoadipyl-CoA transferase, synthetase or hydrolase, C. 3-oxoadipate dehydrogenase, D. 2-fumarylacetate decarboxylase, E. 3-oxopent-4-enoate reductase, F. 3-hydroxypent-4-enoate dehydratase, G. 3-oxoadipyl-CoA reductase, H. 3-hydroxyadipyl-CoA transferase, synthetase or hydrolase, I. 3-hydroxyadipate dehydrogenase, J. 3-hydroxyhex-4-enedioate decarboxylase, K. 3-oxoadipate reductase, L. 2-fumarylacetate reductase., M. 3-hydroxypent-4-enoate decarboxylase, N. 2,4-pentadienoate decarboxylase.

Figure 21:
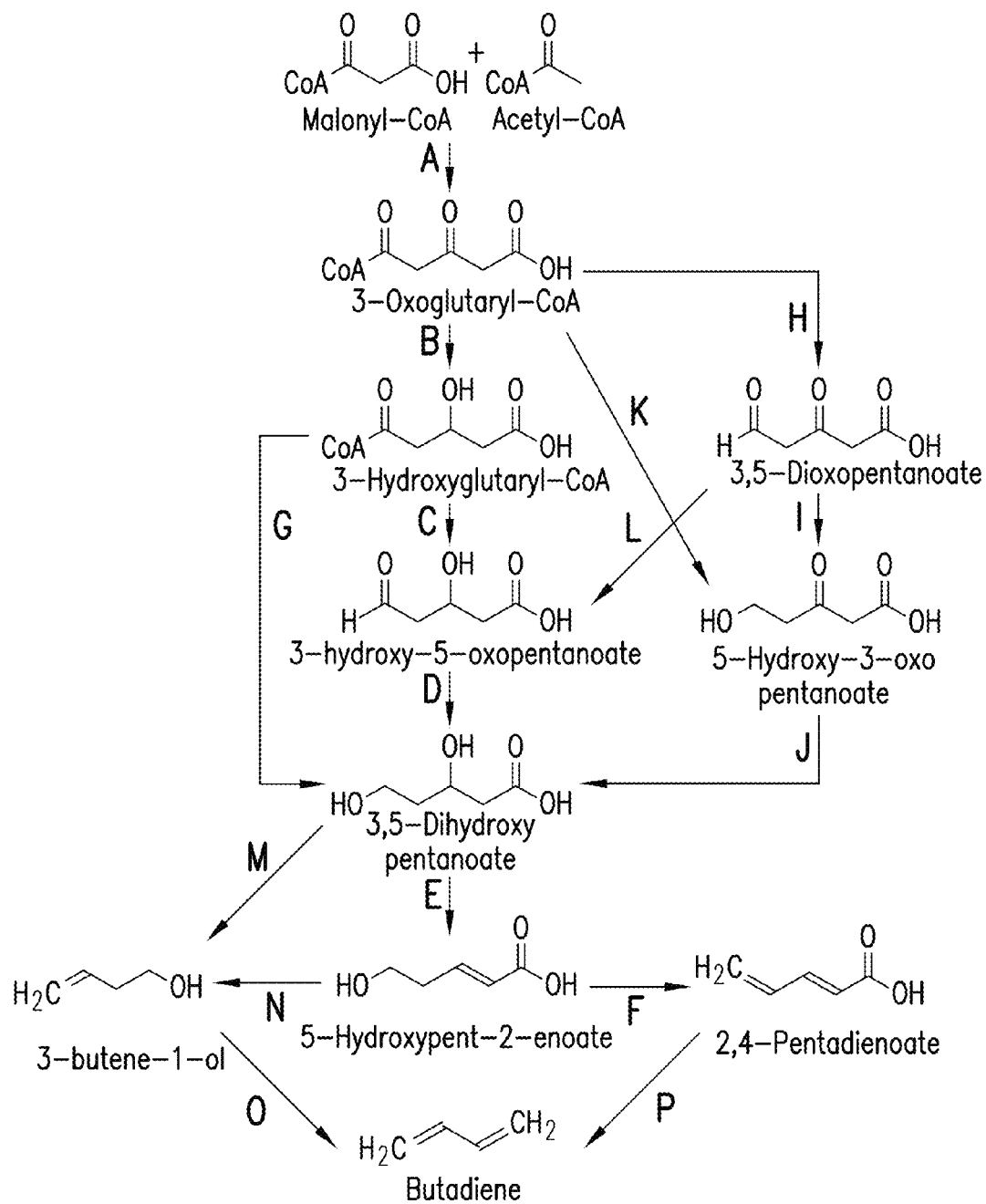

FIG. 21 shows pathways to 3-butene-1-ol, butadiene and 2,4-pentadienoate from malonyl-CoA and acetyl-CoA. Enzymes for transformation of the identified substrates to products include: A. malonyl-CoA:acetyl-CoA acyltransferase, B. 3-oxoglutaryl-CoA reductase (ketone-reducing), C. 3-hydroxyglutaryl-CoA reductase (aldehyde forming), D. 3-hydroxy-5-oxopentanoate reductase, E. 3,5-dihydroxypentanoate dehydratase, F. 5-hydroxypent-2-enoate dehydratase, G. 3-hydroxyglutaryl-CoA reductase (alcohol forming), H. 3-oxoglutaryl-CoA reductase (aldehyde forming), I. 3,5-dioxopentanoate reductase (aldehyde reducing), J. 5-hydroxy-3-oxopentanoate reductase, K. 3-oxoglutaryl-CoA reductase (CoA reducing and alcohol forming), L. 3,5-dioxopentanoate reductase (ketone reducing), M. 3,5-dihydroxypentanoate decarboxylase, N. 5-hydroxypent-2-enoate decarboxylase, O. 3-butene-1-ol dehydratase (or chemical conversion), P. 2,4-pentadiene decarboxylase.

Figure 22:
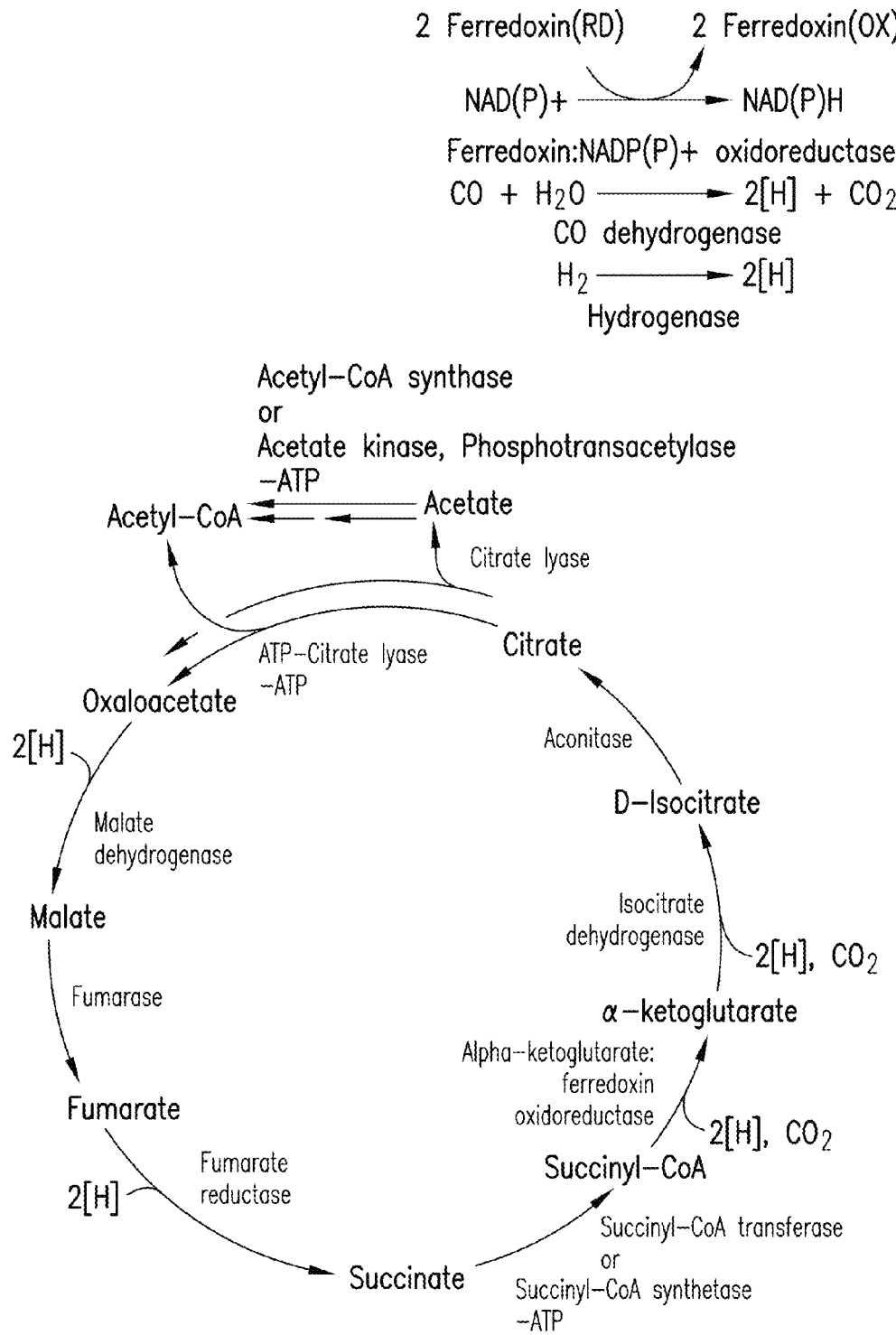

FIG. 22 shows the reverse TCA cycle for fixation of $CO_2$ on carbohydrates as substrates. The enzymatic transformations are carried out by the enzymes as shown.

Figure 23:
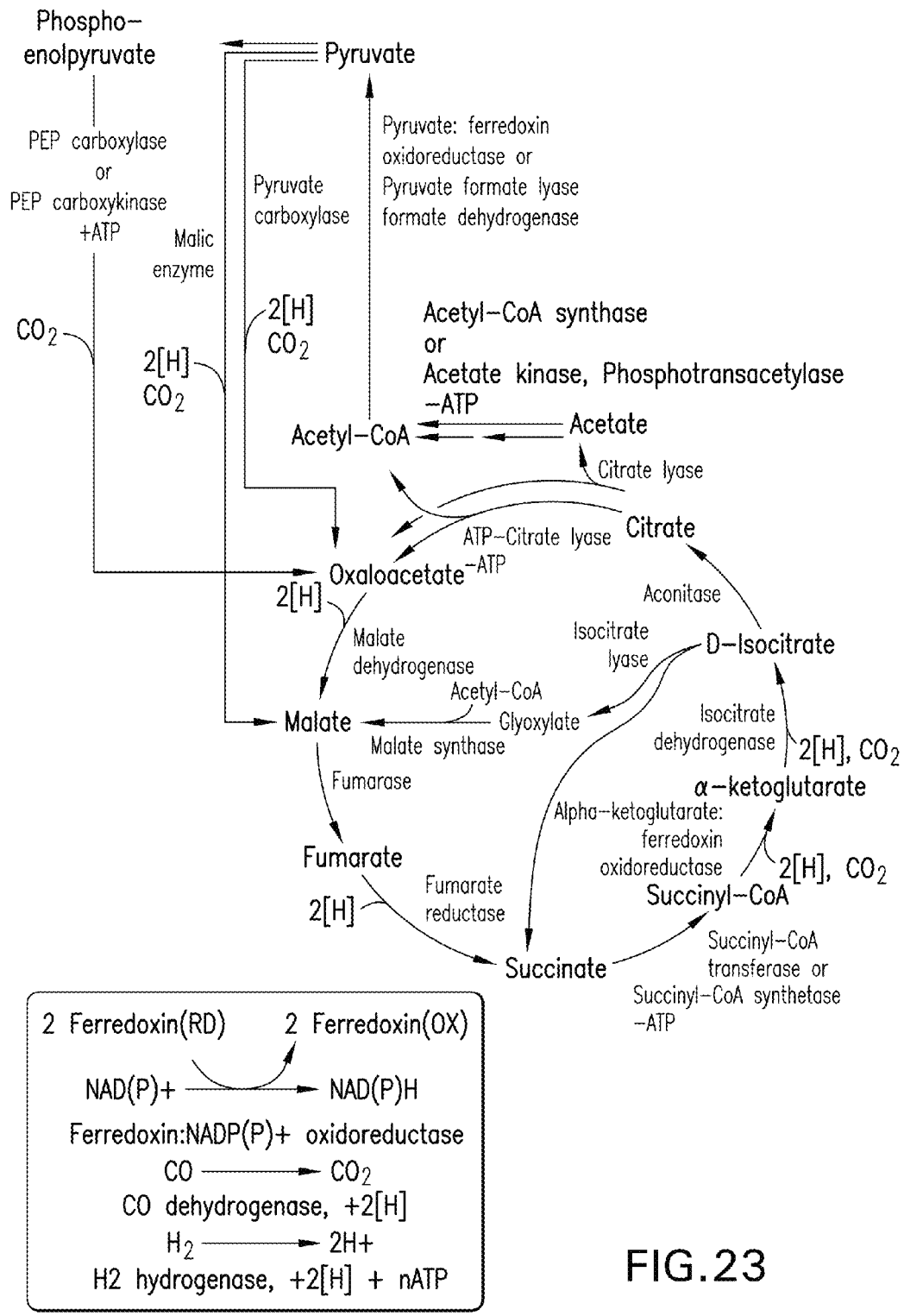

FIG. 23 shows the pathway for the reverse TCA cycle coupled with carbon monoxide dehydrogenase and hydrogenase for the conversion of syngas to acetyl-CoA.

Figure 24:
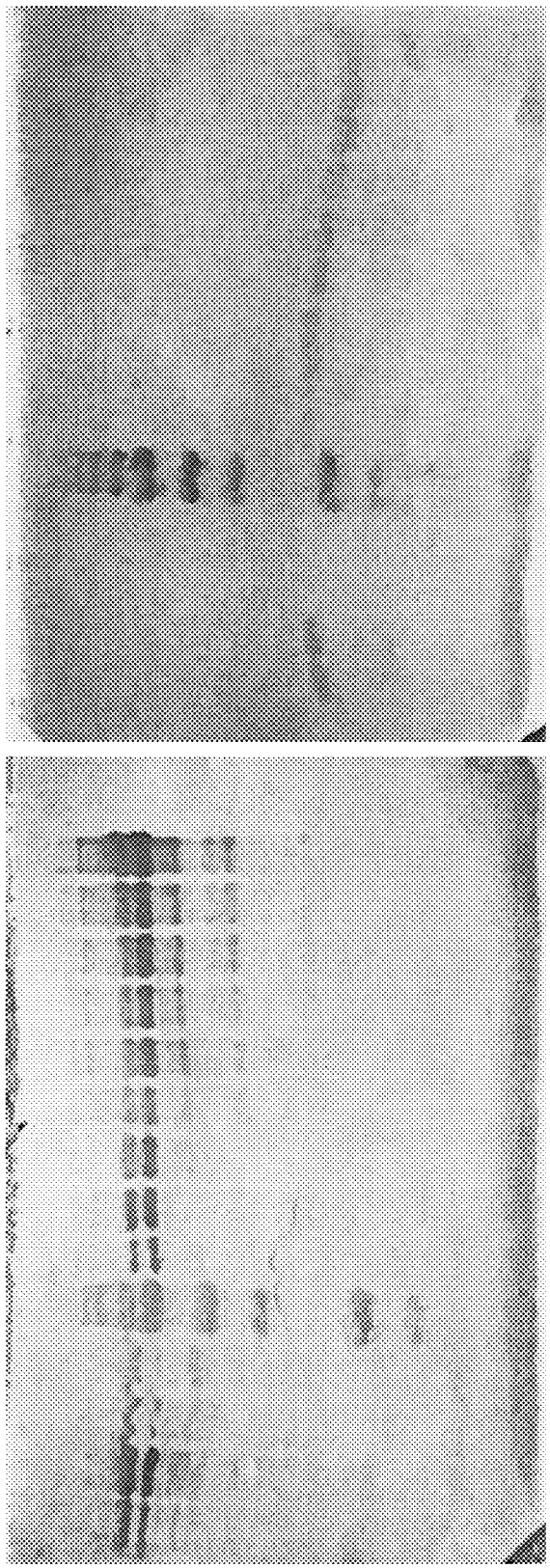

FIG. 24 shows Western blots of 10 micrograms ACS90 (lane 1), ACS91 (lane 2), Mta98/99 (lanes 3 and 4) cell extracts with size standards (lane 5) and controls of *M. thermoacetica* CODH (Moth_1202/1203) or Mtr (Moth_1197) proteins (50, 150, 250, 350, 450, 500, 750, 900, and 1000 ng).

Figure 25:
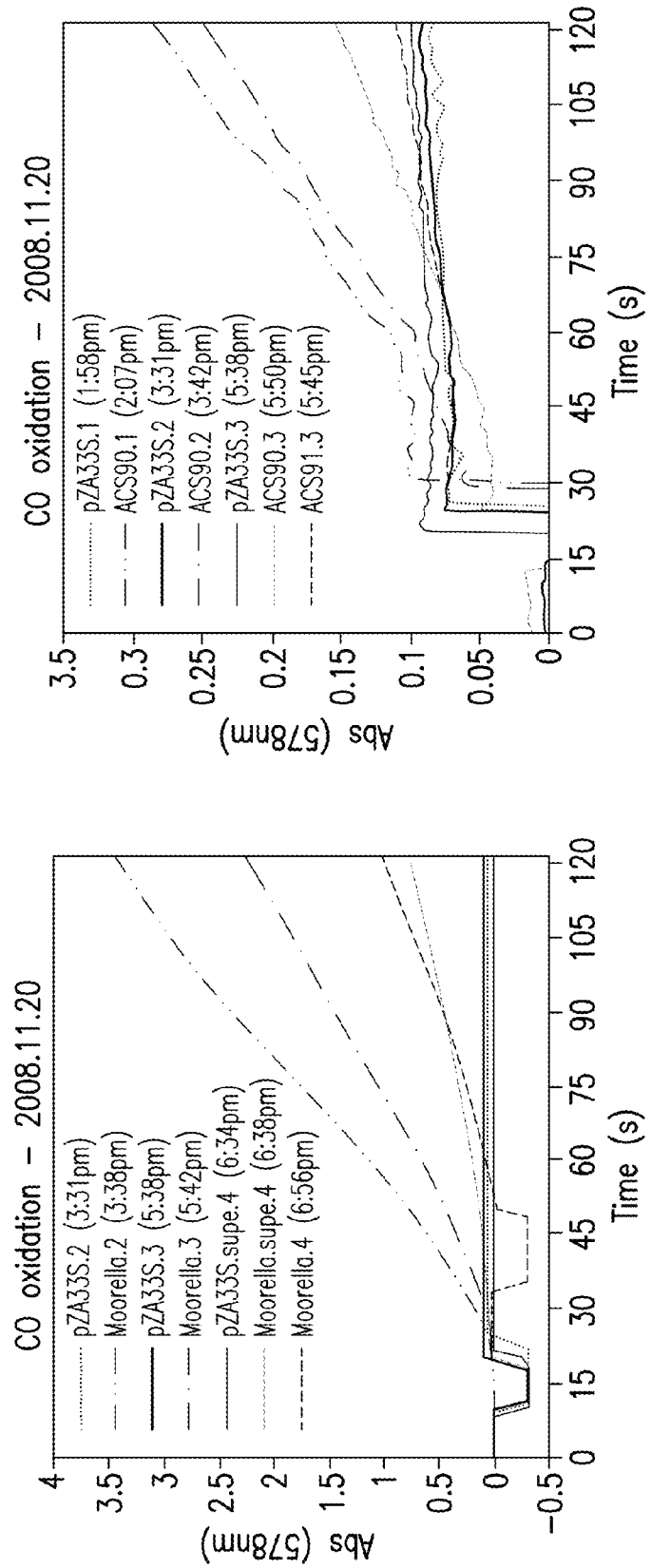

FIG. 25 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

DETAILED DESCRIPTION OF THE INVENTION

The present invention is directed, in part, to the design and production of cells and organisms having biosynthetic production capabilities for toluene, benzene, styrene, 2,4-pentadienoate and 1,3-butadiene. The routes to toluene and benzene, FIGS. 1 and 2, begin with the naturally occurring amino acid phenylalanine and, thus, most organisms will be capable of serving as a host for the construction of a non-naturally occurring organism for the production of toluene and benzene. Strategies for enhancing phenylalanine production are known in the art (Yakandawala et al., *App. Microbiol. Biotech.* 78:283-291 (2008); Lee et al., U.S. Pat. No. 5,008,190).

Figure 3:
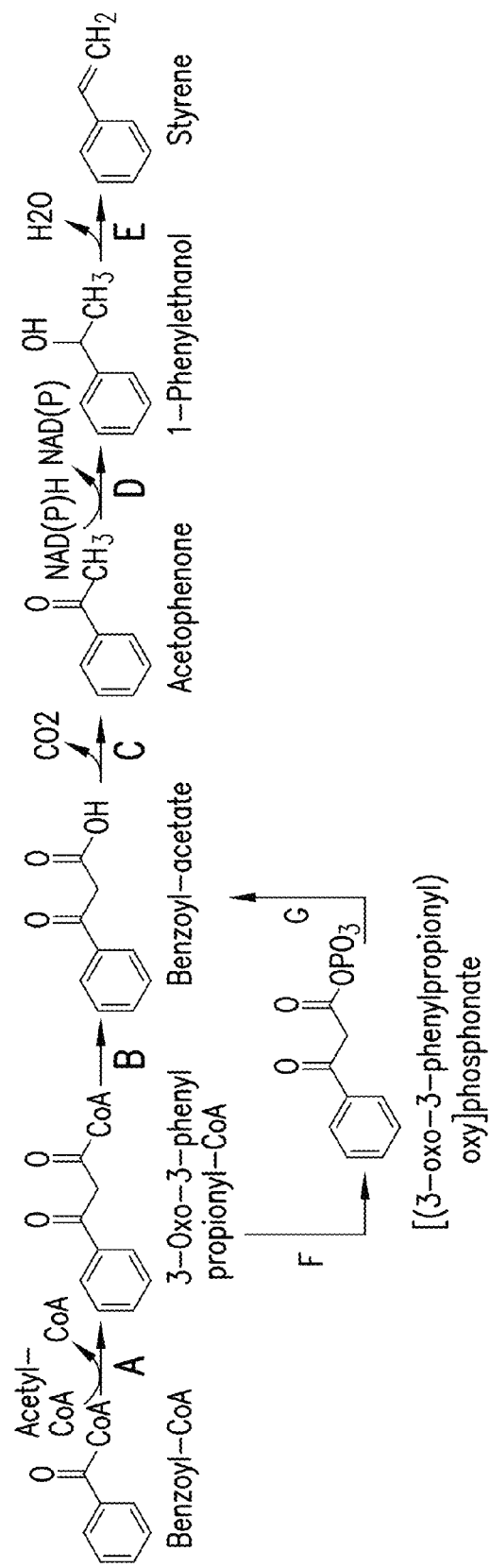
FIG. 3 shows pathways to styrene from benzoyl-CoA. Enzymes are: A. benzoyl-CoA acetyltransferase, B. 3-oxo-3-phenylpropionyl-CoA synthetase, transferase and/or hydrolase, C. benzoyl-acetate decarboxylase, D. acetophenone reductase and E. 1-phenylethanol dehydratase, F. phosphotrans-3-oxo-3-phenylpropionylase, G. benzoyl-acetate kinase.

The route to styrene relies on an organism for generating benzoyl-CoA, as indicated in FIG. 3. Benzoyl-CoA is a key metabolic intermediate of numerous biosynthetic and degradation pathways. Benzoyl-CoA is a key precursor of aromatic natural products such as antibiotics, aromas and defense signals. Biological pathways of benzoyl-CoA biosynthesis are known in the art (Boatright et al., *Plant Physiol* 135:1993-2011 (2004); Xiang et al., *J Bacteriol.* 185:399-404 (2003); Moore et al., *J Nat. Prod* 65:1956-1962 (2002)). Benzoyl-CoA is also a common intermediate of anaerobic and aerobic aromatic compound degradation pathways (Gescher et al., *J Bacteriol.* 184:6301-6315 (2002); Philipp et al., *FEMS Microbiol Lett.* 212:139-143 (2002); Koch et al., *Eur. J Biochem.* 205:195-202 (1992)).

Figure 4:
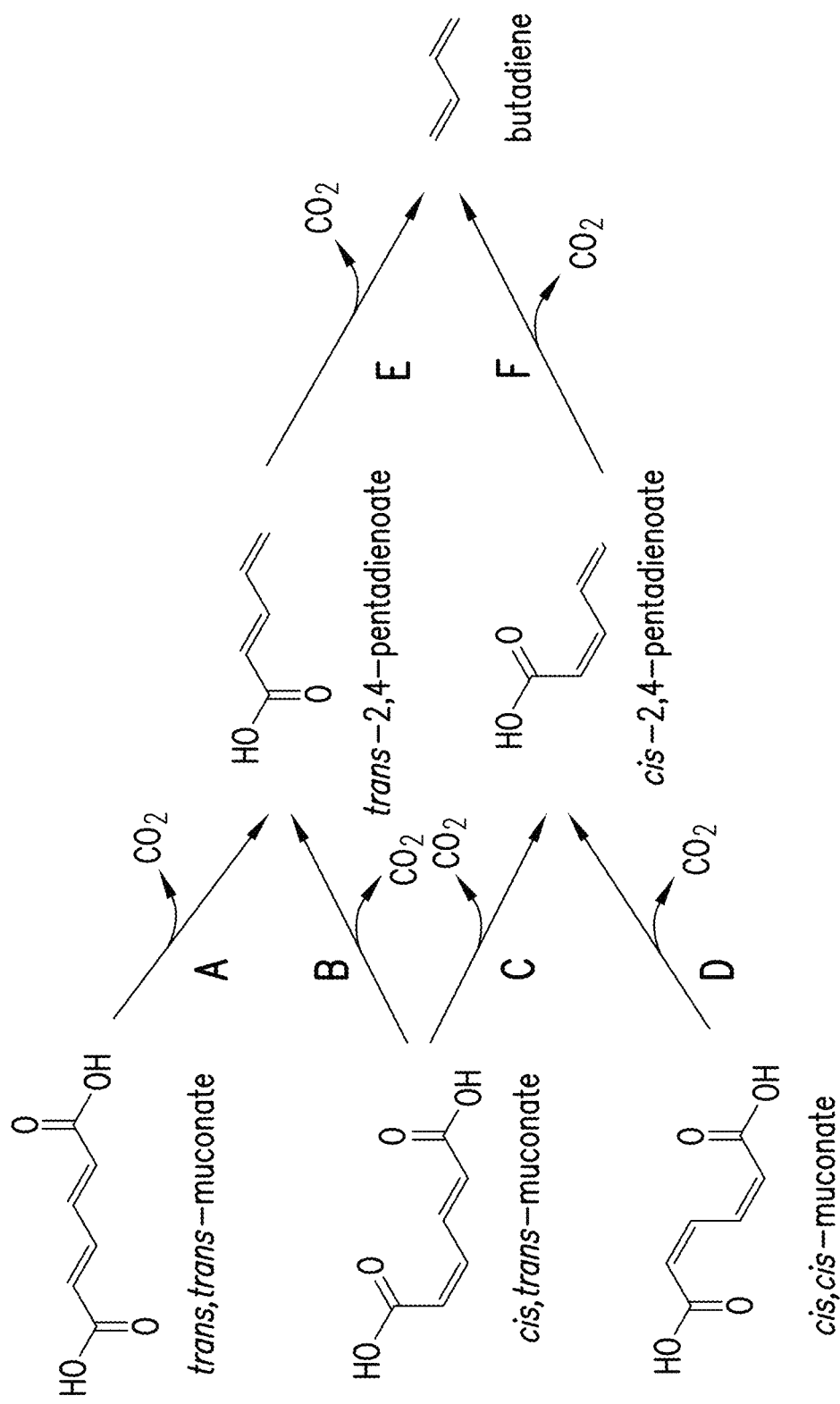
FIG. 4 shows the conversion of muconate stereoisomers to 1,3-butadiene. Enzymes are A. trans,trans-muconate decarboxylase, B. cis,trans-muconate cis-decarboxylase, C. cis, trans-muconate trans-decarboxylase, D. cis, cis-muconate decarboxylase, E. trans-2,4-pentadienoate decarboxylase, F. cis-2,4-pentadienoate decarboxylase.

This invention is also directed, in part, to non-naturally occurring microorganisms that express genes encoding enzymes that catalyze 1,3-butadiene production, as shown in FIG. 4. In some embodiments, pathways for the production of muconate are derived from central metabolic precursors. Muconate is a common degradation product of diverse aromatic compounds in microbes. Several biocatalytic strategies for making cis, cis-muconate have been developed. Engineered *E. coli* strains producing muconate from glucose via shikimate pathway enzymes have been developed in the Frost lab (U.S. Pat. No. 5,487,987 (1996); Niu et al., *Biotechnol Prog.*, 18:201-211 (2002)). These strains are able to produce 36.8 g/L of cis,cis-muconate after 48 hours of culturing under fed-batch fermenter conditions (22% of the maximum theoretical yield from glucose). Muconate has also been produced biocatalytically from aromatic starting materials such as toluene, benzoic acid and catechol. Strains producing muconate from benzoate achieved titers of 13.5 g/L and productivity of 5.5 g/L/hr (Choi et al., *J. Ferment. Bioeng.* 84:70-76 (1997)). Muconate has also been generated from the effluents of a styrene monomer production plant (Wu et al., *Enzyme and Microbiology Technology* 35:598-604 (2004)).

Figure 12:
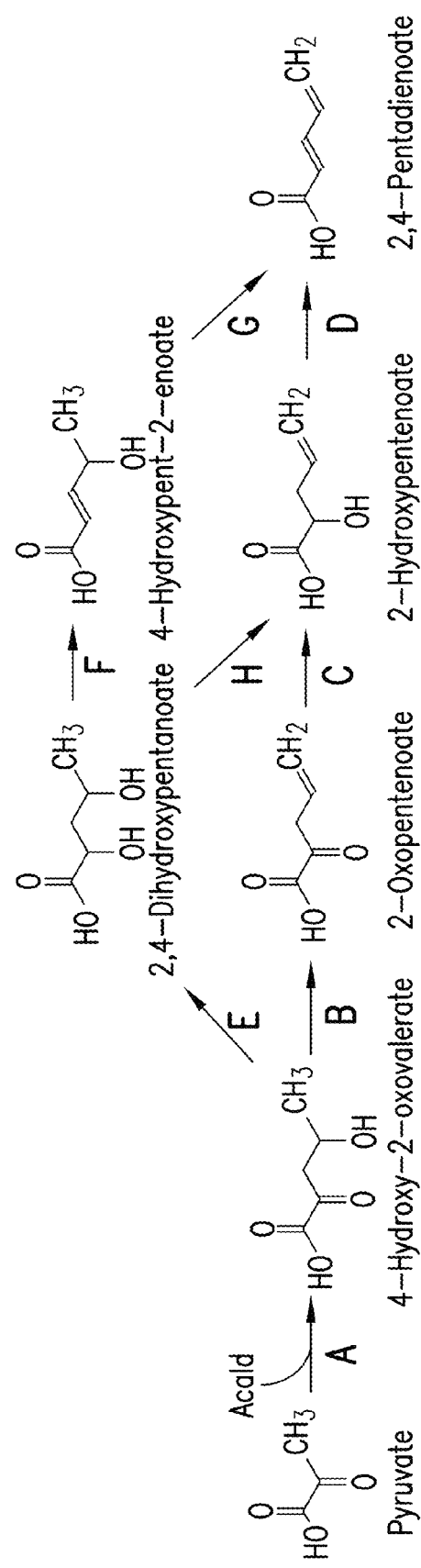
FIG. 12 shows pathways to 2,4-pentadienoate from pyruvate. Enzymes are A. 4-hydroxy-2-oxovalerate aldolase, B. 4-hydroxy-2-oxovalerate dehydratase, C. 2-oxopentenoate reductase, D. 2-hydroxypentenoate dehydratase, E. 4-hydroxy-2-oxovalerate reductase, F. 2,4-dihydroxypentanoate 2-dehydratase, G. 4-hydroxypent-2-enoate dehydratase and H. 2,4-dihydroxypentanoate 4-dehydratase.
Figure 13:
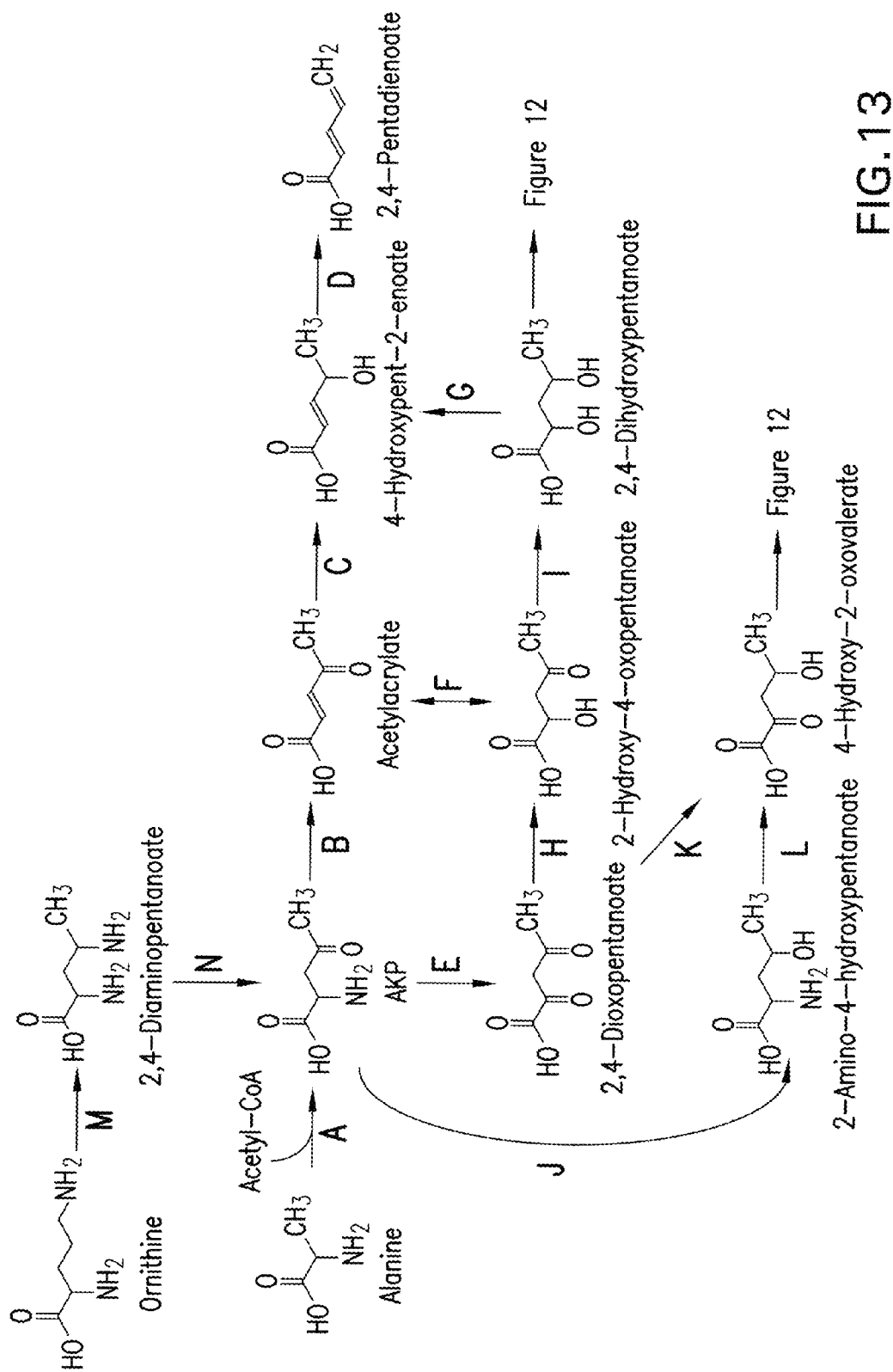
FIG. 13 shows pathways from alanine and ornithine to 2,4-pentadienoate. Enzymes are A. AKP thiolase, B. AKP deaminase, C. acetylacrylate reductase, D. 4-hydroxypent-2-enoate dehydratase, E. AKP aminotransferase and/or dehydrogenase, F. 2-hydroxy-4-oxopentanoate dehydratase, G. 2,4-dihydroxypentanoate 2-dehydratase, H. 2,4-dioxopentanoate 2-reductase, I. 2-hydroxy-4-oxopentanoate reductase, J. AKP reductase, K. 2,4-dioxopentanoate 4-reductase, L. 2-amino-4-hydroxypentanoate aminotransferase and/or dehydrogenase, M. ornithine 4,5-aminomutase, N.

This invention is also directed, in part, to non-naturally occurring microorganisms that express genes encoding enzymes that catalyze 2,4-pentadienoate production, as shown in FIGS. 12-15. Any of these pathways can feed into a further 1,3-butadiene pathway by inclusion of the requisite 2,4-pentadienoate decarboxylase. FIG. 12 shows the overall conversion of pyruvate to 2,4-pentadienoate by three pathways. FIG. 13 shows the overall conversion of ornithine or alanine to 2,4-pentadienoate via common intermediate 2-amino-4-ketopentanoate (AKP). FIG. 13 shows six routes to 2,4-pentadienoate from AKP, three of which intercept intermediates shown in FIG. 12. FIG. 14 shows four additional routes to 2,4-pentadienoate from ornithine. FIG. 15 shows numerous routes to 2,4-pentadienoate from 3-hydroxypropanoyl-CoA (3-HP-CoA) and acryloyl-CoA.

The invention is also directed, in part, to non-naturally occurring microbial organisms that express genes encoding enzymes that catalyze 1,3-butadiene production, as shown in FIGS. 16-17 and 19-21. FIG. 16 shows the decarboxylative dehydration of 3-hydroxypent-4-enoate (3HP4) to 1,3-butadiene, where 3HP4 is available via pathways shown in FIGS. 15 and 19. 3HP4, being important in its own right, is shown in FIG. 18 via intermediate 2,4-pentadienoate via hydration, as well as the via the pathways of FIGS. 15, 19, and 20. Likewise, FIG. 17 shows the tandem decarboxylative dehydration and elimination (further dehydration) of intermediate 3,5-dihydroxypentanoate, which is itself accessible through the pathways shown in FIGS. 15, 19, and 21.

FIG. 19 shows pathways to 1,3-butadiene and 1,3-butadiene intermediates from 3-HP-CoA and acrylyl-CoA. FIG. 20 shows pathways to 1,3-butadiene and 1,3-butadiene intermediates from succinyl-CoA. The requisite succinyl-CoA is a central metabolic intermediate, the yield of which can be enhanced via a reductive TCA cycle as described further herein. Finally, FIG. 21 shows pathways to 1,3-butadiene and 1,3-butadiene intermediates from the condensation of malonyl-CoA and acetyl-CoA, the latter also benefitting from increased throughput via reductive TCA pathways described herein.

The present invention is also directed to the design and production of cells and organisms having biosynthetic production capabilities for p-toluate, terephthalate, (2-hydroxy-3-methyl-4-oxobutoxy)phosphonate, toluene, (2-hydroxy-4-oxobutoxy)phosphonate, benzoate, or benzene. The results described herein indicate that metabolic pathways can be designed and recombinantly engineered to achieve the biosynthesis of p-toluate, terephthalate, (2-hydroxy-3-methyl-4-oxobutoxy)phosphonate, toluene, (2-hydroxy-4-oxobutoxy)phosphonate, benzoate, or benzene in *Escherichia coli* and other cells or organisms. Biosynthetic production of p-toluate, terephthalate, (2-hydroxy-3-methyl-4-oxobutoxy)phosphonate, toluene, (2-hydroxy-4-oxobutoxy)phosphonate, benzoate, or benzene can be confirmed by construction of strains having the designed metabolic genotype. These metabolically engineered cells or organisms also can be subjected to adaptive evolution to further augment p-toluate, terephthalate, (2-hydroxy-3-methyl-4-oxobutoxy)phosphonate, toluene, (2-hydroxy-4-oxobutoxy)phosphonate, benzoate, or benzene biosynthesis, including under conditions approaching theoretical maximum growth.

The shikimate biosynthesis pathway in *E. coli* converts erythrose-4-phosphate to chorismate, an important intermediate that leads to the biosynthesis of many essential metabolites including 4-hydroxybenzoate. 4-Hydroxybenzoate is structurally similar to p-toluate, an industrial precursor of terephthalic acid, and benzene. As disclosed herein, shikimate pathway enzymes are utilized to accept the alternate substrate, (2-hydroxy-3-methyl-4-oxobutoxy)phosphonate (2H3M4OP), and transform it to p-toluate or toluene, or the alternate substrate (2-hydroxy-4-oxobutoxy)phosphonate (2H4OP) and transform it to benzoate or benzene. In addition, a pathway is used to synthesize the 2H3M4OP or 2H4OP precursor using enzymes from the non-mevalonate pathway for isoprenoid biosynthesis.

Disclosed herein are strategies for engineering a microorganism to produce renewable p-toluate, terephthalate (PTA), toluene, benzoate, or benzene from carbohydrate feedstocks. In the toluene series, glyceraldehyde-3-phosphate (G3P) and pyruvate are converted to 2-hydroxy-3-methyl-4-oxobutoxy)phosphonate (2H3M4OP) in three enzymatic steps (see Example III and FIG. 5). The 2H3M4OP intermediate is subsequently transformed to p-toluate by enzymes in the shikimate pathway (see Example IV and FIG. 6). p-Toluate can be further converted to PTA by a microorganism (see Example V and FIG. 7). In the benzene series, 2H4OP is prepared by dehydration and reduction of erythrose-4-phosphate (see Example VI and FIG. 8). The 2H4OP intermediate is subsequently transformed to benzoate by enzymes in the shikimate pathway (see Example VI and FIG. 9). Benzoate and p-toluate are converted to benzene and toluene, respectively (see Example VII, and FIGS. 10 and 11).

The conversion of G3P to p-toluate requires one ATP, two reducing equivalents (NAD(P)H), and two molecules of phosphoenolpyruvate, according to net reaction below.

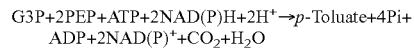

An additional ATP is required to synthesize G3P from glucose. The maximum theoretical p-toluate yield is 0.67 mol/mol (0.51 g/g) from glucose minus carbon required for energy. Under the assumption that 2 ATPs are consumed per p-toluate molecule synthesized, the predicted p-toluate yield from glucose is 0.62 mol/mol (0.46 g/g) p-toluate.

If p-toluate is further converted to PTA by enzymes as described in Example III, the predicted PTA yield from glucose is 0.64 mol/mol (0.58 g/g). In this case, the oxidation of p-toluate to PTA generates an additional net reducing equivalent according to the net reaction:

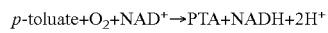

$p\text{-toluate} + O_2 + NAD^+ \rightarrow PTA + NADH + 2H^+$

Enzyme candidates for catalyzing each step of the above pathways are described in the following sections. Successfully engineering pathways for the production of toluene, benzene, styrene, p-toluate, terephthalate, (2-hydroxy-3-methyl-4-oxobutoxy)phosphonate, (2-hydroxy-4-oxobutoxy)phosphonate, benzoate or 1,3-butadiene entails identifying an appropriate set of enzymes with sufficient activity and specificity, cloning their corresponding genes into a production host, optimizing the expression of these genes in the production host, optimizing fermentation conditions, and assaying for product formation following fermentation.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a toluene, benzene, p-toluate, terephthalate, (2-hydroxy-3-methyl-4-oxobutoxy)phosphonate, toluene, (2-hydroxy-4-oxobutoxy)phosphonate, benzoate, styrene, or 1,3-butadiene biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

Figure 5:
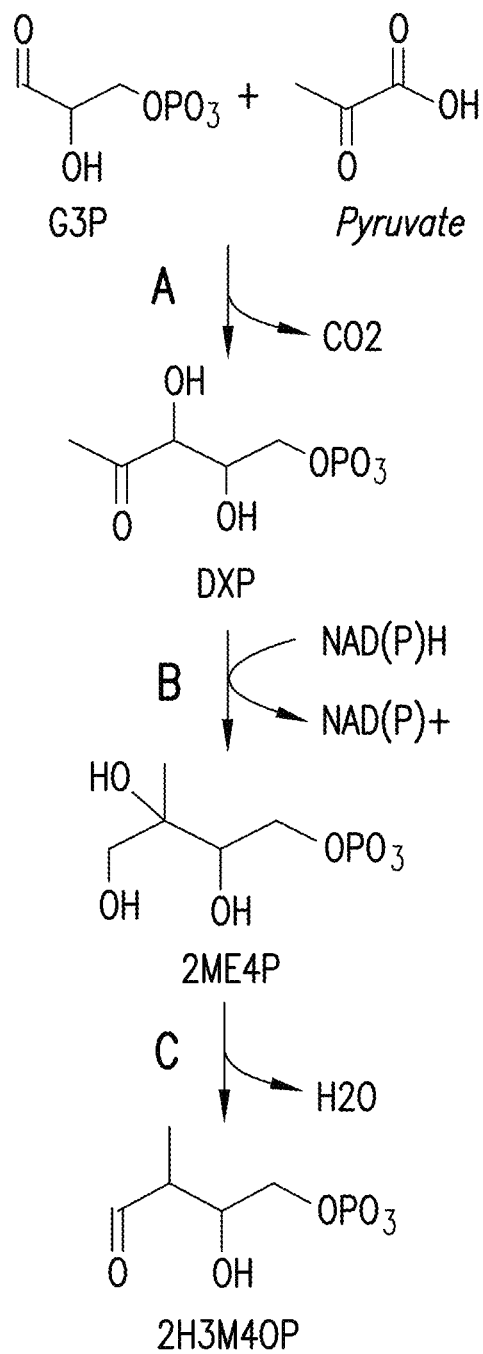
FIG. 5 shows a schematic depiction of an exemplary pathway to (2-hydroxy-3-methyl-4-oxobutoxy)phosphonate (2H3M4OP) from glyceraldehyde-3-phosphate and pyruvate. G3P is glyceraldehyde-3-phosphate, DXP is 1-deoxy-D-xylulose-5-phosphate and 2ME4P is C-methyl-D-erythritol-4-phosphate. Enzymes are (A) DXP synthase; (B) DXP reductoisomerase; and (C) 2ME4P dehydratase.

As used herein, the term "(2-hydroxy-3-methyl-4-oxobutoxy)phosphonate," abbreviated herein as 2H3M4OP, has the chemical formula as shown in FIG. 5. Such a compound can also be described as 3-hydroxy-2-methyl butanal-4-phosphate.

Figure 8:
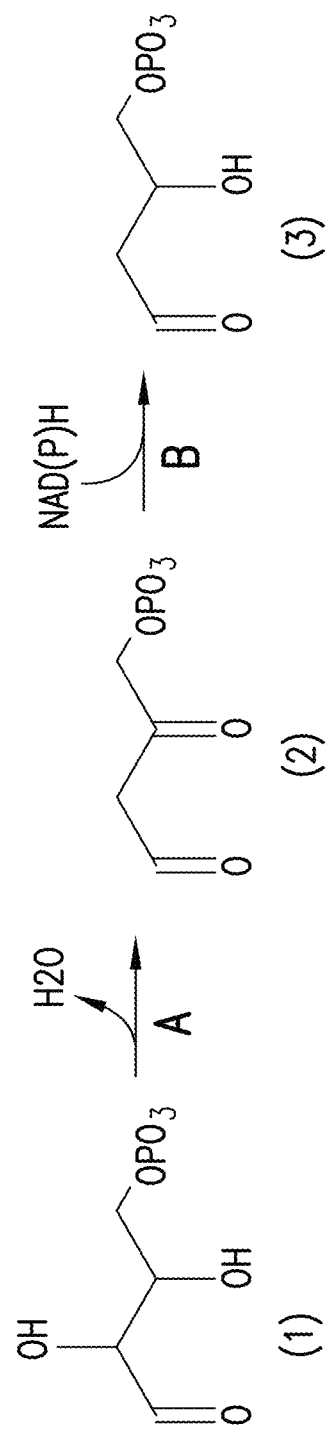
FIG. 8 shows an exemplary pathway to (2-hydroxy-4-oxobutoxy)phosphonate from erythrose-4-phosphate. Enzymes are: A. erythrose-4-phosphate dehydratase, B. (2,4-dioxobutoxy)phosphonate reductase. Compounds are: (1) erythrose-4-phosphate, (2) (2,4-dioxobutoxy)phosphonate and (3) (2-hydroxy-4-oxobutoxy)phosphonate.

As used herein, the term "(2-hydroxy-4-oxobutoxy)phosphonate," abbreviated herein as 2H4OP, has the chemical formula as shown in FIG. 8 (compound 3). Such a compound can also be described as 3-hydroxybutanal-4-phosphate.

As used herein, the term "p-toluate," having the molecular formula $C_8H_7O_2^-$ (see FIG. 6, compound 9)(IUPAC name 4-methylbenzoate) is the ionized form of p-toluic acid, and it is understood that p-toluate and p-toluic acid can be used interchangeably throughout to refer to the compound in any of its neutral or ionized forms, including any salt forms thereof. It is understood by those skilled in the art that the specific form will depend on the pH.

As used herein, the term "benzoate," having the molecular formula $C_7H_6O_2$ (see FIG. 9, compound 9) is the ionized form of benzoic acid, and it is understood that benzoate and benzoic acid can be used interchangeably throughout to refer to the compound in any of it neutral or ionized forms, including any salt forms thereof. It is understood by those skilled in the art that the specific form will depend on the pH.

As used herein, the term "terephthalate," having the molecular formula $C_8H_4O_4^{-2}$ (see FIG. 7, compound 4)(IUPAC name terephthalate) is the ionized form of terephthalic acid, also referred to as p-phthalic acid or PTA, and it is understood that terephthalate and terephthalic acid can be used interchangeably throughout to refer to the compound in any of its neutral or ionized forms, including any salt forms thereof. It is understood by those skilled understand that the specific form will depend on the pH.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiment, the present invention provides a non-naturally occurring microbial organism that includes a microbial organism having a toluene pathway which includes at least one exogenous nucleic acid encoding a toluene pathway enzyme expressed in a sufficient amount to produce toluene. The toluene pathway is selected from (A) 1) one or both of phenylalanine aminotransferase and phenylalanine oxidoreductase (deaminating), 2) phenylpyruvate decarboxylase, and 3) phenylacetaldehyde decarbonylase; (B) 1) one or more of phenylalanine aminotransferase and phenylalanine oxidoreductase (deaminating), 2) phenylpyruvate decarboxylase, 3) one or more of phenylacetaldehyde dehydrogenase and phenylacetaldehyde oxidase, and 4) phenylacetate decarboxylase; and (C) one or more of phenylalanine aminotransferase and phenylalanine oxidoreductase (deaminating), 2) phenylpyruvate oxidase, and 3) phenylacetate decarboxylase, as shown in the alternate pathways in FIG. 1.

The non-naturally occurring microbial organism having the toluene pathway can include two exogenous nucleic acids each encoding a toluene pathway enzyme, three exogenous nucleic acids each encoding a toluene pathway enzyme, four exogenous nucleic acids each encoding a toluene pathway enzyme, or five exogenous nucleic acids each encoding a toluene pathway enzyme. An exemplary non-naturally occurring microbial organism having three exogenous nucleic acids can include an organism having genes encoding 1) phenylalanine aminotransferase and/or oxidoreductase (deaminating), 3) phenylpyruvate oxidase, and 5) phenylacetate decarboxylase. An exemplary non-naturally occurring organism having four exogenous nucleic acids can include an organism having exogenous genes encoding 1) phenylalanine aminotransferase, 2) phenylalanine oxidoreductase (deaminating), 3) phenylpyruvate decarboxylase, and 4) phenylacetaldehyde decarbonylase. An exemplary non-naturally occurring microbial organism having five exogenous nucleic acids can include an organism having genes encoding 1) phenylalanine aminotransferase, 2) phenylalanine oxidoreductase (deaminating), 3) phenylpyruvate decarboxylase, 4) phenylacetaldehyde dehydrogenase and/or oxidase, and 5) phenylacetate decarboxylase. Thus, in particular embodiments, a non-naturally occurring microbial organism can have a complete toluene pathway every gene encoding every enzyme in a complete toluene pathway. In some embodiments the non-naturally occurring microbial organism having a toluene pathway can include at least one exogenous nucleic acid that is a heterologous nucleic acid. Finally, the non-naturally occurring microbial organism having a toluene pathway can be in a substantially anaerobic culture medium.

Figure 2:
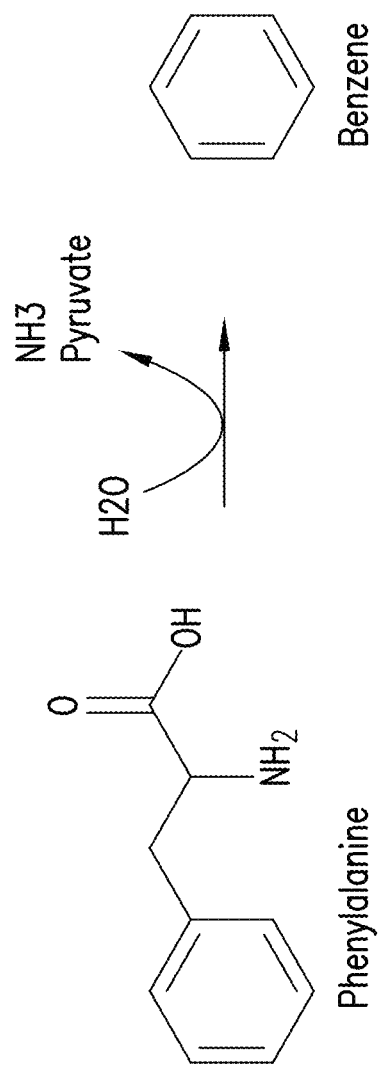
FIG. 2 shows the conversion of phenylalanine to benzene by phenylalanine benzene-lyase.

In some embodiments, the present invention provides a non-naturally occurring microbial organism that includes a microbial organism having a benzene pathway which includes at least one exogenous nucleic acid encoding a benzene pathway enzyme expressed in a sufficient amount to produce benzene. The benzene pathway can include a phenylalanine benzene-lyase as shown in FIG. 2. The at least one exogenous nucleic acid can be phenylalanine benzene-lyase itself or a nucleic acid that affects the production of its precursor phenylalanine. In some embodiments the non-naturally occurring microbial organism having a benzene pathway has at least one exogenous nucleic acid that is a heterologous nucleic acid. In some embodiments, the non-naturally occurring microbial organism having a benzene pathway is in a substantially anaerobic culture medium.

In some embodiments, the present invention provides a non-naturally occurring microbial organism that includes a microbial organism having a styrene pathway which includes at least one exogenous nucleic acid encoding a styrene pathway enzyme expressed in a sufficient amount to produce styrene. The styrene pathway can be selected from (A) 1) benzoyl-CoA acetyltransferase, 2) one or more of 3-oxo-3-phenylpropionyl-CoA synthetase, transferase, and hydrolase, 3) benzoyl-acetate decarboxylase, 4) acetopheone reductase, and 5) 1-phenylethanol dehydratase; and (B) 1) benzoyl-CoA acetyltransferase, 2) phosphotrans-3-oxo-3-phenylpropionylase, 3) benzoyl-acetate kinase, 4) benzoyl-acetate decarboxylase, 5) acetopheone reductase, and 6) 1-phenylethanol dehydratase, as indicated by the alternate pathways in FIG. 3.

In some embodiments, the non-naturally occurring microbial organism having a styrene pathway can include two exogenous nucleic acids each encoding a styrene pathway enzyme, three exogenous nucleic acids each encoding a styrene pathway enzyme, four exogenous nucleic acids each encoding a styrene pathway enzyme, five exogenous nucleic acids each encoding a styrene pathway enzyme, six exogenous nucleic acids each encoding a styrene pathway enzyme, and so on. An exemplary non-naturally occurring organism having five exogenous nucleic acids can include an organism having exogenous genes encoding 1) benzoyl-CoA acetyltransferase, 2) one of 3-oxo-3-phenylpropionyl-CoA synthetase, transferase, and hydrolase, 3) benzoyl-acetate decarboxylase, 4) acetophenone reductase, and 5) 1-phenylethanol dehydratase. An exemplary non-naturally occurring organism having six exogenous nucleic acids can include an organism having exogenous genes encoding 1) benzoyl-CoA acetyltransferase, 2) phosphotrans-3-oxo-3-phenylpropionylase, 3) benzoyl-acetate kinase, 4) benzoyl-acetate decarboxylase, 5) acetopheone reductase, and 6) 1-phenylethanol dehydratase. In some embodiments the non-naturally occurring microbial organism having a styrene pathway has at least one exogenous nucleic acid that is a heterologous nucleic acid. In some embodiments the non-naturally occurring microbial organism having a styrene pathway is in a substantially anaerobic culture medium.

In some embodiments, the present invention provides a non-naturally occurring microbial organism that includes a microbial organism having a 1,3-butadiene pathway which includes at least one exogenous nucleic acid encoding a 1,3-butadiene pathway enzyme expressed in a sufficient amount to produce 1,3-butadiene. The 1,3-butadiene pathway can be selected from (A) 1) trans,trans-muconate decarboxylase and 2) trans-2,4-pentadienoate decarboxylase; (B) 1) cis,trans-muconate cis-decarboxylase and 2) trans-2,4-pentadienoate decarboxylase; (C) 1) cis,trans-muconate trans-decarboxylase 2) cis-2,4-pentadienoate decarboxylase; and (D) 1) cis, cis-muconate decarboxylase and 2) cis-2,4-pentadienoate decarboxylase, as indicated in the alternate pathways in FIG. 4.

In some embodiments, the non-naturally occurring microbial organism having a 1,3-butadiene pathway can include two exogenous nucleic acids each encoding a 1,3-butadiene pathway enzyme. Thus, the two exogenous nucleic acids can encode a set selected from (A) 1) trans,trans-muconate decarboxylase and 2) trans-2,4-pentadienoate decarboxylase; (B) 1) cis, trans-muconate cis-decarboxylase and 2) trans-2,4-pentadienoate decarboxylase; (C) 1) cis, trans-muconate trans-decarboxylase 2) cis-2,4-pentadienoate decarboxylase; and (D) 1) cis, cis-muconate decarboxylase and 2) cis-2,4-pentadienoate decarboxylase, corresponding to the complete pathways shown in FIG. 4. In some embodiments, the non-naturally occurring microbial organism having a 1,3-butadiene pathway has at least one exogenous nucleic acid that is a heterologous nucleic acid. In some embodiments, the non-naturally occurring microbial organism having a 1,3-butadiene pathway is in a substantially anaerobic culture medium.

In some embodiments, the present invention provides a non-naturally occurring microbial organism having a 2,4-pentadienoate pathway that includes at least one exogenous nucleic acid encoding a 2,4-pentadienoate pathway enzyme expressed in a sufficient amount to produce 2,4-pentadienoate. The 2,4-pentadienoate pathway has a set of enzymes capable of converting AKP to 2,4-pentadienoate selected from (A) 1) a 4-hydroxy-2-oxovalerate aldolase, 2) a 4-hydroxy-2-oxovalerate dehydratase, 3) a 2-oxopentenoate reductase, and 4) a 2-hydroxypentenoate dehydratase, as shown in steps A-D of FIG. 12, (B) 1) an AKP deaminase, 2) an acetylacrylate reductase, and 3) a 4-hydroxypent-2-enoate dehydratase, as shown in steps B-D of FIG. 13, (C) 1) an AKP aminotransferase and/or dehydrogenase, 2) a 2,4-dioxopentanoate-2-reductase, 3) a 2-hydroxy-4-oxopentanoate dehydratase, 4) an acetylacrylate reductase, and 5) a 4-hydroxypent-2-enoate dehydratase, as shown in steps E, H, F, C, and D of FIG. 13, (D) 1) an AKP aminotransferase and/or dehydrogenase, 2) a 2,4-dioxopentanoate-4-reductase, 3) a 4-hydroxy-2-oxovalerate dehydratase, 4) a 2-oxopentenoate reductase, and 5) a 2-hydroxypentenoate dehydratase, as shown in steps E and K FIG. 13, along with steps B-D of FIG. 12, and (E) 1) an AKP reductase, 2) a 2-amino-4-hydroxypentanoate aminotransferase and/or dehydrogenase, 3) a 4-hydroxy-2-oxovalerate dehydratase, 4) a 2-oxopentenoate reductase, and 5) a 2-hydroxypentenoate dehydratase, also shown in steps J and L of FIG. 13, along with steps B-D of FIG. 12. In some embodiments, pathways of FIG. 13 that include the intermediate 4-hydroxy-2-oxovalerate, shown in FIG. 12, can also be directed through the 2,4-dihydroxypentanoate pathways shown in FIG. 12 to provide 2,4-pentadienoate. For example, from 4-hydroxy-2-oxovalerate, pathways to 2,4-pentadienoate can include the enzymes in steps E, H, and D or steps E, F, and G, in FIG. 12.

In some embodiments, the present invention also provides a non-naturally occurring microbial organism having a 2,4-pentadienoate pathway that includes at least one exogenous nucleic acid encoding a 2,4-pentadienoate pathway enzyme expressed in a sufficient amount to produce 2,4-pentadienoate. The 2,4-pentadienoate pathway has a set of enzymes selected from (A) 1) 4-hydroxy-2-oxovalerate aldolase, 2) 4-hydroxy-2-oxovalerate reductase, 3) 2,4-dihydroxypentanoate 2-dehydratase, and 4) 4-hydroxypent-2-enoate dehydratase, as shown in steps A, E, F, and G of FIG. 12 and (B) 1) 4-hydroxy-2-oxovalerate aldolase, 2) 4-hydroxy-2-oxovalerate reductase, 3) 2,4-dihydroxypentanoate 4-dehydratase and 4) 2-hydroxypentenoate dehydratase, as shown in steps A, E, H, and D of FIG. 12.

In some embodiments, the present invention also provides a non-naturally occurring microbial organism having a 2,4-pentadienoate pathway that includes at least one exogenous nucleic acid encoding a 2,4-pentadienoate pathway enzyme expressed in a sufficient amount to produce 2,4-pentadienoate. The 2,4-pentadienoate pathway has a set of enzymes selected from (A) 1) AKP aminotransferase and/or dehydrogenase, 2) 2,4-dioxopentanoate 2-reductase, 3) 2-hydroxy-4-oxopentanoate reductase, 4) 2,4-dihydroxypentanoate 2-dehydratase, and 5) 4-hydroxypent-2-enoate dehydratase, as shown in steps E, H, I, G, and D of FIG. 13, and (B) 1) AKP aminotransferase and/or dehydrogenase, 2) 2,4-dioxopentanoate 2-reductase, 3) 2-hydroxy-4-oxopentanoate reductase, along with 4) 2,4-dihydroxypetanoate-2-dehydratase and 5) 4-hydroxypent-2-enoate dehydratase or 4) 2,4-dihydroxypentanoate-4-dehydratase and 5) 2-hydroxypentenoate dehydratase, as shown in steps E, H, and I of FIG. 13, along with steps F and G or H and D of FIG. 12, respectively. That is to say, the double dehydration of 2,4-dihydroxypentanoate can be performed in any order.

In some embodiments, the present invention also provides a non-naturally occurring microbial organism having an AKP pathway that includes at least one exogenous nucleic acid encoding an AKP pathway enzyme expressed in a sufficient amount to produce AKP. The AKP pathway includes an ornithine 4,5-aminomutase and a 2,4-diaminopentanoate 4-aminotransferase and/or 4-dehydrogenase, as shown in steps M and N of FIG. 13. In some embodiments, the microbial organism having an AKP pathway includes two exogenous enzymes encoding an ornithine 4,5-aminomutase and a 2,4-diaminopentanoate 4-aminotransferase or 2,4-diaminopentanoate 4-dehydrogenase. In some embodiments, this AKP pathway can be added to any of the aforementioned 2,4-pentadienoate pathways and as indicated in FIG. 13. Alternatively, AKP can be accessed from alanine by addition of an AKP thiolase, as shown in step A of FIG. 13, and fed into the various 2,4-pentadienoate pathways described herein and shown in FIG. 13, along with FIG. 12.

In some embodiments, the present invention also provides a non-naturally occurring microbial organism having a 2,4-pentadienoate pathway that includes at least one exogenous nucleic acid encoding a 2,4-pentadienoate pathway enzyme expressed in a sufficient amount to produce 2,4-pentadienoate. The 2,4-pentadienoate pathway has a set of enzymes selected from (A) 1) ornithine 2,3-aminomutase, 2) 3,5-diaminopentanoate deaminase, and 3) 5-aminopent-2-enoate deaminase, as shown in steps A-C of FIG. 14, (B) 1) ornithine 2,3-aminomutase, 2) 3,5-diaminopentanoate deaminase, 3) 5-aminopent-2-enoate aminotransferase and/or dehydrogenase, 4) 5-oxopent-2-enoate reductase, and 5) 5-hydroxypent-2-enoate dehydratase, as shown in steps A, B, H, F, and G of FIG. 14, (C) 1) ornithine 2,3-aminomutase, 2) 3,5-diaminopentanoate aminotransferase and/or dehydrogenase, 3) 3-amino-5-oxopentanoate deaminase, 4) 5-oxopent-2-enoate reductase, and 5) 5-hydroxypent-2-enoate dehydratase as shown in steps A, D, E, F, and G of FIG. 14, and (D) 1) ornithine 2,3-aminomutase, 2) 3,5-diaminopentanoate aminotransferase and/or dehydrogenase, 3) 3-amino-5-oxopentanoate reductase, and 4) 3-amino-5-hydroxypentanoate deaminase and 5) 5-hydroxypent-2-enoate dehydratase as shown in steps A, D, I, J, and G of FIG. 14.

In some embodiments, the present invention also provides a non-naturally occurring microbial organism having a 2,4-pentadienoate pathway that includes at least one exogenous nucleic acid encoding a 2,4-pentadienoate pathway enzyme expressed in a sufficient amount to produce 2,4-pentadienoate. The 2,4-pentadienoate pathway has a set of enzymes selected from any of the numerous pathways shown in FIG. 15 starting from 3-HP-CoA or acryloyl-CoA.

Exemplary pathways from 3-HP-CoA include the following enzyme sets (A) 1) 3-hydroxypropanoyl-CoA acetyltransferase, 2) 3-oxo-5-hydroxypentanoyl-CoA reductase, 3) 3,5-dihydroxypentanoyl-CoA dehydratase, 4) 5-hydroxypent-2-enoyl-CoA dehydratase, and 5) pent-2,4-dienoyl-CoA synthetase, transferase and/or hydrolase, as shown in steps A-E of FIG. 15, and (B) 1) 3-hydroxypropanoyl-CoA acetyltransferase, 2) 3-oxo-5-hydroxypentanoyl-CoA synthetase, transferase and/or hydrolase, 3) 3-oxo-5-hydroxypentanoate reductase, 4) 3,5-dihydroxypentanoate dehydratase, and 5) 5-hydroxypent-2-enoate dehydratase, as shown in steps A, F, I, J, and Q of FIG. 15. One skilled in the art will recognize that enzyme sets defining pathways (A) and (B) from 3-HP-CoA can be intermingled via reversible enzymes 3,5-hydroxypentanoyl-CoA synthetase, transferase and/or hydrolase, as shown by step G in FIGS. 15, and 5-hydroxypent-2-enoyl-CoA synthetase, transferase and/or hydrolase, as shown by step H in FIG. 15. Thus, a 3-HP-CoA to 2,4-pentadienoate pathway can include the enzymes in steps A, B, G, J, and Q, or steps A, B, C, H, and Q, or steps A, B, G, J, H, D, and E, or steps A, F, I, G, C, D, and E, or steps, A, F, I, G, C, H, and Q, or steps A, F, I, J, H, D, and E, each shown in FIG. 15.

Exemplary pathways from acryloyl-CoA include the following enzyme sets (C) 1) acryloyl-CoA acetyltransferase, 2) 3-oxopent-4-enoyl-CoA synthetase, transferase and/or hydrolase, 3) 3-oxopent-4-enoate reductase, 4) 3-hydroxypent-4-enoate dehydratase, as shown in steps M, O, P, and S in FIG. 15 and (D), 1) acryloyl-CoA acetyltransferase, 2) 3-oxopent-4-enoyl-CoA reductase, 3) 3-hydroxypent-4-enoyl-CoA dehydratase, and 4) pent-2,4-dienoyl-CoA synthetase, transferase and/or hydrolase, as shown in steps M, N, R, and E. One skilled in the art will recognize that enzyme sets defining pathways (A) and (B) from 3-HP-CoA and (C) and (D) from acryloyl-CoA can be intermingled via reversible enzymes 3-hydroxypropanoyl-CoA dehydratase, as shown in step K of FIG. 15, and 3-oxo-5-hydroxypentanoyl-CoA dehydratase, as shown in step L of FIG. 15. Thus, step K can be added to any of the enumerated pathways from acryloyl-CoA to 2,4-pentadienoate providing 2,4-pentadienoate pathways such as steps K, M, N. R, and E or steps K, M, O, P, and S. Step K can also be used a shuttle alternative to step A to provide 3-oxo-5-hydroxypentanoyl-CoA from 3-HP-CoA via steps K, M, and L. Thus, any of the aforementioned pathways utilizing the enzyme of step A can utilize the enzymes of steps K, M, and L, in its place. The same 3-oxo-5-hydroxypentanoyl-CoA intermediate can be accessed from acryloyl-CoA by pathways via the enzymes of steps K and A or M and L of FIG. 15. Thus, acryloyl-CoA can be used to access all the enumerated pathways that would be accessible from 3-HP-CoA. Thus, for example, an acryloyl-CoA to 2,4-pentadienoate pathway can include enzymes from steps K, A, B, C, D, and E, or steps K, A, F, I, J and Q, or steps K, A, B, G, J, and Q, or steps K, A, B, G, J, H, D, and E, or steps K, A, B, C, H, and Q, or steps K, A, F, I, G, C, D, and E, or steps K, A, F, I, G, C, H, Q, or steps K, A. F, I, J, H, D and E, or steps M, L, B, C, D, and E, or steps M, L, F, I, J and Q, or steps M, L, B, G, J, and Q, or steps M, L, B, G, J, H, D, and E, or steps M, L, B, C, H, and Q, or steps M, L, F, I, G, C, D, and E, or steps M, L, F, I, G, C, H, Q, or steps M, L, F, I, J, H, D and E, all as shown in FIG. 15. Similarly, 3-HP-CoA can feed into the enumerated acryloyl-CoA pathways via intermediate 3-oxopent-4-enoyl-CoA using the enzyme of step L. Thus, a 3-HP-CoA to 2,4-pentadienoate pathway can include enzymes from steps A, L, N, R, and E or steps A, L, O, P, and S, each pathway being shown in FIG. 15.

In some embodiments, the present invention provides a non-naturally occurring microbial organism, that includes a microbial organism having a 2,4-pentadienoate pathway which includes at least one exogenous nucleic acid encoding a 2,4-pentadienoate pathway enzyme expressed in a sufficient amount to produce 2,4-pentadienoate. The 2,4-pentadienoate pathway has a set of enzymes selected from:

1) A. 3-hydroxypropanoyl-CoA acetyltransferase, B. 3-oxo-5-hydroxypentanoyl-CoA reductase, C. 3,5-dihydroxypentanoyl-CoA dehydratase, D. 5-hydroxypent-2-enoyl-CoA dehydratase, E. pent-2,4-dienoyl-CoA synthetase, transferase and/or hydrolase;

2) A. 3-hydroxypropanoyl-CoA acetyltransferase, B. 3-oxo-5-hydroxypentanoyl-CoA reductase, G. 3,5-dihydroxypentanoyl-CoA synthetase, transferase and/or hydrolase, J. 3,5-dihydroxypentanoate dehydratase, H. 5-hydroxypent-2-enoyl-CoA synthetase, transferase and/or hydrolase, D. 5-hydroxypent-2-enoyl-CoA dehydratase, E. pent-2,4-dienoyl-CoA synthetase, transferase and/or hydrolase;

3) A. 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, G. 3,5-dihydroxypentanoyl-CoA synthetase, transferase and/or hydrolase, C. 3,5-dihydroxypentanoyl-CoA dehydratase, D. 5-hydroxypent-2-enoyl-CoA dehydratase, E. pent-2,4-dienoyl-CoA synthetase, transferase and/or hydrolase;

4) A. 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, J. 3,5-dihydroxypentanoate dehydratase, H. 5-hydroxypent-2-enoyl-CoA synthetase, transferase and/or hydrolase, D. 5-hydroxypent-2-enoyl-CoA dehydratase, E. pent-2,4-dienoyl-CoA synthetase, transferase and/or hydrolase;

5) K. 3-hydroxypropanoyl-CoA dehydratase, A. 3-hydroxypropanoyl-CoA acetyltransferase, B. 3-oxo-5-hydroxypentanoyl-CoA reductase, C. 3,5-dihydroxypentanoyl-CoA dehydratase, D. 5-hydroxypent-2-enoyl-CoA dehydratase, E. pent-2,4-dienoyl-CoA synthetase, transferase and/or hydrolase;

6) K. 3-hydroxypropanoyl-CoA dehydratase, A. 3-hydroxypropanoyl-CoA acetyltransferase, B. 3-oxo-5-hydroxypentanoyl-CoA reductase, G. 3,5-dihydroxypentanoyl-CoA synthetase, transferase and/or hydrolase, J. 3,5-dihydroxypentanoate dehydratase, H. 5-hydroxypent-2-enoyl-CoA synthetase, transferase and/or hydrolase, D. 5-hydroxypent-2-enoyl-CoA dehydratase, E. pent-2,4-dienoyl-CoA synthetase, transferase and/or hydrolase;

7) K. 3-hydroxypropanoyl-CoA dehydratase, A. 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, G. 3,5-dihydroxypentanoyl-CoA synthetase, transferase and/or hydrolase, C. 3,5-dihydroxypentanoyl-CoA dehydratase, D. 5-hydroxypent-2-enoyl-CoA dehydratase, E. pent-2,4-dienoyl-CoA synthetase, transferase and/or hydrolase;

8) K. 3-hydroxypropanoyl-CoA dehydratase, A. 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, J. 3,5-dihydroxypentanoate dehydratase, H. 5-hydroxypent-2-enoyl-CoA synthetase, transferase and/or hydrolase, D. 5-hydroxypent-2-enoyl-CoA dehydratase, E. pent-2,4-dienoyl-CoA synthetase, transferase and/or hydrolase;

9) M. acrylyl-CoA acetyltransferase, L. 3-oxo-5-hydroxypentanoyl-CoA dehydratase, B. 3-oxo-5-hydroxypentanoyl-CoA reductase, C. 3,5-dihydroxypentanoyl-CoA dehydratase, D. 5-hydroxypent-2-enoyl-CoA dehydratase, E. pent-2,4-dienoyl-CoA synthetase, transferase and/or hydrolase;

10) M. acrylyl-CoA acetyltransferase, L. 3-oxo-5-hydroxypentanoyl-CoA dehydratase, B. 3-oxo-5-hydroxypentanoyl-CoA reductase, G. 3,5-dihydroxypentanoyl-CoA synthetase, transferase and/or hydrolase, J. 3,5-dihydroxypentanoate dehydratase, H. 5-hydroxypent-2-enoyl-CoA synthetase, transferase and/or hydrolase, D. 5-hydroxypent-2-enoyl-CoA dehydratase, E. pent-2,4-dienoyl-CoA synthetase, transferase and/or hydrolase;

11) M. acrylyl-CoA acetyltransferase, L. 3-oxo-5-hydroxypentanoyl-CoA dehydratase, 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, G. 3,5-dihydroxypentanoyl-CoA synthetase, transferase and/or hydrolase, C. 3,5-dihydroxypentanoyl-CoA dehydratase, D. 5-hydroxypent-2-enoyl-CoA dehydratase, E. pent-2,4-dienoyl-CoA synthetase, transferase and/or hydrolase;

12) M. acrylyl-CoA acetyltransferase, L. 3-oxo-5-hydroxypentanoyl-CoA dehydratase, 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, J. 3,5-dihydroxypentanoate dehydratase, H. 5-hydroxypent-2-enoyl-CoA synthetase, transferase and/or hydrolase, D. 5-hydroxypent-2-enoyl-CoA dehydratase, E. pent-2,4-dienoyl-CoA synthetase, transferase and/or hydrolase;

13) M. acrylyl-CoA acetyltransferase, N. 3-oxopent-4-enoyl-CoA reductase, R. 3-hydroxypent-4-enoyl-CoA dehydratase, E. pent-2,4-dienoyl-CoA synthetase, transferase and/or hydrolase;

14) M. acrylyl-CoA acetyltransferase, N. 3-oxopent-4-enoyl-CoA reductase, T. 3-hydroxypent-4-enoyl-CoA transferase, synthetase or hydrolase, S. 3-hydroxypent-4-enoate dehydratase; and 15) M. acrylyl-CoA acetyltransferase, O. 3-oxopent-4-enoyl-CoA synthetase, transferase and/or hydrolase, P. 3-oxopent-4-enoate reductase, S. 3-hydroxypent-4-enoate dehydratase;

16) A. 3-hydroxypropanoyl-CoA acetyltransferase, L. 3-oxo-5-hydroxypentanoyl-CoA dehydratase, N. 3-oxopent-4-enoyl-CoA reductase, R. 3-hydroxypent-4-enoyl-CoA dehydratase, E. pent-2,4-dienoyl-CoA synthetase, transferase and/or hydrolase;

17) A. 3-hydroxypropanoyl-CoA acetyltransferase, L. 3-oxo-5-hydroxypentanoyl-CoA dehydratase, N. 3-oxopent-4-enoyl-CoA reductase, T. 3-hydroxypent-4-enoyl-CoA transferase, synthetase or hydrolase, S. 3-hydroxypent-4-enoate dehydratase; and 18) A. 3-hydroxypropanoyl-CoA acetyltransferase, L. 3-oxo-5-hydroxypentanoyl-CoA dehydratase, O. 3-oxopent-4-enoyl-CoA synthetase, transferase and/or hydrolase, P. 3-oxopent-4-enoate reductase, S. 3-hydroxypent-4-enoate dehydratase.

In some embodiments, the non-naturally occurring microbial organism of the invention includes two, three, four, five, six, seven, or eight exogenous nucleic acids each encoding a 2,4-pentadienoate pathway enzyme. In some embodiments, the non-naturally occurring microbial organism of the invention has at least one exogenous nucleic acid is a heterologous nucleic acid. In some embodiments, the non-naturally occurring microbial organism of the invention is in a substantially anaerobic culture medium. In some embodiments, the non-naturally occurring microbial organism of the invention further includes a 2,4-pentadiene decarboxylase to convert 2,4-pentadienoate to 1,3-butadiene.

In some embodiments, a non-naturally occurring microbial organism includes a microbial organism having a 1,3-butadiene pathway which includes at least one exogenous nucleic acid encoding a 1,3-butadiene pathway enzyme expressed in a sufficient amount to produce 1,3-butadiene. The 1,3-butadiene pathway has a set of enzymes selected from:

1) M. acrylyl-CoA acetyltransferase, N. 3-oxopent-4-enoyl-CoA reductase, T. 3-hydroxypent-4-enoyl-CoA transferase, synthetase or hydrolase, Y. 3-hydroxypent-4-enoate decarboxylase;

2) M. acrylyl-CoA acetyltransferase, O. 3-oxopent-4-enoyl-CoA synthetase, transferase and/or hydrolase, P. 3-oxopent-4-enoate reductase, Y. 3-hydroxypent-4-enoate decarboxylase;

3) K. 3-hydroxypropanoyl-CoA dehydratase, M. acrylyl-CoA acetyltransferase, N. 3-oxopent-4-enoyl-CoA reductase, T. 3-hydroxypent-4-enoyl-CoA transferase, synthetase or hydrolase, Y. 3-hydroxypent-4-enoate decarboxylase;

4) K. 3-hydroxypropanoyl-CoA dehydratase, M. acrylyl-CoA acetyltransferase, O. 3-oxopent-4-enoyl-CoA synthetase, transferase and/or hydrolase, P. 3-oxopent-4-enoate reductase, Y. 3-hydroxypent-4-enoate decarboxylase;

5) A. 3-hydroxypropanoyl-CoA acetyltransferase, L. 3-oxo-5-hydroxypentanoyl-CoA dehydratase, N. 3-oxopent-4-enoyl-CoA reductase, T. 3-hydroxypent-4-enoyl-CoA transferase, synthetase or hydrolase, Y. 3-hydroxypent-4-enoate decarboxylase;

6) A. 3-hydroxypropanoyl-CoA acetyltransferase, L. 3-oxo-5-hydroxypentanoyl-CoA dehydratase, O. 3-oxopent-4-enoyl-CoA synthetase, transferase and/or hydrolase, P. 3-oxopent-4-enoate reductase, Y. 3-hydroxypent-4-enoate decarboxylase;

In some embodiments, the non-naturally occurring microbial organism of the invention includes two, three, four, or five exogenous nucleic acids each encoding a 1,3-butadiene pathway enzyme. In some embodiments, the non-naturally occurring microbial organism of the invention includes at least one exogenous nucleic acid that is a heterologous nucleic acid. In some embodiments, the non-naturally occurring microbial organism of the invention is in a substantially anaerobic culture medium.

In some embodiments, the present invention provides a non-naturally occurring microbial organism, that includes a microbial organism having a 1,3-butadiene pathway which includes at least one exogenous nucleic acid encoding a 3-butene-1-ol pathway enzyme expressed in a sufficient amount to produce 3-butene-1-ol. The 3-butene-1-ol pathway has a set of enzymes selected from:

1) A. 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, U. 3,5-dihydroxypentanoate decarboxylase;

2) A. 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, J. 3,5-dihydroxypentanoate dehydratase, V. 5-hydroxypent-2-enoate decarboxylase;

3) A. 3-hydroxypropanoyl-CoA acetyltransferase, B. 3-oxo-5-hydroxypentanoyl-CoA reductase, G. 3,5-dihydroxypentanoyl-CoA synthetase, transferase and/or hydrolase, U. 3,5-dihydroxypentanoate decarboxylase;

4) A. 3-hydroxypropanoyl-CoA acetyltransferase, B. 3-oxo-5-hydroxypentanoyl-CoA reductase, G. 3,5-dihydroxypentanoyl-CoA synthetase, transferase and/or hydrolase, J. 3,5-dihydroxypentanoate dehydratase, V. 5-hydroxypent-2-enoate decarboxylase;

5) A. 3-hydroxypropanoyl-CoA acetyltransferase, B. 3-oxo-5-hydroxypentanoyl-CoA reductase, C. 3,5-dihydroxypentanoyl-CoA dehydratase, H. 5-hydroxypent-2-enoyl-CoA synthetase, transferase and/or hydrolase, V. 5-hydroxypent-2-enoate decarboxylase;

6) M. acrylyl-CoA acetyltransferase, L. 3-oxo-5-hydroxypentanoyl-CoA dehydratase, F. 3-oxo-5-hydroxypentanoyl-CoA synthetase, transferase and/or hydrolase, I. 3-oxo-5-hydroxypentanoate reductase, U. 3,5-dihydroxypentanoate decarboxylase;

7) M. acrylyl-CoA acetyltransferase, L. 3-oxo-5-hydroxypentanoyl-CoA dehydratase, F. 3-oxo-5-hydroxypentanoyl-CoA synthetase, transferase and/or hydrolase, I. 3-oxo-5-hydroxypentanoate reductase, J. 3,5-dihydroxypentanoate dehydratase, V. 5-hydroxypent-2-enoate decarboxylase;

8) M. acrylyl-CoA acetyltransferase, L. 3-oxo-5-hydroxypentanoyl-CoA dehydratase, B. 3-oxo-5-hydroxypentanoyl-CoA reductase, G. 3,5-dihydroxypentanoyl-CoA synthetase, transferase and/or hydrolase, U. 3,5-dihydroxypentanoate decarboxylase;

9) M. acrylyl-CoA acetyltransferase, L. 3-oxo-5-hydroxypentanoyl-CoA dehydratase, B. 3-oxo-5-hydroxypentanoyl-CoA reductase, G. 3,5-dihydroxypentanoyl-CoA synthetase, transferase and/or hydrolase, J. 3,5-dihydroxypentanoate dehydratase, V. 5-hydroxypent-2-enoate decarboxylase;

10) M. acrylyl-CoA acetyltransferase, L. 3-oxo-5-hydroxypentanoyl-CoA dehydratase, B. 3-oxo-5-hydroxypentanoyl-CoA reductase, C. 3,5-dihydroxypentanoyl-CoA dehydratase, H. 5-hydroxypent-2-enoyl-CoA synthetase, transferase and/or hydrolase, V. 5-hydroxypent-2-enoate decarboxylase;

11) K. 3-hydroxypropanoyl-CoA dehydratase, A. 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, U. 3,5-dihydroxypentanoate decarboxylase;

12) K. 3-hydroxypropanoyl-CoA dehydratase, A. 3-hydroxypropanoyl-CoA acetyltransferase, F. 3-oxo-5-hydroxypentanoyl-CoA synthetase, transferase and/or hydrolase, I. 3-oxo-5-hydroxypentanoate reductase, J. 3,5-dihydroxypentanoate dehydratase, V. 5-hydroxypent-2-enoate decarboxylase;

13) K. 3-hydroxypropanoyl-CoA dehydratase, A. 3-hydroxypropanoyl-CoA acetyltransferase, B. 3-oxo-5-hydroxypentanoyl-CoA reductase, G. 3,5-dihydroxypentanoyl-CoA synthetase, transferase and/or hydrolase, U. 3,5-dihydroxypentanoate decarboxylase;

14) K. 3-hydroxypropanoyl-CoA dehydratase, A. 3-hydroxypropanoyl-CoA acetyltransferase, B. 3-oxo-5-hydroxypentanoyl-CoA reductase, G. 3,5-dihydroxypentanoyl-CoA synthetase, transferase and/or hydrolase, J. 3,5-dihydroxypentanoate dehydratase, V. 5-hydroxypent-2-enoate decarboxylase;

15) K. 3-hydroxypropanoyl-CoA dehydratase, A. 3-hydroxypropanoyl-CoA acetyltransferase, B. 3-oxo-5-hydroxypentanoyl-CoA reductase, C. 3,5-dihydroxypentanoyl-CoA dehydratase, H. 5-hydroxypent-2-enoyl-CoA synthetase, transferase and/or hydrolase, V. 5-hydroxypent-2-enoate decarboxylase;

16) K. 3-hydroxypropanoyl-CoA dehydratase, M. acrylyl-CoA acetyltransferase, L. 3-oxo-5-hydroxypentanoyl-CoA dehydratase, F. 3-oxo-5-hydroxypentanoyl-CoA synthetase, transferase and/or hydrolase, I. 3-oxo-5-hydroxypentanoate reductase, U. 3,5-dihydroxypentanoate decarboxylase;

17) K. 3-hydroxypropanoyl-CoA dehydratase, M. acrylyl-CoA acetyltransferase, L. 3-oxo-5-hydroxypentanoyl-CoA dehydratase, F. 3-oxo-5-hydroxypentanoyl-CoA synthetase, transferase and/or hydrolase, I. 3-oxo-5-hydroxypentanoate reductase, J. 3,5-dihydroxypentanoate dehydratase, V. 5-hydroxypent-2-enoate decarboxylase;

18) K. 3-hydroxypropanoyl-CoA dehydratase, M. acrylyl-CoA acetyltransferase, L. 3-oxo-5-hydroxypentanoyl-CoA dehydratase, B. 3-oxo-5-hydroxypentanoyl-CoA reductase, G. 3,5-dihydroxypentanoyl-CoA synthetase, transferase and/or hydrolase, U. 3,5-dihydroxypentanoate decarboxylase;

19) K. 3-hydroxypropanoyl-CoA dehydratase, M. acrylyl-CoA acetyltransferase, L. 3-oxo-5-hydroxypentanoyl-CoA dehydratase, B. 3-oxo-5-hydroxypentanoyl-CoA reductase, G. 3,5-dihydroxypentanoyl-CoA synthetase, transferase and/or hydrolase, J. 3,5-dihydroxypentanoate dehydratase, V. 5-hydroxypent-2-enoate decarboxylase;

20) K. 3-hydroxypropanoyl-CoA dehydratase, M. acrylyl-CoA acetyltransferase, L. 3-oxo-5-hydroxypentanoyl-CoA dehydratase, B. 3-oxo-5-hydroxypentanoyl-CoA reductase, C. 3,5-dihydroxypentanoyl-CoA dehydratase, FL 5-hydroxypent-2-enoyl-CoA synthetase, transferase and/or hydrolase, V. 5-hydroxypent-2-enoate decarboxylase;

In some embodiments, the non-naturally occurring microbial organism of the invention includes two, three, four, five, six, or seven, exogenous nucleic acids each encoding a 3-butene-1-ol pathway enzyme. In some embodiments, the non-naturally occurring microbial organism of the invention has at least one exogenous nucleic acid that is a heterologous nucleic acid. In some embodiments, the non-naturally occurring microbial organism of the invention is in a substantially anaerobic culture medium. In some embodiments, the non-naturally occurring microbial organism of the invention further includes a 3-butene-1-ol dehydratase to convert 3-butene-1-ol to 1,3-butadiene.

In some embodiments, non-naturally occurring microbial organism of the invention can include two exogenous nucleic acids each encoding a 2,4-pentadienoate pathway enzyme. In some embodiments, non-naturally occurring microbial organism of the invention can include three exogenous nucleic acids each encoding a 2,4-pentadienoate pathway enzyme. For example, the non-naturally occurring microbial organism of the invention can include three exogenous nucleic acids encoding i) an AKP deaminase, ii) an acetylacrylate reductase, and iii) a 4-hydroxypent-2-enoate dehydratase, thus providing an alanine or ornithine accessible pathway to 2,4-pentadienoate via AKP. One skilled in the art will recognize that this is merely exemplary and that three exogenous nucleic acids can be the basis of any 2,4-pentadienoate-producing non-naturally occurring organism in any of the enumerated pathways of FIG. 12-15.

In some embodiments, the non-naturally occurring microbial organism of the invention microbial can include any four exogenous nucleic acids each encoding a 2,4-pentadienoate pathway enzyme. For example, a non-naturally occurring microbial organism can include four exogenous nucleic acids encoding i) a 4-hydroxy-2-oxovalerate aldolase, ii) a 4-hydroxy-2-oxovalerate dehydratase, iii) a 2-oxopentenoate reductase, and iv) a 2-hydroxypentenoate dehydratase, thus defining a complete pathway from pyruvate to 2,4-pentadienoate, as shown in FIG. 12. One skilled in the art will recognize that this is merely exemplary and that four exogenous nucleic acids can be the basis of any 2,4-pentadienoate-producing non-naturally occurring organism in any of the enumerated pathways of FIG. 12-15.

In still further embodiments, the non-naturally occurring microbial organism of the invention can include five exogenous nucleic acids each encoding a 2,4-pentadienoate pathway enzyme. Exemplary non-naturally occurring microbial organism of the invention having five exogenous nucleic acids can include enzymes encoding (A) i) an AKP aminotransferase and/or dehydrogenase, ii) a 2,4-dioxopentanoate-2-reductase, iii) a 2-hydroxy-4-oxopentanoate dehydratase, iv) an acetylacrylate reductase, and v) a 4-hydroxypent-2-enoate dehydratase, as shown in steps E, H, F, C, and D in FIG. 13, or (B) i) an AKP aminotransferase and/or dehydrogenase, ii) a 2,4-dioxopentanoate-4-reductase, iii) a 4-hydroxy-2-oxovalerate dehydratase, iv) a 2-oxopentenoate reductase, and v) a 2-hydroxypentenoate dehydratase, as shown in steps E and K of FIG. 13, along with steps B, C, and D of FIG. 12, or i) an AKP reductase, ii) a 2-amino-4-hydroxypentanoate aminotransferase and/or dehydrogenase, iii) a 4-hydroxy-2-oxovalerate dehydratase, iv) a 2-oxopentenoate reductase, and v) a 2-hydroxypentenoate dehydratase, as shown in steps J and L of FIG. 13, along with steps B, C, and D of FIG. 12. One skilled in the art will recognize that this is merely exemplary and that five exogenous nucleic acids can be the basis of any 2,4-pentadienoate-producing non-naturally occurring organism in any of the enumerated pathways of FIG. 12-15. Thus, in some embodiments two, three, four, five, six, up to all of the enzymes in a 2,4-pentadienoate pathway can be provided insertion of exogenous nucleic acids. In some embodiments, the non-naturally occurring microbial organism of the invention has at least one exogenous nucleic acid is a heterologous nucleic acid. Moreover, in some embodiments, the non-naturally occurring microbial organism of the invention can be provided in a substantially anaerobic culture medium.

In some embodiments, the non-naturally occurring microbial organism of the invention can further include a 2,4-pentadienoate decarboxylase expressed in a sufficient amount to produce 1,3-butadiene by conversion of 2,4-pentadienoate to 1,3-butadiene. Thus, any 2,4-pentadienoate pathway of FIG. 12 can form the basis of further production of 1,3 butadiene, as indicated by the conversion of cis or trans 2,4-pentadienoate to 1,3-butadiene in FIG. 4.

In some embodiments, the invention provides a non-naturally occurring microbial organism having a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway, wherein the non-naturally occurring microbial organism comprises at least one exogenous nucleic acid encoding an enzyme or protein that converts a substrate to a product. For example, in a toluene pathway (FIG. 1), such substrate to product is selected from the group consisting of phenylalanine to phenylpyruvate, phenylpyruvate to phenylacetaldehyde, phenylpyruvate to phenylacetate, phenylacetaldehyde to phenylacetate, phenylacetaldehyde to toluene, and phenylacetate to toluene. In a styrene pathway (FIG. 3), such a substrate to product is selected from the group consisting of benzoyl-CoA to 3-oxo-3-phenylpropionyl-CoA, 3-oxo-3-phenylpropionyl-CoA to [(3-oxo-3-phenylpropionyl)oxy]phosphonate, [(3-oxo-3-phenylpropionyl)oxy]phosphonate to benzoyl-acetate, 3-oxo-3-phenylpropionyl-CoA to benzoyl-acetate, benzoyl-acetate to acetophenone, acetophenone to 1-phenylethanol, and 1-phenylethanol to styrene. In a 1,3-butadiene pathway (FIG. 4), such substrate to product is selected from trans, trans-muconate to trans-2,4-pentadienoate, cis,trans-muconate to trans-2,4-pentadienoate, cis,trans-muconate to cis-2,4-pentadienoate, cis,cis-muconate to cis-2,4-pentadienoate, trans-2,4-pentadienoate to 1,3-butadiene, and cis-2,4-pentadienoate to 1,3-butadiene. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein.

In a 2,4-pentadienoate pathway, such a substrate to product is selected from pyruvate to 4-hydroxy-2-oxovalerate, 4-hydroxy-2-oxovalerate to 2-oxopentenoate, 2-oxopentenoate to 2-hydroxypentenoate, 2-hydroxypentenoate to 2,4-pentadienoate, AKP to acetylacrylate, acetylacrylate to 4-hydroxypent-2-enoate, 4-hydroxypent-2-enoate to 2,4-pentadienoate, AKP to 2,4-dioxopentanoate, 2,4-dioxopentanoate to 4-hydroxy-2-oxovalerate, AKP to 2-amino-4-hydroxypentanoate, 2-amino-4-hydroxypentanoate to 4-hydroxy-2-oxovalerate, ornithine to 2,4-diaminopentanoate, 2,4-diaminopentanoate to AKP, alanine to AKP, and so on.

The invention also provides a non-naturally occurring microbial organism, comprising a microbial organism having a (2-hydroxy-3-methyl-4-oxobutoxy)phosphonate pathway comprising at least one exogenous nucleic acid encoding a (2-hydroxy-3-methyl-4-oxobutoxy)phosphonate pathway enzyme expressed in a sufficient amount to produce (2-hydroxy-3-methyl-4-oxobutoxy)phosphonate, the (2-hydroxy-3-methyl-4-oxobutoxy)phosphonate pathway comprising 2-C-methyl-D-erythritol-4-phosphate dehydratase (see Example III and FIG. 5, step C). A non-naturally occurring microbial organism comprising a (2-hydroxy-3-methyl-4-oxobutoxy)phosphonate pathway can further comprise 1-deoxyxylulose-5-phosphate synthase or 1-deoxy-D-xylulose-5-phosphate reductoisomerase (see Example III and FIG. 5, steps A and B). Thus, a (2-hydroxy-3-methyl-4-oxobutoxy)phosphonate can comprise 5 2-C-methyl-D-erythritol-4-phosphate dehydratase, 1-deoxyxylulose-5-phosphate synthase and 1-deoxy-D-xylulose-5-phosphate reductoisomerase.

Figure 6:
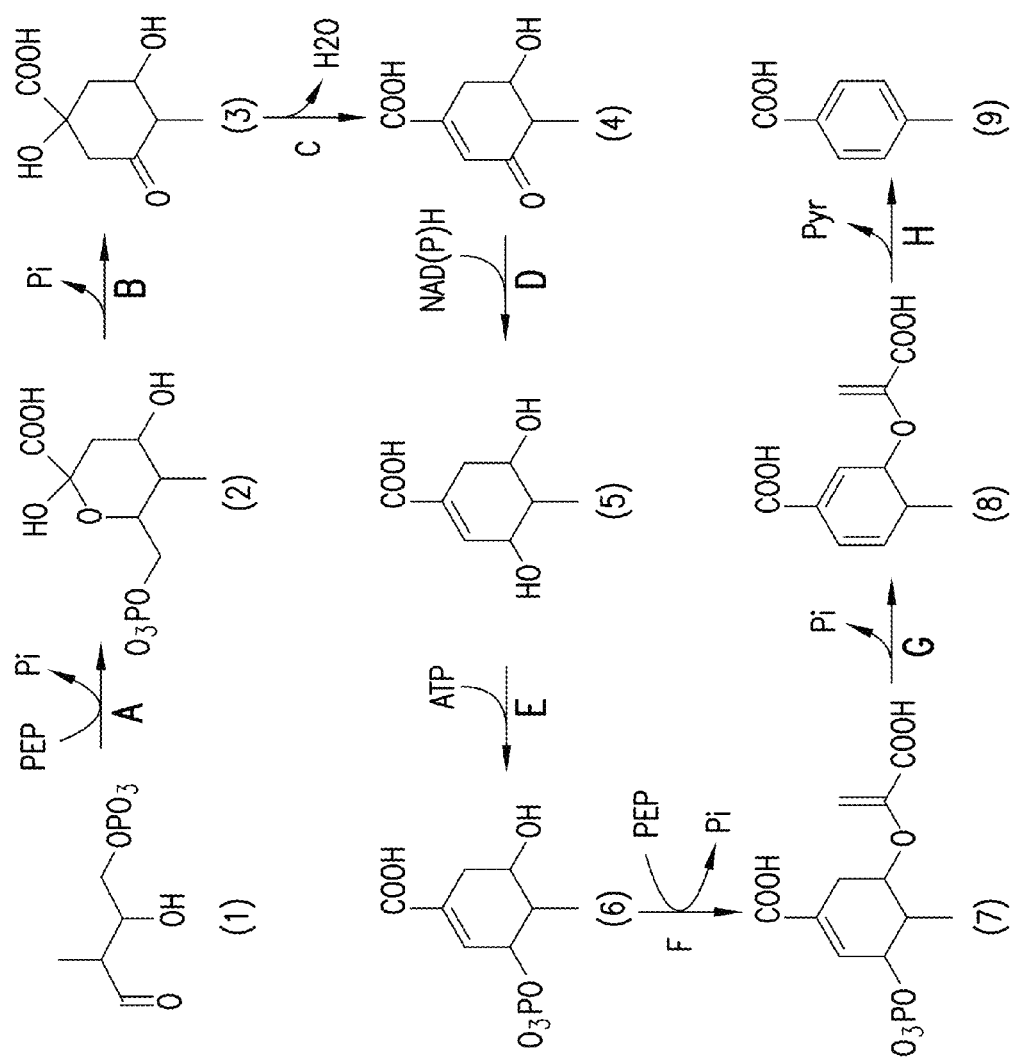
FIG. 6 shows a schematic depiction of an exemplary alternate shikimate pathway to p-toluate. Enzymes are: (A) 2-dehydro-3-deoxyphosphoheptonate synthase; (B) 3-dehydroquinate synthase; (C) 3-dehydroquinate dehydratase; (D) shikimate dehydrogenase; (E) Shikimate kinase; (F) 3-phosphoshikimate-2-carboxyvinyltransferase; (G) chorismate synthase; and (H) chorismate lyase. Compounds are: (1) (2-hydroxy-3-methyl-4-oxobutoxy)phosphonate; (2) 2,4-dihydroxy-5-methyl-6-[(phosphonooxy)methyl]oxane-2-carboxylate; (3) 1,3-dihydroxy-4-methyl-5-oxocyclohexane-1-carboxylate; (4) 5-hydroxy-4-methyl-3-oxocyclohex-1-ene-1-carboxylate; (5) 3,5-dihydroxy-4-methylcyclohex-1-ene-1-carboxylate; (6) 5-hydroxy-4-methyl-3-(phosphonooxy)cyclohex-1-ene-1-carboxylate; (7) 5-[(1-carboxyeth-1-en-1-yl)oxy]-4-methyl-3-(phosphonooxy)cyclohex-1-ene-1-carboxylate; (8) 3-[(1-carboxyeth-1-en-1-yl)oxy]-4-methylcyclohexa-1,5-diene-1-carboxylate; and (9) p-toluate.

The invention also provides a non-naturally occurring microbial organism, comprising a microbial organism having a p-toluate pathway comprising at least one exogenous nucleic acid encoding a p-toluate pathway enzyme expressed in a sufficient amount to produce p-toluate, the p-toluate pathway comprising 2-dehydro-3-deoxyphosphoheptonate synthase; 3-dehydroquinate synthase; 3-dehydroquinate dehydratase; shikimate dehydrogenase; shikimate kinase; 3-phosphoshikimate-2-carboxyvinyltransferase; chorismate synthase; or chorismate lyase (see Example IV and FIG. 6, steps A-H). A non-naturally occurring microbial organism having a p-toluate pathway can further comprise a (2-hydroxy-3-methyl-4-oxobutoxy)phosphonate pathway (FIG. 5). A (2-hydroxy-3-methyl-4-oxobutoxy)phosphonate pathway can comprise, for example, 2-C-methyl-D-erythritol-4-phosphate dehydratase, 1-deoxyxylulose-5-phosphate synthase or 1-deoxy-D-xylulose-5-phosphate reductoisomerase (FIG. 5).

Figure 7:
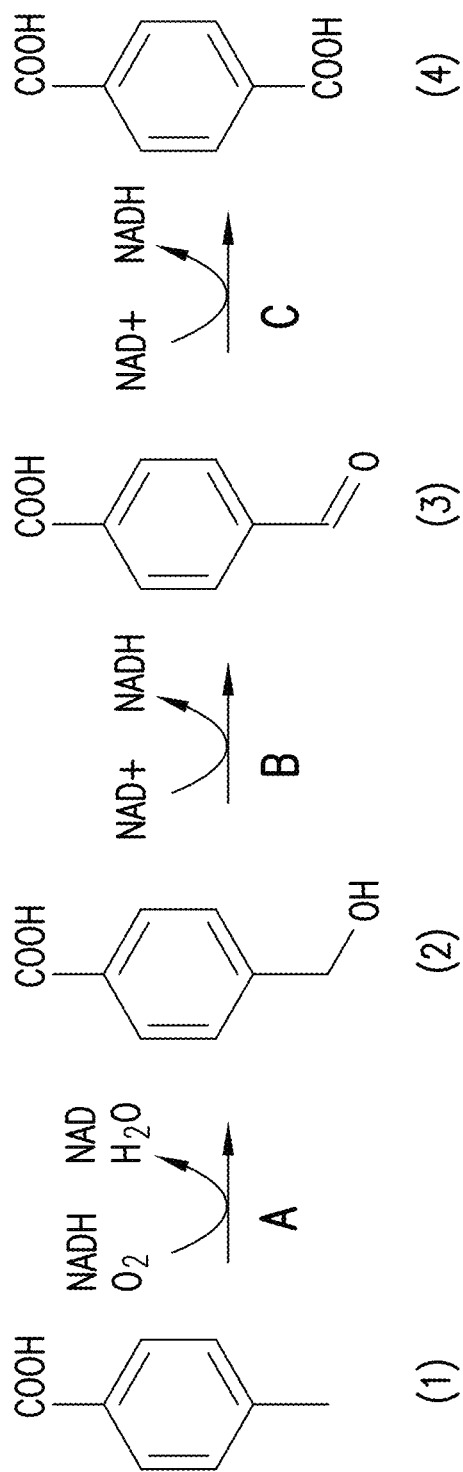
FIG. 7 shows an exemplary pathway for conversion of p-toluate to terephthalic acid (PTA). Reactions A, B and C are catalyzed by p-toluate methyl-monooxygenase reductase, 4-carboxybenzyl alcohol dehydrogenase and 4-carboxybenzyl aldehyde dehydrogenase, respectively. The compounds shown are (1)p-toluic acid; (2) 4-carboxybenzyl alcohol; (3) 4-carboxybenzaldehyde and (4) terephthalic acid.

The invention additionally provides a non-naturally occurring microbial organism, comprising a microbial organism having a terephthalate pathway comprising at least one exogenous nucleic acid encoding a terephthalate pathway enzyme expressed in a sufficient amount to produce terephthalate, the terephthalate pathway comprising p-toluate methyl-monooxygenase reductase; 4-carboxybenzyl alcohol dehydrogenase; or 4-carboxybenzyl aldehyde dehydrogenase (see Example V and FIG. 7). Such an organism containing a terephthalate pathway can additionally comprise a p-toluate pathway, wherein the p-toluate pathway comprises 2-dehydro-3-deoxyphosphoheptonate synthase; 3-dehydroquinate synthase; 3-dehydroquinate dehydratase; shikimate dehydrogenase; shikimate kinase; 3-phosphoshikimate-2-carboxyvinyltransferase; chorismate synthase; or chorismate lyase (see Examples IV and V and FIGS. 6 and 7). Such a non-naturally occurring microbialorganism having a terephthalate pathway and a p-toluate pathway can further comprise a (2-hydroxy-3-methyl-4-oxobutoxy)phosphonate pathway (see Example III and FIG. 5). A (2-hydroxy-3-methyl-4-oxobutoxy)phosphonate pathway can comprise, for example, 2-C-methyl-D-erythritol-4-phosphate dehydratase, 1-deoxyxylulose-5-phosphate synthase or 1-deoxy-D-xylulose-5-phosphate reductoisomerase (see Example III and FIG. 5).

In some embodiments, the present invention provides a non-naturally occurring microbial organism having a toluene pathway comprising at least one exogenous nucleic acid encoding a toluene pathway enzyme expressed in a sufficient amount to produce toluene. The toluene pathway is selected from a set of pathway enzymes selected from: a) p-toluate decarboxylase; b) p-toluate reductase and p-methylbenzaldehyde decarbonylase; c) p-toluate kinase, (p-methylbenzoyloxy)phosphonate reductase, and p-methylbenzaldehyde decarbonylase; d) (p-methylbenzoyl-CoA synthetase, transferase and/or hydrolase), phosphotrans-p-methylbenzoylase, (p-methylbenzoyloxy)phosphonate reductase, and p-methylbenzaldehyde decarbonylase; and e) (p-methylbenzoyl-CoA synthetase, transferase and/or hydrolase), p-methylbenzoyl-CoA reductase and p-methylbenzaldehyde decarbonylase.

In some embodiments, the present invention provides a non-naturally occurring microbial organism having a (2-hydroxy-4-oxobutoxy)phosphonate pathway comprising at least one exogenous nucleic acid encoding a (2-hydroxy-4-oxobutoxy)phosphonate pathway enzyme expressed in a sufficient amount to produce (2-hydroxy-4-oxobutoxy)phosphonate. The (2-hydroxy-4-oxobutoxy)phosphonate pathway includes erythrose-4-phosphate dehydratase and (2,4-dioxobutoxy)phosphonate reductase.

In some embodiments, the present invention provides a non-naturally occurring microbial organism having a benzoate pathway comprising at least one exogenous nucleic acid encoding a benzoate pathway enzyme expressed in a sufficient amount to produce benzoate. The benzoate pathway includes 2-dehydro-3-deoxyphosphoheptonate synthase; 3-dehydroquinate synthase; 3-dehydroquinate dehydratase; shikimate dehydrogenase; shikimate kinase; 3-phosphoshikimate-2-carboxyvinyltransferase; chorismate synthase; and chorismate lyase.

In some embodiments, the present invention provides a non-naturally occurring microbial organism having a benzene pathway comprising at least one exogenous nucleic acid encoding a benzene pathway enzyme expressed in a sufficient amount to produce benzene. The benzene pathway is selected from a set of pathway enzymes selected from: a) benzoate decarboxylase; b) benzoate reductase and benzaldehyde decarbonylase; c) benzoate kinase, (benzoyloxy) phosphonate reductase, and benzaldehyde decarbonylase; d) (benzoyl-CoA synthetase, transferase and/or hydrolase), phosphotransbenzoylase, (benzoyloxy)phosphonate reductase, and benzaldehyde decarbonylase; and e) (benzoyl-CoA synthetase, transferase and/or hydrolase), benzoyl-CoA reductase and benzaldehyde decarbonylase.

In an additional embodiment, the invention provides a non-naturally occurring microbial organism having a (2-hydroxy-3-methyl-4-oxobutoxy)phosphonate, p-toluate, terephthalate, toluene, (2-hydroxy-4-oxobutoxy)phosphonate, benzoate, or benzene pathway, wherein the non-naturally occurring microbial organism comprises at least one exogenous nucleic acid encoding an enzyme or protein that converts a substrate to a product. For example, in a (2-hydroxy-3-methyl-4-oxobutoxy)phosphonate pathway, the substrates and products can be selected from the group consisting of glyceraldehyde-3-phosphate and pyruvate to 1-deoxy-D-xylulose-5-phosphate; 1-deoxy-D-xylulose-5-phosphate to C-methyl-D-erythritol-4-phosphate; and C-methyl-D-erythritol-4-phosphate to (2-hydroxy-3-methyl-4-oxobutoxy)phosphonate (see Example III and FIG. 5). In another embodiment, a p-toluate pathway can comprise substrates and products selected from (2-hydroxy-3-methyl-4-oxobutoxy)phosphonate to 2,4-dihydroxy-5-methyl-6-[(phosphonooxy)methyl]oxane-2-carboxylate; 2,4-dihydroxy-5-methyl-6-[(phosphonooxy)methyl]oxane-2-carboxylate to 1,3-dihydroxy-4-methyl-5-oxocyclohexane-1-carboxylate; 1,3-dihydroxy-4-methyl-5-oxocyclohexane-1-carboxylate to 5-hydroxy-4-methyl-3-oxocyclohex-1-ene-1-carboxylic acid; 5-hydroxy-4-methyl-3-oxocyclohex-1-ene-1-carboxylic acid to 3,5-dihydroxy-4-methylcyclohex-1-ene-1-carboxylate; 3,5-dihydroxy-4-methylcyclohex-1-ene-1-carboxylate to 5-hydroxy-4-methyl-3-(phosphonooxy)cyclohex-1-ene-1-carboxylate; 5-hydroxy-4-methyl-3-(phosphonooxy)cyclohex-1-ene-1-carboxylate to 5-[(1-carboxyeth-1-en-1-yl)oxy]-4-methyl-3-(phosphonooxy)cyclohex-1-ene-1-carboxylate; 5-[(1-carboxyeth-1-en-1-yl)oxy]-4-methyl-3-(phosphonooxy)cyclohex-1-ene-1-carboxylate to 3-[(1-carboxyeth-1-en-1-yl)oxy]-4-methylcyclohexa-1,5-diene-1-carboxylate; and 3-[(1-carboxyeth-1-en-1-yl)oxy]-4-methylcyclohexa-1,5-diene-1-carboxylate to p-toluate (see Example IV and FIG. 6). In still another embodiment, a terephthalate pathway can comprise substrates and products selected from p-toluate to 4-carboxybenzyl alcohol; 4-carboxybenzyl alcohol to 4-carboxybenzaldehyde; and 4-carboxybenzaldehyde to and terephthalic acid (see Example V and FIG. 7). In another embodiment, a toluene pathway can comprise substrates and products selected from p-toluate to toluene; p-toluate to p-methyl benzoyl-CoA; p-methyl benzoyl-CoA to p-methylbenzoyloxy phosphate or p-methylbenzaldehyde; p-methylbenzoyloxy phosphonate to p-methylbenzaldehyde; and p-methylbenzaldehyde to toluene (see Example VII and FIG. 11). In another embodiment, a 2H4OP pathway can comprise substrates and products selected from erythrose-4-phosphate to (2,4-dioxobutoxy)phosphonate; and (2,4-dioxobutoxy)phosphonate to 2H4OP (see Example VI and FIG. 8). In another embodiment, a benzoate pathway can comprise substrates and products selected from (2-hydroxy-4-oxobutoxy)phosphonate to 2,4-dihydroxy-6-[(phosphonooxy)methyl]oxane-2-carboxylate; 2,4-dihydroxy-6-[(phosphonooxy)methyl]oxane-2-carboxylate to 1,3-dihydroxy-5-oxocyclohexane-1-carboxylate; 1,3-dihydroxy-5-oxocyclohexane-1-carboxylate to 5-hydroxy-3-oxocyclohex-1-ene-1-carboxylate; 5-hydroxy-3-oxocyclohex-1-ene-1-carboxylate to 3,5-dihydroxycyclohex-1-ene-1-carboxylate, 3,5-dihydroxycyclohex-1-ene-1-carboxylate to 5-hydroxy-3-(phosphonooxy)cyclohex-1-ene-1-carboxylate; 5-hydroxy-3-(phosphonooxy)cyclohex-1-ene-1-carboxylate to 5-[(1-carboxyeth-1-en-1-yl)oxy]-3-(phosphonooxy)cyclohex-1-ene-1-carboxylate; 5-[(1-carboxyeth-1-en-1-yl)oxy]-3-(phosphonooxy)cyclohex-1-ene-1-carboxylate to 3-[(1-carboxyeth-1-en-1-yl)oxy]cyclohexa-1,5-diene-1-carboxylate; and 3-[(1-carboxyeth-1-en-1-yl)oxy]cyclohexa-1,5-diene-1-carboxylate to benzoate (see Example VI and FIG. 9). In another embodiment, a benzene pathway can comprise substrates and products selected from benzoate to benzene; benzoate to benzoyl-CoA, (benzoyloxy)phosphonate or benzaldehyde; benzoyl-CoA to (benzoyloxy)phosphonate or benzaldehyde; (benzoyloxy)phosphonate to benzaldehyde; and benzaldehyde to benzene. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein.

As disclosed herein, a (2-hydroxy-3-methyl-4-oxobutoxy)phosphonate pathway is exemplified in FIG. 5 (see Example III). Therefore, in addition to a microbial organism containing a (2-hydroxy-3-methyl-4-oxobutoxy)phosphonate pathway that produces (2-hydroxy-3-methyl-4-oxobutoxy)phosphonate, the invention additionally provides a non-naturally occurring microbial organism comprising at least one exogenous nucleic acid encoding a (2-hydroxy-3-methyl-4-oxobutoxy)phosphonate pathway enzyme, where the microbial organism produces a (2-hydroxy-3-methyl-4-oxobutoxy)phosphonate pathway intermediate, for example, 1-deoxy-D-xylulose-5-phosphate or C-methyl-D-erythritol-4-phosphate. Similarly, the invention also provides a non-naturally occurring microbial organism containing a p-toluate pathway that produces p-toluate, wherein the non-naturally occurring microbial organism comprises at least one exogenous nucleic acid encoding a p-toluate pathway enzyme, where the microbial organism produces a p-toluate pathway intermediate, for example, 2,4-dihydroxy-5-methyl-6-[(phosphonooxy)methyl]oxane-2-carboxylate, 1,3-dihydroxy-4-methyl-5-oxocyclohexane-1-carboxylate, 5-hydroxy-4-methyl-3-oxocyclohex-1-ene-1-carboxylate, 3,5-dihydroxy-4-methylcyclohex-1-ene-1-carboxylate, 5-hydroxy-4-methyl-3-(phosphonooxy)cyclohex-1-ene-1-carboxylate, 5-[(1-carboxyeth-1-en-1-yl)oxy]-4-methyl-3-(phosphonooxy)cyclohex-1-ene-1-carboxylate, or 3-[(1-carboxyeth-1-en-1-yl)oxy]-4-methylcyclohexa-1,5-diene-1-carboxylate. Further, the invention additionally provides a non-naturally occurring microbial organism containing a terephthalate pathway enzyme, where the microbial organism produces a terephthalate pathway intermediate, for example, 4-carboxybenzyl alcohol or 4-carboxybenzaldehyde.

Similarly, the invention also provides a non-naturally occurring microbial organism containing a toluene pathway that produces toluene, wherein the non-naturally occurring microbial organism comprises at least one exogenous nucleic acid encoding a toluene pathway enzyme, where the microbial organism produces a toluene pathway intermediate, for example, p-methylbenzoyl-CoA, (p-methylbenzoyloxy)phosphonate, or p-methylbenzaldehyde.

Figure 10:
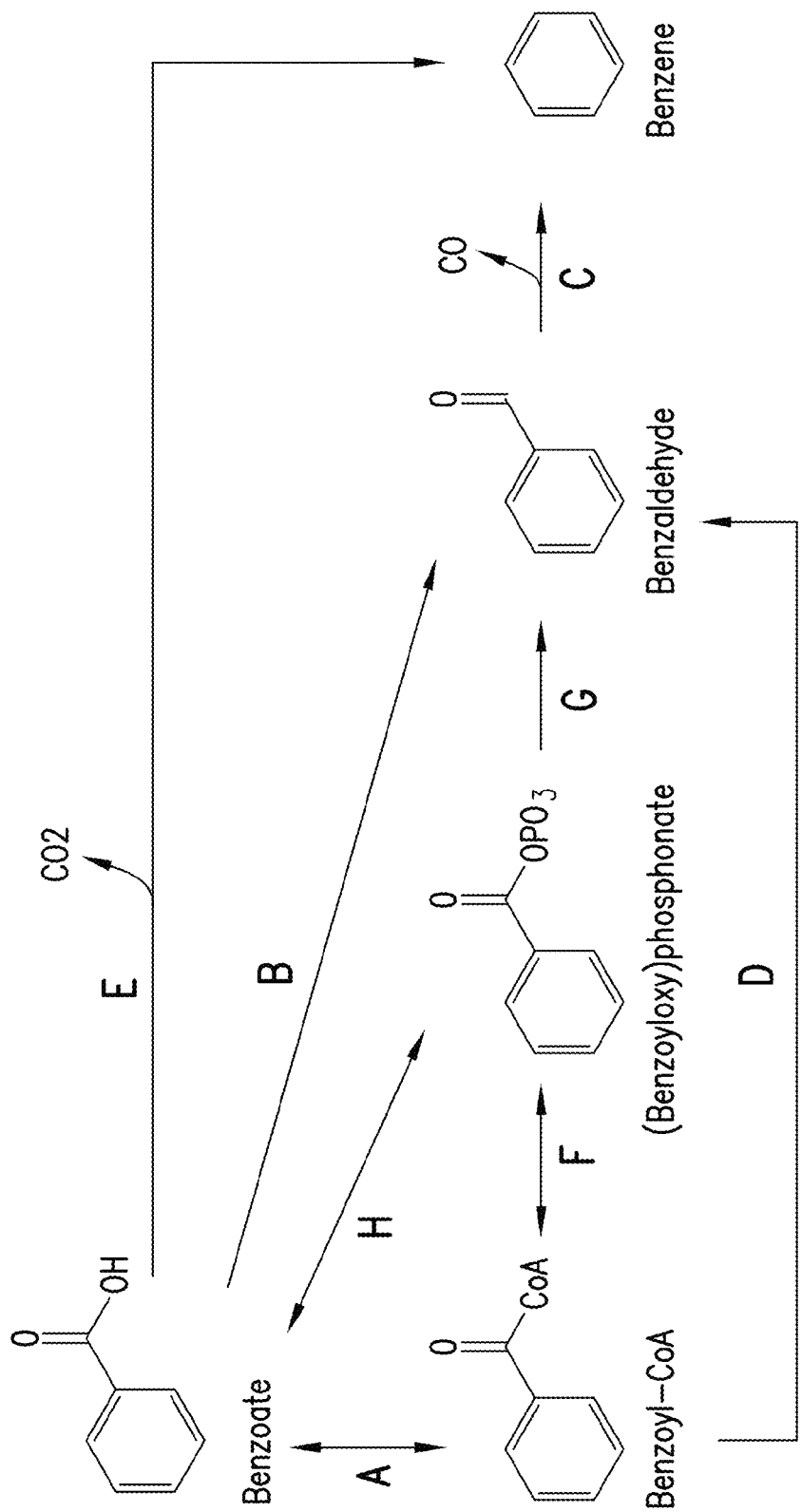
FIG. 10 shows pathways from benzoate and benzoyl-CoA to benzene. Enzymes are A. benzoyl-CoA synthetase, transferase and/or hydrolase, B. benzoate reductase, C. benzaldehyde decarbonylase, D. benzoyl-CoA reductase, E. benzoate decarboxylase, F. phosphotransbenzoylase, G. (benzoyloxy)phosphonate reductase (dephosphorylating), H. benzoate kinase.

Similarly, the invention also provides a non-naturally occurring microbial organism containing a benzene pathway that produces benzene, wherein the non-naturally occurring microbial organism comprises at least one exogenous nucleic acid encoding a benzene pathway enzyme, where the microbial organism produces a benzene pathway intermediate, for example, benzoyl-CoA, (benzoyloxy)phosphonate, and benzaldehyde (FIG. 10).

Figure 9:
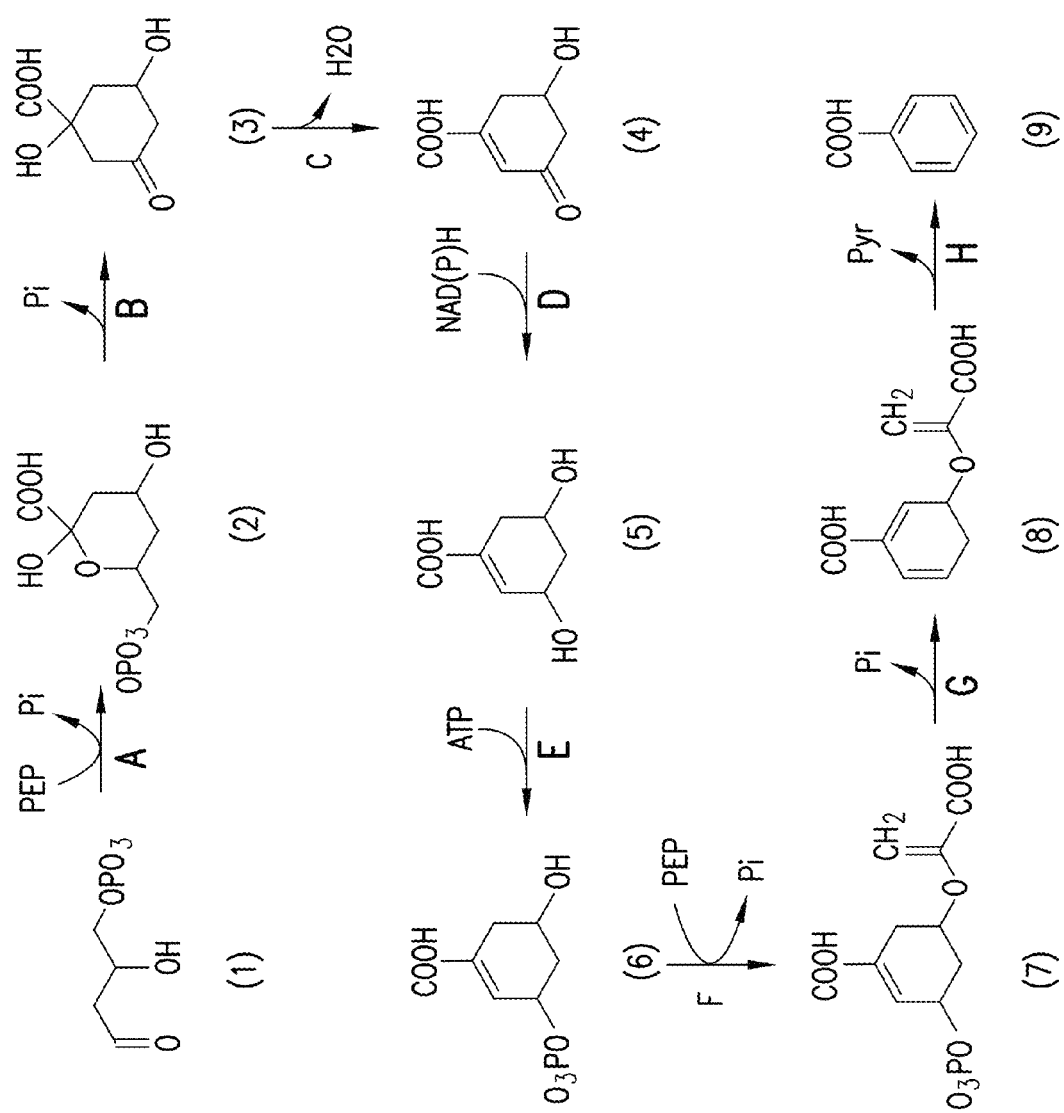
FIG. 9 shows an alternate shikimate pathway from (2-hydroxy-4-oxobutoxy)phosphonate to benzoate. Enzymes are: A. 2-dehydro-3-deoxyphosphoheptonate synthase, B. 3-dehydroquinate synthase, C. 3-dehydroquinate dehydratase, D. shikimate dehydrogenase, E. shikimate kinase, F. 3-phosphoshikimate-2-carboxyvinyltransferase, G. chorismate synthase, H. chorismate lyase. Compounds are: 1. (2-hydroxy-4-oxobutoxy)phosphonate, 2. 2,4-dihydroxy-6-[(phosphonooxy)methyl]oxane-2-carboxylate, 3. 1,3-dihydroxy-5-oxocyclohexane-1-carboxylate, 4. 5-hydroxy-3-oxocyclohex-1-ene-1-carboxylate, 5. 3,5-dihydroxycyclohex-1-ene-1-carboxylate, 6. 5-hydroxy-3-(phosphonooxy)cyclohex-1-ene-1-carboxylate, 7. 5-[(1-carboxyeth-1-en-1-yl)oxy]-3-(phosphonooxy)cyclohex-1-ene-1-carboxylate, 8. 3-[(1-carboxyeth-1-en-1-yl)oxy]cyclohexa-1,5-diene-1-carboxylate, 9. benzoate.

Similarly, the invention also provides a non-naturally occurring microbial organism containing a benzoate pathway that produces benzoate, wherein the non-naturally occurring microbial organism comprises at least one exogenous nucleic acid encoding a benzoate pathway enzyme, where the microbial organism produces a benzoate pathway intermediate, for example, (2-hydroxy-4-oxobutoxy)phosphonate, 2,4-dihydroxy-6-[(phosphonooxy)methyl]oxane-2-carboxylate, 1,3-dihydroxy-5-oxocyclohexane-1-carboxylate, 5-hydroxy-3-oxocyclohex-1-ene-1-carboxylate, 3,5-dihydroxycyclohex-1-ene-1-carboxylate, 5-hydroxy-3-(phosphonooxy)cyclohex-1-ene-1-carboxylate, 5-[(1-carboxyeth-1-en-1-yl)oxy]-3-(phosphonooxy)cyclohex-1-ene-1-carboxylate, and 3-[(1-carboxyeth-1-en-1-yl)oxy] cyclohexa-1,5-diene-1-carboxylate (FIG. 9).

Thus, the invention provides a non-naturally occurring microbial organism containing at least one exogenous nucleic acid encoding an enzyme or protein, where the enzyme or protein converts the substrates and products of a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway, such as those shown in FIGS. 1-11.

While generally described herein as a microbial organism that contains a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway, it is understood that the invention additionally provides a non-naturally occurring microbial organism comprising at least one exogenous nucleic acid encoding a toluene, benzene, p-toluate, terephthalate, (2-hydroxy-3-methyl-4-oxobutoxy) phosphonate, (2-hydroxy-4-oxobutoxy)phosphonate, benzoate, styrene, 2,4-pentadienoate, 3-butene-1ol or 1,3-butadiene pathway enzyme expressed in a sufficient amount to produce an intermediate of a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway. For example, as disclosed herein, toluene, benzene, styrene, and 1,3-butadiene pathways are exemplified in FIGS. 1-23. Therefore, in addition to a microbial organism containing a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway that produces toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene, the invention additionally provides a non-naturally occurring microbial organism comprising at least one exogenous nucleic acid encoding a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway enzyme, where the microbial organism produces a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway intermediate, for example, phenylpyruvate, phenylacetaldehyde, phenylacetate, 3-oxo-3-phenylpropionyl-CoA, [(3-oxo-3-phenylpropionyl)oxy]phosphonate, benzoyl-acetate, acetophenone, 1-phenylethanol, DXP, 2ME4P, benzoyl-CoA, (benzoyloxy)phosphonate, benzaldehyde, trans-2,4-pentadienoate, and cis-2,4-pentadienoate, as well as any shikimate pathway intermediate shown in FIGS. 6 and 9.

It is understood that any of the pathways disclosed herein, as described in the Examples and exemplified in the Figures, including the pathways of FIGS. 1-11, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more toluene, benzene, p-toluate, terephthalate, (2-hydroxy-3-methyl-4-oxobutoxy) phosphonate, (2-hydroxy-4-oxobutoxy)phosphonate, benzoate, styrene, 2,4-pentadienoate, 3-butene-1ol or 1,3-butadiene biosynthetic pathways. Depending on the host microbial organism chosen for biosynthesis, nucleic acids for some or all of a particular toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae. Schizosaccharomyces pombe, Kluyveromyces lactis, Kluyveromyces marxianus, Aspergillus terreus, Aspergillus niger, Pichia pastoris, Rhizopus arrhizus, Rhizopus oryzae*, and the like. *E. coli* is a particularly useful host organisms since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathway constituents of a selected host microbial organism, the non-naturally occurring microbial organisms of the invention will include at least one exogenously expressed toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway-encoding nucleic acid and up to all encoding nucleic acids for one or more toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathways. For example, toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthesis can be established in a host deficient in a pathway enzyme or protein through exogenous expression of the corresponding encoding nucleic acid. In a host deficient in all enzymes or proteins of a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene can be included, such as phenylalanine aminotransferase and/or phenylalanine oxidoreductase (deaminating), phenylpyruvate decarboxylase, phenylacetaldehyde dehydrogenase and/or oxidase, phenylpyruvate oxidase, phenylacetate decarboxylase, phenylacetaldehyde decarbonylase, phenylalanine benzene-lyase, benzoyl-CoA acetyltransferase, 3-oxo-3-phenylpropionyl-CoA synthetase, transferase and/or hydrolase, benzoyl-acetate decarboxylase, acetophenone reductase, 1-phenylethanol dehydratase, phosphotrans-3-oxo-3-phenylpropionylase, benzoyl-acetate kinase, trans,trans-muconate decarboxylase, cis,trans-muconate cis-decarboxylase, cis,trans-muconate trans-decarboxylase, cis, cis-muconate decarboxylase, trans-2,4-pentadienoate decarboxylase, and cis-2,4-pentadienoate decarboxylase.

For example, all enzymes in a p-toluate pathway can be included, such as 2-dehydro-3-deoxyphosphoheptonate synthase; 3-dehydroquinate synthase; 3-dehydroquinate dehydratase; shikimate dehydrogenase; shikimate kinase; 3-phosphoshikimate-2-carboxyvinyltransferase; chorismate synthase; and chorismate lyase. In addition, all enzymes in a terephthalate pathway can be included, such as p-toluate methyl-monooxygenase reductase; 4-carboxybenzyl alcohol dehydrogenase; and 4-carboxybenzyl aldehyde dehydrogenase. Furthermore, all enzymes in a (2-hydroxy-3-methyl-4-oxobutoxy)phosphonate pathway can be included, such as 2-C-methyl-D-erythritol-4-phosphate dehydratase, 1-deoxyxylulose-5-phosphate synthase and 1-deoxy-D-xylulose-5-phosphate reductoisomerase. Likewise, all enzymes in a toluene pathway can be included, such as p-methylbenzoyl-CoA synthetase, transferase and/or hydrolase, p-toluate reductase, p-methylbenzaldehyde decarbonylase, p-methylbenzoyl-CoA reductase, p-toluate decarboxylase, phosphotrans-p-methylbenzoylase, (p-methylbenzoyloxy)phosphonate reductase (dephosphorylating), and p-toluate kinase.

Likewise, all enzymes in a (2-hydroxy-4-oxobutoxy) phosphonate pathway can be included, such as erythrose-4-phosphate dehydratase and (2,4-dioxobutoxy)phosphonate reductase.

Likewise, all enzymes in a benzozate pathway can be included, such as 2-dehydro-3-deoxyphosphoheptonate synthase, 3-dehydroquinate synthase, 3-dehydroquinate dehydratase, shikimate dehydrogenase, shikimate kinase, 3-phosphoshikimate-2-carboxyvinyltransferase, chorismate synthase, and chorismate lyase.

Likewise, all enzymes in a benzene pathway can be included, such as benzoyl-CoA synthetase, transferase and/or hydrolase, benzoate reductase, benzaldehyde decarbonylase, benzoyl-CoA reductase, benzoate decarboxylase, phosphotransbenzoylase, (benzoyloxy)phosphonate reductase (dephosphorylating), and benzoate kinase.

Given the teachings and guidance provided herein, those skilled in the art will understand that the number of encoding nucleic acids to introduce in an expressible form will, at least, parallel the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway deficiencies of the selected host microbial organism. Therefore, a non-naturally occurring microbial organism of the invention can have one, two, three, four, five, six, seven, eight, that is, up to all nucleic acids encoding the enzymes or proteins constituting a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathway disclosed herein. In some embodiments, the non-naturally occurring microbial organisms also can include other genetic modifications that facilitate or optimize toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthesis or that confer other useful functions onto the host microbial organism. One such other functionality can include, for example, augmentation of the synthesis of one or more of the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway precursors such as phenylalanine, phenylpyruvate, phenylacetaldehyde, phenylacetate, benzoyl-CoA, 3-oxo-3-phenylpropionyl-CoA, [(3-oxo-3-phenylpropionyl)oxy]phosphonate, benzoyl acetate, acetophenone, 1-phenylethanol, trans,trans-muconate, cis,trans-muconate, cis,cis-muconate, trans-2,4-pentadienoate, cis-2,4-pentadienoate, 4-hydroxy-2-oxovalerate, 2-oxopentenoate, 2-hydroxypentenoate, 2,4-dihydroxypentanoate, 4-hydroxypent-2-enoate, 2,4-diaminopentanoate, AKP, acetylacrylate, 2,4-dioxopentanoate, 2-hydroxy-4-oxo-pentanoate, 2-amino-4-hydroxypentanoate, 3,5-diaminopentanoate, 5-aminopent-2-enoate, 3-amino-5-oxopentanoate, 5-oxopent-2-enoate, 5-hydroxypent-2-enoate, 3-amino-5-hydroxypentanoate, 3-HP-CoA, acryloyl-CoA, 3-oxo-5-hydroxypentanoyl-CoA, 3-oxo-5-hydroxypentanoate, 3,5-dihydroxypentanoate, 3,5-dihydroxypentanoyl-CoA, 5-hydroxypent-2-enoyl-CoA, 2,4-pentadienoyl-CoA, 3-oxopent-4-enoyl-CoA, 3-hydroxypent-4-enoyl-CoA, 3-oxopent-4-enoate, and 3-hydroxypent-4-enoate glyceraldehyde-3-phosphate, pyruvate, (2-hydroxy-3-methyl-4-oxobutoxy)phosphonate or p-toluate. Furthermore, as disclosed herein, multiple pathways can be included in a single organism such as the pathway to produce p-toluate (FIG. 6), terephthalate (FIG. 7) toluene (FIG. 11) and (2-hydroxy-3-methyl-4-oxobutoxy)phosphonate (FIG. 5), as desired, or 2H4OP (FIG. 8), benzoate (FIG. 9) and benzene (FIG. 10).

Generally, a host microbial organism is selected such that it produces the precursor of a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway, either as a naturally produced molecule or as an engineered product that either provides de novo production of a desired precursor or increased production of a precursor naturally produced by the host microbial organism. For example, cis, cis-muconate is produced naturally in a host organism such as E. coli. As a further example, glyceraldehyde-3-phosphate and phosphoenolpyruvate are produced naturally in a host organism such as E. coli. A host organism can be engineered to increase production of a precursor, as disclosed herein. In addition, a microbial organism that has been engineered to produce a desired precursor can be used as a host organism and further engineered to express enzymes or proteins of a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway.

In some embodiments, a non-naturally occurring microbial organism of the invention is generated from a host that contains the enzymatic capability to synthesize toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene. In this specific embodiment it can be useful to increase the synthesis or accumulation of a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway product to, for example, drive toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway reactions toward toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene production. Increased synthesis or accumulation can be accomplished by, for example, overexpression of nucleic acids encoding one or more of the above-described toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway enzymes or proteins. Over expression the enzyme or enzymes and/or protein or proteins of the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene, through overexpression of one, two, three, four, five, six, seven, eight, that is, up to all nucleic acids encoding toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathway enzymes or proteins. In addition, a non-naturally occurring organism can be generated by mutagenesis of an endogenous gene that results in an increase in activity of an enzyme in the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathway onto the microbial organism. Alternatively, encoding nucleic acids can be introduced to produce an intermediate microbial organism having the biosynthetic capability to catalyze some of the required reactions to confer toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic capability. For example, a non-naturally occurring microbial organism having a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathway can comprise at least two exogenous nucleic acids encoding desired enzymes or proteins, such as the combination of phenylalanine aminotransferase and/or phenylalanine oxidoreductase (deaminating) and phenylpyruvate decarboxylase, phenylalanine aminotransferase and/or phenylalanine oxidoreductase (deaminating) and phenylacetaldehyde dehydrogenase and/or oxidase, phenylalanine aminotransferase and/or phenylalanine oxidoreductase (deaminating) and phenylpyruvate oxidase, phenylpyruvate oxidase and phenylacetate decarboxylase, phenylalanine aminotransferase and/or phenylalanine oxidoreductase (deaminating) and phenylacetate decarboxylase, phenylalanine aminotransferase and/or phenylalanine oxidoreductase (deaminating) and phenylacetaldehyde decarbonylase, phenylpyruvate decarboxylase and phenylacetaldehyde dehydrogenase, phenypyruvate decarboxylase and phenylacetate decarboxylase, phenylpyruvate decarboxylase and phenylacetaldehyde decarbonylase, and phenylacetaldehyde dehydrogenase and/or oxidase and phenylacetate decarboxylase, in a toluene pathway. Similarly, in a styrene pathway the combination of at least two exogenous nucleic acids can include benzoyl-CoA acetyltransferase and 3-oxo-3-phenylpropionyl-CoA synthetase, benzoyl-CoA acetyltransferase and benzoyl-acetate decarboxylase, benzoyl-CoA acetyltransferase and acetophenone reductase, benzoyl-CoA acetyltransferase and 1-phenylethanol dehydratase, benzoyl-CoA acetyltransferase and phosphotrans-3-oxo-3-phenylpropionylase, benzoyl-CoA acetyltransferase and benzoyl-acetate kinase, 3-oxo-3-phenylpropionyl-CoA synthetase and benzoyl-acetate decarboxylase, 3-oxo-3-phenylpropionyl-CoA synthetase and acetopheonone reductase, 3-oxo-3-phenylpropionyl-CoA synthetase and 1-phenylethanol dehydratase, and so on.

Similarly, in a (2-hydroxy-3-methyl-4-oxobutoxy)phosphonate pathway, a combination of the enzymes expressed can be a combination of 2-C-methyl-D-erythritol-4-phosphate dehydratase and 1-deoxyxylulose-5-phosphate synthase, or 2-C-methyl-D-erythritol-4-phosphate dehydratase and 1-deoxy-D-xylulose-5-phosphate reductoisomerase. In a p-toluate pathway, a combination of the enzymes expressed can be a combination of 2-dehydro-3-deoxyphosphoheptonate synthase and 3-dehydroquinate dehydratase; shikimate kinase and 3-phosphoshikimate-2-carboxyvinyltransferase; shikimate kinase and shikimate dehydrogenase and, and the like. Similarly, in a terephthalate pathway, a combination of the expressed enzymes can be p-toluate methyl-monooxygenase reductase and 4-carboxybenzyl alcohol dehydrogenase; or 4-carboxybenzyl alcohol dehydrogenase and 4-carboxybenzyl aldehyde dehydrogenase, and the like. Thus, it is understood that any combination of two or more enzymes or proteins of a biosynthetic pathway can be included in a non-naturally occurring microbial organism of the invention.

Similarly, it is understood that any combination of three or more enzymes or proteins of a biosynthetic pathway can be included in a non-naturally occurring microbial organism of the invention, and so forth, as desired, so long as the combination of enzymes and/or proteins of the desired biosynthetic pathway results in production of the corresponding desired product. Such combination of three enzymes can include, for example, 3-dehydroquinate synthase, shikimate dehydrogenase and shikimate kinase; shikimate kinase, chorismate synthase and chorismate lyase; 3-dehydroquinate dehydratase, chorismate synthase and chorismate lyase, and so forth, as desired, so long as the combination of enzymes and/or proteins of the desired biosynthetic pathway results in production of the corresponding desired product.

Similarly, any combination of four, five, six, or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene as described herein, the non-naturally occurring microbial organisms and methods of the invention also can be utilized in various combinations with each other and with other microbial organisms and methods well known in the art to achieve product biosynthesis by other routes. For example, one alternative to produce toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene other than use of the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ot or 1,3-butadiene producers is through addition of another microbial organism capable of converting a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway intermediate to toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene. One such procedure includes, for example, the fermentation of a microbial organism that produces a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway intermediate. The toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway intermediate can then be used as a substrate for a second microbial organism that converts the toluene, benzene, p-toluate, terephthalate, (2-hydroxy-3-methyl-4-oxobutoxy) phosphonate, (2-hydroxy-4-oxobutoxy)phosphonate, benzoate, styrene, 2,4-pentadienoate, 3-butene-1ol or 1,3-butadiene pathway intermediate to toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene. The toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway intermediate can be added directly to another culture of the second organism or the original culture of the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene can be accomplished by constructing a microbial organism that contains biosynthetic pathways for conversion of one pathway intermediate to another pathway intermediate or the product. Alternatively, toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene also can be biosynthetically produced from microbial organisms through co-culture or co-fermentation using two organisms in the same vessel, where the first microbial organism produces a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene intermediate and the second microbial organism converts the intermediate to toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene.

Sources of encoding nucleic acids for a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Mycobacterium tuberculosis, Agrobacterium tumefaciens, Bacillus subtilis, Synechocystis* species, *Arabidopsis thaliana, Zymomonas mobilis, Klebsiella oxytoca, Salmonella typhimurium, Salmonella typhi, Lactobacullus collinoides, Klebsiella pneumoniae, Clostridium pasteuranum, Citrobacter freundii, Clostridium butyricum, Roseburia inulinivorans, Sulfolobus solfataricus, Neurospora crassa, Sinorhizobium fredii, Helicobacter pylori, Pyrococcus furiosus, Haemophilus influenzae, Erwinia chrysanthemi, Staphylococcus aureus, Dunaliella salina, Streptococcus pneumoniae, Saccharomyces cerevisiae, Aspergillus nidulans, Pneumocystis carinii, Streptomyces coelicolor,* species from the genera *Burkholderia, Alcaligenes, Pseudomonas, Shingomonas* and *Comamonas,* for example, *Comamonas testosteroni,* as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathway exists in an unrelated species, toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene.

Methods for constructing and testing the expression levels of a non-naturally occurring toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the present invention provides a method for producing toluene that includes culturing a non-naturally occurring microbial organism having a toluene pathway. The toluene pathway includes at least one exogenous nucleic acid encoding a toluene pathway enzyme expressed in a sufficient amount to produce toluene, under conditions and for a sufficient period of time to produce toluene. The toluene pathway can be selected from (A) 1) one or both of phenylalanine aminotransferase and phenylalanine oxidoreductase (deaminating), 2) phenylpyruvate decarboxylase, and 3) phenylacetaldehyde decarbonylase; (B) 1) one or more of phenylalanine aminotransferase and phenylalanine oxidoreductase (deaminating), 2) phenylpyruvate decarboxylase, 3) one or more of phenylacetaldehyde dehydrogenase and phenylacetaldehyde oxidase, and 4) phenylacetate decarboxylase; and (C) 1) one or more of phenylalanine aminotransferase and phenylalanine oxidoreductase (deaminating), 2) phenylpyruvate oxidase, and 3) phenylacetate decarboxylase, as indicated in the alternate pathways shown in FIG. 1. In some embodiments, the method includes culturing the non-naturally occurring microbial organism is in a substantially anaerobic culture medium.

In some embodiments, methods of the invention for producing toluene include culturing a non-naturally microbial organism, that includes two exogenous nucleic acids each encoding a toluene pathway enzyme, three exogenous nucleic acids each encoding a toluene pathway enzyme, four exogenous nucleic acids each encoding a toluene pathway enzyme, five exogenous nucleic acids each encoding a toluene pathway, and so on. Exemplary organisms having four exogenous nucleic acids can encode 1) phenylalanine aminotransferase, 2) phenylalanine oxidoreductase (deaminating), 3) phenylpyruvate decarboxylase, and 4) phenylacetaldehyde decarbonylase. Exemplary organisms having five exogenous nucleic acids can encode 1) phenylalanine aminotransferase, 2) phenylalanine oxidoreductase (deaminating), 3) phenylpyruvate decarboxylase, 4) phenylacetaldehyde dehydrogenase and/or oxidase, and 5) phenylacetate decarboxylase. In some embodiments, methods of the invention for producing toluene can include culturing a non-naturally occurring microbial organism that has at least one exogenous nucleic acid that is a heterologous nucleic acid.

In some embodiments, the present invention provides a method for producing benzene that includes culturing a non-naturally occurring microbial organism having a benzene pathway. The benzene pathway can include at least one exogenous nucleic acid encoding a benzene pathway enzyme expressed in a sufficient amount to produce benzene, under conditions and for a sufficient period of time to produce benzene. The benzene pathway can include a phenylalanine benzene-lyase, as shown in FIG. 2. In some embodiments, the at least one exogenous nucleic acid is the phenylalanine benzene-lyase itself, while in alternate embodiments, the at least one exogenous nucleic acid can affect the production of the precursor metabolite phenylalanine. In some embodiments the at least one exogenous nucleic acid of the benzene pathway is a heterologous nucleic acid. In some embodiments, methods of the invention for producing benzene can include culturing a non-naturally occurring microbial organism that is in a substantially anaerobic culture medium.

In some embodiments, the present invention provides a method for producing styrene that includes culturing a non-naturally occurring microbial organism having a styrene pathway. The styrene pathway can include at least one exogenous nucleic acid encoding a styrene pathway enzyme expressed in a sufficient amount to produce styrene, under conditions and for a sufficient period of time to produce styrene. The styrene pathway can be selected from (A) 1) benzoyl-CoA acetyltransferase, 2) one or more of 3-oxo-3-phenylpropionyl-CoA synthetase, transferase, and hydrolase, 3) benzoyl-acetate decarboxylase, 4) acetopheone reductase, and 5) 1-phenylethanol dehydratase; and (B) 1) benzoyl-CoA acetyltransferase, 2) phosphotrans-3-oxo-3-phenylpropionylase, 3) benzoyl-acetate kinase, 4) benzoyl-acetate decarboxylase, 5) acetopheone reductase, and 6) 1-phenylethanol dehydratase, as indicated in the alternate pathways in FIG. 3. In some embodiments, methods of the invention for producing styrene can include culturing a non-naturally occurring microbial organism that is in a substantially anaerobic culture medium.

In some embodiments, methods of the invention for producing styrene include culturing a non-naturally microbial organism, that includes two exogenous nucleic acids each encoding a styrene pathway enzyme, three exogenous nucleic acids each encoding a styrene pathway enzyme, four exogenous nucleic acids each encoding a styrene pathway enzyme, five exogenous nucleic acids each encoding a styrene pathway enzyme, six exogenous nucleic acids each encoding a styrene pathway enzyme, and so on. An exemplary organism having five exogenous nucleic acids can encode 1) benzoyl-CoA acetyltransferase, 2) one of 3-oxo-3-phenylpropionyl-CoA synthetase, transferase, and hydrolase, 3) benzoyl-acetate decarboxylase, 4) acetopheone reductase, and 5) 1-phenylethanol dehydratase. An exemplary organism having six exogenous nucleic acids encode 1) benzoyl-CoA acetyltransferase, 2) phosphotrans-3-oxo-3-phenylpropionylase, 3) benzoyl-acetate kinase, 4) benzoyl-acetate decarboxylase, 5) acetopheone reductase, and 6) 1-phenylethanol dehydratase. In some embodiments, methods of the present invention for producing styrene can include culturing a non-naturally occurring microbial organism in which at least one exogenous nucleic acid is a heterologous nucleic acid.

In some embodiments, the present invention provides a method for producing 1,3-butadiene that includes culturing a non-naturally occurring microbial organism having a 1,3-butadiene pathway. The 1,3-butadiene pathway includes at least one exogenous nucleic acid encoding a 1,3-butadiene pathway enzyme expressed in a sufficient amount to produce 1,3-butadiene, under conditions and for a sufficient period of time to produce 1,3-butadiene. The 1,3-butadiene pathway can be selected from (A) 1) trans,trans-muconate decarboxylase and 2) trans-2,4-pentadienoate decarboxylase; (B) 1) cis,trans-muconate cis-decarboxylase and 2) trans-2,4-pentadienoate decarboxylase; (C) 1) cis,trans-muconate trans-decarboxylase 2) cis-2,4-pentadienoate decarboxylase; and (D) 1) cis, cis-muconate decarboxylase and 2) cis-2,4-pentadienoate decarboxylase, as indicated by the alternate pathways in FIG. 4. In some embodiments, the method of producing 1,3-butadiene can include culturing a non-naturally occurring microbial organism that is in a substantially anaerobic culture medium.

In some embodiments, methods of the invention can include culturing a non-naturally occurring microbial organism that has two exogenous nucleic acids each encoding a 1,3-butadiene pathway enzyme. Exemplary organisms having two exogenous nucleic acids can include genes encoding a set of enzymes selected from (A) 1) trans,trans-muconate decarboxylase and 2) trans-2,4-pentadienoate decarboxylase; (B) 1) cis,trans-muconate cis-decarboxylase and 2) trans-2,4-pentadienoate decarboxylase; (C) 1) cis,trans-muconate trans-decarboxylase 2) cis-2,4-pentadienoate decarboxylase; and (D) 1) cis, cis-muconate decarboxylase and 2) cis-2,4-pentadienoate decarboxylase. In some embodiments, methods of the invention can include culturing a non-naturally occurring microbial organism that has at least one exogenous nucleic acid that is a heterologous nucleic acid.

The invention additionally provides a method for producing (2-hydroxy-3-methyl-4-oxobutoxy)phosphonate, comprising culturing the non-naturally occurring microbial organism containing a (2-hydroxy-3-methyl-4-oxobutoxy)phosphonate pathway under conditions and for a sufficient period of time to produce (2-hydroxy-3-methyl-4-oxobutoxy)phosphonate. Such a microbial organism can have a (2-hydroxy-3-methyl-4-oxobutoxy)phosphonate pathway comprising at least one exogenous nucleic acid encoding a (2-hydroxy-3-methyl-4-oxobutoxy)phosphonate pathway enzyme expressed in a sufficient amount to produce (2-hydroxy-3-methyl-4-oxobutoxy)phosphonate, the (2-hydroxy-3-methyl-4-oxobutoxy)phosphonate pathway comprising 2-C-methyl-D-erythritol-4-phosphate dehydratase (see Example III and FIG. 5, step C). A (2-hydroxy-3-methyl-4-oxobutoxy)phosphonate pathway can optionally further comprise 1-deoxyxylulose-5-phosphate synthase and/or 1-deoxy-D-xylulose-5-phosphate reductoisomerase (see Example III and FIG. 5, steps A and B).

In another embodiment, the invention provides a method for producing p-toluate, comprising culturing the non-naturally occurring microbial organism comprising a p-toluate pathway under conditions and for a sufficient period of time to produce p-toluate. A p-toluate pathway can comprise at least one exogenous nucleic acid encoding a p-toluate pathway enzyme expressed in a sufficient amount to produce p-toluate, the p-toluate pathway comprising 2-dehydro-3-deoxyphosphoheptonate synthase; 3-dehydroquinate synthase; 3-dehydroquinate dehydratase; shikimate dehydrogenase; shikimate kinase; 3-phosphoshikimate-2-carboxyvinyltransferase; chorismate synthase; and/or chorismate lyase (see Example IV and FIG. 6, steps A-H). In another embodiment, a method of the invention can utilize a non-naturally occurring microbial organism that further comprises a (2-hydroxy-3-methyl-4-oxobutoxy)phosphonate pathway (see Example III and FIG. 5). Such a (2-hydroxy-3-methyl-4-oxobutoxy)phosphonate pathway can comprise 2-C-methyl-D-erythritol-4-phosphate dehydratase, 1-deoxyxylulose-5-phosphate synthase and/or 1-deoxy-D-xylulose-5-phosphate reductoisomerase (see Example III and FIG. 5).

The invention further provides a method for producing terephthalate, comprising culturing a non-naturally occurring microbial organism containing a terephthalate pathway under conditions and for a sufficient period of time to produce terephthalate. Such a terephthalate pathway can comprise at least one exogenous nucleic acid encoding a terephthalate pathway enzyme expressed in a sufficient amount to produce terephthalate, the terephthalate pathway comprising p-toluate methyl-monooxygenase reductase; 4-carboxybenzyl alcohol dehydrogenase; and/or 4-carboxybenzyl aldehyde dehydrogenase. Such a microbial organism can further comprise a p-toluate pathway, wherein the p-toluate pathway comprises 2-dehydro-3-deoxyphosphoheptonate synthase; 3-dehydroquinate synthase; 3-dehydroquinate dehydratase; shikimate dehydrogenase; shikimate kinase; 3-phosphoshikimate-2-carboxyvinyltransferase; chorismate synthase; and/or chorismate lyase (see Examples IV and V and FIGS. 6 and 7). In another embodiment, the non-naturally occurring microbial organism can further comprise a (2-hydroxy-3-methyl-4-oxobutoxy)phosphonate pathway (see Example III and FIG. 5). In some embodiments, the present invention provides a method for producing toluene, comprising culturing a non-naturally occurring microbial organism having a toluene pathway comprising at least one exogenous nucleic acid encoding a toluene pathway enzyme expressed in a sufficient amount to produce toluene. The toluene pathway can be selected from a set of pathway enzymes selected from: a) p-toluate decarboxylase; b) p-toluate reductase and p-methylbenzaldehyde decarbonylase; c) p-toluate kinase, (p-methylbenzoyloxy)phosphonate reductase, and p-methylbenzaldehyde decarbonylase; d) (p-methylbenzoyl-CoA synthetase, transferase and/or hydrolase), phosphotrans-p-methylbenzoylase, (p-methylbenzoyloxy)phosphonate reductase, and p-methylbenzaldehyde decarbonylase; and e) (p-methylbenzoyl-CoA synthetase, transferase and/or hydrolase), p-methylbenzoyl-CoA reductase and p-methylbenzaldehyde decarbonylase. The non-naturally occurring microbial organism can be cultured under conditions and for a sufficient period of time to produce toluene. In a particular embodiment, the invention provides a non-naturally occurring microbial organism and methods of use, in which the microbial organism contains p-toluate, terephthalate or toluene, and (2-hydroxy-3-methyl-4-oxobutoxy)phosphonate pathways.

In some embodiments, the present invention provides a method for producing (2-hydroxy-4-oxobutoxy)phosphonate, comprising culturing a non-naturally occurring microbial organism having a (2-hydroxy-4-oxobutoxy)phosphonate pathway comprising at least one exogenous nucleic acid encoding a (2-hydroxy-4-oxobutoxy)phosphonate pathway enzyme expressed in a sufficient amount to produce (2-hydroxy-4-oxobutoxy)phosphonate. The (2-hydroxy-4-oxobutoxy)phosphonate pathway can include erythrose-4-phosphate dehydratase and (2,4-dioxobutoxy)phosphonate reductase.

In some embodiments, the present invention provides a method for producing benzoate, comprising culturing a non-naturally occurring microbial organism having a benzoate pathway comprising at least one exogenous nucleic acid encoding a benzoate pathway enzyme expressed in a sufficient amount to produce benzoate. The benzoate pathway includes 2-dehydro-3-deoxyphosphoheptonate synthase; 3-dehydroquinate synthase; 3-dehydroquinate dehydratase; shikimate dehydrogenase; shikimate kinase; 3-phosphoshikimate-2-carboxyvinyltransferase; chorismate synthase; and chorismate lyase. The method includes culturing the non-naturally occurring organism under conditions and for a sufficient period of time to produce benzoate.

In some embodiments, the present invention provides a method for producing benzene, comprising culturing the non-naturally occurring microbial organism having a benzene pathway comprising at least one exogenous nucleic acid encoding a benzene pathway enzyme expressed in a sufficient amount to produce benzene. The benzene pathway is selected from a set of pathway enzymes selected from: a) benzoate decarboxylase; b) benzoate reductase and benzaldehyde decarbonylase; c) benzoate kinase, (benzoyloxy)phosphonate reductase, and benzaldehyde decarbonylase; d) (benzoyl-CoA synthetase, transferase and/or hydrolase), phosphotransbenzoylase, (benzoyloxy)phosphonate reductase, and benzaldehyde decarbonylase; and e) (benzoyl-CoA synthetase, transferase and/or hydrolase), benzoyl-CoA reductase and benzaldehyde decarbonylase. The non-naturally occurring microbial organism can be cultured under conditions and for a sufficient period of time to produce benzene. In a particular embodiment, the invention provides a non-naturally occurring microbial organism and methods of use, in which the microbial organism contains (2-hydroxy-4-oxobutoxy)phosphonate, benzoate, and benzene pathways.

In some embodiments, the present invention provides a method for producing 2,4-pentadienoate that includes culturing a non-naturally occurring microbial organism having a 2,4-pentadienoate pathway. The pathway includes at least one exogenous nucleic acid encoding a 2,4-pentadienoate pathway enzyme expressed in a sufficient amount to produce 2,4-pentadienoate, under conditions and for a sufficient period of time to produce 2,4-pentadienoate. The 2,4-pentadienoate pathway selected from A) i) a 4-hydroxy-2-oxovalerate aldolase, ii) a 4-hydroxy-2-oxovalerate dehydratase, iii) a 2-oxopentenoate reductase, and iv) a 2-hydroxypentenoate dehydratase; B) i) an AKP deaminase, ii) an acetylacrylate reductase, and iii) a 4-hydroxypent-2-enoate dehydratase; C) i) an AKP aminotransferase and/or dehydrogenase, ii) a 2,4-dioxopentanoate-2-reductase, iii) a 2-hydroxy-4-oxopentanoate dehydratase, iv) an acetylacrylate reductase, and v) a 4-hydroxypent-2-enoate dehydratase; D) i) an AKP aminotransferase and/or dehydrogenase, ii) a 2,4-dioxopentanoate-4-reductase, iii) a 4-hydroxy-2-oxovalerate dehydratase, iv) a 2-oxopentenoate reductase, and v) a 2-hydroxypentenoate dehydratase; and E) i) an AKP reductase, ii) a 2-amino-4-hydroxypentanoate aminotransferase and/or dehydrogenase, iii) a 4-hydroxy-2-oxovalerate dehydratase, iv) a 2-oxopentenoate reductase, and v) a 2-hydroxypentenoate dehydratase.

In some embodiments, the methods of the invention utilize a non-naturally occurring microbial organism having a 2,4-pentadienoate pathway that includes at least one exogenous nucleic acid encoding a 2,4-pentadienoate pathway enzyme expressed in a sufficient amount to produce 2,4-pentadienoate. The 2,4-pentadienoate pathway has a set of enzymes selected from (A) 1) 4-hydroxy-2-oxovalerate aldolase, 2) 4-hydroxy-2-oxovalerate reductase, 3) 2,4-dihydroxypentanoate 2-dehydratase, and 4) 4-hydroxypent-2-enoate dehydratase, as shown in steps A, E, F, and G of FIG. 12 and (B) 1) 4-hydroxy-2-oxovalerate aldolase, 2) 4-hydroxy-2-oxovalerate reductase, 3) 2,4-dihydroxypentanoate 4-dehydratase and 4) 2-hydroxypentenoate dehydratase, as shown in steps A, E, H, and D of FIG. 12.

In some embodiments, the present methods of the invention utilize a non-naturally occurring microbial organism having a 2,4-pentadienoate pathway that includes at least one exogenous nucleic acid encoding a 2,4-pentadienoate pathway enzyme expressed in a sufficient amount to produce 2,4-pentadienoate. The 2,4-pentadienoate pathway has a set of enzymes selected from (A) 1) AKP aminotransferase and/or dehydrogenase, 2) 2,4-dioxopentanoate 2-reductase, 3) 2-hydroxy-4-oxopentanoate reductase, 4) 2,4-dihydroxypentanoate 2-dehydratase, and 5) 4-hydroxypent-2-enoate dehydratase, as shown in steps E, H, I, G, and D of FIG. 13, and (B) 1) AKP aminotransferase and/or dehydrogenase, 2) 2,4-dioxopentanoate 2-reductase, 3) 2-hydroxy-4-oxopentanoate reductase, along with 4) 2,4-dihydroxypetanoate-2-dehydratase and 5) 4-hydroxypent-2-enoate dehydratase or 4) 2,4-dihydroxypentanoate-4-dehydratase and 5) 2-hydroxypentenoate dehydratase, as shown in steps E, H, and I of FIG. 13, along with steps F and G or H and D of FIG. 12, respectively. That is to say, the double dehydration of 2,4-dihydroxypentanoate can be performed in any order.

In some embodiments, the methods of the invention utilize a non-naturally occurring microbial organism having an AKP pathway that includes at least one exogenous nucleic acid encoding an AKP pathway enzyme expressed in a sufficient amount to produce AKP. The AKP pathway includes an ornithine 4,5-aminomutase and a 2,4-diaminopentanoate 4-aminotransferase and/or 4-dehydrogenase, as shown in steps M and N of FIG. 13. In some embodiments, the microbial organism having an AKP pathway includes two exogenous enzymes encoding an ornithine 4,5-aminomutase and a 2,4-diaminopentanoate 4-aminotransferase or 2,4-diaminopentanoate 4-dehydrogenase. In some embodiments, this AKP pathway can be added to any of the aforementioned 2,4-pentadienoate pathways and as indicated in FIG. 13. Alternatively, AKP can be accessed from alanine by addition of an AKP thiolase, as shown in step A of FIG. 13, and fed into the various 2,4-pentadienoate pathways described herein and shown in FIG. 13, along with FIG. 12.

In some embodiments, the methods of the invention utilize a non-naturally occurring microbial organism having a 2,4-pentadienoate pathway that includes at least one exogenous nucleic acid encoding a 2,4-pentadienoate pathway enzyme expressed in a sufficient amount to produce 2,4-pentadienoate. The 2,4-pentadienoate pathway has a set of enzymes selected from (A) 1) ornithine 2,3-aminomutase, 2) 3,5-diaminopentanoate deaminase, and 3) 5-aminopent-2-enoate deaminase, as shown in steps A-C of FIG. 14, (B) 1) ornithine 2,3-aminomutase, 2) 3,5-diaminopentanoate deaminase, 3) 5-aminopent-2-enoate aminotransferase and/or dehydrogenase, 4) 5-oxopent-2-enoate reductase, and 5) 5-hydroxypent-2-enoate dehydratase, as shown in steps A, B, H, F, and G of FIG. 14, (C) 1) ornithine 2,3-aminomutase, 2) 3,5-diaminopentanoate aminotransferase and/or dehydrogenase, 3) 3-amino-5-oxopentanoate deaminase, 4) 5-oxopent-2-enoate reductase, and 5) 5-hydroxypent-2-enoate dehydratase as shown in steps A, D, E, F, and G of FIG. 14, and (D) 1) ornithine 2,3-aminomutase, 2) 3,5-diaminopentanoate aminotransferase and/or dehydrogenase, 3) 3-amino-5-oxopentanoate reductase, and 4) 3-amino-5-hydroxypentanoate deaminase and 5) 5-hydroxypent-2-enoate dehydratase as shown in steps A, D, I, J. and G of FIG. 14.

In some embodiments, the methods of the invention utilize a non-naturally occurring microbial organism having a 2,4-pentadienoate pathway that includes at least one exogenous nucleic acid encoding a 2,4-pentadienoate pathway enzyme expressed in a sufficient amount to produce 2,4-pentadienoate. The 2,4-pentadienoate pathway has a set of enzymes selected from any of the numerous pathways shown in FIG. 15 starting from 3-HP-CoA or acryloyl-CoA.

Exemplary pathways from 3-HP include the following enzyme sets (A) 1) 3-hydroxypropanoyl-CoA acetyltransferase, 2) 3-oxo-5-hydroxypentanoyl-CoA reductase, 3) 3,5-dihydroxypentanoyl-CoA dehydratase, 4) 5-hydroxypent-2-enoyl-CoA dehydratase, and 5) pent-2,4-dienoyl-CoA synthetase, transferase and/or hydrolase, as shown in steps A-E of FIG. 15, and (B) 1) 3-hydroxypropanoyl-CoA acetyltransferase, 2) 3-oxo-5-hydroxypentanoyl-CoA synthetase, transferase and/or hydrolase, 3) 3-oxo-5-hydroxypentanoate reductase, 4) 3,5-dihydroxypentanoate dehydratase, and 5 5-hydroxypent-2-enoate dehydratase, as shown in steps A, F, I, J, and Q of FIG. 15. One skilled in the art will recognize that enzyme sets defining pathways (A) and (B) from 3-HP-CoA can be intermingled via reversible enzymes 3,5-hydroxypentanoyl-CoA synthetase, transferase and/or hydrolase, as shown by step G in FIG. 15, and 5-hydroxypent-2-enoyl-CoA synthetase, transferase and/or hydrolase, as shown by step H in FIG. 15. Thus, a 3-HP-CoA to 2,4-pentadienoate pathway can include the enzymes in steps A, B, G, J, and Q, or steps A, B, C, H, and Q, or steps A, B, G, J, H, D, and E, or steps A, F, I, G, C, D, and E, or steps, A, F, I, G, C, H, and Q, or steps A, F, I, J, H, D, and E, each shown in FIG. 15.

Exemplary pathways from acryloyl-CoA include the following enzyme sets (C) 1) acryloyl-CoA acetyltransferase, 2) 3-oxopent-4-enoyl-CoA synthetase, transferase and/or hydrolase, 3) 3-oxopent-4-enoate reductase, 4) 3-hydroxypent-4-enoate dehydratase, as shown in steps M, O, P, and S in FIG. 15 and (D), 1) acryloyl-CoA acetyltransferase, 2) 3-oxopent-4-enoyl-CoA reductase, 3) 3-hydroxypent-4-enoyl-CoA dehydratase, and 4) pent-2,4-dienoyl-CoA synthetase, transferase and/or hydrolase, as shown in steps M, N, R, and E. One skilled in the art will recognize that enzyme sets defining pathways (A) and (B) from 3-HP-CoA and (C) and (D) from acryloyl-CoA can be intermingled via reversible enzymes 3-hydroxypropanoyl-CoA dehydratase, as shown in step K of FIG. 15, and 3-oxo-5-hydroxypentanoyl-CoA dehydratase, as shown in step L of FIG. 15. Thus, step K can be added to any of the enumerated pathways from acryloyl-CoA to 2,4-pentadienoate providing 2,4-pentadienoate pathways such as steps K, M, N, R, and E or steps K, M, O, P, and S. Step K can also be used a shuttle alternative to step A to provide 3-oxo-5-hydroxypentanoyl-CoA from 3-HP-CoA via steps K, M, and L. Thus, any of the aforementioned pathways utilizing the enzyme of step A can utilize the enzymes of steps K, M, and L, in its place. The same 3-oxo-5-hydroxypentanoyl-CoA intermediate can be accessed from acryloyl-CoA by pathways via the enzymes of steps K and A or M and L of FIG. 15. Thus, acryloyl-CoA can be used to access all the enumerated pathways that would be accessible from 3-HP-CoA. Thus, for example, an acryloyl-CoA to 2,4-pentadienoate pathway can include enzymes from steps K, A, B, C, D, and E, or steps K, A, F, I, J and Q, or steps K, A, B, G, J, and Q, or steps K, A, B, G, J, H, D, and E, or steps K, A, B, C, H, and Q, or steps K, A, F, I, G, C, D, and E, or steps K, A, F, I, G, C, H, Q, or steps K, A, F, I, J, H, D and E, or steps M, L, B, C, D, and E, or steps M, L, F, I, J and Q, or steps M, L, B, G, J, and Q, or steps M, L, B, G, J, H, D, and E, or steps M, L, B, C, H, and Q, or steps M, L, F, I, G, C, D, and E, or steps M, L, F, I, G, C, H, Q, or steps M, L, F, I, J, H, D and E, all as shown in FIG. 15. Similarly, 3-HP-CoA can feed into the enumerated acryloyl-CoA pathways via intermediate 3-oxopent-4-enoyl-CoA using the enzyme of step L. Thus, a 3-HP-CoA to 2,4-pentadienoate pathway can include enzymes from steps A, L, N, R, and E or steps A, L, O, P, and S, each pathway being shown in FIG. 15.

In some embodiments, non-naturally occurring microbial organism used in methods of the invention can include two exogenous nucleic acids each encoding a 2,4-pentadienoate pathway enzyme. In some embodiments, non-naturally occurring microbial organism of the invention can include three exogenous nucleic acids each encoding a 2,4-pentadienoate pathway enzyme. For example, the non-naturally occurring microbial organism of the invention can include three exogenous nucleic acids encoding i) an AKP deaminase, ii) an acetylacrylate reductase, and iii) a 4-hydroxypent-2-enoate dehydratase, thus providing an alanine or ornithine accessible pathway to 2,4-pentadienoate via AKP. One skilled in the art will recognize that this is merely exemplary and that three exogenous nucleic acids can be the basis of any 2,4-pentadienoate-producing non-naturally occurring organism in any of the enumerated pathways of FIG. 12-15.

In some embodiments, the non-naturally occurring microbial organism used in methods of the invention microbial can include any four exogenous nucleic acids each encoding a 2,4-pentadienoate pathway enzyme. For example, a non-naturally occurring microbial organism can include four exogenous nucleic acids encoding i) a 4-hydroxy-2-oxovalerate aldolase, ii) a 4-hydroxy-2-oxovalerate dehydratase, iii) a 2-oxopentenoate reductase, and iv) a 2-hydroxypentenoate dehydratase, thus defining a complete pathway from pyruvate to 2,4-pentadienoate, as shown in FIG. 12. One skilled in the art will recognize that this is merely exemplary and that four exogenous nucleic acids can be the basis of any 2,4-pentadienoate-producing non-naturally occurring organism in any of the enumerated pathways of FIG. 12-15.

In still further embodiments, the non-naturally occurring microbial organism used in methods of the invention can include five exogenous nucleic acids each encoding a 2,4-pentadienoate pathway enzyme. Exemplary non-naturally occurring microbial organism of the invention having five exogenous nucleic acids can include enzymes encoding (A) i) an AKP aminotransferase and/or dehydrogenase, ii) a 2,4-dioxopentanoate-2-reductase, iii) a 2-hydroxy-4-oxopentanoate dehydratase, iv) an acetylacrylate reductase, and v) a 4-hydroxypent-2-enoate dehydratase, as shown in steps E, H, F, C, and D in FIG. 13, or (B) i) an AKP aminotransferase and/or dehydrogenase, ii) a 2,4-dioxopentanoate-4-reductase, i(i) a 4-hydroxy-2-oxovalerate dehydratase, (v) a 2-oxopentenoate reductase, and v) a 2-hydroxypentenoate dehydratase, as shown in steps E and K of FIG. 13, along with steps B, C, and D of FIG. 12, or i) an AKP reductase, ii) a 2-amino-4-hydroxypentanoate aminotransferase and/or dehydrogenase, iii) a 4-hydroxy-2-oxovalerate dehydratase, iv) a 2-oxopentenoate reductase, and v) a 2-hydroxypentenoate dehydratase, as shown in steps J and L of FIG. 13, along with steps B, C, and D of FIG. 12. One skilled in the art will recognize that this is merely exemplary and that five exogenous nucleic acids can be the basis of any 2,4-pentadienoate-producing non-naturally occurring organism in any of the enumerated pathways of FIG. 12-15. Thus, in some embodiments two, three, four, five, six, up to all of the enzymes in a 2,4-pentadienoate pathway can be provided insertion of exogenous nucleic acids. In some embodiments, the non-naturally occurring microbial organism of the invention has at least one exogenous nucleic acid is a heterologous nucleic acid. Moreover, in some embodiments, the methods employing non-naturally occurring microbial organism of the invention can utilize a substantially anaerobic culture medium.

In some embodiments, the non-naturally occurring microbial organism used in methods of the invention can further include a 2,4-pentadienoate decarboxylase expressed in a sufficient amount to produce 1,3-butadiene by conversion of 2,4-pentadienoate to 1,3-butadiene. Thus, any 2,4-pentadienoate pathway of FIG. 12 can form the basis of further production of 1,3 butadiene, as indicated by the conversion of cis or trans 2,4-pentadienoate to 1,3-butadiene in FIG. 4.

In some embodiments, the present invention provides a method for producing 2,4-pentadienoate, comprising culturing a non-naturally occurring microbial organism according to the aforementioned pathways described herein under conditions and for a sufficient period of time to produce 2,4-pentadienoate. In some such embodiments, the microbial organism includes two, three, four, five, six, seven, or eight exogenous nucleic acids each encoding a 2,4-pentadienoate pathway enzyme. In some such embodiments, at least one exogenous nucleic acid is a heterologous nucleic acid. In some such embodiments thenon-naturally occurring microbial organism is in a substantially anaerobic culture medium.

In some embodiments, the present invention provides a method for producing 1,3-butadiene that includes culturing a non-naturally occurring microbial organism according to the aforementioned pathways described herein, under conditions and for a sufficient period of time to produce 1,3-butadiene. In some such embodiments, the microbial organism includes two, three, four, five, six, seven, or eight exogenous nucleic acids each encoding a 1,3-butadiene pathway enzyme. In some such embodiments, at least one exogenous nucleic acid is a heterologous nucleic acid. In some such embodiments, the non-naturally occurring microbial organism is in a substantially anaerobic culture medium.

In some embodiments, the present invention provides a method for producing 3-butene-1-ol which includes culturing a non-naturally occurring microbial organism according to the aforementioned pathway described herein, under conditions and for a sufficient period of time to produce 3-butene-1-ol. In some such embodiments, the microbial organism includes two, three, four, five, six, or seven exogenous nucleic acids each encoding a 3-butene-1-ol pathway enzyme. In some such embodiments, at least one exogenous nucleic acid is a heterologous nucleic acid. In some such embodiments, the non-naturally occurring microbial organism is in a substantially anaerobic culture medium. In some such embodiments, methods of the invention further include the chemical dehydration of 3-butene-1-ol to provide 1,3-butadiene.

3-butene-1-ol can be chemically dehydrated with formation of 1,3-butadiene, starting with pure 3-butene-1-ol isolated from the fermentation solution or starting with an aqueous or organic solutions of 3-butene-1-ol, isolated in work up of the fermentation solution. Such solutions of 3-butene-1-ol can also be concentrated before the dehydration step, for example by means of distillation, optionally in the presence of a suitable entrainer.

The dehydration reaction can be carried out in liquid phase or in the gas phase. The dehydration reaction can be carried out in the presence of a catalyst, the nature of the catalyst employed depending on whether a gas-phase or a liquid-phase reaction is carried out.

Suitable dehydration catalysts include both acidic catalysts and alkaline catalysts. Acidic catalysts, in particular can exhibit a decreased tendency to form oligomers. The dehydration catalyst can be employed as a homogeneous catalyst, a heterogeneous catalyst, or combinations thereof. Heterogeneous catalysts can be used in conjunction with a suitable support material. Such a support can itself be acidic or alkaline and provide the acidic or alkaline dehydration catalyst or a catalyst can be applied to an inert support.

Suitable supports which serve as dehydration catalysts include natural or synthetic silicates such as mordenite, montmorillonite, acidic zeolites; supports which are coated with monobasic, dibasic or polybasic inorganic acids, such as phosphoric acid, or with acidic salts of inorganic acids, such as oxides or silicates, for example $Al_2O_3$, $TiO_2$; oxides and mixed oxides such as $\gamma$-$Al_2O_3$ and ZnO—$Al_2O_3$ mixed oxides of heteropolyacids. Alkaline substances which act both as dehydration catalyst and as a support a support material include alkali, alkaline earth, lanthanum, lanthoids or a combinations thereof as their oxides. A further class of materials that can effect dehydration are ion exchangers which can be used in either alkaline or acidic form.

Suitable homogeneous dehydration catalysts include inorganic acids, such as phosphorus-containing acids such as phosphoric acid. Inorganic acids can be immobilized on the support material by immersion or impregnation.

In some embodiments, dehydration reaction is carried out in the gas phase using conventional apparatuses known in the art, for example tubular reactors, shell-and-tube heat exchangers and reactors which comprise thermoplates as heat exchangers. In some embodiments, gas-phase dehydration can utilize isolated 3-butene-1-ol or solutions of butene-1-ol, the butene-1-ol being introduced into a reactor with fixed-bed catalysts. Thermal dehydration in the liquid phase can be carried out in a temperature range of between 200° C. and 350° C., and in some embodiments between 250 and 300° C.

Suitable purification and/or assays to test for the production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. For example, the activity of phenylpyruvate decarboxylase can be measured using a coupled photometric assay with alcohol dehydrogenase as an auxiliary enzyme as described by Weiss et al (Weiss et al., *Biochem*, 27:2197-2205 (1988). NADH- and NADPH-dependent enzymes such as acetophenone reductase can be followed spectrophotometrically at 340 nm as described by Schlieben et al (Schlieben et al, *J. Mol. Biol.*, 349:801-813 (2005)). For typical hydrocarbon assay methods, see Manual on Hydrocarbon Analysis (ASTM Manula Series, A. W. Drews, ed., 6th edition, 1998, American Society for Testing and Materials, Baltimore, Md. P-toluate methyl-monooxygenase activity can be assayed by incubating purified enzyme with NADH, $FeSO_4$ and the p-toluate substrate in a water bath, stopping the reaction by precipitation of the proteins, and analysis of the products in the supernatant by HPLC (Locher et al., J. Bacteriol. 173:3741-3748 (1991)).

The toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene producers can be cultured for the biosynthetic production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene.

For the production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United States publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch.

Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene.

In addition to renewable feedstocks such as those exemplified above, the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene microbial organisms of the invention also can be modified for growth on syngas as its source of carbon. In this specific embodiment, one or more proteins or enzymes are expressed in the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

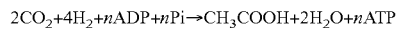

$$2CO_2+4H_2+n\text{ADP}+n\text{Pi} \rightarrow CH_3COOH+2H_2O+n\text{ATP}$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains the complete reductive TCA pathway will confer syngas utilization ability.

In some embodiments, the invention provides a non-naturally occurring microbial organism, comprising a microbial organism having a 1,3-butadiene pathway comprising at least one exogenous nucleic acid encoding a 1,3-butadiene pathway enzyme expressed in a sufficient amount to produce 1,3-butadiene, said 1,3-butadiene pathway selected from: (A) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate dehydrogenase; a 2-fumarylacetate decarboxylase; a 3-oxopent-4-enoate reductase; and a 3-hydroxypent-4-enoate decarboxylase; (B) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate dehydrogenase; a 2-fumarylacetate decarboxylase; a 3-oxopent-4-enoate reductase; a 3-hydroxypent-4-enoate dehydratase; and a 2,4-pentadienoate decarboxylase; (C) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate dehydrogenase; a 2-fumarylacetate reductase; a 3-hydroxyhex-4-enedioate decarboxylase; and a 3-hydroxypent-4-enoate decarboxylase; (D) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate dehydrogenase; a 2-fumarylacetate reductase; a 3-hydroxyhex-4-enedioate decarboxylase; a 3-hydroxypent-4-enoate dehydratase; and a 2,4-pentadienoate decarboxylase; (E) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate reductase; a 3-hydroxyadipate dehydrogenase; a 3-hydroxyhex-4-enedioate decarboxylase; and a 3-hydroxypent-4-enoate decarboxylase; (F) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate reductase; a 3-hydroxyadipate dehydrogenase; a 3-hydroxyhex-4-enedioate decarboxylase; a 3-hydroxypent-4-enoate dehydratase; and a 2,4-pentadienoate decarboxylase; (G) a succinyl-CoA:acetyl-CoA acyltransferase; a 3-oxoadipyl-CoA reductase; a 3-hydroxyadipyl-CoA transferase, a 3-hydroxyadipyl-CoA synthetase or a 3-hydroxyadipyl-CoA hydrolase; a 3-hydroxyadipate dehydrogenase; a 3-hydroxyhex-4-enedioate decarboxylase; and a 3-hydroxypent-4-enoate decarboxylase; and (H) a succinyl-CoA:acetyl-CoA acyltransferase; a 3-oxoadipyl-CoA reductase; a 3-hydroxyadipyl-CoA transferase, a 3-hydroxyadipyl-CoA synthetase or a 3-hydroxyadipyl-CoA hydrolase; a 3-hydroxyadipate dehydrogenase; a 3-hydroxyhex-4-enedioate decarboxylase; a 3-hydroxypent-4-enoate dehydratase; and a 2,4-pentadienoate decarboxylase.

In some aspects, the non-naturally occurring microbial organism comprises two, three, four, five, six or seven exogenous nucleic acids each encoding a 1,3-butadiene pathway enzyme. For example, the microbial organism can comprise exogenous nucleic acids encoding each of the enzymes selected from: (A) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate dehydrogenase; a 2-fumarylacetate decarboxylase; a 3-oxopent-4-enoate reductase; and a 3-hydroxypent-4-enoate decarboxylase; (B) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate dehydrogenase; a 2-fumarylacetate decarboxylase; a 3-oxopent-4-enoate reductase; a 3-hydroxypent-4-enoate dehydratase; and a 2,4-pentadienoate decarboxylase; (C) a succinyl-CoA:acetyl-CoA acyltransferase; a 3-oxoadipyl-CoA transferase; a 3-oxoadipyl-CoA synthetase or a 3-oxoadipyl-CoA hydrolase; a 3-oxoadipate dehydrogenase; a 2-fumarylacetate reductase; a 3-hydroxyhex-4-enedioate decarboxylase; and a 3-hydroxypent-4-enoate decarboxylase; (D) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate dehydrogenase; a 2-fumarylacetate reductase; a 3-hydroxyhex-4-enedioate decarboxylase; a 3-hydroxypent-4-enoate dehydratase; and a 2,4-pentadienoate decarboxylase; (E) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate reductase; a 3-hydroxyadipate dehydrogenase; a 3-hydroxyhex-4-enedioate decarboxylase; and a 3-hydroxypent-4-enoate decarboxylase; (F) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate reductase; a 3-hydroxyadipate dehydrogenase; a 3-hydroxyhex-4-enedioate decarboxylase; a 3-hydroxypent-4-enoate dehydratase; and a 2,4-pentadienoate decarboxylase; (G) a succinyl-CoA:acetyl-CoA acyltransferase; a 3-oxoadipyl-CoA reductase; a 3-hydroxyadipyl-CoA transferase, a 3-hydroxyadipyl-CoA synthetase or a 3-hydroxyadipyl-CoA hydrolase; a 3-hydroxyadipate dehydrogenase; a 3-hydroxyhex-4-enedioate decarboxylase; and a 3-hydroxypent-4-enoate decarboxylase; and (H) a succinyl-CoA:acetyl-CoA acyltransferase; a 3-oxoadipyl-CoA reductase; a 3-hydroxyadipyl-CoA transferase, a 3-hydroxyadipyl-CoA synthetase or a 3-hydroxyadipyl-CoA hydrolase; a 3-hydroxyadipate dehydrogenase; a 3-hydroxyhex-4-enedioate decarboxylase; a 3-hydroxypent-4-enoate dehydratase; and a 2,4-pentadienoate decarboxylase.

In some embodiments, the invention provides a non-naturally occurring microbial organism as described above, wherein said microbial organism further comprises: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an H2 hydrogenase; or (iii) at least one exogenous nucleic acid encodes an enzyme selected from a CO dehydrogenase, an H2 hydrogenase, and combinations thereof. In some aspects of the invention, the microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In some aspects of the invention, the microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In some embodiments, the invention provides a non-naturally occurring microbial organism of as described above, wherein said microbial organism comprising (i)

comprises four exogenous nucleic acids encoding an ATP-citrate lyase, citrate lyase, a fumarate reductase, and an alpha-ketoglutarate:ferredoxin oxidoreductase; wherein said microbial organism comprising (ii) comprises five exogenous nucleic acids encoding a pyruvate:ferredoxin oxidoreductase, a phosphoenolpyruvate carboxylase, a phosphoenolpyruvate carboxykinase, a CO dehydrogenase, and an $H_2$ hydrogenase; or wherein said microbial organism comprising (iii) comprises two exogenous nucleic acids encoding a CO dehydrogenase and an $H_2$ hydrogenase.

In some aspects, the invention provides that the non-naturally occurring microbial organism as described herein, wherein said at least one exogenous nucleic acid is a heterologous nucleic acid. In another aspect, the non-naturally occurring microbial organism is in a substantially anaerobic culture medium. In some embodiments, the invention provides a method for producing 1,3-butadiene, comprising culturing a non-naturally occurring microbial organism as described herein under conditions and for a sufficient period of time to produce 1,3-butadiene.

In some embodiments, the invention provides a non-naturally occurring microbial organism, comprising a microbial organism having a 2,4-pentadienoate pathway comprising at least one exogenous nucleic acid encoding a 2,4-pentadienoate pathway enzyme expressed in a sufficient amount to produce 2,4-pentadienoate, said 2,4-pentadienoate pathway selected from: (A) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate dehydrogenase; a 2-fumarylacetate decarboxylase; a 3-oxopent-4-enoate reductase; and a 3-hydroxypent-4-enoate dehydratase; (B) a succinyl-CoA:acetyl-CoA acyltransferase; a 3-oxoadipyl-CoA transferase, a 3-oxoadipyl-CoA synthetase or a 3-oxoadipyl-CoA hydrolase; a 3-oxoadipate dehydrogenase; a 2-fumarylacetate reductase; a 3-hydroxyhex-4-enedioate decarboxylase; and a 3-hydroxypent-4-enoate dehydratase; (C) a succinyl-CoA:acetyl-CoA acyltransferase; a 3-oxoadipyl-CoA transferase, a 3-oxoadipyl-CoA synthetase ora 3-oxoadipyl-CoA hydrolase; a 3-oxoadipate reductase; a 3-hydroxyadipate dehydrogenase; a 3-hydroxyhex-4-enedioate decarboxylase; and a 3-hydroxypent-4-enoate dehydratase; and (D) a succinyl-CoA:acetyl-CoA acyltransferase; a 3-oxoadipyl-CoA reductase; a 3-hydroxyadipyl-CoA transferase, a 3-hydroxyadipyl-CoA synthetase or a 3-hydroxyadipyl-CoA hydrolase; a 3-hydroxyadipate dehydrogenase; a 3-hydroxyhex-4-enedioate decarboxylase; and a 3-hydroxypent-4-enoate dehydratase.

In some aspects, the microbial organism comprises two, three, four, five, or six exogenous nucleic acids each encoding a 2,4-pentadienoate pathway enzyme. For example, the microbial organism can comprise exogenous nucleic acids encoding each of the enzymes selected from: (A) a succinyl-CoA:acetyl-CoA acyltransferase; a 3-oxoadipyl-CoA transferase, a 3-oxoadipyl-CoA synthetase ora 3-oxoadipyl-CoA hydrolase; a 3-oxoadipate dehydrogenase; a 2-fumarylacetate decarboxylase; a 3-oxopent-4-enoate reductase; and a 3-hydroxypent-4-enoate dehydratase; (B) a succinyl-CoA:acetyl-CoA acyltransferase; a 3-oxoadipyl-CoA transferase, a 3-oxoadipyl-CoA synthetase ora 3-oxoadipyl-CoA hydrolase; a 3-oxoadipate dehydrogenase; a 2-fumarylacetate reductase; a 3-hydroxyhex-4-enedioate decarboxylase; and a 3-hydroxypent-4-enoate dehydratase; (C) a succinyl-CoA:acetyl-CoA acyltransferase; a 3-oxoadipyl-CoA transferase, a 3-oxoadipyl-CoA synthetase ora 3-oxoadipyl-CoA hydrolase; a 3-oxoadipate reductase; a 3-hydroxyadipate dehydrogenase; a 3-hydroxyhex-4-enedioate decarboxylase; and a 3-hydroxypent-4-enoate dehydratase; and (D) a succinyl-CoA:acetyl-CoA acyltransferase; a 3-oxoadipyl-CoA reductase; a 3-hydroxyadipyl-CoA transferase, a 3-hydroxyadipyl-CoA synthetase or a 3-hydroxyadipyl-CoA hydrolase; a 3-hydroxyadipate dehydrogenase; a 3-hydroxyhex-4-enedioate decarboxylase; and a 3-hydroxypent-4-enoate dehydratase.

In some embodiments, the invention provides a non-naturally occurring microbial organism as described above, wherein said microbial organism further comprises: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an H2 hydrogenase; or (iii) at least one exogenous nucleic acid encodes an enzyme selected from a CO dehydrogenase, an H2 hydrogenase, and combinations thereof. In some aspects, the microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In some aspects, the microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In some aspects, the non-naturally occurring microbial orgnaism comprising (i) comprises four exogenous nucleic acids encoding an ATP-citrate lyase, citrate lyase, a fumarate reductase, and an alpha-ketoglutarate:ferredoxin oxidoreductase; wherein said microbial organism comprising (ii) comprises five exogenous nucleic acids encoding a pyruvate:ferredoxin oxidoreductase, a phosphoenolpyruvate carboxylase, a phosphoenolpyruvate carboxykinase, a CO dehydrogenase, and an $H_2$ hydrogenase; or wherein said microbial organism comprising (iii) comprises two exogenous nucleic acids encoding a CO dehydrogenase and an $H_2$ hydrogenase.

In some aspects, the invention provides that the non-naturally occurring microbial organism as disclosed above, wherein said at least one exogenous nucleic acid is a heterologous nucleic acid. In some aspects, the non-naturally occurring microbial organism is in a substantially anaerobic culture medium.

In some embodiments, the invention provides a method for producing 2,4-pentadienoate, comprising culturing a non-naturally occurring microbial organism as described herein under conditions and for a sufficient period of time to produce 2,4-pentadienoate.

In some embodiments, the invention provides a non-naturally occurring microbial organism, comprising a microbial organism having a 1,3-butadiene pathway comprising at least one exogenous nucleic acid encoding a 1,3-butadiene pathway enzyme expressed in a sufficient amount to produce 1,3-butadiene, said 1,3-butadiene pathway selected from: (A) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate dehydratase; a 5-hydroxypent-2-enoate dehydratase; and a 2,4-pentadiene decarboxylase; (B) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate dehydratase; a 5-hydroxypent-2-enoate decarboxylase; and a 3-butene-1-ol dehydratase; (C) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate decarboxylase; and a 3-butene-1-ol dehydratase; (D) a malonyl-CoA:acetyl-CoA acyltransferase; a 3-oxoglutaryl-CoA reductase (CoA reducing and alcohol forming); a 5-hydroxy-3-oxopentanoate reductase; a 3,5-dihydroxypentanoate dehydratase; a 5-hydroxypent-2-enoate dehydratase; and a 2,4-pentadiene decarboxylase; (E) a malonyl-CoA:acetyl-CoA acyltransferase; a 3-oxoglutaryl-CoA reductase (CoA reducing and alcohol forming); a 5-hydroxy-3-oxopentanoate reductase; a 3,5-dihydroxypentanoate dehydratase; a 5-hydroxypent-2-enoate decarboxylase; and a 3-butene-1-ol dehydratase; (F) a malonyl-CoA:acetyl-CoA acyltransferase; a 3-oxoglutaryl-CoA reductase (CoA reducing and alcohol forming); a 5-hydroxy-3-oxopentanoate reductase; a 3,5-dihydroxypentanoate decarboxylase; and a 3-butene-1-ol dehydratase; (G) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate dehydratase; a 5-hydroxypent-2-enoate dehydratase; and a 2,4-pentadiene decarboxylase; (H) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate dehydratase; a 5-hydroxypent-2-enoate decarboxylase; and a 3-butene-1-ol dehydratase; (I) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate decarboxylase; and a 3-butene-1-ol dehydratase; (J) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate dehydratase; a 5-hydroxypent-2-enoate dehydratase; and a 2,4-pentadiene decarboxylase; (K) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate dehydratase; a 5-hydroxypent-2-enoate decarboxylase; and a 3-butene-1-ol dehydratase; (M) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate dehydratase; a 5-hydroxypent-2-enoate dehydratase; and a 2,4-pentadiene decarboxylase; (N) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate dehydratase; a 5-hydroxypent-2-enoate decarboxylase; and a 3-butene-1-ol dehydratase; and (O) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate decarboxylase; and a 3-butene-1-ol dehydratase.

In some embodiments, the invention provides a nonnaturally occurring microbial organism as described above, wherein said microbial organism comprises two, three, four, five, six or seven exogenous nucleic acids each encoding a 1,3-butadiene pathway enzyme. For example, in some aspects, the microbial organism comprises exogenous nucleic acids encoding each of the enzymes selected from: (A) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate dehydratase; a 5-hydroxypent-2-enoate dehydratase; and a 2,4-pentadiene decarboxylase; (B) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate dehydratase; a 5-hydroxypent-2-enoate decarboxylase; and a 3-butene-1-ol dehydratase; (C) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate decarboxylase; and a 3-butene-1-ol dehydratase; (D) a malonyl-CoA:acetyl-CoA acyltransferase; a 3-oxoglutaryl-CoA reductase (CoA reducing and alcohol forming); a 5-hydroxy-3-oxopentanoate reductase; a 3,5-dihydroxypentanoate dehydratase; a 5-hydroxypent-2-enoate dehydratase; and a 2,4-pentadiene decarboxylase; (E) a malonyl-CoA:acetyl-CoA acyltransferase; a 3-oxoglutaryl-CoA reductase (CoA reducing and alcohol forming); a 5-hydroxy-3-oxopentanoate reductase; a 3,5-dihydroxypentanoate dehydratase; a 5-hydroxypent-2-enoate decarboxylase; and a 3-butene-1-ol dehydratase; (F) a malonyl-CoA:acetyl-CoA acyltransferase; a 3-oxoglutaryl-CoA reductase (CoA reducing and alcohol forming); a 5-hydroxy-3-oxopentanoate reductase; a 3,5-dihydroxypentanoate decarboxylase; and a 3-butene-1-ol dehydratase; (G) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate dehydratase; a 5-hydroxypent-2-enoate dehydratase; and a 2,4-pentadiene decarboxylase; (H) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate dehydratase; a 5-hydroxypent-2-enoate decarboxylase; and a 3-butene-1-ol dehydratase; (I) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate decarboxylase; and a 3-butene-1-ol dehydratase; (J) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate dehydratase; a 5-hydroxypent-2-enoate dehydratase; and a 2,4-pentadiene decarboxylase; (K) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate dehydratase; a 5-hydroxypent-2- enoate decarboxylase; and a 3-butene-1-ol dehydratase; (L) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate decarboxylase; and a 3-butene-1-ol dehydratase; (M) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate dehydratase; a 5-hydroxypent-2-enoate dehydratase; and a 2,4-pentadiene decarboxylase; (N) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate dehydratase; a 5-hydroxypent-2-enoate decarboxylase; and a 3-butene-1-ol dehydratase; and (O) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate decarboxylase; and a 3-butene-1-ol dehydratase.

In some embodiments, the invention provides a non-naturally occurring microbial organism as disclosed above, wherein said microbial organism further comprises: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an H2 hydrogenase; or (iii) at least one exogenous nucleic acid encodes an enzyme selected from a CO dehydrogenase, an H2 hydrogenase, and combinations thereof. In some aspects, the non-naturally occurring microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In some aspects, the microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof. In some aspects, the microbial organism comprising (i) comprises four exogenous nucleic acids encoding an ATP-citrate lyase, citrate lyase, a fumarate reductase, and an alpha-ketoglutarate:ferredoxin oxidoreductase; wherein said microbial organism comprising (ii) comprises five exogenous nucleic acids encoding a pyruvate:ferredoxin oxidoreductase, a phosphoenolpyruvate carboxylase, a phosphoenolpyruvate carboxykinase, a CO dehydrogenase, and an $H_2$ hydrogenase; or wherein said microbial organism comprising (iii) comprises two exogenous nucleic acids encoding a CO dehydrogenase and an $H_2$ hydrogenase.

In some aspects, the non-naturally occurring microbial organism as disclosed herein includes, wherein said at least one exogenous nucleic acid is a heterologous nucleic acid. In some aspects, the non-naturally occurring microbial organism is in a substantially anaerobic culture medium.

In some embodiments, the invention provides a method for producing 1,3-butadiene, comprising culturing a non-naturally occurring microbial organism as disclosed herein under conditions and for a sufficient period of time to produce 1,3-butadiene.

In some embodiments, the invention provides a non-naturally occurring microbial organism, comprising a microbial organism having a 2,4-pentadienoate pathway comprising at least one exogenous nucleic acid encoding a 2,4-pentadienoate pathway enzyme expressed in a sufficient amount to produce 2,4-pentadienoate, said 2,4-pentadienoate pathway selected from: (A) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate dehydratase; and a 5-hydroxypent-2-enoate dehydratase; (B) a malonyl-CoA:acetyl-CoA acyltransferase; a 3-oxoglutaryl-CoA reductase (CoA reducing and alcohol forming); a 5-hydroxy-3-oxopentanoate reductase; a 3,5-dihydroxypentanoate dehydratase; and a 5-hydroxypent-2-enoate dehydratase; (C) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate dehydratase; and a 5-hydroxypent-2-enoate dehydratase; (D) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate dehydratase; and a 5-hydroxypent-2-enoate dehydratase; and (E) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate dehydratase; and a 5-hydroxypent-2-enoate dehydratase.

In some aspects, the non-naturally occurring microbial organism as disclosed above comprises two, three, four, five or six exogenous nucleic acids each encoding a 2,4-pentadienoate pathway enzyme. For example, the microbial organism comprises exogenous nucleic acids encoding each of the enzymes selected from: (A) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate dehydratase; and a 5-hydroxypent-2-enoate dehydratase; (B) a malonyl-CoA:acetyl-CoA acyltransferase; a 3-oxoglutaryl-CoA reductase (CoA reducing and alcohol forming); a 5-hydroxy-3-oxopentanoate reductase; a 3,5-dihydroxypentanoate dehydratase; and a 5-hydroxypent-2-enoate dehydratase; (C) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate dehydratase; and a 5-hydroxypent-2-enoate dehydratase; (D) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate dehydratase; and a 5-hydroxypent-2-enoate dehydratase; and (E) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate dehydratase; and a 5-hydroxypent-2-enoate dehydratase.

In some embodiments, the invention provides a non-naturally occurring microbial organism as disclosed above, wherein said microbial organism further comprises: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an H2 hydrogenase; or (iii) at least one exogenous nucleic acid encodes an enzyme selected from a CO dehydrogenase, an H2 hydrogenase, and combinations thereof. In some aspects, the microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In some aspects, the non-naturally occurring microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In some aspects, the microbial organism as disclose above comprising (i) comprises four exogenous nucleic acids encoding an ATP-citrate lyase, citrate lyase, a fumarate reductase, and an alpha-ketoglutarate:ferredoxin oxidoreductase; wherein said microbial organism comprising (ii) comprises five exogenous nucleic acids encoding a pyruvate:ferredoxin oxidoreductase, a phosphoenolpyruvate carboxylase, a phosphoenolpyruvate carboxykinase, a CO dehydrogenase, and an $H_2$ hydrogenase; or wherein said microbial organism comprising (iii) comprises two exogenous nucleic acids encoding a CO dehydrogenase and an $H_2$ hydrogenase.

In some aspects, the non-naturally occurring microbial organism as disclosed herein includes, wherein said at least one exogenous nucleic acid is a heterologous nucleic acid. In some aspects, the non-naturally occurring microbial organism is in a substantially anaerobic culture medium.

In some embodiments, the invention provides a method for producing 2,4-pentadienoate, comprising culturing a non-naturally occurring microbial organism as disclosed above under conditions and for a sufficient period of time to produce 2,4-pentadienoate.

In some embodiments, the invention provides a non-naturally occurring microbial organism, comprising a microbial organism having a 3-butene-1-ol pathway comprising at least one exogenous nucleic acid encoding a 3-butene-1-ol pathway enzyme expressed in a sufficient amount to produce 3-butene-1-ol, said 3-butene-1-ol pathway selected from: (A) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate dehydratase; and a 5-hydroxypent-2-enoate decarboxylase; (B) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; and a 3,5-dihydroxypentanoate decarboxylase; (C) a malonyl-CoA:acetyl-CoA acyltransferase; a 3-oxoglutaryl-CoA reductase (CoA reducing and alcohol forming); a 5-hydroxy-3-oxopentanoate reductase; a 3,5-dihydroxypentanoate dehydratase; and a 5-hydroxypent-2-enoate decarboxylase; (D) a malonyl-CoA:acetyl-CoA acyltransferase; a 3-oxoglutaryl-CoA reductase (CoA reducing and alcohol forming); a 5-hydroxy-3-oxopentanoate reductase; and a 3,5-dihydroxypentanoate decarboxylase; (E) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate dehydratase; and a 5-hydroxypent-2-enoate decarboxylase; (F) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; and a 3,5-dihydroxypentanoate decarboxylase; (G) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate dehydratase; and a 5-hydroxypent-2-enoate decarboxylase; (H) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; and a 3,5-dihydroxypentanoate decarboxylase; (I) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate dehydratase; and a 5-hydroxypent-2-enoate decarboxylase; and (J) a malonyl-CoA:acetyl-CoA acyltransferase; a 3-oxoglutaryl-CoA reductase (ketone-reducing); a 3-hydroxyglutaryl-CoA reductase (alcohol forming); and a 3,5-dihydroxypentanoate decarboxylase.

In some aspects, the non-naturally occurring microbial organism as disclosed above comprises two, three, four or five exogenous nucleic acids each encoding a 3-butene-1-ol pathway enzyme. For example, in some aspects, microbial organism comprises exogenous nucleic acids encoding each of the enzymes selected from: (A) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; a 3,5-dihydroxypentanoate dehydratase; and a 5-hydroxypent-2-enoate decarboxylase; (B) a malonyl-CoA:acetyl-CoA acyltransferase; a 3-oxoglutaryl-CoA reductase (aldehyde forming); a 3,5-dioxopentanoate reductase (aldehyde reducing); a 5-hydroxy-3-oxopentanoate reductase; and a 3,5-dihydroxypentanoate decarboxylase; (C) a malonyl-CoA: acetyl-CoA acyltransferase; a 3-oxoglutaryl-CoA reductase (CoA reducing and alcohol forming); a 5-hydroxy-3-oxopentanoate reductase; a 3,5-dihydroxypentanoate dehydratase; and a 5-hydroxypent-2-enoate decarboxylase; (D) a malonyl-CoA:acetyl-CoA acyltransferase; a 3-oxoglutaryl-CoA reductase (CoA reducing and alcohol forming); a 5-hydroxy-3-oxopentanoate reductase; and a 3,5-dihydroxypentanoate decarboxylase; (E) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; a 3,5-dihydroxypentanoate dehydratase; and a 5-hydroxypent-2-enoate decarboxylase; (F) a malonyl-CoA:acetyl-CoA acyltransferase; a 3-oxoglutaryl-CoA reductase (aldehyde forming); a 3,5-dioxopentanoate reductase (ketone reducing); a 3-hydroxy-5-oxopentanoate reductase; and a 3,5-dihydroxypentanoate decarboxylase; (G) a malonyl-CoA: acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate dehydratase; and a 5-hydroxypent-2-enoate decarboxylase; (H) a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; and a 3,5-dihydroxypentanoate decarboxylase; (I) a malonyl-CoA:acetyl-CoA acyltransferase; a 3-oxoglutaryl-CoA reductase (ketone-reducing); a 3-hydroxyglutaryl-CoA reductase (alcohol forming); a 3,5-dihydroxypentanoate dehydratase; and a 5-hydroxypent-2-enoate decarboxylase; and (J) a malonyl-CoA:acetyl-CoA acyltransferase; a 3-oxoglutaryl-CoA reductase (ketone-reducing); a 3-hydroxyglutaryl-CoA reductase (alcohol forming); and a 3,5-dihydroxypentanoate decarboxylase.

In some embodiments, the invention provides a non-naturally occurring microbial organism as disclosed above, wherein said microbial organism further comprises: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an H2 hydrogenase; or (iii) at least one exogenous nucleic acid encodes an enzyme selected from a CO dehydrogenase, an H2 hydrogenase, and combinations thereof. In some aspects, the non-naturally occurring microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In some aspects, the non-naturally occurring microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof. In some aspects, the non-naturally occurring microbial comprising (i) comprises four exogenous nucleic acids encoding an ATP-citrate lyase, citrate lyase, a fumarate reductase, and an alpha-ketoglutarate:ferredoxin oxidoreductase; wherein said microbial organism comprising (ii) comprises five exogenous nucleic acids encoding a pyruvate:ferredoxin oxidoreductase, a phosphoenolpyruvate carboxylase, a phosphoenolpyruvate carboxykinase, a CO dehydrogenase, and an $H_2$ hydrogenase; or wherein said microbial organism comprising (iii) comprises two exogenous nucleic acids encoding a CO dehydrogenase and an $H_2$ hydrogenase.

In some aspects, the non-naturally occurring microbial organism as disclosed herein includes, wherein said at least one exogenous nucleic acid is a heterologous nucleic acid. In some aspects, the non-naturally occurring microbial organism is in a substantially anaerobic culture medium.

In some embodiments, the invention provides a method for producing 3-butene-1-ol, comprising culturing a non-naturally occurring microbial organism as disclosed above under conditions and for a sufficient period of time to produce 3-butene-1-ol.

In some embodiments, the invention provides a method for producing 1,3-butadiene comprising, culturing a non-naturally occurring microbial organism that can produce 3-butene-1-ol as disclosed above under conditions and for a sufficient period of time to produce 3-butene-1-ol, and chemically converting said 3-butene-1-ol to 1,3-butadiene. It is understood that methods for chemically converting 3-butene-1-ol to 1,3-butadiene are well know in the art.

This invention is also directed, in part to engineered biosynthetic pathways to improve carbon flux through a central metabolism intermediate en route to 2,4-pentadienoate, 3-butene-1-ol, or 1,3-butadiene. The present invention provides non-naturally occurring microbial organisms having one or more exogenous genes encoding enzymes that can catalyze various enzymatic transformations en route to 2,4-pentadienoate, 3-butene-1-ol, or 1,3-butadiene. In some embodiments, these enzymatic transformations are part of the reductive tricarboxylic acid (RTCA) cycle and are used to improve product yields, including but not limited to, from carbohydrate-based carbon feedstock.

In numerous engineered pathways, realization of maximum product yields based on carbohydrate feedstock is hampered by insufficient reducing equivalents or by loss of reducing equivalents and/or carbon to byproducts. In accordance with some embodiments, the present invention increases the yields of 2,4-pentadienoate, 3-butene-1-ol, or 1,3-butadiene by (i) enhancing carbon fixation via the reductive TCA cycle, and/or (ii) accessing additional reducing equivalents from gaseous carbon sources and/or syngas components such as CO, $CO_2$, and/or $H_2$. In addition to syngas, other sources of such gases include, but are not limited to, the atmosphere, either as found in nature or generated.

The $CO_2$-fixing reductive tricarboxylic acid (RICA) cycle is an endergenic anabolic pathway of $CO_2$ assimilation which uses reducing equivalents and ATP (FIG. 22). One turn of the RICA cycle assimilates two moles of $CO_2$ into one mole of acetyl-CoA, or four moles of $CO_2$ into one mole of oxaloacetate. This additional availability of acetyl-CoA improves the maximum theoretical yield of product molecules derived from carbohydrate-based carbon feedstock. Exemplary carbohydrates include but are not limited to glucose, sucrose, xylose, arabinose and glycerol.

In some embodiments, the reductive TCA cycle, coupled with carbon monoxide dehydrogenase and/or hydrogenase enzymes, can be employed to allow syngas, $CO_2$, CO, $H_2$, and/or other gaseous carbon source utilization by microorganisms. Synthesis gas (syngas), in particular is a mixture of primarily $H_2$ and CO, sometimes including some amounts of $CO_2$, that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. In addition to coal, biomass of many types has been used for syngas production and represents an inexpensive and flexible feedstock for the biological production of renewable chemicals and fuels. Carbon dioxide can be provided from the atmosphere or in condensed from, for example, from a tank cylinder, or via sublimation of solid $CO_2$. Similarly, CO and hydrogen gas can be provided in reagent form and/or mixed in any desired ratio. Other gaseous carbon forms can include, for example, methanol or similar volatile organic solvents.

The components of synthesis gas and/or other carbon sources can provide sufficient $CO_2$, reducing equivalents, and ATP for the reductive TCA cycle to operate. One turn of the RTCA cycle assimilates two moles of $CO_2$ into one mole of acetyl-CoA and requires 2 ATP and 4 reducing equivalents. CO and/or $H_2$ can provide reducing equivalents by means of carbon monoxide dehydrogenase and hydrogenase enzymes, respectively. Reducing equivalents can come in the form of NADH, NADPH, FADH, reduced quinones, reduced ferredoxins, reduced flavodoxins and thioredoxins. The reducing equivalents, particularly NADH, NADPH, and reduced ferredoxin, can serve as cofactors for the RTCA cycle enzymes, for example, malate dehydrogenase, fumarate reductase, alpha-ketoglutarate:ferredoxin oxidoreductase (alternatively known as 2-oxoglutarate:ferredoxin oxidoreductase, alpha-ketoglutarate synthase, or 2-oxoglutarate synthase), pyruvate:ferredoxin oxidoreductase and isocitrate dehydrogenase. The electrons from these reducing equivalents can alternatively pass through an ion-gradient producing electron transport chain where they are passed to an acceptor such as oxygen, nitrate, oxidized metal ions, protons, or an electrode. The ion-gradient can then be used for ATP generation via an ATP synthase or similar enzyme.

The reductive TCA cycle was first reported in the green sulfur photosynthetic bacterium *Chlorobium limicola* (Evans et al., *Proc. Natl. Acad. Sci. U.S.A.* 55:928-934 (1966)). Similar pathways have been characterized in some prokaryotes (proteobacteria, green sulfur bacteria and thermophillic Knallgas bacteria) and sulfur-dependent archaea (Hugler et al., *J. Bacteriol.* 187:3020-3027 (2005; Hugler et al., *Environ. Microbiol.* 9:81-92 (2007). In some cases, reductive and oxidative (Krebs) TCA cycles are present in the same organism (Hugler et al., supra (2007); Siebers et al., *J Bacteriol.* 186:2179-2194 (2004)). Some methanogens and obligate anaerobes possess incomplete oxidative or reductive TCA cycles that may function to synthesize biosynthetic intermediates (Ekiel et al., *J. Bacteriol.* 162:905-908 (1985); Wood et al., *FEMS Microbiol. Rev.* 28:335-352 (2004)).

The key carbon-fixing enzymes of the reductive TCA cycle are alpha-ketoglutarate:ferredoxin oxidoreductase, pyruvate:ferredoxin oxidoreductase and isocitrate dehydrogenase. Additional carbon may be fixed during the conversion of phosphoenolpyruvate to oxaloacetate by phosphoenolpyruvate carboxylase or phosphoenolpyruvate carboxykinase carboxykinase or by conversion of pyruvate to malate by malic enzyme.

Many of the enzymes in the TCA cycle are reversible and can catalyze reactions in the reductive and oxidative directions. However, some TCA cycle reactions are irreversible in vivo and thus different enzymes are used to catalyze these reactions in the directions required for the reverse TCA cycle. These reactions are: (1) conversion of citrate to oxaloacetate and acetyl-CoA, (2) conversion of fumarate to succinate, and (3) conversion of succinyl-CoA to alpha-ketoglutarate. In the TCA cycle, citrate is formed from the condensation of oxaloacetate and acetyl-CoA. The reverse reaction, cleavage of citrate to oxaloacetate and acetyl-CoA, is ATP-dependent and catalyzed by ATP-citrate lyase, or citryl-CoA synthetase and citryl-CoA lyase. Alternatively, citrate lyase can be coupled to acetyl-CoA synthetase, an acetyl-CoA transferase, or phosphotransacetylase and acetate kinase to form acetyl-CoA and oxaloacetate from citrate. The conversion of succinate to fumarate is catalyzed by succinate dehydrogenase while the reverse reaction is catalyzed by fumarate reductase. In the TCA cycle succinyl-CoA is formed from the $NAD(P)^+$ dependent decarboxylation of alpha-ketoglutarate by the alpha-ketoglutarate dehydrogenase complex. The reverse reaction is catalyzed by alpha-ketoglutarate:ferredoxin oxidoreductase.

An organism capable of utilizing the reverse tricarboxylic acid cycle to enable production of acetyl-CoA-derived products on 1) CO, 2) $CO_2$ and $H_2$, 3) CO and $CO_2$, 4) synthesis gas comprising CO and $H_2$, and 5) synthesis gas or other gaseous carbon sources comprising CO, $CO_2$, and $H_2$ can include any of the following enzyme activities: ATP-citrate lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, acetate kinase, phosphotransacetylase, acetyl-CoA synthetase, acetyl-CoA transferase, pyruvate:ferredoxin oxidoreductase, NAD(P)H:ferredoxin oxidoreductase, carbon monoxide dehydrogenase, hydrogenase, and ferredoxin (see FIG. 23). Enzymes and the corresponding genes required for these activities are described herein above.

Carbon from syngas or other gaseous carbon sources can be fixed via the reverse TCA cycle and components thereof. Specifically, the combination of certain carbon gas-utilization pathway components with the pathways for formation of 2,4-pentadienoate, 3-butene-1-ol, or 1,3-butadiene from acetyl-CoA results in high yields of these products by providing an efficient mechanism for fixing the carbon present in carbon dioxide, fed exogenously or produced endogenously from CO, into acetyl-CoA.

In some embodiments, a 2,4-pentadienoate, 3-butene-1-ol, or 1,3-butadiene pathway in a non-naturally occurring microbial organism of the invention can utilize any combination of (1) CO, (2) $CO_2$, (3) $H_2$, or mixtures thereof to enhance the yields of biosynthetic steps involving reduction, including addition to driving the reductive TCA cycle.

In some embodiments a non-naturally occurring microbial organism having an 2,4-pentadienoate, 3-butene-1-ol, or 1,3-butadiene pathway includes at least one exogenous nucleic acid encoding a reductive TCA pathway enzyme. The at least one exogenous nucleic acid is selected from an ATP-citrate lyase, citrate lyase, a fumarate reductase, isocitrate dehydrogenase, aconitase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$.

In some embodiments a method includes culturing a non-naturally occurring microbial organism having a 2,4-pentadienoate, 3-butene-1-ol, or 1,3-butadiene pathway also comprising at least one exogenous nucleic acid encoding a reductive TCA pathway enzyme. The at least one exogenous nucleic acid is selected from an ATP-citrate lyase, citrate lyase, a fumarate reductase, isocitrate dehydrogenase, aconitase, and an alpha-ketoglutarate:ferredoxin oxidoreductase. Additionally, such an organism can also include at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$ to produce a product.

In some embodiments a non-naturally occurring microbial organism having an 2,4-pentadienoate, 3-butene-1-01, or 1,3-butadiene pathway further includes at least one exogenous nucleic acid encoding a reductive TCA pathway enzyme expressed in a sufficient amount to enhance carbon flux through acetyl-CoA. The at least one exogenous nucleic acid is selected from an ATP-citrate lyase, citrate lyase, a fumarate reductase, a pyruvate:ferredoxin oxidoreductase, isocitrate dehydrogenase, aconitase and an alpha-ketoglutarate:ferredoxin oxidoreductase.

In some embodiments a non-naturally occurring microbial organism having an 2,4-pentadienoate, 3-butene-1-ol, or 1,3-butadiene pathway includes at least one exogenous nucleic acid encoding an enzyme expressed in a sufficient amount to enhance the availability of reducing equivalents in the presence of carbon monoxide and/or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H:ferredoxin oxidoreductase, and a ferredoxin. In some embodiments, the present invention provides a method for enhancing the availability of reducing equivalents in the presence of carbon monoxide or hydrogen thereby increasing the yield of redox-limited products via carbohydrate-based carbon feedstock, such as sugars or gaseous carbon sources, the method includes culturing this non-naturally occurring microbial organism under conditions and for a sufficient period of time to produce 2,4-pentadienoate, 3-butene-1-ol, or 1,3-butadiene.

In some embodiments, the non-naturally occurring microbial organism having an 2,4-pentadienoate, 3-butene-1-ol, or 1,3-butadiene pathway includes two exogenous nucleic acids, each encoding a reductive TCA pathway enzyme. In some embodiments, the non-naturally occurring microbial organism having an 2,4-pentadienoate, 3-butene-1-ol, or 1,3-butadiene pathway includes three exogenous nucleic acids each encoding a reductive TCA pathway enzyme. In some embodiments, the non-naturally occurring microbial organism includes three exogenous nucleic acids encoding an ATP-citrate lyase, a fumarate reductase, and an alpha-ketoglutarate:ferredoxin oxidoreductase. In some embodiments, the non-naturally occurring microbial organism includes three exogenous nucleic acids encoding a citrate lyase, a fumarate reductase, and an alpha-ketoglutarate: ferredoxin oxidoreductase.

In some embodiments, the non-naturally occurring microbial organisms having an 2,4-pentadienoate, 3-butene-1-ol, or 1,3-butadiene pathway further include an exogenous nucleic acid encoding an enzyme selected from a pyruvate: ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, and combinations thereof In some embodiments, the non-naturally occurring microbial organism having an 2,4-pentadienoate, 3-butene-1-ol, or 1,3-butadiene pathway further includes an exogenous nucleic acid encoding an enzyme selected from carbon monoxide dehydrogenase, acetyl-CoA synthase, ferredoxin, NAD(P)H:ferredoxin oxidoreductase and combinations thereof.

In some embodiments, the non-naturally occurring microbial organism having an 2,4-pentadienoate, 3-butene-1-ol, or 1,3-butadiene pathway utilizes a carbon feedstock selected from (1) CO, (2) $CO_2$, (3) $CO_2$ and $H_2$, (4) CO and $H_2$, or (5) CO, $CO_2$, and $H_2$. In some embodiments, the non-naturally occurring microbial organism having an 2,4-pentadienoate, 3-butene-1-ol, or 1,3-butadiene pathway utilizes hydrogen for reducing equivalents. In some embodiments, the non-naturally occurring microbial organism having an 2,4-pentadienoate, 3-butene-1-ol, or 1,3-butadiene pathway utilizes CO for reducing equivalents. In some embodiments, the non-naturally occurring microbial organism having an 2,4-pentadienoate, 3-butene-1-ol, or 1,3-butadiene pathway utilizes combinations of CO and hydrogen for reducing equivalents.

In some embodiments, the non-naturally occurring microbial organism having an 2,4-pentadienoate, 3-butene-1-ol, or 1,3-butadiene pathway further includes one or more nucleic acids encoding an enzyme selected from a phosphoenolpyruvate carboxylase, a phosphoenolpyruvate carboxykinase, a pyruvate carboxylase, and a malic enzyme.

In some embodiments, the non-naturally occurring microbial organism having an 2,4-pentadienoate, 3-butene-1-ol, or 1,3-butadiene pathway further includes one or more nucleic acids encoding an enzyme selected from a malate dehydrogenase, a fumarase, a fumarate reductase, a succinyl-CoA synthetase, and a succinyl-CoA transferase.

In some embodiments, the non-naturally occurring microbial organism having an 2,4-pentadienoate, 3-butene-1-ol, or 1,3-butadiene pathway further includes at least one exogenous nucleic acid encoding a citrate lyase, an ATP-citrate lyase, a citryl-CoA synthetase, a citryl-CoA lyase an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, and a ferredoxin.

In some embodiments, the carbon feedstock and other cellular uptake sources such as phosphate, ammonia, sulfate, chloride and other halogens can be chosen to alter the isotopic distribution of the atoms present in 1,3-butadiene or any 1,3-butadiene pathway intermediate. The various carbon feedstock and other uptake sources enumerated above will be referred to herein, collectively, as "uptake sources." Uptake sources can provide isotopic enrichment for any atom present in the product toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway or any intermediate en route thereto. The various carbon feedstock and other uptake sources enumerated above will be referred to herein, collectively, as "uptake sources." Uptake sources can provide isotopic enrichment for any atom present in the product toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene or toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway intermediate including any toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene impurities generated in diverging away from the pathway at any point. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, a target isotopic ratio of an uptake source can be obtained via synthetic chemical enrichment of the uptake source. Such isotopically enriched uptake sources can be purchased commercially or prepared in the laboratory. In some embodiments, a target isotopic ratio of an uptake source can be obtained by choice of origin of the uptake source in nature. In some such embodiments, a source of carbon, for example, can be selected from a fossil fuel-derived carbon source, which can be relatively depleted of carbon-14, or an environmental carbon source, such as $CO_2$, which can possess a larger amount of carbon-14 than its petroleum-derived counterpart.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

In some embodiments, the present invention provides toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene or a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene intermediate that has a carbon-12, carbon-13, and carbon-14 ratio that reflects an atmospheric carbon uptake source. In some such embodiments, the uptake source is $CO_2$. In some embodiments, In some embodiments, the present invention provides toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene, intermediate that has a carbon-12, carbon-13, and carbon-14 ratio that reflects petroleum-based carbon uptake source. In some embodiments, the present invention provides toluene, benzene, p-toluate, terephthalate, (2-hydroxy-3-methyl-4-oxobutoxy) phosphonate, (2-hydroxy-4-oxobutoxy)phosphonate, benzoate, styrene, 2,4-pentadienoate, 3-butene-1ol or 1,3-butadiene or a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene intermediate that has a carbon-12, carbon-13, and carbon-14 ratio that is obtained by a combination of an atmospheric carbon uptake source with a petroleum-based uptake source. Such combination of uptake sources is one means by which the carbon-12, carbon-13, and carbon-14 ratio can be varied.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, toluene, benzene, p-toluate, terephthalate, (2-hydroxy-3-methyl-4-oxobutoxy) phosphonate, (2-hydroxy-4-oxobutoxy)phosphonate, benzoate, styrene, 2,4-pentadienoate, 3-butene-1ol or 1,3-butadiene and any of the intermediate metabolites in the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway. All that is required is to engineer in one or more of the required enzyme or protein activities to achieve biosynthesis of the desired compound or intermediate including, for example, inclusion of some or all of the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene biosynthetic pathways. Accordingly, the invention provides a non-naturally occurring microbial organism that produces and/or secretes toluene, benzene, p-toluate, terephthalate, (2-hydroxy-3-methyl-4-oxobutoxy)phosphonate, (2-hydroxy-4-oxobutoxy) phosphonate, benzoate, styrene, 2,4-pentadienoate, 3-butene-1ol or 1,3-butadiene when grown on a carbohydrate or other carbon source and produces and/or secretes any of the intermediate metabolites shown in the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway when grown on a carbohydrate or other carbon source. The toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene producing microbial organisms of the invention can initiate synthesis from an intermediate, for example, phenylalanine, phenylpyruvate, phenylacetaldehyde, phenylacetate, benzoyl-CoA, 3-oxo-3-phenylpropionyl-CoA, [(3-oxo-3-phenylpropionyl)oxy]phosphonate, benzoyl acetate, acetophenone, 1-phenylethanol, trans,trans-muconate, cis,trans-muconate, cis,cis-muconate, trans-2,4-pentadienoate, and cis-2,4-pentadienoate. As a further example, a (2-hydroxy-3-methyl-4-oxobutoxy)phosphonate pathway intermediate can be 1-deoxy-D-xylulose-5-phosphate or C-methyl-D-erythritol-4-phosphate (see Example III and FIG. 5). A p-toluate pathway intermediate can be, for example, 2,4-dihydroxy-5-methyl-6-[(phosphonooxy)methyl]oxane-2-carboxylate, 1,3-dihydroxy-4-methyl-5-oxocyclohexane-1-carboxylate, 5-hydroxy-4-methyl-3-oxocyclohex-1-ene-1-carboxylate, 3,5-dihydroxy-4-methylcyclohex-1-ene-1-carboxylate, 5-hydroxy-4-methyl-3-(phosphonooxy) cyclohex-1-ene-1-carboxylate, 5-[(1-carboxyeth-1-en-1-yl) oxy]-4-methyl-3-(phosphonooxy)cyclohex-1-ene-1-carboxylate, or 3-[(1-carboxyeth-1-en-1-yl)oxy]-4-methylcyclohexa-1,5-diene-1-carboxylate (see Example IV and FIG. 6). A terephthalate intermediate can be, for example, 4-carboxybenzyl alcohol or 4-carboxybenzaldehyde (see Example V and FIG. 7).

As disclosed herein, p-toluate and benzoate are exemplary intermediates that can be the subject of a non-naturally occurring microbial organism. Such carboxylates can occur in ionized form or fully protonated form. Accordingly, the suffix "-ate," or the acid form, can be used interchangeably to describe both the free acid form as well as any deprotonated form, in particular since the ionized form is known to depend on the pH in which the compound is found. It is understood that propionate products accessible in accordance with the present invention include ester forms, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl propionate, ethyl propionate, and n-propyl propionate. Other biosynthetically accessible 0-propionates can include medium to long chain groups, that is C7-C22, O-propionate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-propionate esters can also be accessed via a biochemical or chemical process, such as esterification of a free carboxylic acid product or transesterification of an O- or S-propionate. S-carboxylates are exemplified by CoA S-esters, cysteinyl S-esters, alkylthioesters, and various aryl and heteroaryl thioesters.

The non-naturally occurring microbial organisms of the invention are constructed using methods well known in the art as exemplified herein to exogenously express at least one nucleic acid encoding a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene pathway enzyme or protein in sufficient amounts to produce toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene. It is understood that the microbial organisms of the invention are cultured under conditions sufficient to produce toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene. Following the teachings and guidance provided herein, the non-naturally occurring microbial organisms of the invention can achieve biosynthesis of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene resulting in intracellular concentrations between about 0.1-200 mM or more. Generally, the intracellular concentration of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene producers can synthesize toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene at intracellular concentrations of 5-10 mM or more as well as all other concentrations exemplified herein. It is understood that, even though the above description refers to intracellular concentrations, toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene producing microbial organisms can produce toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene intracellularly and/or secrete the product into the culture medium.

In addition to the culturing and fermentation conditions disclosed herein, growth condition for achieving biosynthesis of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene. Generally, and as with non-continuous culture procedures, the continuous and/or near-continuous production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene will include culturing a non-naturally occurring toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene producing organism of the invention in sufficient nutrients and medium to sustain and/or nearly sustain growth in an exponential phase. Continuous culture under such conditions can be include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene producers of the invention for continuous production of substantial quantities of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene, the toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene producers also can be, for example, simultaneously subjected to chemical synthesis procedures to convert the product to other compounds or the product can be separated from the fermentation culture and sequentially subjected to chemical conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/

00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organisms ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ot or 1,3-butadiene pathway can be introduced into a host organism. In some cases, it can be desirable to modify an activity of a toluene, benzene, p-toluate, terephthalate, (2-hydroxy-3-methyl-4-oxobutoxy) phosphonate, (2-hydroxy-4-oxobutoxy)phosphonate, benzoate, styrene, 2,4-pentadienoate, 3-butene-1ol or 1,3-butadiene pathway enzyme or protein to increase production of toluene, benzene, p-toluate, terephthalate, (2-hydroxy-3-methyl-4-oxobutoxy)phosphonate, (2-hydroxy-4-oxobutoxy)phosphonate, benzoate, styrene, 2,4-pentadienoate, 3-butene-1ol or 1,3-butadiene. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >104). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a toluene, benzene, p-toluate, terephthalate, (2-hydroxy-3-methyl-4-oxobutoxy) phosphonate, (2-hydroxy-4-oxobutoxy)phosphonate, benzoate, styrene, 2,4-pentadienoate, 3-butene-1ol or 1,3-butadiene pathway enzyme or protein. Such methods include, but are not limited to EpPCR, which introduces random point mutations by reducing the fidelity of DNA polymerase in PCR reactions (Pritchard et al., J. Theor. Biol. 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., Nucleic Acids Res. 32:e145 (2004); and Fujii et al., Nat. Protoc. 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, Proc. Natl. Acad. Sci. U.S.A. 91:10747-10751 (1994); and Stemmer, Nature 370:389-391 (1994)); Staggered Extension (StEP), which entails template priming followed by repeated cycles of 2 step PCR with denaturation and very short duration of annealing/extension (as short as 5 sec) (Zhao et al., Nat. Biotechnol. 16:258-261 (1998)); Random Priming Recombination (RPR), in which random sequence primers are used to generate many short DNA fragments complementary to different segments of the template (Shao et al., Nucleic Acids Res 26:681-683 (1998)).

Additional methods include Heteroduplex Recombination, in which linearized plasmid DNA is used to form heteroduplexes that are repaired by mismatch repair (Volkov et al. Nucleic Acids Res. 27:e18 (1999); and Volkov et al., Methods Enzymol. 328:456-463 (2000)); Random Chimeragenesis on Transient Templates (RACHITT), which employs Dnase I fragmentation and size fractionation of single stranded DNA (ssDNA) (Coco et al., Nat. Biotechnol. 19:354-359 (2001)); Recombined Extension on Truncated templates (RETT), which entails template switching of unidirectionally growing strands from primers in the presence of unidirectional ssDNA fragments used as a pool of templates (Lee et al., J. Molec. Catalysis 26:119-129 (2003)); Degenerate Oligonucleotide Gene Shuffling (DOGS), in which degenerate primers are used to control recombination between molecules; (Bergquist and Gibbs, Methods Mol. Biol. 352:191-204 (2007); Bergquist et al., *Biomol. Eng*. 22:63-72 (2005); Gibbs et al., Gene 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. U.S.A.* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res.* 29:E16 (2001)); SCRATCHY, which combines two methods for recombining genes, ITCHY and DNA shuffling (Lutz et al., *Proc. Natl. Acad. Sci. U.S.A.* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., Nat. Biotechnol. 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., Methods Enzymol. 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. Methods Enzymol. 208:564-586 (1991); and Reidhaar-Olson et al. Science 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., Angew. Chem. Int. Ed Engl. 40:3589-3591 (2001)); the Mutator Strains technique, in which conditional ts mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., Appl. Environ. Microbiol. 67:3645-3649 (2001)); Low et al., J. Mol. Biol. 260:359-3680 (1996)).

Additional exemplary methods include Look-Through Mutagenesis (LTM), which is a multidimensional mutagenesis method that assesses and optimizes combinatorial mutations of selected amino acids (Rajpal et al., Proc. Natl. Acad. Sci. U.S.A. 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., Proc. Natl. Acad. Sci. U.S.A. 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., Nat. Protoc. 2:891-903 (2007); and Reetz et al., Angew. Chem. Int. Ed Engl. 45:7745-7751 (2006)).

Any of the aforementioned methods for mutagenesis can be used alone or in any combination. Additionally, any one or combination of the directed evolution methods can be used in conjunction with adaptive evolution techniques, as described herein.

Example I

Pathways to Benzene and Toluene

This example shows pathways from phenylalanine to toluene, phenylalanine to benzene and benzoyl-CoA to styrene.

Figure 1:
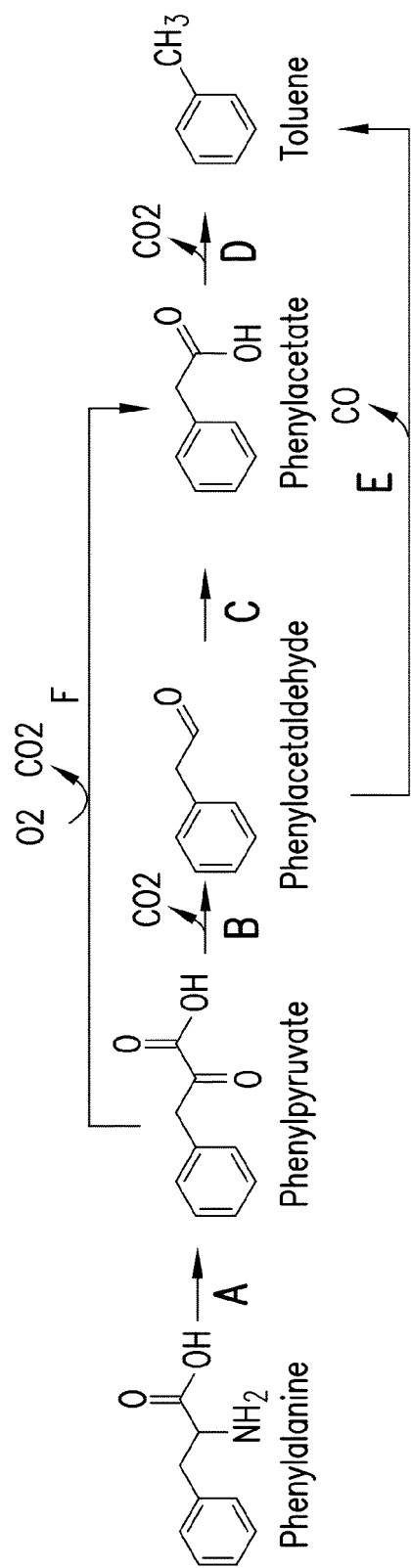
FIG. 1 shows the conversion of phenylalanine to toluene via phenylacetate. Enzymes are A. phenylalanine aminotransferase and/or phenylalanine oxidoreductase (deaminating), B. phenylpyruvate decarboxylase, C. phenylacetaldehyde dehydrogenase and/or oxidase, D. phenylacetate decarboxylase, E. phenylacetaldehyde decarbonylase, and F. phenylpyruvate oxidase.

Pathways for enzymatic conversion of phenylalanine are shown in FIG. 1. The first step entails conversion of phenylalanine to phenylpyruvate, a transformation that can be accomplished by an aminotransferase or a deaminating oxidoreductase. Phenylpyruvate is then decarboxylated to phenylacetaldehyde in Step B of FIG. 1. Toluene may be produced directly from phenylacetaldehyde by decarbonylation (FIG. 1, Step E), or indirectly via a phenylacetate intermediate (FIG. 1, Steps C and D). Phenylacetate can be oxidized to phenylacetate (FIG. 1, Step C) by either a phenylacetaldehyde dehydrogenase or a phenylacetaldehyde oxidase. An alternate pathway is the direct oxidative decarboxylation of phenylpyruvate to phenylacetate by phenylpyruvate oxidase (FIG. 1, StepF).

A one-step pathway for enzymatic conversion of phenylalanine to benzene is shown in FIG. 2. The conversion of phenylalanine and water to benzene, pyruvate and ammonia is catalyzed by an enzyme with phenylalanine benzene-lyase activity.

Enzymatic pathways to styrene from benzoyl-CoA are shown in FIG. 3. Benzoyl-CoA is a common metabolic intermediate of numerous biosynthetic and degradation pathways. Pathways involving the biosynthesis of benzoyl-CoA, and also the generation of benzoyl-CoA as a degradation product, are known in the art. In the proposed styrene pathways, benzoyl-CoA and acetyl-CoA are first converted to 3-oxo-3-phenylpropionyl-CoA by a beta-ketothiolase (FIG. 3, Step A). The CoA moiety of 3-oxo-3-phenylpropionyl-CoA is then released by a CoA hydrolase, transferase or synthase (FIG. 3, Step B). Alternately, 3-oxo-3-phenylpropionyl-CoA is converted to benzoyl-acetate in two enzymatic steps by a phosphotrans-3-oxo-3-phenylpropionylase and benzoyl-acetate kinase (FIG. 3, Steps F and G). Once formed, benzoyl-acetate is decarboxylated, reduced and dehydrated to form styrene (FIG. 3, Steps C, D and E).

Enzymes for catalyzing the transformations shown in FIGS. 1-3 are categorized by EC number (Table 1) and described further below.

| Label | Function | Step |
|---|---|---|
| 1.1.1.a | Oxidoreductase (oxo to alcohol) | 3D |
| 1.2.1.a | Oxidoreductase (aldehyde to acid) | 1C |
| 1.2.3.a | Aldehyde oxidase | 1C/F |
| 1.4.1.a | Oxidoreductase (aminating/deaminating) | 1A |
| 2.3.1.a | Acyltransferase (transferring phosphate group to CoA) | 3F |
| 2.3.1.b | Beta-ketothiolase | 3A |
| 2.6.1.a | Aminotransferase | 1A |
| 2.7.2.a | Phosphotransferase, carboxyl group acceptor (kinase) | 3G |
| 2.8.3.a | Coenzyme-A transferase | 3B |
| 3.1.2.a | Thiolester hydrolase (CoA specific) | 3B |
| 4.1.1.a | Carboxy-lyase | 1B/D, 3C |
| 4.1.99.a | Decarbonylase | 1E |
| 4.1.99.b | Lyase | 2 |
| 4.2.1.a | Hydro-lyase | 3E |
| 6.2.1.a | Acid-thiol ligase | 3B |

1.1.1.a Oxidoreductase (oxo to alcohol): The reduction of acetophenone to 1-phenylethanol (Step D of FIG. 3) is catalyzed by a ketone reductase with acetophenone reductase activity. Enzymes with this activity have been characterized in numerous organisms, and product formation is generally stereoselective. An exemplary enzyme with this activity is the R-specific short-chain dehydrogenase/reductase of *Lactobacillus brevis*, which has been extensively studied, structurally characterized and re-engineered to prefer NADH to NADPH as a cosubstrate (Schlieben et al., *J. Mol. Biol.* 349:801-813 (2005)). Additional enzymes with acetophenone reductase activity are encoded by adhF1 of *Pseudomonas fluorescens* (Hildebrandt et al., *Appl. Microbiol Biotechnol.* 59:483-487 (2002)), adh of *Thermus thermophilus* (Pennacchio et al., *Appl. Environ. Microbiol* 74:3949-3958 (2008)) and LSADH of *Leifsonia* sp. S749 (Inoue et al., *Biosci. Biotechnol. Biochem.* 70:418-426 (2006)). An S-specific enzyme was characterized in the ethylbenzene degradation pathway of the denitrifying bacterium *Aromatoleum aromaticum* EbN1 (Kniemeyer et al., *Arch. Microbiol.* 176:129-135 (2001)). This enzyme, encoded by ped, favors the reductive direction at low pH (4), while the oxidative direction is favored at neutral pH.

| Gene | GenBank Accession No. | GI No. | Organism |
|---|---|---|---|
| LVIS_0347 | YP_794544.1 | 116333017 | *Lactobacillus brevis* |
| adhF1 | AAL79772.1 | 18860822 | *Pseudomonas fluorescens* |
| adhTt | YP_003977.1 | 46198310 | *Thermus thermophilus* |
| LSADH | BAD99642.1 | 67625613 | *Leifsonia* sp. S749 |
| ped | YP_158329.1 | 56476740 | *Aromatoleum aromaticum* EbN1 |

A variety of alcohol dehydrogenase enzymes catalyze the reduction of a ketone to an alcohol functional group. These enzymes are also suitable for catalyzing the reduction of acetophenone. Two such enzymes in *E. coli* are encoded by malate dehydrogenase (mdh) and lactate dehydrogenase (ldhA). The lactate dehydrogenase from *Ralstonia eutropha* has been shown to demonstrate high activities on 2-ketoacids of various chain lengths including lactate, 2-oxobutyrate, 2-oxopentanoate and 2-oxoglutarate (Steinbuchel et al., *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). An additional oxidoreductase is the mitochondrial 3-hydroxybutyrate dehydrogenase (bdh) from the human heart which has been cloned and characterized (Marks et al., *J. Biol. Chem.* 267:15459-15463 (1992)). Alcohol dehydrogenase enzymes of *C. beijerinckii* (Ismaiel et al., *J. Bacteriol.* 175:5097-5105 (1993)) and *T. brockii* (Lamed et al., *Biochem. J.* 195:183-190 (1981); Peretz et al., *Biochemistry* 28:6549-6555 (1989)) convert acetone to isopropanol. Methyl ethyl ketone reductase, or alternatively, 2-butanol dehydrogenase, catalyzes the reduction of MEK to form 2-butanol. Exemplary MEK reductase enzymes can be found in *Rhodococcus ruber* (Kosjek et al., *Biotechnol Bioeng.* 86:55-62 (2004)) and *Pyrococcus furiosus* (van der et al., *Eur. J. Biochem.* 268:3062-3068 (2001)).

| Gene | GenBank Accession No. | GI No. | Organism |
|---|---|---|---|
| Mdh | AAC76268.1 | 1789632 | *Escherichia coli* |
| ldhA | NP_415898.1 | 16129341 | *Escherichia coli* |
| Ldh | YP_725182.1 | 113866693 | *Ralstonia eutropha* |
| bdh | AAA58352.1 | 177198 | *Homo sapiens* |
| adh | AAA23199.2 | 60592974 | *Clostridium beijerinckii* NRRL B593 |
| adh | P14941.1 | 113443 | *Thermoanaerobacter brockii* HTD4 |
| adhA | AAC25556 | 3288810 | *Pyrococcus furiosus* |
| sadh | CAD36475 | 21615553 | *Rhodococcus ruber* |

1.2.1.a Oxidoreductase (aldehyde to acid): Oxidation of phenylacetaldehyde to phenylacetate is catalyzed by phenylacetaldehyde dehydrogenase (Step C of FIG. 1), enzyme in the EC class 1.2.1. NAD$^+$-dependent phenylacetaldehyde dehydrogenase enzymes (EC 1.2.1.39) have been characterized in *E. coli*, *Pseudomonas putida* and *Antirrhinum majus* (Long et al., *Plant J* 59:256-265 (2009); Arias et al., *Environ. Microbiol* 10:413-432 (2008); Ferrandez et al., *FEBS Lett.* 406:23-27 (1997)). NAD$^+$-dependent aldehyde dehydrogenase enzymes with high activity on phenylacetaldehyde have also been characterized in mammals such as *Bos taurus*, *Rattus norvegicus* and *Homo sapiens* (Klyosov, *Biochemistry* 35:4457-4467 (1996a); Lindahl et al., *J Biol. Chem.* 259:11991-11996 (1984)). Two aldehyde dehydrogenases found in human liver, ALDH-1 and ALDH-2, have broad substrate ranges for a variety of aliphatic, aromatic and polycyclic aldehydes with demonstrated activity on phenylacetaldehyde (Klyosov, *Biochemistry* 35:4457-4467 (1996b)). The NADP$^+$-dependent benzaldehyde dehydrogenase of *Pseudomonas putida* encoded by badh also demonstrated activity on phenylacetaldehyde (Yeung et al., *Biochim. Biophys. Acta* 1784:1248-1255 (2008)). NAD$^+$-dependent aldehyde dehydrogenase enzymes with high activity on phenylacetaldehyde have also been characterized in mammals such as *Bos taurus, Rattus norvegicus* and *Homo sapiens* (Klyosov, *Biochemistry* 35:4457-4467 (1996a); Lindahl et al., *J Biol. Chem.* 259:11991-11996 (1984)). Two aldehyde dehydrogenases found in human liver, ALDH-1 and ALDH-2, have broad substrate ranges for a variety of aliphatic, aromatic and polycyclic aldehydes with demonstrated activity on phenylacetaldehyde (Klyosov, *Biochemistry* 35:4457-4467 (1996b)).

| Gene | GenBank Accession No. | GI No. | Organism |
|---|---|---|---|
| feaB | AAC74467.2 | 87081896 | Escherichia coli |
| peaE | ABR57205.1 | 150014683 | Pseudomonas putida |
| BALDH | ACM89738.1 | 223452696 | Antirrhinum majus |
| ALDH-2 | P05091.2 | 118504 | Homo sapiens |
| badh | P39849.1 | 731175 | Pseudomonas putida |

1.2.3.a Aldehyde oxidase: An $O_2$-dependent aldehyde oxidase enzyme can be employed to convert phenylacetaldehyde or phenylpyruvate to phenylacetate (Steps C and F of FIG. 1). Phenylacetaldehyde oxidase enzymes convert phenylacetaldehyde, water and $O_2$ to phenylacetate and hydrogen peroxide. Exemplary phenylacetaldehyde oxidase enzymes are found in *Methylobacillus* sp., *Pseudomonas* sp., *Streptomyces moderatus*, *Cavia porcellus* and *Zea mays* (Koshiba et al., Plant Physiol 110:781-789 (1996)). The two flavin- and molybdenum-containing aldehyde oxidases of *Zea mays* are encoded by zmAO-1 and zmAO-2 (Sekimoto et al., J Biol. Chem. 272:15280-15285 (1997)). Phenylacetaldehyde oxidase activity has also been demonstrated in the indole-3-acetaldehyde oxidase (EC 1.2.3.7) of *Avena sativa*, although the genes associated with this activity have not been identified to date and bear no significant homology to the aldehyde oxidase genes of *Zea mays* (Rajagopal, Physiol. Plant 24:272-281 (1971)). Additional phenylacetaldehyde oxidases can be inferred by sequence homology to the *Z. mays* genes and are shown below.

| Gene | GenBank Accession No. | GI No. | Organism |
|---|---|---|---|
| zmAO-1 | NP_001105308.1 | 162458742 | Zea mays |
| zmAO-2 | BAA23227.1 | 2589164 | Zea mays |
| Aox1 | O54754.2 | 20978408 | Mus musculus |
| ALDO1_ORYSJ | Q7XH05.1 | 75296231 | Oryza sativa |
| AAO3 | BAA82672.1 | 5672672 | Arabidopsis thaliana |
| XDH | DAA24801.1 | 296482686 | Bos taurus |

Phenylpyruvate oxidase enzymes convert phenylpyruvate and 02 to phenylacetate, CO2 and water (Step F of FIG. 1). The 4-hydroxyphenylpyruvate oxidase (EC 1.2.3.13) from *Arthrobacter globiformis* was shown catalyze the 02-dependent oxidation of phenylpyruvate to phenylacetate during tyrosine catabolism (Blakley, Can. J Microbiol 23:1128-1139 (1977)). This enzymatic activity was demonstrated in cell extracts; however, the gene encoding this enzyme has not been identified to date.

1.4.1.a Oxidoreductase (deaminating): The NAD(P)+-dependent oxidation of phenylalanine to phenylpyruvate (Step A of FIG. 1) is catalyzed by phenylalanine oxidoreductase (deaminating), also called phenylalanine dehydrogenase. NAD+-dependent phenylalanine dehydrogenase enzymes encoded by pdh genes have been characterized in *Bacillus badius*, *Lysinibacillus sphaericus* and *Thermoactinomyces intermedius* (Yamada et al., Biosci. Biotechnol. Biochem. 59:1994-1995 (1995); Takada et al., J Biochem. 109:371-376 (1991); Okazaki et al., Gene 63:337-341 (1988)).

| Gene | GenBank Accession No. | GI No. | Organism |
|---|---|---|---|
| pdh | BAA08816.1 | 1228936 | Bacillus badius |
| pdh | AAA22646.1 | 529017 | Lysinibacillus sphaericus |
| pdh | P22823.1 | 118598 | Thermoactinomyces intermedius |

2.3.1.a Acyltransferase (phosphotransacylase): An enzyme with phosphotransbenzoylase activity is required to phosphorylate 3-oxo-3-phenylpropionyl-CoA to [(3-oxo-3-phenylpropionyl)oxy]phosphoate (Step F of FIG. 3). An enzyme with this activity has not been characterized to date. Exemplary phosphate-transferring acyltransferases include phosphotransacetylase (EC 2.3.1.8) and phosphotransbutyrylase (EC 2.3.1.19). The pta gene from *E. coli* encodes a phosphotransacetylase that reversibly converts acetyl-CoA into acetyl-phosphate (Suzuki, Biochim. Biophys. Acta 191:559-569 (1969)). Phosphotransacetylase enzymes in several organisms also catalyze the conversion of propionyl-CoA to propionylphosphate. Such enzymes include the pta gene products of *E. coli* (Hesslinger et al., Mol. Microbiol 27:477-492 (1998)), *Bacillus subtilis* (Rado et al., Biochim. Biophys. Acta 321:114-125 (1973)), *Clostridium kluyveri* (Stadtman, 1:596-599 (1955)), and *Thermotoga maritima* (Bock et al., J Bacteriol. 181:1861-1867 (1999)). The ptb gene from *C. acetobutylicum* encodes phosphotransbutyrylase, an enzyme that reversibly converts butyryl-CoA into butyryl-phosphate (Wiesenborn et al., Appl Environ. Microbiol 55:317-322 (1989); Walter et al., Gene 134:107-111 (1993)). Additional ptb genes are found in butyrate-producing bacterium L2-50 (Louis et al., J. Bacteriol. 186:2099-2106 (2004)) and *Bacillus megaterium* (Vazquez et al., Curr. Microbiol 42:345-349 (2001)).

| Gene | GenBank Accession No. | GI No. | Organism |
|---|---|---|---|
| pta | NP_416800.1 | 71152910 | Escherichia coli |
| pta | P39646 | 730415 | Bacillus subtilis |
| pta | A5N801 | 146346896 | Clostridium kluyveri |
| pta | Q9X0L4 | 6685776 | Thermotoga maritime |
| ptb | NP_349676 | 34540484 | Clostridium acetobutylicum |
| ptb | AAR19757.1 | 38425288 | butyrate-producing bacterium L2-50 |
| ptb | CAC07932.1 | 10046659 | Bacillus megaterium |

2.3.1.b Beta-ketothiolase. A beta-ketothiolase enzyme is required to convert benzoyl-CoA and acetyl-CoA to 3-oxo-3-phenylpropionyl-CoA (Step A of FIG. 3). This transformation is not known to occur naturally. Suitable beta-ketothiolase enzymes include 3-oxoadipyl-CoA thiolase (EC 2.3.1.174), 3-oxopimeloyl-CoA:glutaryl-CoA acyltransferase (EC 2.3.1.16), 3-oxovaleryl-CoA thiolase and acetoacetyl-CoA thiolase (EC 2.1.3.9).

3-Oxoadipyl-CoA thiolase (EC 2.3.1.174) converts beta-ketoadipyl-CoA to succinyl-CoA and acetyl-CoA, and is a key enzyme of the beta-ketoadipate pathway for aromatic compound degradation. The enzyme is widespread in soil bacteria and fungi including *Pseudomonas putida* (Harwood et al., J Bacteriol. 176:6479-6488 (1994)) and *Acinetobacter calcoaceticus* (Doten et al., J Bacteriol. 169:3168-3174 (1987)). The gene products encoded by pcaF in *Pseudomonas* strain B13 (Kaschabek et al., J Bacteriol. 184:207-215 (2002)), phaD in *Pseudomonas putida* U (Olivera et al., Proc. Natl. Acad. Sci U.S.A 95:6419-6424 (1998)), paaE in *Pseudomonas fluorescens* ST (Di et al., Arch. Microbiol 188:117-125 (2007)), and paaJ from *E. coli* (Nogales et al., Microbiology 153:357-365 (2007)) also catalyze this transformation. Several beta-ketothiolases exhibit significant and selective activities in the oxoadipyl-CoA forming direction including bkt from *Pseudomonas putida*, pcaF and bkt from *Pseudomonas aeruginosa* PAO1, bkt from *Burkholderia ambifaria* AMMD, paaJ from *E. coli*, and phaD from *P. putida*.

| Gene name | GI# | GenBank Accession # | Organism |
| --- | --- | --- | --- |
| paaJ | 16129358 | NP_415915.1 | Escherichia coli |
| pcaF | 17736947 | AAL02407 | Pseudomonas knackmussii (B13) |
| phaD | 3253200 | AAC24332.1 | Pseudomonas putida |
| pcaF | 506695 | AAA85138.1 | Pseudomonas putida |
| pcaF | 141777 | AAC37148.1 | Acinetobacter calcoaceticus |
| paaE | 106636097 | ABF82237.1 | Pseudomonas fluorescens |
| bkt | 115360515 | YP_777652.1 | Burkholderia ambifaria AMMD |
| bkt | 9949744 | AAG06977.1 | Pseudomonas aeruginosa PAO1 |
| pcaF | 9946065 | AAG03617.1 | Pseudomonas aeruginosa PAO1 |

3-Oxopimeloyl-CoA thiolase catalyzes the condensation of glutaryl-CoA and acetyl-CoA into 3-oxopimeloyl-CoA (EC 2.3.1.16). An enzyme catalyzing this transformation is encoded by genes bktB and bktC in Ralstonia eutropha (formerly known as Alcaligenes eutrophus) (Slater et al., J. Bacteriol. 180:1979-1987 (1998); Haywood et al., FEMS Microbiology Letters 52:91-96 (1988)). The sequence of the BktB protein is known but the sequence of the BktC protein has not been reported to date. The pim operon of Rhodopseudomonas palustris also encodes a beta-ketothiolase, encoded by pimB, predicted to catalyze this transformation in the degradative direction during benzoyl-CoA degradation (Harrison et al., Microbiology 151:727-736 (2005)). A beta-ketothiolase enzyme in S. aciditrophicus was identified by sequence homology to bktB (43% identity, evalue=1e-93).

| Gene name | GI# | GenBank Accession # | Organism |
| --- | --- | --- | --- |
| bktB | 11386745 | YP_725948 | Ralstonia eutropha |
| pimB | 39650633 | CAE29156 | Rhodopseudomonas palustris |
| syn_02642 | 85860483 | YP_462685.1 | Syntrophus aciditrophicus |

Beta-ketothiolase enzymes catalyzing the formation of 3-oxovalerate from acetyl-CoA and propionyl-CoA may also be able to catalyze the formation of 3-oxo-3-phenyl-propionyl-CoA. Zoogloea ramigera possesses two ketothiolases that can form β-ketovaleryl-CoA from propionyl-CoA and acetyl-CoA and R. eutropha has a β-oxidation ketothiolase that is also capable of catalyzing this transformation (Gruys et al., (1999)). The sequences of these genes or their translated proteins have not been reported, but several genes in R. eutropha, Z. ramigera, or other organisms can be identified based on sequence homology to bktB from R. eutropha and are listed below.

| Gene name | GI# | GenBank Accession # | Organism |
| --- | --- | --- | --- |
| phaA | 113867452 | YP_725941.1 | Ralstonia eutropha |
| h16_A1713 | 113867716 | YP_726205.1 | Ralstonia eutropha |
| pcaF | 116694155 | YP_728366.1 | Ralstonia eutropha |
| h16_B1369 | 116695312 | YP_840888.1 | Ralstonia eutropha |
| h16_A0170 | 113866201 | YP_724690.1 | Ralstonia eutropha |
| h16_A0462 | 113866491 | YP_724980.1 | Ralstonia eutropha |
| h16_A1528 | 113867539 | YP_726028.1 | Ralstonia eutropha |
| h16_B0381 | 116694334 | YP_728545.1 | Ralstonia eutropha |
| h16_B0662 | 116694613 | YP_728824.1 | Ralstonia eutropha |
| h16_B0759 | 116694710 | YP_728921.1 | Ralstonia eutropha |
| h16_B0668 | 116694619 | YP_728830.1 | Ralstonia eutropha |
| h16_A1720 | 113867723 | YP_726212.1 | Ralstonia eutropha |
| h16_A1887 | 113867867 | YP_726356.1 | Ralstonia eutropha |
| phbA | 135759 | P07097.4 | Zoogloea ramigera |
| bktB | 194289475 | YP_002005382.1 | Cupriavidus taiwanensis |
| Rmet_1362 | 94310304 | YP_583514.1 | Ralstonia metallidurans |
| Bphy_0975 | 186475740 | YP_001857210.1 | Burkholderia phymatum |

Additional enzymes include beta-ketothiolases that are known to convert two molecules of acetyl-CoA into acetoacetyl-CoA (EC 2.1.3.9). Exemplary acetoacetyl-CoA thiolase enzymes include the gene products of atoB from E. coli (Martin et al., Nat. Biotechnol 21:796-802 (2003)), thlA and thlB from C. acetobutylicum (Hanai et al., Appl Environ Microbiol 73:7814-7818 (2007); Winzer et al., J. Mol. Microbiol Biotechnol 2:531-541 (2000)), and ERG10 from S. cerevisiae (Hiser et al., J. Biol. Chem. 269:31383-31389 (1994)).

| Gene name | GI# | GenBank Accession # | Organism |
| --- | --- | --- | --- |
| atoB | 16130161 | NP_416728 | Escherichia coli |
| thlA | 15896127 | NP_349476.1 | Clostridium acetobutylicum |
| thlB | 15004782 | NP_149242.1 | Clostridium acetobutylicum |
| ERG10 | 6325229 | NP_015297 | Saccharomyces cerevisiae |

2.6.1.a Aminotransferase: A phenylalanine aminotransferase or transaminase in the EC class 2.6.1 is required to convert phenylalanine to phenylpyruvate (Step A of FIG. 1). A variety of enzymes catalyze this transformation, including phenylacetate aminotransferase, aromatic amino acid aminotransferase, tryptophan aminotransferase, aspartate aminotransferase, branched chain amino acid aminotransferase and others. Enzymes with phenylalanine aminotransferase activity in E. coli are encoded by tyrB, ilvE and aspC (Lee-Peng et al., J Bacteriol. 139:339-345 (1979); Powell et al., Eur. J Biochem. 87:391-400 (1978)). Exemplary enzymes with phenylalanine aminotransferase activity in other organisms include the aromatic amino acid aminotransferase of S. cerevisiae encoded by ARO9 (Iraqui et al., Mol. Gen. Genet. 257:238-248 (1998)) and the tryptophan aminotransferase of Arabidopsis thaliana, encoded by TAA1 (Tao et al., Cell 133:164-176 (2008)).

| Gene | GenBank Accession No. | GI No. | Organism |
| --- | --- | --- | --- |
| tyrB | AAC77024.1 | 1790488 | Escherichia coli |
| ilvE | AAT48207.1 | 48994963 | Escherichia coli |
| aspC | NP_415448.1 | 16128895 | Escherichia coli |
| ARO9 | NP_012005.1 | 6321929 | Saccharomyces cerevisiae |
| TAA1 | NP_177213.1 | 15223183 | Arabidopsis thaliana |

2.7.2.a Phosphotransferase: Phosphotransferase enzymes in the EC class 2.7.2 convert carboxylic acids to phosphonic acids with concurrent hydrolysis of one ATP. In Step G of FIG. 3, a phosphotransferase is required to convert [(3-oxo-3-phenylpropionyl)oxy]phosphonate and ADP to benzoyl-acetate and ATP. An enzyme with this exact activity has not been characterized to date. Exemplary enzymes include butyrate kinase (EC 2.7.2.7), isobutyrate kinase (EC 2.7.2.14), aspartokinase (EC 2.7.2.4), acetate kinase (EC 2.7.2.1) and gamma-glutamyl kinase (EC 2.7.2.11). Aspartokinase catalyzes the ATP-dependent phosphorylation of aspartate and participates in the synthesis of several amino acids. The aspartokinase III enzyme in E. coli, encoded by lysC, has a broad substrate range that includes the aromatic compound aspartic acid 1-benzyl ester, and the catalytic residues involved in substrate specificity have been elucidated (Keng et al., Arch. Biochem. Biophys. 335:73-81 (1996)). Two additional kinases in E. coli include acetate kinase and gamma-glutamyl kinase. The E. coli acetate kinase, encoded by ackA (Skarstedt et al., J. Biol. Chem. 251:6775-6783 (1976)), phosphorylates propionate in addition to acetate (Hesslinger et al., Mol. Microbiol 27:477-492 (1998)). The E. coli gamma-glutamyl kinase, encoded by proB (Smith et al., J. Bacteriol. 157:545-551 (1984)), phosphorylates the gamma carbonic acid group of glutamate. Butyrate kinase carries out the reversible conversion of butyryl-phosphate to butyrate during acidogenesis in *C. acetobutylicum* (Cary et al., *Appl. Environ. Microbiol* 56:1576-1583 (1990)). This enzyme is encoded by either of the two buk gene products (Huang et al., *J Mol. Microbiol Biotechnol* 2:33-38 (2000)). Other butyrate kinase enzymes are found in *C. butyricum* and *C. tetanomorphum* (TWAROG et al., *J Bacteriol.* 86:112-117 (1963)). A related enzyme, isobutyrate kinase from *Thermotoga maritime*, was expressed in *E. coli* and crystallized (Diao et al., *J Bacteriol.* 191:2521-2529 (2009); Diao et al., *Acta Crystallogr. D. Biol. Crystallogr.* 59:1100-1102 (2003)).

| Gene name | GI# | GenBank Accession # | Organism |
| --- | --- | --- | --- |
| lysC | 16131850 | NP_418448.1 | *Escherichia coli* |
| ackA | 16130231 | NP_416799.1 | *Escherichia coli* |
| proB | 16128228 | NP_414777.1 | *Escherichia coli* |
| buk1 | 15896326 | NP_349675 | *Clostridium acetobutylicum* |
| buk2 | 20137415 | Q97II1 | *Clostridium acetobutylicum* |
| buk2 | 6685256 | Q9X278.1 | *Thermotoga maritima* |

2.8.3.a CoA transferase: CoA transferases catalyze the reversible transfer of a CoA moiety from one molecule to another. Step B of FIG. 3 is catalyzed by an enzyme with 3-oxo-3-phenylpropionyl-CoA transferase activity. In this transformation, benzoyl-acetate is formed from 3-oxo-3-phenylpropionyl-CoA by the transfer of the CoA to a CoA acceptor such as acetate, succinate or others. Exemplary CoA transferase enzymes that react with similar substrates include cinnamoyl-CoA transferase (EC 2.8.3.17) and benzylsuccinyl-CoA transferase. Cinnamoyl-CoA transferase, encoded by fldA in *Clostridium sporogenes*, transfers a CoA moiety from cinnamoyl-CoA to a variety of aromatic acid substrates including phenylacetate, 3-phenylpropionate and 4-phenylbutyrate (Dickert et al., *Eur. J Biochem.* 267:3874-3884 (2000)). Benzylsuccinyl-CoA transferase utilizes succinate or maleate as the CoA acceptor, forming benzylsuccinate from benzylsuccinyl-CoA. This enzyme was characterized in the reverse direction in denitrifying bacteria *Thauera aromatica*, where it is encoded by bbsEF (Leutwein et al., *J Bacteriol.* 183:4288-4295 (2001)).

| Gene | GenBank Accession No. | GI No. | Organism |
| --- | --- | --- | --- |
| fldA | AAL18808.1 | 16417587 | *Clostridium sporogenes* |
| bbsE | AAF89840.1 | 9622535 | *Thauera aromatica* |
| bbsF | AAF89841.1 | 9622536 | *Thauera aromatica* |

Additional CoA transferase enzymes with diverse substrate ranges include succinyl-CoA transferase, 4-hydroxybutyryl-CoA transferase, butyryl-CoA transferase, glutaconyl-CoA transferase and acetoacetyl-CoA transferase. The gene products of cat1, cat2, and cat3 of *Clostridium kluyveri* have been shown to exhibit succinyl-CoA, 4-hydroxybutyryl-CoA, and butyryl-CoA transferase activity, respectively (Seedorf et al., *Proc. Natl. Acad. Sci U.S.A* 105:2128-2133 (2008); Sohling et al., *J Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). The glutaconyl-CoA-transferase (EC 2.8.3.12) from the anaerobic bacterium *Acidaminococcus fermentans* reacts with glutaconyl-CoA and 3-butenoyl-CoA (Mack et al., *Eur. J. Biochem.* 226:41-51 (1994)). The genes encoding this enzyme are gctA and gctB. This enzyme exhibits reduced but detectable activity with several alternate substrates including glutaryl-CoA, 2-hydroxyglutaryl-CoA, adipyl-CoA, crotonyl-CoA and acrylyl-CoA (Buckel et al., *Eur. J Biochem.* 118:315-321 (1981)). The enzyme has been cloned and expressed in *E. coli* (Mack et al., *Eur. J. Biochem.* 226:41-51 (1994)). Glutaconate CoA-transferase activity has also been detected in *Clostridium sporosphaeroides* and *Clostridium symbiosum*. Acetoacetyl-CoA transferase utilizes acetyl-CoA as the CoA donor. This enzyme is encoded by the *E. coli* atoA (alpha subunit) and atoD (beta subunit) genes (Korolev et al., *Acta Crystallogr. D. Biol. Crystallogr.* 58:2116-2121 (2002); Vanderwinkel et al., *Biochem. Biophys. Res. Commun.* 33:902-908 (1968)). This enzyme has a broad substrate range (Sramek et al., *Arch. Biochem. Biophys.* 171:14-26 (1975)) and has been shown to transfer the CoA moiety from acetyl-CoA to a variety of substrates, including isobutyrate (Matthies et al., *Appl Environ. Microbiol* 58:1435-1439 (1992)), valerate and butanoate (Vanderwinkel et al., *Biochem. Biophys. Res. Commun.* 33:902-908 (1968)). Similar enzymes exist in *Corynebacterium glutamicum* ATCC 13032 (Duncan et al., *Appl. Environ. Microbiol* 68:5186-5190 (2002)), *Clostridium acetobutylicum* (Cary et al., *Appl. Environ. Microbiol* 56:1576-1583 (1990); Wiesenborn et al., *Appl. Environ. Microbiol* 55:323-329 (1989)), and *Clostridium saccharoperbutylacetonicum* (Kosaka et al., *Biosci. Biotechnol Biochem.* 71:58-68 (2007)).

| Gene | GenBank Accession No. | GI No. | Organism |
| --- | --- | --- | --- |
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| gctA | CAA57199.1 | 559392 | *Acidaminococcus fermentans* |
| gctB | CAA57200.1 | 559393 | *Acidaminococcus fermentans* |
| gctA | ACJ24333.1 | 212292816 | *Clostridium symbiosum* |
| gctB | ACJ24326.1 | 212292808 | *Clostridium symbiosum* |
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* |
| cg0592 | YP_224801.1 | 62389399 | *Corynebacterium glutamicum* |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

3.1.2.a CoA hydrolase: 3-Oxo-3-phenylpropionyl-CoA can be hydrolyzed to its corresponding acid by a CoA hydrolase or thioesterase in the EC class 3.1.2 (Step B of FIG. 3). Exemplary CoA thioesters that hydrolyze aromatic substrates include benzoyl-CoA hydrolase, 4-hydroxybenzoyl-CoA hydrolase (EC 3.1.2.23) and phenylacetyl-CoA hydrolase (EC 3.1.2.25). The *Azoarcus evansii* gene orf1 encodes an enzyme with benzoyl-CoA hydrolase activity that participates in benzoate metabolism (Ismail, *Arch. Microbiol* 190:451-460 (2008)). This enzyme, when heterologously expressed in *E. coli*, demonstrated activity on a number of alternate substrates. Additional benzoyl-CoA hydrolase enzymes were identified in benzonate degradation gene clusters of *Magnetospirillum magnetotacticum, Jannaschia* sp. CCS1 and *Sagittula stellata* E-37 by sequence similarity (Ismail, *Arch. Microbiol* 190:451-460 (2008)). The 4-hydroxybenzoyl-CoA hydrolase of *Pseudomonas* sp. CBS3 exhibits activity on the alternate substrates benzoyl-CoA and p-methylbenzoyl-CoA, and has been heterologously expressed and characterized in *E. coli* (Song et al., *Bioorg. Chem.* 35:1-10 (2007)). Additional enzymes with aryl-CoA hydrolase activity include the palmitoyl-CoA hydrolase of *Mycobacterium tuberculosis* (Wang et al., *Chem. Biol.* 14:543-551 (2007)) and the acyl-CoA hydrolase of *E. coli* encoded by entH (Guo et al., *Biochemistry* 48:1712-1722 (2009)).

4.1.1a. Carboxy-lyase: Decarboxylase enzymes in the EC class 4.1.1 are required to catalyze several transformations in FIGS. 1-3. Conversion of phenylpyruvate to phenylacetaldehyde (Step B of FIG. 1) is catalyzed by a keto-acid decarboxylase. Decarboxylation of phenylacetate to toluene (Step D of FIG. 1) is catalyzed by an enzyme with phenylacetate decarboxylase activity. A 3-oxoacid decarboxylase is required to decarboxylate benzoyl-acetate to acetophenone (Step C of FIG. 7). Decarboxylases (also known as carboxy lyases) catalyze the loss of carbon dioxide from an organic compound or a cellular metabolite possessing a carboxylic acid function. Decarboxylases are prevalent in nature and can require either pyridoxal phosphate or pyruvate as a co-factor, although many require no bound co-factors. Over 50 decarboxylase enzymes have been reported and characterized by biochemical and/or analytical methods.

A phenylacetate decarboxylase is required to catalyze the decarboxylation of phenylacetate to toluene (Step D of FIG. 1). Such an activity has not been detected in characterized decarboxylase enzymes to date. An enzyme catalyzing a similar reaction is 4-hydroxyphenylacetate decarboxylase (EC 4.1.1.83), which naturally decarboxylates 4-hydroxyphenylacetate to p-cresol. Characterized 4-hydroxyphenylacetate decarboxylase enzymes from *Clostridium difficile* and *Clostridium scatologenes* are composed of two subunits and require activation by a specific activating enzyme (Yu et

| Gene | GenBank Accession No. | GI No. | Organism |
|---|---|---|---|
| orf1 | AAN39365.1 | 23664428 | *Azoarcus evansii* |
| Magn03011230 | ZP_00207794 | 46200680 | *Magnetospirillum magnetotacticum* |
| Jann_0674 | YP_508616 | 89053165 | *Jannaschia* sp. CCS1 |
| SSE37_24444 | ZP_01745221 | 126729407 | *Sagittula stellata* |
| EF569604.1: 4745 . . . 5170 | ABQ44580.1 | 146761194 | *Pseudomonas* sp. CBS3 |
| Rv0098 | NP_214612.1 | 15607240 | *Mycobacterium tuberculosis* |
| entH | AAC73698.1 | 1786813 | *Escherichia coli* |

Several additional CoA hydrolases with broad substrate ranges are suitable for hydrolyzing benzoyl-CoA and/or p-methylbenzoyl-CoA. For example, the enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)). The closest *E. coli* homolog to this enzyme, tesB, can also hydrolyze a range of CoA thioesters (Naggert et al., *J Biol Chem* 266:11044-11050 (1991)). A similar enzyme has also been characterized in the rat liver (Deana R., *Biochem Int* 26:767-773 (1992)). Additional enzymes with hydrolase activity in *E. coli* include ybgC, paaI, and ybdB (Kuznetsova, et al., FEMS Microbiol Rev, 2005, 29(2):263-279; Song et al., J Biol Chem, 2006, 281(16):11028-38).

| Gene name | GenBank Accession # | GI# | Organism |
|---|---|---|---|
| acot12 | NP_570103.1 | 18543355 | *Rattus norvegicus* |
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* | al., *Biochemistry* 45:9584-9592 (2006); Andrei et al., *Eur. J Biochem.* 271:2225-2230 (2004)). These enzymes, encoded by csdABC in *C. scatologenes* and hpdABC in *C. difficile*, have been heterologously expressed in *E. coli*. Another suitable enzyme is the arylmalonate decarboxylase (EC 4.1.1.76) of *Enterobacter cloacae*, which has activity on the structurally related substrate, 2-phenylpropionate (Yatake et al., *Appl. Microbiol Biotechnol.* 78:793-799 (2008)). The sequence of this enzyme is available in the publication by Yatake et al; however this enzyme has not been assigned a GenBank Accession number to date. A related enzyme from *Bordetella bronchiseptica* (98% amino acid identity) encoded by AMDA_BORBR was recently crystallized (Kuettner et al., *J Mol. Biol.* 377:386-394 (2008)).

| Gene name | GenBank Accession # | GI# | Organism |
|---|---|---|---|
| csdA | ABB05048.1 | 77863917 | *Clostridium scatologenes* |
| csdB | ABB05046.1 | 77863915 | *Clostridium scatologenes* |
| csdC | ABB05047.1 | 77863916 | *Clostridium scatologenes* |
| hpdA | CAD65891.1 | 28300943 | *Clostridium difficile* |
| hpdB | CAD65889.1 | 28300939 | *Clostridium difficile* |
| hpdC | CAD65890.1 | 28300941 | *Clostridium difficile* |
| AMDA_BORBR | Q05115.1 | 728844 | *Bordetella bronchiseptica* |

The conversion of phenylpyruvate to phenylacetaldehyde (FIG. 1, Step B) is catalyzed by an enzyme with phenylpyruvate decarboxylase activity. Several keto-acid decarboxylase enzymes have demonstrated activity on phenylpyruvate including phenylpyruvate decarboxylase (EC 4.1.1.43), pyruvate decarboxylase (EC 4.1.1.1), branched-chain alpha-ketoacid decarboxylase (EC 4.1.1.72) and benzylformate decarboxylase (EC 4.1.1.7). An exemplary phenylpyruvate decarboxylase is encoded by the ipdC gene of *Azospirillum brasilense* (Spaepen et al., *J Bacteriol.* 189:7626-7633 (2007)). Phenylpyruvate is the favored substrate of this enzyme. The *Saccharomyces cerevisiae* enzymes encoded by the genes PDC1, PDC5, PDC6 and ARO10 also exhibit phenylpyruvate decarboxylase activity (Dickinson et al., *J Biol. Chem.* 278:8028-8034 (2003)). Other enzymes with phenylpyruvate decarboxylase activity include the pyruvate dehydrogenase enzyme *Zygosaccharomyces bisporus* (Neuser et al., *Biol. Chem.* 381:349-353 (2000)), the branched chain 2-oxoacid decarboxylase enzymes of *Mycobacterium tuberculosis* H37Rv and *Lactococcus lactis* (Gocke et al., *Adv. Synth. Catal.* 349:1425-1435 (2007); Werther et al., *J Biol. Chem.* 283:5344-5354 (2008)), and the benzylformate decarboxylase enzyme of *Pseudomonas putida* (Siegert et al., *Protein Eng Des Sel* 18:345-357 (2005)). Another suitable enzyme is the pyruvate decarboxylase from *Zymomonas mobilus*, as this enzyme has a broad substrate range and has been a subject of directed engineering studies to alter the substrate specificity (Siegert et al., *Protein Eng Des Sel* 18:345-357 (2005)).

| Protein | GenBank ID | GI Number | Organism |
| --- | --- | --- | --- |
| ipdC | P51852.1 | 1706320 | *Azospirillum brasilense* |
| PDC1 | P06169.7 | 30923172 | *Saccharomyces cerevisiae* |
| PDC5 | P16467.4 | 1352225 | *Saccharomyces cerevisiae* |
| PDC6 | P26263.3 | 118389 | *Saccharomyces cerevisiae* |
| ARO10 | Q06408.1 | 50400299 | *Saccharomyces cerevisiae* |
| pdc1 | CAB65554.1 | 6689662 | *Zygosaccharomyces bisporus* |
| Rv0853c | NP_215368.1 | 15607993 | *Mycobacterium tuberculosis* H37Rv |
| kdcA | AAS49166.1 | 44921617 | *Lactococcus lactis* |
| mdlC | P20906.2 | 3915757 | *Pseudomonas putida* |
| pdc | P06672.1 | 118391 | *Zymomonas mobilis* |

The decarboxylation of benzoyl-acetate to acetophenone (Step C of FIG. 3) is catalyzed by an enzyme with benzoyl-acetate decarboxylase activity. An ATP-dependent enzyme with this activity, acetophenone carboxylase, operates in the reverse (carboxylation) direction during ethylbenzene degradation in *Aromatoleum aromaticum* EbN1 (Rabus et al., *Arch. Microbiol* 178:506-516 (2002)). This enzyme is composed of five subunits encoded by apc1-5 and is ATP-dependent (AMP forming) in the direction of carboxylation. Similar enzymes are found by sequence homology in *Azotobacter vinelandii* and *Rubrobacter xylanophilus*.

| Gene name | GenBank Accession # | GI# | Organism |
| --- | --- | --- | --- |
| apc1 | YP_158351.1 | 56476762 | *Aromatoleum aromaticum* EbN1 |
| apc2 | YP_158350.1 | 56476761 | *Aromatoleum aromaticum* EbN1 |
| apc3 | YP_158349.1 | 56476760 | *Aromatoleum aromaticum* EbN1 |
| apc4 | YP_158348.1 | 56476759 | *Aromatoleum aromaticum* EbN1 |
| apc5 | YP_158347.1 | 56476758 | *Aromatoleum aromaticum* EbN1 |
| apc1 | YP_002798345.1 | 226943272 | *Azotobacter vinelandii* |
| apc2 | ACO77369.1 | 226718198 | *Azotobacter vinelandii* |
| apc3 | YP_002798343.1 | 226943270 | *Azotobacter vinelandii* |
| apc4 | YP_002798342.1 | 226943269 | *Azotobacter vinelandii* |
| apc1 | YP_644617.1 | 108804680 | *Rubrobacter xylanophilus* |
| apc2 | YP_644616.1 | 108804679 | *Rubrobacter xylanophilus* |
| apc3 | YP_644615.1 | 108804678 | *Rubrobacter xylanophilus* |
| apc4 | YP_644614.1 | 108804677 | *Rubrobacter xylanophilus* |
| apc5 | YP_644613.1 | 108804676 | *Rubrobacter xylanophilus* |

Alternatively, a 3-oxoacid decarboxylase can convert benzoyl-acetate to acetophenone. An exemplary 3-oxoacid decarboxylase is acetoacetate decarboxylase (EC 4.1.1.4), which naturally converts acetoacetate into acetone and $CO_2$. The enzyme from *Clostridium acetobutylicum*, encoded by adc, has a broad substrate range and has been shown to catalyze the desired decarboxylation of benzoyl-acetate to acetophenone (Rozzel et al., *J. Am. Chem. Soc.* 106:4937-4941 (1984); Benner et al., *J. Am. Chem. Soc.* 103:993-994 (1981); Autor et al., *J Biol. Chem.* 245:5214-5222 (1970)). A related acetoacetate decarboxylase has been characterized in *Clostridium beijerinckii* (Ravagnani et al., *Mol. Microbiol* 37:1172-1185 (2000)). The acetoacetate decarboxylase from *Bacillus polymyxa*, characterized in cell-free extracts, also has a broad substrate specificity for 3-keto acids and can decarboxylate 3-oxopentanoate (Matiasek et al., *Curr. Microbiol* 42:276-281 (2001)). The gene encoding this enzyme has not been identified to date and the genome sequence of *B. polymyxa* is not yet available. Another adc is found in *Clostridium saccharoperbutylacetonicum* (Kosaka, et al., *Biosci. Biotechnol Biochem.* 71:58-68 (2007)). Additional genes in other organisms, including *Clostridium botulinum* and *Bacillus amyloliquefaciens* FZB42, can be inferred by sequence homology.

| Protein | GenBank ID | GI Number | Organism |
| --- | --- | --- | --- |
| adc | NP_149328.1 | 15004868 | *Clostridium acetobutylicum* |
| adc | AAP42566.1 | 31075386 | *Clostridium saccharoperbutylacetonicum* |
| adc | YP_001310906.1 | 150018652 | *Clostridium beijerinckii* |
| CLL_A2135 | YP_001886324.1 | 187933144 | *Clostridium botulinum* |
| RBAM_030030 | YP_001422565.1 | 154687404 | *Bacillus amyloliquefaciens* |

4.1.99.a Decarbonylase: A decarbonylase enzyme is required to convert phenylacetaldehyde to toluene (Step E of FIG. 1). Decarbonylase enzymes catalyze the final step of alkane biosynthesis in plants, mammals, insects and bacteria (Dennis et al., *Arch. Biochem. Biophys.* 287:268-275 (1991)). Non-oxidative decarbonylases transfom aldehydes into alkanes with the concurrent release of CO, whereas oxidative decarboxylases are cytochrome P450 enzymes that utilize NADPH and $O_2$ as cofactors and release $CO_2$, water and $NADP^+$. Exemplary decarbonylase enzymes include octadecanal decarbonylase (EC 4.1.99.5), sterol desaturase and fatty aldehyde decarbonylase. A cobalt-porphyrin containing decarbonylase was purified and characterized in the algae *Botryococcus braunii*; however, no gene is associated with this activity to date (Dennis et al., *Proc. Natl. Acad. Sci. U.S.A* 89:5306-5310 (1992)). A copper-containing decarbonylase from *Pisum sativum* was also purified and characterized (Schneider-Belhaddad et al., *Arch. Biochem. Biophys.* 377:341-349 (2000)). The CER1 gene of *Arabidopsis thaliana* encodes a fatty acid decarbonylase involved in epicuticular wax formation (U.S. Pat. No. 6,437,218). Additional fatty acid decarbonylases are found in *Medicago truncatula*, *Vitis vinifera* and *Oryza sativa* (US Patent Application 2009/0061493).

| Protein | GenBank ID | GI Number | Organism |
|---|---|---|---|
| CER1 | NP_850932 | 145361948 | *Arabidopsis thaliana* |
| MtrDRAFT_AC153128g2v2 | ABN07985 | 124359969 | *Medicago truncatula* |
| VITISV_029045 | CAN60676 | 147781102 | *Vitis vinifera* |
| OSJNBa0004N05.14 | CAE03390.2 | 38345317 | *Oryza sativa* |

Oxidative decarbonylase enzymes are encoded by the CYP4G2v1 and CYP4G1gene products of *Musca domestica* and *Drosophila melanogaster* (US Patent Application 2010/0136595). Additional enzymes with oxidative decarbonylase activity can be identified in other organisms, for example *Mamestra brassicae*, *Helicoverpa zea* and *Acyrthosiphon pisum*, by sequence homology.

| Protein | GenBank ID | GI Number | Organism |
|---|---|---|---|
| CYP4G2v1 | ABV48808.1 | 157382740 | *Musca domestica* |
| CYP4G1 | NP_525031.1 | 17933498 | *Drosophila melanogaster* |
| CYP4G25 | BAD81026.1 | 56710314 | *Antheraea yamamai* |
| CYP4M6 | AAM54722.1 | 21552585 | *Helicoverpa zea* |
| LOC100164072 | XP_001944205.1 | 193650239 | *Acyrthosiphon pisum* |

4.1.99.b Lyase: The conversion of phenylalanine to benzene in FIG. 2 is catalyzed by an enzyme with phenylalanine benzene-lyase activity. The required novel activity is similar to that of tyrosine phenol-lyase (EC 4.1.99.2), which reversibly interconverts tyrosine and phenol, with concomitant release of pyruvate and ammonia. The enzyme from *Pantoea agglomerans* (formerly *Erwinia herbicola*), encoded by tutA, reacts with a range of substituted derivatives including dihydroxyphenylalanine (Foor et al., *Appl. Environ. Microbiol* 59:3070-3075 (1993)). This enzyme was heterologously expressed in *E. coli* and utilized to synthesize dihydroxyphenylalanine from catechol, pyruvate and ammonia. Additional tyrosine phenol-lyase enzymes include are found in *Citrobacter intermedius* (Nagasawa et al., *Eur. J Biochem.* 117:33-40 (1981)), *Citrobacter freundii* (Phillips et al., *Biochim. Biophys. Acta* 1647:167-172 (2003)) and *Symbiobacterium thermophilum* (Hirahara et al., *Appl. Microbiol Biotechnol.* 39:341-346 (1993)). The *Citrobacter freundii* enzyme has been structurally characterized and residues involved in substrate binding were identified (Milic et al., *J Biol. Chem.* 283:29206-29214 (2008)). Phenylalanine is not a natural substrate of any characterized tyrosine phenol-lyase enzyme; rather it has been shown to act as inhibitor of some enzymes. Directed evolution or other protein engineering approaches well known in the art will likely be required to gain this activity and improve performance.

| Protein | GenBank ID | GI Number | Organism |
|---|---|---|---|
| tutA | AAA66390.1 | 806897 | *Pantoea agglomerans* |
| tpl | ABI75028.1 | 114451977 | *Citrobacter freundii* |
| tpl | BAA00763.1 | 216675 | *Citrobacter intermedius* |
| tpl | YP_076671.1 | 51893980 | *Symbiobacterium thermophilum* |

An enzyme catalyzing a similar reaction is tryptophan indole-lyase (EC 4.1.99.1), also called tryptophanase, which converts tryptophan and water to indole and pyruvate. Exemplary tryptophan indole-lyase enzymes include the gene products of tnaA of *E. coli*, tna1 of *Symbiobacterium thermophilum* and tnaA of *Enterobacter aerogenes* (Kogan et al., *Acta Crystallogr. D. Biol. Crystallogr.* 60:2073-2075 (2004); Kawasaki et al., *Biosci. Biotechnol. Biochem.* 59:1938-1943 (1995); Suzuki et al., *Agric. Biol. Chem.* 55:3059-3066 (1991)).

| Protein | GenBank ID | GI Number | Organism |
|---|---|---|---|
| tnaA | NP_418164.4 | 90111643 | *Escherichia coli* |
| tna1 | BAA24688.1 | 2842554 | *Symbiobacterium thermophilum* |
| tnaA | Q59342.1 | 2501228 | *Enterobacter aerogenes* |

4.2.1.a Dehydratase: Step E of FIG. 3 employs a dehydratase (EC 4.1.2.-) to convert 1-phenylethanol to styrene. Exemplary enzymes for catalyzing this reaction include fumarase (EC 4.2.1.2), citramalate hydratase (EC 4.2.1.34) and dimethylmaleate hydratase (EC 4.2.1.85). Fumarase enzymes naturally catalyze the reversible dehydration of malate to fumarate. Although the suitability of 1-phenylethanol as a substrate for fumarase enzymes has not been described in the literature to date, a wealth of structural information is available for this enzyme and researchers have successfully engineered the enzyme to alter activity, inhibition and localization (Weaver, 61:1395-1401 (2005)). *E. coli* has three fumarases: FumA, FumB, and FumC that are regulated by growth conditions. FumB is oxygen sensitive and only active under anaerobic conditions. FumA is active under microanaerobic conditions, and FumC is the only enzyme active during aerobic growth (Tseng et al., 183:461-467 (2001); Woods et al., 954:14-26 (1988); Guest et al., *J Gen Microbiol* 131:2971-2984 (1985)). Additional enzymes are found in *Campylobacter jejuni* (Smith et al., *Int. J Biochem. Cell Biol* 31:961-975 (1999)), *Thermus* thermophilus (Mizobata et al., Arch. Biochem. Biophys. 355:49-55 (1998)) and Rattus norvegicus (Kobayashi et al., 89:1923-1931 (1981)). Similar enzymes with high sequence homology include fum1 from Arabidopsis thaliana and fumC from Corynebacterium glutamicum. The mmcBC fumarase from Pelotomaculum thermopropionicum is another class of fumarase with two subunits (Shimoyama et al., 270:207-213 (2007)). Citramalate hydrolyase naturally dehydrates 2-methylmalate to mesaconate. This enzyme has been studied in Methanocaldococcus jannaschii in the context of the pyruvate pathway to 2-oxobutanoate, where it has been shown to have a broad substrate specificity (Drevland et al., J Bacteriol. 189:4391-4400 (2007)). This enzyme activity was also detected in Clostridium tetanomorphum, Morganella morganii, Citrobacter amalonaticus where it is thought to participate in glutamate degradation (Kato and Asano, Arch. Microbiol 168:457-463 (1997)). The M. jannaschii protein sequence does not bear significant homology to genes in these organisms. Dimethylmaleate hydratase is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in Eubacterium barkeri (Alhapel et al., supra; Kollmann-Koch et al., Hoppe Seylers. Z. Physiol Chem. 365:847-857 (1984)).

277-287 (2004)). Directed evolution or engineering can be used to modify this enzyme to operate at the physiological temperature of the host organism. The enzymes from A. fulgidus, H. marismortui and P. aerophilum have all been cloned, functionally expressed, and characterized in E. coli (Brasen and Schonheit, Arch. Microbiol 182:277-287 (2004); Musfeldt and Schonheit, J Bacteria 184:636-644 (2002)). An additional enzyme is encoded by sucCD in E. coli, which naturally catalyzes the formation of succinyl-CoA from succinate with the concomitant consumption of one ATP, a reaction which is reversible in vivo (Buck et al., Biochemistry 24:6245-6252 (1985)). The acyl CoA ligase from Pseudomonas putida has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., Appl. Environ. Microbiol. 59:1149-1154 (1993)). A related enzyme, malonyl CoA synthetase (6.3.4.9) from Rhizobium leguminosarum could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., J. Am. Chem. Soc. 123:5822-5823 (2001)).

| Protein | GenBank ID | GI Number | Organism |
| --- | --- | --- | --- |
| fumA | NP_416129.1 | 16129570 | Escherichia coli |
| fumB | NP_418546.1 | 16131948 | Escherichia coli |
| fumC | NP_416128.1 | 16129569 | Escherichia coli |
| fumC | O69294 | 9789756 | Campylobacter jejuni |
| fumC | P84127 | 75427690 | Thermus thermophilus |
| fumH | P14408 | 120605 | Rattus norvegicus |
| fum1 | P93033 | 39931311 | Arabidopsis thaliana |
| fumC | Q8NRN8 | 39931596 | Corynebacterium glutamicum |
| mmcB | YP_001211906 | 147677691 | Pelotomaculum thermopropionicum |
| mmcC | YP_001211907 | 147677692 | Pelotomaculum thermopropionicum |
| leuD | Q58673.1 | 3122345 | Methanocaldococcus jannaschii |
| dmdA | ABC88408 | 86278276 | Eubacterium barkeri |
| dmdB | ABC88409.1 | 86278277 | Eubacterium barkeri |

6.2.1.a Acid-thiol ligase: The conversion of 3-oxo-3-phenylpropionyl-CoA to benzoyl-acetate (Step B of FIG. 3) can be catalyzed by a CoA synthetase or acid-thiol ligase in the EC class 6.2.1. ATP-forming CoA synthetases catalyzing this exact transformation have not been characterized to date; however, several enzymes with broad substrate specificities have been described in the literature. The ADP-forming acetyl-CoA synthetase (ACD, EC 6.2.1.13) from Archaeoglobus fulgidus, encoded by AF1211, was shown to operate on a variety of linear and branched-chain substrates including isobutyrate, isopentanoate, and fumarate (Musfeldt et al., J Bacteriol. 184:636-644 (2002)). A second reversible ACD in Archaeoglobus fulgidus, encoded by AF1983, was also shown to have a broad substrate range with high activity on aromatic compounds phenylacetate and indoleacetate (Musfeldt et al., supra). The enzyme from Haloarcula marismortui, annotated as a succinyl-CoA synthetase, accepts propionate, butyrate, and branched-chain acids (isovalerate and isobutyrate) as substrates, and was shown to operate in the forward and reverse directions (Brasen et al., Arch. Microbiol 182:277-287 (2004)). The ACD encoded by PAE3250 from hyperthermophilic crenarchaeon Pyrobaculum aerophilum showed the broadest substrate range of all characterized ACDs, reacting with acetyl-CoA, isobutyryl-CoA (preferred substrate) and phenylacetyl-CoA (Brasen and Schonheit, Arch. Microbiol 182:

| Gene | GenBank Accession No. | GI No. | Organism |
| --- | --- | --- | --- |
| AF1211 | NP_070039.1 | 11498810 | Archaeoglobus fulgidus |
| AF1983 | NP_070807.1 | 11499565 | Archaeoglobus fulgidus |
| scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| paaF | AAC24333.2 | 22711873 | Pseudomonas putida |
| matB | AAC83455.1 | 3982573 | Rhizobium leguminosarum |

Example II

Pathways to 1,3-Butadiene from Muconate Isomers

This example shows pathways from muconate isomers to 1,3-butadiene.

FIG. 4 shows the conversion of muconate isomers to 1,3-butadiene by decarboxylase enzymes. Cis,cis-muconate, cis,trans-muconate or trans,trans-muconate is first decarboxylated to either cis-2,4-pentadienoate or trans-2,4-pentadienoate (Steps A, B, C and D of FIG. 4). 2,4-Pentadienoate is subsequently decarboxylated to form 1,3-butadiene (Steps E, F of FIG. 4).

It is understood that the decarboxylation of any muconate isomer can serve as part of a pathway to 1,3-butadiene. The biological production of cis,cis-muconate is well-known in the art (Draths and Frost. J Am Chem Soc. 116:399-400 (1994); Niu et al. Biotechnol Prog. 18:201-211 (2002); Bang and Choi. J Ferm Bioeng. 79(4):381-383 (1995)). Isomers of muconate can be interconverted by muconate isomerase enzymes in the EC class 5.2.1.

It is further understood that decarboxylation of either isomer of 2,4-pentadienoate will form 1,3-butadiene. Isomers of 2,4-pentadienoate can alternatively be formed from starting materials other than muconate (e.g., introduction of second double bond via dehydrogenation of pent-2-enoate or pent-4-enoate; removal of CoA from 2,4-pentadienoyl-CoA via a hydrolase, synthetase, or transferase, dehydrogenation of 2,4-pentadienal or 2,4-pentadienol via an aldehyde or aldehyde/alcohol dehydrogenase, respectively). Isomers of 2,4-pentadienoate can be interconverted by isomerase enzymes in the EC class: 5.2.1.

Numerous decarboxylase enzymes have been characterized and shown to decarboxylate structurally similar substrates to muconate or 2,4-pentadienoate isomers. Exemplary enzymes include sorbic acid decarboxylase, aconitate decarboxylase (EC 4.1.1.16), 4-oxalocrotonate decarboxylase (EC 4.1.1.77), cinnamate decarboxylase and ferulic acid decarboxylase. These enzymes are applicable for use in the present invention to decarboxylate muconate and/or 2,4-pentadienoate as shown in FIG. 4.

One decarboxylase enzyme with closely related function is sorbic acid decarboxylase which converts sorbic acid to 1,3-pentadiene. Sorbic acid decarboxylation by *Aspergillus niger* requires three genes: padA1, ohbA1, and sdrA (Plumridge et al. Fung. Genet. Bio, 47:683-692 (2010). PadA1 is annotated as a phenylacrylic acid decarboxylase, ohbA1 is a putative 4-hydroxybenzoic acid decarboxylase, and sdrA is a sorbic acid decarboxylase regulator. Additional species have also been shown to decarboxylate sorbic acid including several fungal and yeast species (Kinderlerler and Hatton, Food Addit Contam., 7(5):657-69 (1990); Casas et al., Int J Food Micro., 94(1):93-96 (2004); Pinches and Apps, Int. J. Food Microbiol. 116: 182-185 (2007)). For example, *Aspergillus oryzae* and *Neosartorya fischeri* have been shown to decarboxylate sorbic acid and have close homologs to padA1, ohbA1, and sdrA.

| Gene name | GenBankID | GI Number | Organism |
| --- | --- | --- | --- |
| padA1 | XP_001390532.1 | 145235767 | *Aspergillus niger* |
| ohbA1 | XP_001390534.1 | 145235771 | *Aspergillus niger* |
| sdrA | XP_001390533.1 | 145235769 | *Aspergillus niger* |
| padA1 | XP_001818651.1 | 169768362 | *Aspergillus oryzae* |
| ohbA1 | XP_001818650.1 | 169768360 | *Aspergillus oryzae* |
| sdrA | XP_001818649.1 | 169768358 | *Aspergillus oryzae* |
| padA1 | XP_001261423.1 | 119482790 | *Neosartorya fischeri* |
| ohbA1 | XP_001261424.1 | 119482792 | *Neosartorya fischeri* |
| sdrA | XP_001261422.1 | 119482788 | *Neosartorya fischeri* |

Aconitate decarboxylase is another useful enzyme for this invention. This enzyme catalyzes the final step in itaconate biosynthesis in a strain of *Candida* and also in the filamentous fungus *Aspergillus terreus*. (Bonnarme et al. *J Bacteriol.* 177:3573-3578 (1995); Willke and Vorlop, *Appl Microbiol. Biotechnol.* 56:289-295 (2001)) Aconitate decarboxylase has been purified and characterized from *Aspergillus terreus*. (Dwiarti et al., *J Biosci. Bioeng.* 94(1): 29-33 (2002)) The gene and protein sequence for the cis-aconitic acid decarboxylase (CAD) enzyme were reported previously (EP 2017344 A1; WO 2009/014437 A1), along with several close homologs listed in the table below.

| Gene name | GenBankID | GI Number | Organism |
| --- | --- | --- | --- |
| CAD | XP_001209273 | 115385453 | *Aspergillus terreus* |
| | XP_001217495 | 115402837 | *Aspergillus terreus* |
| | XP_001209946 | 115386810 | *Aspergillus terreus* |
| | BAE66063 | 83775944 | *Aspergillus oryzae* |
| | XP_001393934 | 145242722 | *Aspergillus niger* |
| | XP_391316 | 46139251 | *Gibberella zeae* |
| | XP_001389415 | 145230213 | *Aspergillus niger* |
| | XP_001383451 | 126133853 | *Pichia stipitis* |
| | YP_891060 | 118473159 | *Mycobacterium smegmatis* |
| | NP_961187 | 41408351 | *Mycobacterium avium* subsp. *pratuberculosis* |
| | YP_880968 | 118466464 | *Mycobacterium avium* |
| | ZP_01648681 | 119882410 | *Salinispora arenicola* |

4-Oxalocronate decarboxylase catalyzes the decarboxylation of 4-oxalocrotonate to 2-oxopentanoate. This enzyme has been isolated from numerous organisms and characterized. Genes encoding this enzyme include dmpH and dmpE in *Pseudomonas* sp. (strain 600) (Shingler et al., 174:711-724 (1992)), xylII and xylIII from *Pseudomonas putida* (Kato et al., *Arch. Microbiol* 168:457-463 (1997); Stanley et al., *Biochemistry* 39:3514 (2000); Lian et al., *J. Am. Chem. Soc.* 116:10403-10411 (1994)) and Reut_B5691 and Reut_B5692 from *Ralstonia eutropha* JMP134 (Hughes et al., 158:79-83 (1984)). The genes encoding the enzyme from *Pseudomonas* sp. (strain 600) have been cloned and expressed in *E. coli* (Shingler et al., 174:711-724 (1992)).

| Gene name | GenBankID | GI Number | Organism |
| --- | --- | --- | --- |
| dmpH | CAA43228.1 | 45685 | *Pseudomonas* sp. CF600 |
| dmpE | CAA43225.1 | 45682 | *Pseudomonas* sp. CF600 |
| xylII | YP_709328.1 | 111116444 | *Pseudomonas putida* |
| xylIII | YP_709353.1 | 111116469 | *Pseudomonas putida* |
| Reut_B5691 | YP_299880.1 | 73539513 | *Ralstonia eutropha* JMP134 |
| Reut_B5692 | YP_299881.1 | 73539514 | *Ralstonia eutropha* JMP134 |

Finally, a class of decarboxylases has been characterized that catalyze the conversion of cinnamate (phenylacrylate) and substituted cinnamate derivatives to their corresponding styrene derivatives. These enzymes are common in a variety of organisms and specific genes encoding these enzymes that have been cloned and expressed in *E. coli* include: pad 1 from *Saccharomyces cerevisae* (Clausen et al., *Gene* 142:107-112 (1994)), pdc from *Lactobacillus plantarum* (Barthelmebs et al., 67:1063-1069 (2001); Qi et al., *Metab Eng* 9:268-276 (2007); Rodriguez et al., *J. Agric. Food Chem.* 56:3068-3072 (2008)), pofK (pad) from *Klebsiella oxytoca* (Uchiyama et al., *Biosci. Biotechnol. Biochem.* 72:116-123 (2008); Hashidoko et al., *Biosci. Biotech. Biochem.* 58:217-218 (1994)), *Pedicoccus pentosaceus* (Barthelmebs et al., 67:1063-1069 (2001)), and padC from *Bacillus subtilis* and *Bacillus pumilus* (Shingler et al., 174: 711-724 (1992)). A ferulic acid decarboxylase from *Pseudomonas fluorescens* also has been purified and characterized (Huang et al., *J. Bacteriol.* 176:5912-5918 (1994)). Enzymes in this class are stable and do not require either exogenous or internally bound co-factors, thus making these enzymes ideally suitable for biotransformations (Sariaslani, *Annu. Rev. Microbiol.* 61:51-69 (2007)).

| Gene name | GenBankID | GI Number | Organism |
|---|---|---|---|
| pad1 | BAG32372.1 | 188496949 | Saccharomyces cerevisiae |
| pdc | AAC45282.1 | 1762616 | Lactobacillus plantarum |
| pofK (pad) | BAF65031.1 | 149941607 | Klebsiella oxytoca |
| padC | AAC46254.1 | 2394282 | Bacillus subtilis |
| pad | CAC16793.1 | 11322457 | Pedicoccus pentosaceus |
| pad | CAC18719.1 | 11691810 | Bacillus pumilus |

Each of the decarboxylases listed above represents a possible suitable enzyme for the desired transformations shown in FIG. 4. If the desired activity or productivity of the enzyme is not observed in the desired conversions (e.g., muconate to 2,4-pentadienoate, 2,4-pentadienoate to butadiene), the decarboxylase enzymes can be evolved using known protein engineering methods to achieve the required performance. Importantly, it was shown through the use of chimeric enzymes that the C-terminal region of decarboxylases appears to be responsible for substrate specificity (Barthelmebs, L.; Divies, C.; Cavin, J.-F. 2001. Expression in *Escherichia coli* of Native and Chimeric Phenolic Acid Decarboxylases with Modified Enzymatic Activities and Method for Screening Recombinant *E. coli* Strains Expressing These Enzymes, Appl. Environ. Microbiol. 67, 1063-1069.). Accordingly, directed evolution experiments to broaden the specificity of decarboxylases in order to gain activity with muconate or 2,4-pentadienoate can be focused on the C-terminal region of these enzymes.

Some of the decarboxylases required to catalyze the transformations in FIG. 4 may exhibit higher activity on specific isomers of muconate or 2,4-pentadienoate. Isomerase enzymes can be applied to convert less desirable isomers of muconate and 2,4-pentadienoate into more desirable isomers for decarboxylation. Exemplary isomerases that catalyze similar transformations and thus represent suitable enzymes for this invention include maleate cis-trans isomerase (EC 5.2.1.1), maleylacetone cis-trans isomerase (EC 5.2.1.2) and fatty acid cis-trans isomerase. Maleate cis-trans isomerase converts fumarate to maleate. This enzyme is encoded by the maiA gene from *Alcaligenes faecalis* (Hatakeyama, et al., 1997, Gene Cloning and Characterization of Maleate cis-trans Isomerase from *Alcaligenes faecalis*, Biochem. Biophys. Research Comm. 239, 74-79) or *Serratia marcescens* (Hatakeyama et al., Biosci. Biotechnol. Biochem. 64:1477-1485 (2000)). Similar genes that can be identified by sequence homology include those from *Geobacillus stearothermophilus*, *Ralstonia pickettii* 12D, and *Ralstonia eutropha* H16. Additional maleate cis-trans isomerase enzymes are encoded by the enzymes whose amino acid sequences are provided as sequence ID's 1 through 4 in ref (Mukouyama et al., U.S. Pat. No. 6,133, 014). Maleylacetone cis,trans-isomerase catalyzes the conversion of 4-maleyl-acetoacetate to 4-fumaryl-acetyacetate, a cis to trans conversion. This enzyme is encoded by maiA in *Pseudomonas aeruginosa* (Fernandez-Canon et al., *J Biol. Chem.* 273:329-337 (1998))) and *Vibrio cholera* (Seltzer, *J Biol. Chem.* 248:215-222 (1973)). A similar enzyme was identified by sequence homology in *E. coli* O157. The cti gene product catalyzes the conversion of cis-unsaturated fatty acids (UFA) to trans-UFA. The enzyme has been characterized in *P. putida* (Junker et al., *J Bacteriol.* 181: 5693-5700 (1999)). Similar enzymes are found in *Shewanella* sp. MR-4 and *Vibrio cholerae*.

| Gene name | GenBankID | GI Number | Organism |
|---|---|---|---|
| maiA | BAA23002.1 | 2575787 | Alcaligenes faecalis |
| maiA | BAA96747.1 | 8570038 | Serratia marcescens |
| maiA | BAA77296 | 4760466 | Geobacillus stearothermophilus |
| Rpic12DDRAFT_0600 | ZP_02009633 | 153888491 | Ralstonia pickettii 12D |
| maiA | YP_725437 | 113866948 | Ralstonia eutropha H16 |
| maiA | NP_250697 | 15597203 | Pseudomonas aeruginosa |
| maiA | NP_230991 | 15641359 | Vibrio cholerae |
| maiA | EDU73766 | 189355347 | Escherichia coli O157 |
| cti | AAD41252 | 5257178 | Pseudomonas putida |
| cti | YP_732637 | 113968844 | Shewanella sp. MR-4 |
| cti | ZP_04395785 | 229506276 | Vibrio cholerae |

Example III

Exemplary Pathway for Producing (2-Hydroxy-3-methyl-4-oxobutoxy)phosphonate

This example describes an exemplary pathway for producing the terephthalic acid (PTA) precursor (2-hydroxy-3-methyl-4-oxobutoxy)phosphonate (2H3M4OP).

The precursor to the p-toluate and PTA pathways is 2H3M4OP. This chemical can be derived from central metabolites glyceraldehyde-3-phosphate (G3P) and pyruvate in three enzymatic steps as shown in FIG. 5. The first two steps are native to *E. coli* and other organisms that utilize the methylerythritol phosphate (non-mevalonate) pathway for isoprenoid biosynthesis. Pyruvate and G3P are first condensed to form 1-deoxy-D-xylulose 5-phosphate (DXP) by DXP synthase. Subsequent reduction and rearrangement of the carbon backbone is catalyzed by DXP reductoisomerase. Finally, a novel diol dehydratase transforms 2-C-methyl-D-erythritol-4-phosphate to the p-toluate precursor 2H3M4OP.

A. 1-Deoxyxylulose-5-phosphate (DXP) synthase. Pyruvate and G3P are condensed to form DXP by DXP synthase (EC 2.2.1.7). This enzyme catalyzes the first step in the non-mevalonate pathway of isoprenoid biosynthesis. The enzyme requires thiamine diphosphate as a cofactor, and also requires reduced FAD, although there is no net redox change. A crystal structure of the *E. coli* enzyme is available (Xiang et al., *J. Biol. Chem.* 282:2676-2682 (2007)). Other enzymes have been cloned and characterized in *M. tuberculosis* (Bailey et al., Glycobiology 12:813-820 (2002) and *Agrobacterium tumefaciens* (Lee et al., J. Biotechnol. 128: 555-566 (2007)). DXP synthase enzymes from *B. subtilis* and *Synechocystis* sp. PCC 6803 were cloned into *E. coli* (Harker and Bramley, *FEBS Lett.* 448:115-119 (1999)).

| Gene | GenBank Accession No. | GI No. | Organism |
|---|---|---|---|
| dxs | AAC73523.1 | 1786622 | Escherichia coli |
| dxs | P0A554.1 | 61222979 | M. tuberculosis |
| dxs11 | AAP56243.1 | 37903541 | Agrobacterium tumefaciens |
| dxs | P54523.1 | 1731052 | Bacillus subtilis |
| sll1945 | BAA17089.1 | 1652165 | Synechocystis sp. PCC 6803 |

B. 1-Deoxy-D-xylulose-5-phosphate reductoisomerase (EC 1.1.1.267). The NAD(P)H-dependent reduction and rearrangement of 1-deoxy-D-xylulose-5-phosphate (DXP) to 2-C-methyl-D-erythritol-4-phosphate is catalyzed by DXP reductoisomerase (DXR, EC 1.1.1.267) in the second step of the non-mevalonate pathway for isoprenoid biosynthesis. The NADPH-dependent E. coli enzyme is encoded by dxr (Takahashi et al., Proc. Natl. Acad. Sci. USA 95:9879-9884 (1998)). A recombinant enzyme from Arabidopsis thaliana was functionally expressed in E. coli (Carretero-Paulet et al., Plant Physiol. 129:1581-1591 (2002)). DXR enzymes from Zymomonas mobilis and Mycobacterium tuberculosis have been characterized and crystal structures are available (Grolle et al., FEMS Microbiol. Lett. 191:131-137 (2000)); Henriksson et al., Acta Crystallogr. D. Biol. Crystallogr. 62:807-813 (2006)). Most characterized DXR enzymes are strictly NADPH dependent, but the enzymes from A. thaliana and M. tuberculosis react with NADH at a reduced rate (Argyrou and Blanchard, Biochemistry 43:4375-4384 (2004)); Rohdich et al., FEBS 1 273:4446-4458 (2006)).

| Gene | GenBank Accession No. | GI No. | Organism |
|---|---|---|---|
| dxr | AAC73284.1 | 1786369 | Escherichia coli |
| dxr | AAF73140.1 | 8131928 | Arabisopsis thaliana |
| dxr | CAB60758.1 | 6434139 | Zymomonas mobilis |
| dxr | NP_217386.2 | 57117032 | Mycobacterium tuberculosis |

C. 2-C-Methyl-D-erythritol-4-phosphate dehydratase. A diol dehydratase is required to convert 2-C-methyl-D-erythritol-4-phosphate into the p-toluate precursor (Altmiller and Wagner, Arch. Biochem. Biophys. 138:160-170 (1970)). Although this transformation has not been demonstrated experimentally, several enzymes catalyze similar transformations including dihydroxy-acid dehydratase (EC 4.2.1.9), propanediol dehydratase (EC 4.2.1.28), glycerol dehydratase (EC 4.2.1.30) and myo-inositose dehydratase (EC 4.2.1.44).

Diol dehydratase or propanediol dehydratase enzymes (EC 4.2.1.28) capable of converting the secondary diol 2,3-butanediol to 2-butanone are excellent candidates for this transformation. Adenosylcobalamin-dependent diol dehydratases contain alpha, beta and gamma subunits, which are all required for enzyme function. Exemplary gene candidates are found in Klebsiella pneumoniae (Tobimatsu et al., Biosci. Biotechnol. Biochem. 62:1774-1777 (1998); Toraya et al., Biochem. Biophys. Res. Commun. 69:475-480 (1976)), Salmonella typhimurium (Bobik et a)., J. Bacteriol. 179:6633-6639 (1997)), Klebsiella oxytoca (Tobimatsu et al., J. Biol. Chem. 270:7142-7148 (1995)) and Lactobacillus collinoides (Sauvageot et al., FEMS Microbiol. Lett. 209: 69-74 (2002)). Methods for isolating diol dehydratase gene candidates in other organisms are well known in the art (see, for example, U.S. Pat. No. 5,686,276).

| Gene | GenBank Accession No. | GI No. | Organism |
|---|---|---|---|
| pddA | BAA08099.1 | 868006 | Klebsiella oxytoca |
| pddB | BAA08100.1 | 868007 | Klebsiella oxytoca |
| pddC | BAA08101.1 | 868008 | Klebsiella oxytoca |
| pduC | AAB84102.1 | 2587029 | Salmonella typhimurium |
| pduD | AAB84103.1 | 2587030 | Salmonella typhimurium |
| pduE | AAB84104.1 | 2587031 | Salmonella typhimurium |
| pduC | CAC82541.1 | 18857678 | Lactobacullus collinoides |
| pduD | CAC82542.1 | 18857679 | Lactobacullus collinoides |
| pduE | CAD01091.1 | 18857680 | Lactobacullus collinoides |
| pddA | AAC98384.1 | 4063702 | Klebsiella pneumoniae |
| pddB | AAC98385.1 | 4063703 | Klebsiella pneumoniae |
| pddC | AAC98386.1 | 4063704 | Klebsiella pneumoniae |

Enzymes in the glycerol dehydratase family (EC 4.2.1.30) can also be used to dehydrate 2-C-methyl-D-erythritol-4-phosphate. Exemplary gene candidates encoded by gldABC and dhaB123 in Klebsiella pneumoniae (WO 2008/137403) and (Toraya et al., Biochem. Biophys. Res. Commun. 69:475-480 (1976)), dhaBCE in Clostridium pasteuranum (Macis et al., FEMS Microbiol Lett. 164:21-28 (1998)) and dhaBCE in Citrobacter freundii (Seyfried et al., J Bacteriol. 178:5793-5796 (1996)). Variants of the B12-dependent diol dehydratase from K. pneumoniae with 80- to 336-fold enhanced activity were recently engineered by introducing mutations in two residues of the beta subunit (Qi et al., J. Biotechnol. 144:43-50 (2009)). Diol dehydratase enzymes with reduced inactivation kinetics were developed by DuPont using error-prone PCR (WO 2004/056963).

| Gene | GenBank Accession No. | GI No. | Organism |
|---|---|---|---|
| gldA | AAB96343.1 | 1778022 | Klebsiella pneumoniae |
| gldB | AAB96344.1 | 1778023 | Klebsiella pneumoniae |
| gldC | AAB96345.1 | 1778024 | Klebsiella pneumoniae |
| dhaB1 | ABR78884.1 | 150956854 | Klebsiella pneumoniae |
| dhaB2 | ABR78883.1 | 150956853 | Klebsiella pneumoniae |
| dhaB3 | ABR78882.1 | 150956852 | Klebsiella pneumoniae |
| dhaB | AAC27922.1 | 3360389 | Clostridium pasteuranum |
| dhaC | AAC27923.1 | 3360390 | Clostridium pasteuranum |
| dhaE | AAC27924.1 | 3360391 | Clostridium pasteuranum |
| dhaB | P45514.1 | 1169287 | Citrobacter freundii |
| dhaC | AAB48851.1 | 1229154 | Citrobacter freundii |
| dhaE | AAB48852.1 | 1229155 | Citrobacter freundii |

If a B12-dependent diol dehydratase is utilized, heterologous expression of the corresponding reactivating factor is recommended. B12-dependent diol dehydratases are subject to mechanism-based suicide activation by substrates and some downstream products. Inactivation, caused by a tight association with inactive cobalamin, can be partially overcome by diol dehydratase reactivating factors in an ATP-dependent process. Regeneration of the B12 cofactor requires an additional ATP. Diol dehydratase regenerating factors are two-subunit proteins. Exemplary candidates are found in Klebsiella oxytoca (Mori et al., J. Biol. Chem. 272:32034-32041 (1997)), Salmonella typhimurium (Bobik et al., J. Bacteriol. 179:6633-6639 (1997); Chen et al., J. Bacteriol. 176:5474-5482 (1994)), Lactobacillus collinoides (Sauvageot et al., FEMS Microbiol. Lett. 209:69-74 (2002)), and Klebsiella pneumonia (WO 2008/137403).

| Gene | GenBank Accession No. | GI No. | Organism |
|---|---|---|---|
| ddrA | AAC15871.1 | 3115376 | Klebsiella oxytoca |
| ddrB | AAC15872.1 | 3115377 | Klebsiella oxytoca |

| Gene | GenBank Accession No. | GI No. | Organism |
|---|---|---|---|
| pduG | AAL20947.1 | 16420573 | Salmonella typhimurium |
| pduH | AAL20948.1 | 16420574 | Salmonella typhimurium |
| pduG | YP_002236779 | 206579698 | Klebsiella pneumoniae |
| pduH | YP_002236778 | 206579863 | Klebsiella pneumoniae |
| pduG | CAD01092 | 29335724 | Lactobacillus collinoides |
| pduH | CAD01093 | 29335725 | Lactobacillus collinoides |

B12-independent diol dehydratase enzymes utilize S-adenosylmethionine (SAM) as a cofactor, function under strictly anaerobic conditions, and require activation by a specific activating enzyme (Frey et al., Chem. Rev. 103: 2129-2148 (2003)). The glycerol dehydrogenase and corresponding activating factor of Clostridium butyricum, encoded by dhaB1 and dhaB2, have been well-characterized (O'Brien et al., Biochemistry 43:4635-4645 (2004); Raynaud et al., Proc. Natl. Acad. Sci USA 100:5010-5015 (2003)). This enzyme was recently employed in a 1,3-propanediol overproducing strain of E. coli and was able to achieve very high titers of product (Tang et al., Appl. Environ. Microbiol. 75:1628-1634 (2009)). An additional B12-independent diol dehydratase enzyme and activating factor from Roseburia inulinivorans was shown to catalyze the conversion of 2,3-butanediol to 2-butanone (US publication 2009/09155870).

| Gene | GenBank Accession No. | GI No. | Organism |
|---|---|---|---|
| dhaB1 | AAM54728.1 | 27461255 | Clostridium butyricum |
| dhaB2 | AAM54729.1 | 27461256 | Clostridium butyricum |
| rdhtA | ABC25539.1 | 83596382 | Roseburia inulinivorans |
| rdhtB | ABC25540.1 | 83596383 | Roseburia inulinivorans |

Dihydroxy-acid dehydratase (DHAD, EC 4.2.1.9) is a B12-independent enzyme participating in branched-chain amino acid biosynthesis. In its native role, it converts 2,3-dihydroxy-3-methylvalerate to 2-keto-3-methyl-valerate, a precursor of isoleucine. In valine biosynthesis, the enzyme catalyzes the dehydration of 2,3-dihydroxy-isovalerate to 2-oxoisovalerate. The DHAD from Sulfolobus solfataricus has a broad substrate range, and activity of a recombinant enzyme expressed in E. coli was demonstrated on a variety of aldonic acids (Kim and Lee, J. Biochem. 139:591-596 (2006)). The S. solfataricus enzyme is tolerant of oxygen unlike many diol dehydratase enzymes. The E. coli enzyme, encoded by ilvD, is sensitive to oxygen, which inactivates its iron-sulfur cluster (Flint et al., J. Biol. Chem. 268:14732-14742 (1993)). Similar enzymes have been characterized in Neurospora crassa (Altmiller and Wagner, Arch. Biochem. Biophys. 138:160-170 (1970)) and Salmonella typhimurium (Armstrong et al., Biochim. Biophys. Acta 498:282-293 (1977)).

| Gene | GenBank Accession No. | GI No. | Organism |
|---|---|---|---|
| ilvD | NP_344419.1 | 15899814 | Sulfolobus solfataricus |
| ilvD | AAT48208.1 | 48994964 | Escherichia coli |
| ilvD | NP_462795.1 | 16767180 | Salmonella typhimurium |
| ilvD | XP_958280.1 | 85090149 | Neurospora crassa |

The diol dehydratase myo-inosose-2-dehydratase (EC 4.2.1.44) is another exemplary candidate. Myo-inosose is a six-membered ring containing adjacent alcohol groups. A purified enzyme encoding myo-inosose-2-dehydratase functionality has been studied in Klebsiella aerogenes in the context of myo-inositol degradation (Berman and Magasanik, J. Biol. Chem. 241:800-806 (1966)), but has not been associated with a gene to date. The myo-inosose-2-dehydratase of Sinorhizobium fredii was cloned and functionally expressed in E. coli (Yoshida et al., Biosci. Biotechnol. Biochem. 70:2957-2964 (2006)). A similar enzyme from B. subtilis, encoded by iolE, has also been studied (Yoshida et al., Microbiology 150:571-580 (2004)).

| Gene | GenBank Accession No. | GI No. | Organism |
|---|---|---|---|
| iolE | P42416.1 | 1176989 | Bacillus subtilis |
| iolE | AAX24114.1 | 60549621 | Sinorhizobium fredii |

Example IV

Exemplary Pathway for Synthesis of p-Toluate from (2-Hydroxy-3-methyl-4-oxobutoxy)phosphonate by Shikimate Pathway Enzymes This example describes exemplary pathways for synthesis of p-toluate using shikimate pathway enzymes.

The chemical structure of p-toluate closely resembles p-hydroxybenzoate, a precursor of the electron carrier ubiquinone. 4-Hydroxybenzoate is synthesized from central metabolic precursors by enzymes in the shikimate pathway, found in bacteria, plants and fungi. The shikimate pathway is comprised of seven enzymatic steps that transform D-erythrose-4-phosphate (E4P) and phosphoenolpyruvate (PEP) to chorismate. Pathway enzymes include 2-dehydro-3-deoxyphosphoheptonate (DAHP) synthase, dehydroquinate (DHQ) synthase, DHQ dehydratase, shikimate dehydrogenase, shikimate kinase, 5-enolpyruvylshikimate-3-phosphate (EPSP) synthase and chorismate synthase. In the first step of the pathway, erythrose-4-phosphate and phosphoenolpyruvate are joined by DAHP synthase to form 3-deoxy-D-arabino-heptulosonate-7-phosphate. This compound is then dephosphorylated, dehydrated and reduced to form shikimate. Shikimate is converted to chorismate by the actions of three enzymes: shikimate kinase, 3-phosphoshikimate-2-carboxyvinyltransferase and chorismate synthase. Subsequent conversion of chorismate to 4-hydroxybenzoate is catalyzed by chorismate lyase.

The synthesis of p-toluate proceeds in an analogous manner as shown in FIG. 6. The pathway originates with PEP and 2H3M4OP, a compound analogous to E4P with a methyl group in place of the 3-hydroxyl group of E4P. The hydroxyl group of E4P does not directly participate in the chemistry of the shikimate pathway reactions, so the methyl-substituted 2H3M4OP precursor is expected to react as an alternate substrate. Directed or adaptive evolution can be used to improve preference for 2H3M4OP and downstream derivatives as substrates. Such methods are well-known in the art.

Strain engineering strategies for improving the efficiency of flux through shikimate pathway enzymes are also applicable here. The availability of the pathway precursor PEP can be increased by altering glucose transport systems (Yi et al., Biotechnol. Prog. 19:1450-1459 (2003)). 4-Hydroxybenzoate-overproducing strains were engineered to improve flux through the shikimate pathway by means of overexpression of a feedback-insensitive isozyme of 3-deoxy-D-arabinoheptulosonic acid-7-phosphate synthase (Barker and Frost, Biotechnol. Bioeng. 76:376-390 (2001)). Additionally, expression levels of shikimate pathway enzymes and chorismate lyase were enhanced. Similar strategies can be employed in a strain for overproducing p-toluate.

A. 2-Dehydro-3-deoxyphosphoheptonate synthase (EC 2.5.1.54). The condensation of erythrose-4-phosphate and phosphoenolpyruvate is catalyzed by 2-dehydro-3-deoxyphosphoheptonate (DAHP) synthase (EC 2.5.1.54). Three isozymes of this enzyme are encoded in the E. coli genome by aroG, aroF and aroH and are subject to feedback inhibition by phenylalanine, tyrosine and tryptophan, respectively. In wild-type cells grown on minimal medium, the aroG, aroF and aroH gene products contributed 80%, 20% and 1% of DAHP synthase activity, respectively (Hudson and Davidson, J. Mol. Biol. 180:1023-1051 (1984)). Two residues of AroG were found to relieve inhibition by phenylalanine (Kikuchi et al., Appl. Environ. Microbiol. 63:761-762 (1997)). The feedback inhibition of AroF by tyrosine was removed by a single base-pair change (Weaver and Herrmann, J. Bacteriol. 172:6581-6584 (1990)). The tyrosine-insensitive DAHP synthase was overexpressed in a 4-hydroxybenzoate-overproducing strain of E. coli (Barker and Frost, Biotechnol. Bioeng. 76:376-390 (2001)). The aroG gene product was shown to accept a variety of alternate 4- and 5-carbon length substrates (Sheflyan et al., J. Am. Chem. Soc. 120(43):11027-11032 (1998); Williamson et al., Bioorg. Med. Chem. Lett. 15:2339-2342 (2005)). The enzyme reacts efficiently with (3S)-2-deoxyerythrose-4-phosphate, a substrate analogous to erythrose-4-phosphate but lacking the alcohol at the 2-position (Williamson et al., supra 2005). Enzymes from Helicobacter pylori and Pyrococcus furiosus also accept this alternate substrate (Schofield et al., Biochemistry 44:11950-11962 (2005)); Webby et al., Biochem. J. 390:223-230 2005)) and have been expressed in E. coli. An evolved variant of DAHP synthase, differing from the wild type E. coli AroG enzyme by 7 amino acids, was shown to exhibit a 60-fold improvement in Kcat/KM (Ran and Frost, J. Am. Chem. Soc. 129:6130-6139 (2007)).

| Gene | GenBank Accession No. | GI No. | Organism |
|---|---|---|---|
| aroG | AAC73841.1 | 1786969 | Escherichia coli |
| aroF | AAC75650.1 | 1788953 | Escherichia coli |
| aroH | AAC74774.1 | 1787996 | Escherichia coli |
| aroF | Q9ZMU5 | 81555637 | Helicobacter pylori |
| PF1690 | NP_579419.1 | 18978062 | Pyrococcus furiosus |

B. 3-Dehydroquinate Synthase (EC 4.2.3.4). The dephosphorylation of substrate (2)(2,4-dihydroxy-5-methyl-6-[(phosphonooxy)methyl]oxane-2-carboxylate) to substrate (3)(1,3-dihydroxy-4-methylcylohex-1-ene-1-carboxylate) as shown in FIG. 2 is analogous to the dephosphorylation of 3-deoxy-arabino-heptulonate-7-phosphate by 3-dehydroquinate synthase. The enzyme has been characterized in E. coli (Mehdi et al., Methods Enzymol. 142:306-314 (1987), B. subtilis (Hasan and Nester, J. Biol. Chem. 253:4999-5004 (1978)) and Mycobacterium tuberculosis H37Rv (de Mendonca et al., J. Bacteriol. 189:6246-6252 (2007)). The E. coli enzyme is subject to inhibition by L-tyrosine (Barker and Frost, Biotechnol. Bioeng. 76:376-390 2001)).

| Gene | GenBank Accession No. | GI No. | Organism |
|---|---|---|---|
| aroB | AAC76414.1 | 1789791 | Escherichia coli |
| aroB | NP_390151.1 | 16079327 | Bacillus subtilis |
| aroB | CAB06200.1 | 1781064 | Mycobacterium tuberculosis |

C. 3-Dehydroquinate Dehydratase (EC 4.2.1.10). 3-Dehydroquinate dehydratase, also termed 3-dehydroquinase (DHQase), naturally catalyzes the dehydration of 3-dehydroquinate to 3-dehydroshikimate, analogous to step C in the p-toluate pathway of FIG. 2. DHQase enzymes can be divided into two classes based on mechanism, stereochemistry and sequence homology (Gourley et al., Nat. Struct. Biol. 6:521-525. (1999)). Generally the type 1 enzymes are involved in biosynthesis, while the type 2 enzymes operate in the reverse (degradative) direction. Type 1 enzymes from E. coli (Kinghorn et al., Gene 14:73-80. 1981)), Salmonella typhi (Kinghorn et al., supra 1981; Servos et al., J. Gen. Microbiol. 137:147-152 (1991)) and B. subtilis (Warburg et al., Gene 32:57-66 1984)) have been cloned and characterized. Exemplary type II 3-dehydroquinate dehydratase enzymes are found in Mycobacterium tuberculosis, Streptomyces coelicolor (Evans et al., FEBS Lett. 530:24-30 (2002)) and Helicobacter pylori (Lee et al., Proteins 51:616-7 (2003)).

| Gene | GenBank Accession No. | GI No. | Organism |
|---|---|---|---|
| aroD | AAC74763.1 | 1787984 | Escherichia coli |
| aroD | P24670.2 | 17433709 | Salmonella typhi |
| aroC | NP_390189.1 | 16079365 | Bacillus subtilis |
| aroD | P0A4Z6.2 | 61219243 | Mycobacterium tuberculosis |
| aroQ | P15474.3 | 8039781 | Streptomyces coelicolor |
| aroQ | Q48255.2 | 2492957 | Helicobacter pylori |

D. Shikimate Dehydrogenase (EC 1.1.1.25). Shikimate dehydrogenase catalyzes the NAD(P)H dependent reduction of 3-dehydroshikimate to shikimate, analogous to Step D of FIG. 2. The E. coli genome encodes two shikimate dehydrogenase paralogs with different cofactor specificities. The enzyme encoded by aroE is NADPH specific, whereas the ydiB gene product is a quinate/shikimate dehydrogenase which can utilize NADH (preferred) or NADPH as a cofactor (Michel et al., J. Biol. Chem. 278:19463-19472 (2003)). NADPH-dependent enzymes from Mycobacterium tuberculosis (Zhang et al., J. Biochem. Mol. Biol. 38:624-631 (2005)), Haemophilus influenzae (Ye et al., J. Bacteriol. 185:4144-4151 (2003)) and Helicobacter pylori (Han et al., FEBS 1 273:4682-4692 (2006)) have been functionally expressed in E. coli.

| Gene | GenBank Accession No. | GI No. | Organism |
|---|---|---|---|
| aroE | AAC76306.1 | 1789675 | Escherichia coli |
| ydiB | AAC74762.1 | 1787983 | Escherichia coli |
| aroE | NP_217068.1 | 15609689 | Mycobacterium tuberculosis |
| aroE | P43876.1 | 1168510 | Haemophilus influenzae |
| aroE | AAW22052.1 | 56684731 | Helicobacter pylori |

E. Shikimate Kinase (EC 2.7.1.71). Shikimate kinase catalyzes the ATP-dependent phosphorylation of the 3-hydroxyl group of shikimate analogous to Step E of FIG. 2. Two shikimate kinase enzymes are encoded by aroK (SK1) and aroL (SK2) in E. coli (DeFeyter and Pittard, J. Bacteriol.

165:331-333 (1986); Lobner-Olesen and Marinus, *J. Bacteriol.* 174:525-529 (1992)). The Km of SK2, encoded by aroL, is 100-fold lower than that of SK1, indicating that this enzyme is responsible for aromatic biosynthesis (DeFeyter et al., supra 1986). Additional shikimate kinase enzymes from *Mycobacterium tuberculosis* (Gu et al., *J. Mol. Biol.* 319:779-789 (2002)); Oliveira et al., *Protein Expr. Purif.* 22:430-435 (2001)(doi:10.1006/prep.2001.1457, doi; S1046-5928(01)91457-3, pii), *Helicobacter pylori* (Cheng et al., *J. Bacteriol.* 187:8156-8163 (2005)) and *Erwinia chrysanthemi* (Krell et al., *Protein Sci.* 10:1137-1149 (2001)) have been cloned in *E. coli*.

| Gene | GenBank Accession No. | GI No. | Organism |
|---|---|---|---|
| aroK | YP_026215.2 | 90111581 | Escherichia coli |
| aroL | NP_414922.1 | 16128373 | Escherichia coli |
| aroK | CAB06199.1 | 1781063 | Mycobacterium tuberculosis |
| aroK | NP_206956.1 | 15644786 | Helicobacter pylori |
| SK | CAA32883.1 | 42966 | Erwinia chrysanthemi |

F. 3-Phosphoshikimate-2-carboxyvinyltransferase (EC 2.5.1.19). 3-Phosphoshikimate-2-carboxyvinyltransferase, also known as 5-enolpyruvylshikimate-3-phosphate synthase (EPSPS), catalyzes the transfer of the enolpyruvyl moiety of phosphoenolpyruvate to the 5-hydroxyl of shikimate-3-phosphate. The enzyme is encoded by aroA in *E. coli* (Anderson et al., *Biochemistry* 27:1604-1610 (1988)). EPSPS enzymes from *Mycobacterium tuberculosis* (Oliveira et al., *Protein Expr. Purif* 22:430-435 (2001)), *Dunaliella salina* (Yi et al., *J. Microbiol.* 45:153-157 (2007)) and *Staphylococcus aureus* (Priestman et al., *FEBS Lett.* 579:728-732 (2005)) have been cloned and functionally expressed in *E. coli*.

| Gene | GenBank Accession No. | GI No. | Organism |
|---|---|---|---|
| aroA | AAC73994.1 | 1787137 | Escherichia coli |
| aroA | AAA25356.1 | 149928 | Mycobacterium tuberculosis |
| aroA | AAA71897.1 | 152956 | Staphylococcus aureus |
| aroA | ABM68632.1 | 122937807 | Dunaliella salina |

G. Chorismate Synthase (EC 4.2.3.5). Chorismate synthase is the seventh enzyme in the shikimate pathway, catalyzing the transformation of 5-enolpyruvylshikimate-3-phosphate to chorismate. The enzyme requires reduced flavin mononucleotide (FMN) as a cofactor, although the net reaction of the enzyme does not involve a redox change. In contrast to the enzyme found in plants and bacteria, the chorismate synthase in fungi is also able to reduce FMN at the expense of NADPH (Macheroux et al., *Planta* 207:325-334 (1999)). Representative monofunctional enzymes are encoded by aroC of *E. coli* (White et al., *Biochem. J.* 251:313-322 (1988)) and *Streptococcus pneumoniae* (Maclean and Ali, *Structure* 11:1499-1511 (2003)(doi: S0969212603002648, pii). Bifunctional fungal enzymes are found in *Neurospora crassa*(Kitzing et al., *J Biol. Chem.* 276:42658-42666 (2001)) and *Saccharomyces cerevisiae* (Jones et al., *Mol. Microbiol.* 5:2143-2152 (1991)).

| Gene | GenBank Accession No. | GI No. | Organism |
|---|---|---|---|
| aroC | NP_416832.1 | 16130264 | Escherichia coli |
| aroC | ACH47980.1 | 197205483 | Streptococcus pneumoniae |
| U25818.1:19..1317 | AAC49056.1 | 976375 | Neurospora crassa |
| ARO2 | CAA42745.1 | 3387 | Saccharomyces cerevisiae |

H. Chorismate Lyase (EC 4.1.3.40). Chorismate lyase catalyzes the first committed step in ubiquinone biosynthesis: the removal of pyruvate from chorismate to form 4-hydroxybenzoate. The enzymatic reaction is rate-limited by the slow release of the 4-hydroxybenzoate product (Gallagher et al., *Proteins* 44:304-311 (2001)), which is thought to play a role in delivery of 4-hydroxybenzoate to downstream membrane-bound enzymes. The chorismate lyase of *E. coli* was cloned and characterized and the enzyme has been crystallized (Gallagher et al., supra 2001; Siebert et al., *FEBS Lett.* 307:347-350 (1992)). Structural studies implicate the G90 residue as contributing to product inhibition (Smith et al., *Arch. Biochem. Biophys.* 445:72-80 (2006)). Modification of two surface-active cysteine residues reduced protein aggregation (Holden et al., *Biochim. Biophys. Acta* 1594:160-167 (2002)). A recombinant form of the *Mycobacterium tuberculosis* chorismate lyase was cloned and characterized in *E. coli* (Stadthagen et al., *J. Biol. Chem.* 280:40699-40706 2005)).

| Gene | GenBank Accession No. | GI No. | Organism |
|---|---|---|---|
| ubiC | AAC77009.2 | 87082361 | Escherichia coli |
| Rv2949c | NP_217465.1 | 15610086 | Mycobacterium tuberculosis |

B-F. Multifunctional AROM Protein. In most bacteria, the enzymes of the shikimate pathway are encoded by separate polypeptides. In microbial eukaryotes, five enzymatic functions are catalyzed by a polyfunctional protein encoded by a pentafunctional supergene (Campbell et al., *Int. J. Parasitol.* 34:5-13 (2004)). The multifunctional AROM protein complex catalyzes reactions analogous to reactions B-F of FIG. 2. The AROM protein complex has been characterized in fungi including *Aspergillus nidulans, Neurospora crassa, Saccharomyces cerevisiae* and *Pneumocystis carinii* (Banerji et al., *J. Gen. Microbiol.* 139:2901-2914 (1993); Charles et al., *Nucleic Acids Res.* 14:2201-2213 (1986); Coggins et al., *Methods Enzymol.* 142:325-341 (1987); Duncan, K., *Biochem.* 1 246:375-386 (1987)). Several components of AROM have been shown to function independently as individual polypeptides. For example, dehydroquinate synthase (DHQS) forms the amino-terminal domain of AROM, and can function independently when cloned into *E. coli* (Moore et al., *Biochem. J.* 301 (Pt 1):297-304 (1994)). Several crystal structures of AROM components from *Aspergillus nidulans* provide insight into the catalytic mechanism (Carpenter et al., *Nature* 394:299-302 (1998)).

| Gene | GenBank Accession No. | GI No. | Organism |
|------|----------------------|-----------|----------------------|
| AROM | P07547.3 | 238054389 | *Aspergillus nidulans* |
| AROM | P08566.1 | 114166 | *Saccharomyces cerevisiae* |
| AROM | P07547.3 | 238054389 | *Aspergillus nidulans* |
| AROM | Q12659.1 | 2492977 | *Pneumocystis carinii* |

Example V

Exemplary Pathway for Enzymatic Transformation of p-Toluate to Terephthalic Acid This example describes exemplary pathways for conversion of p-toluate to terephthalic acid (PTA).

P-toluate can be further transformed to PTA by oxidation of the methyl group to an acid in three enzymatic steps as shown in FIG. 3. The pathway is comprised of a p-toluate methyl-monooxygenase reductase, a 4-carboxybenzyl alcohol dehydrogenase and a 4-carboxybenzyl aldehyde dehydrogenase. In the first step, p-toluate methyl-monooxygenase oxidizes p-toluate to 4-carboxybenzyl alcohol in the presence of $O_2$. The *Comamonas testosteroni* enzyme (tsaBM), which also reacts with 4-toluene sulfonate as a substrate, has been purified and characterized (Locher et al., *J. Bacteriol.* 173:3741-3748 (1991)). 4-Carboxybenzyl alcohol is subsequently converted to an aldehyde by 4-carboxybenzyl alcohol dehydrogenase (tsaC). The aldehyde to acid transformation is catalyzed by 4-carboxybenzaldehyde dehydrogenase (tsaD). Enzymes catalyzing these reactions are found in *Comamonas testosteroni* T-2, an organism capable of utilizing p-toluate as the sole source of carbon and energy (Junker et al., *J. Bacteriol.* 179:919-927 (1997)). Additional genes to transform p-toluate to PTA can be found by sequence homology, in particular to proteobacteria in the genera *Burkholderia, Alcaligenes, Pseudomonas, Shingomonas* and *Comamonas* (U.S. Pat. No. 6,187,569 and US publication 2003/0170836). Genbank identifiers associated with the *Comamonas testosteroni* enzymes are listed below.

| Gene | GenBank Accession No. | GI No. | Organism |
|------|----------------------|---------|-----------------------|
| tsaB | AAC44805.1 | 1790868 | *Comamonas testosteroni* |
| tsaM | AAC44804.1 | 1790867 | *Comamonas testosteroni* |
| tsaC | AAC44807.1 | 1790870 | *Comamonas testosteroni* |
| tsaD | AAC44808.1 | 1790871 | *Comamonas testosteroni* |

Example VI

Synthesis of Benzoate from 2H4OP

This example shows the synthesis of benzoate from 2H4OP by shikimate pathway enzymes (FIG. 9) and an exemplary pathway for producing the benzoate pathway precursor 2H4OP (FIG. 8).

Like p-toluate, the chemical structure of benzoate resembles p-hydroxybenzoate, a product of the shikimate pathway described above in Example IV. In this Example shikimate pathway enzymes are utilized to synthesize benzoate from the pathway precursor (2-hydroxy-4-oxobutoxy) phosphonate (2H4OP) by the pathway shown in FIG. 9. The reactivity of shikimate pathway enzymes on 2H4OP and the alternate substrates used in benzoate formation are optionally optimized by directed or adaptive evolution to improve preference for 2H4OP and downstream derivatives as substrates. Such methods are well-known in the art and described herein.

An exemplary and novel pathway for synthesizing the benzoate pathway precursor (2-hydroxy-4-oxobutoxy)phosphonate (2H4OP) is shown in FIG. 8. In this pathway, 2H4OP is derived from the central metabolite erythrose-4-phosphate in two enzymatic steps. In the first step, a diol dehydratase transforms erythrose-4-phosphate to (2,4-dioxobutoxy)phosphonate (24DBP). The 2-keto group of 24DBP is subsequently reduced to the alcohol of 2H4OP by an oxidoreductase with 24DBP reductase activity. Exemplary enzymes for Steps A and B of FIG. 8 are presented below.

A. Erythrose-4-phosphate dehydratase: Diol dehydratase enzymes in the EC class 4.2.1 are used to convert erythrose-4-phosphate into 24DBP (FIG. 4, Step A). Although enzymes catalyzing this transformation have not been indicated, several enzymes catalyze similar transformations including dihydroxy-acid dehydratase (EC 4.2.1.9), propanediol dehydratase (EC 4.2.1.28), glycerol dehydratase (EC 4.2.1.30) and myo-inositose dehydratase (EC 4.2.1.44). Exemplary diol dehydratase enzymes are described above in Example III.

Diol dehydratase or propanediol dehydratase enzymes (EC 4.2.1.28) capable of converting the secondary diol 2,3-butanediol to 2-butanone can be used for this transformation. Adenosylcobalamin- or B12-dependent diol dehydratases contain alpha, beta and gamma subunits, all of which are used for enzyme function. Exemplary genes are found in *Klebsiella pneumoniae* (Tobimatsu et al., *Biosci. Biotechnol. Biochem.* 62:1774-1777 (1998); Toraya et al.,. *Biochem. Biophys. Res. Commun.* 69:475-480 (1976)), *Salmonella typhimurium* (Bobik et al., *J. Bacteriol.* 179:6633-6639 (1997)), *Klebsiella oxytoca* (Tobimatsu et al., *J. Biol. Chem.* 270:7142-7148 (1995)) and *Lactobacillus collinoides* (Sauvageot et al., *FEMS Microbiol. Lett.* 209:69-74 (2002)). Methods for isolating diol dehydratase genes in other organisms are well known in the art as exemplified in U.S. Pat. No. 5,686,276, which is incorporated herein by reference in its entirety.

| Gene | GenBank Accession No. | GI No. | Organism |
|------|----------------------|---------|---------------------------|
| pddA | BAA08099.1 | 868006 | *Klebsiella oxytoca* |
| pddB | BAA08100.1 | 868007 | *Klebsiella oxytoca* |
| pddC | BAA08101.1 | 868008 | *Klebsiella oxytoca* |
| pduC | AAB84102.1 | 2587029 | *Salmonella typhimurium* |
| pduD | AAB84103.1 | 2587030 | *Salmonella typhimurium* |
| pduE | AAB84104.1 | 2587031 | *Salmonella typhimurium* |
| pduC | CAC82541.1 | 18857678 | *Lactobacullus collinoides* |
| pduD | CAC82542.1 | 18857679 | *Lactobacullus collinoides* |
| pduE | CAD01091.1 | 18857680 | *Lactobacullus collinoides* |
| pddA | AAC98384.1 | 4063702 | *Klebsiella pneumoniae* |
| pddB | AAC98385.1 | 4063703 | *Klebsiella pneumoniae* |
| pddC | AAC98386.1 | 4063704 | *Klebsiella pneumoniae* |

Enzymes in the glycerol dehydratase family (EC 4.2.1.30) can also be used to dehydrate erythrose-4-phosphate. Exemplary genes include gldABC and dhaB123 in *Klebsiella pneumoniae* (WO 2008/137403) and (Toraya et al., *Biochem. Biophys. Res. Commun.* 69:475-480 (1976)), dhaBCE in *Clostridium pasteuranum* (Macis et al., *FEMS Microbiol Lett.* 164:21-28 (1998)) and dhaBCE in *Citrobacter freundii* (Seyfried et al., *J. Bacteriol.* 178:5793-5796 (1996)). Variants of the B12-dependent diol dehydratase from *K. pneumoniae* with 80- to 336-fold enhanced activity were recently engineered by introducing mutations in two residues of the beta subunit (Qi et al., *J. Biotechnol.* 144:43-50 (2009)). Diol dehydratase enzymes with reduced inactivation kinetics were developed by DuPont using error-prone PCR (WO 2004/056963).

| Gene | GenBank Accession No. | GI No. | Organism |
|---|---|---|---|
| gldA | AAB96343.1 | 1778022 | *Klebsiella pneumoniae* |
| gldB | AAB96344.1 | 1778023 | *Klebsiella pneumoniae* |
| gldC | AAB96345.1 | 1778024 | *Klebsiella pneumoniae* |
| dhaB1 | ABR78884.1 | 150956854 | *Klebsiella pneumoniae* |
| dhaB2 | ABR78883.1 | 150956853 | *Klebsiella pneumoniae* |
| dhaB3 | ABR78882.1 | 150956852 | *Klebsiella pneumoniae* |
| dhaB | AAC27922.1 | 3360389 | *Clostridium pasteuranum* |
| dhaC | AAC27923.1 | 3360390 | *Clostridium pasteuranum* |
| dhaE | AAC27924.1 | 3360391 | *Clostridium pasteuranum* |
| dhaB | P45514.1 | 1169287 | *Citrobacter freundii* |
| dhaC | AAB48851.1 | 1229154 | *Citrobacter freundii* |
| dhaE | AAB48852.1 | 1229155 | *Citrobacter freundii* |

If a B12-dependent diol dehydratase is utilized, heterologous expression of the corresponding reactivating factor is useful. B12-dependent diol dehydratases are subject to mechanism-based suicide activation by substrates and some downstream products. Inactivation, caused by a tight association with inactive cobalamin, can be partially overcome by diol dehydratase reactivating factors in an ATP-dependent process. Regeneration of the B12 cofactor is ATP-dependent. Diol dehydratase regenerating factors are two-subunit proteins. Exemplary genes are found in *Klebsiella oxytoca* (Mori et al., *J. Biol. Chem.* 272:32034-32041 (1997)), *Salmonella typhimurium* (Bobik et al., *J. Bacteriol.* 179:6633-6639 (1997); Chen et al., *J. Bacteriol.* 176:5474-5482 (1994)), *Lactobacillus collinoides* (Sauvageot et al., *FEMS Microbiol. Lett.* 209:69-74 (2002)), and *Klebsiella pneumonia* (WO 2008/137403).

| Gene | GenBank Accession No. | GI No. | Organism |
|---|---|---|---|
| ddrA | AAC15871.1 | 3115376 | *Klebsiella oxytoca* |
| ddrB | AAC15872.1 | 3115377 | *Klebsiella oxytoca* |
| pduG | AAL20947.1 | 16420573 | *Salmonella typhimurium* |
| pduH | AAL20948.1 | 16420574 | *Salmonella typhimurium* |
| pduG | YP_002236779 | 206579698 | *Klebsiella pneumonia* |
| pduH | YP_002236778 | 206579863 | *Klebsiella pneumonia* |
| pduG | CAD01092 | 29335724 | *Lactobacillus collinoides* |
| pduH | CAD01093 | 29335725 | *Lactobacillus collinoides* |

B12-independent diol dehydratase enzymes utilize S-adenosylmethionine (SAM) as a cofactor, function under strictly anaerobic conditions, and require activation by a specific activating enzyme (Frey et al., *Chem. Rev.* 103: 2129-2148 (2003)). The glycerol dehydrogenase and corresponding activating factor of *Clostridium butyricum*, encoded by dhaB1 and dhaB2, have been well-characterized (O'Brien et al., *Biochemistry* 43:4635-4645 (2004); Raynaud et al., *Proc. Natl. Acad. Sci USA* 100:5010-5015 (2003)). This enzyme was recently employed in a 1,3-propanediol overproducing strain of *E. coli* and was able to achieve very high titers of product (Tang et al., *Appl. Environ. Microbiol.* 75:1628-1634 (2009)). An additional B12-independent diol dehydratase enzyme and activating factor from *Roseburia inulinivorans* was shown to catalyze the conversion of 2,3-butanediol to 2-butanone (US publication 2009/09155870).

| Gene | GenBank Accession No. | GI No. | Organism |
|---|---|---|---|
| dhaB1 | AAM54728.1 | 27461255 | *Clostridium butyricum* |
| dhaB2 | AAM54729.1 | 27461256 | *Clostridium butyricum* |
| rdhtA | ABC25539.1 | 83596382 | *Roseburia inulinivorans* |
| rdhtB | ABC25540.1 | 83596383 | *Roseburia inulinivorans* |

Dihydroxy-acid dehydratase (DHAD, EC 4.2.1.9) is a B12-independent enzyme participating in branched-chain amino acid biosynthesis. In its native role, it converts 2,3-dihydroxy-3-methylvalerate to 2-keto-3-methyl-valerate, a precursor of isoleucine. In valine biosynthesis, the enzyme catalyzes the dehydration of 2,3-dihydroxy-isovalerate to 2-oxoisovalerate. The DHAD from *Sulfolobus solfataricus* has a broad substrate range, and activity of a recombinant enzyme expressed in *E. coli* was demonstrated on a variety of aldonic acids (Kim and Lee, *J. Biochem.* 139:591-596 (2006)). The *S. solfataricus* enzyme is tolerant of oxygen unlike many diol dehydratase enzymes. The *E. coli* enzyme, encoded by ilvD, is sensitive to oxygen, which inactivates its iron-sulfur cluster (Flint et al., *J. Biol. Chem.* 268:14732-14742 (1993)). Similar enzymes have been characterized in *Neurospora crassa* (Altmiller and Wagner, *Arch. Biochem. Biophys.* 138:160-170 (1970)) and *Salmonella typhimurium* (Armstrong et al., *Biochim. Biophys. Acta* 498:282-293 (1977)).

| Gene | GenBank Accession No. | GI No. | Organism |
|---|---|---|---|
| ilvD | NP_344419.1 | 15899814 | *Sulfolobus solfataricus* |
| ilvD | AAT48208.1 | 48994964 | *Escherichia coli* |
| ilvD | NP_462795.1 | 16767180 | *Salmonella typhimurium* |
| ilvD | XP_958280.1 | 85090149 | *Neurospora crassa* |

The diol dehydratase myo-inosose-2-dehydratase (EC 4.2.1.44) is another exemplary enzyme. Myo-inosose is a six-membered ring containing adjacent alcohol groups. A purified enzyme encoding myo-inosose-2-dehydratase functionality has been studied in *Klebsiella aerogenes* in the context of myo-inositol degradation (Berman and Magasanik, *J Biol. Chem.* 241:800-806 (1966)), but has not been associated with a gene to date. The myo-inosose-2-dehydratase of *Sinorhizobium fredii* was cloned and functionally expressed in *E. coli* (Yoshida et al., *Biosci. Biotechnol. Biochem.* 70:2957-2964 (2006)). A similar enzyme from *B. subtilis*, encoded by iolE, has also been studied (Yoshida et al., *Microbiology* 150:571-580 (2004)).

| Gene | GenBank Accession No. | GI No. | Organism |
|---|---|---|---|
| iolE | P42416.1 | 1176989 | *Bacillus subtilis* |
| iolE | AAX24114.1 | 60549621 | *Sinorhizobium fredii* |

B. (2,4-Dioxobutoxy)phosphonate reductase: An enzyme with (2,4-dioxobutoxy)phosphonate reductase activity is used to convert 24DBP to 2H4OP. Although this compound is not a known substrate of alcohol dehydrogenase enzymes, several enzymes in the EC class 1.1.1 catalyze similar reactions. Exemplary enzymes that reduce ketones of phosphorylated substrates include glycerol-3-phosphate dehydrogenase (EC 1.1.1.8), 3-phosphoglycerate dehydrogenase (EC 1.1.1.95) and erythronate-4-phosphate dehydrogenase (EC 1.1.1.290). Glycerol-3-phosphate dehydrogenase catalyzes the NAD(P)H-dependent reduction of dihydroxyacetone-phosphate to glycerol-3-phosphate. This enzyme is encoded by gpsA of *E. coli* (Kito et al., *J Biol. Chem.* 244:3316-3323 (1969)). 3-Phosphoglycerate dehydrogenase catalyzes the first step of serine biosynthesis in several organisms including *E. coli*, where it is encoded by the gene serA (Tobey et al., *J Biol. Chem.* 261:12179-12183 (1986)). Erythronate-4-phosphate dehydrogenase (EC 1.1.1.290) catalyzes the reversible reduction of 2-oxo-3-hydroxy-4-phosphobutanoate to erythronate-4-phosphate. This enzyme, encoded by pdxB of *E. coli*, normally operates in the reverse direction in the context of pyridoxal 5'-phosphate biosynthesis (Schoenlein et al., *J Bacteriol.* 171:6084-6092 (1989)). A similar enzyme encoded by pdxB in *Pseudomonas aeruginosa* has been characterized and heterologously expressed in *E. coli* (Ha et al., *Acta Crystallogr. Sect. F. Struct. Biol. Cryst. Commun.* 62:139-141 (2006)).

| Gene | GenBank Accession No. | GI No. | Organism |
|---|---|---|---|
| gpsA | AAC76632.1 | 1790037 | *Escherichia coli* |
| serA | AAC75950.1 | 1789279 | *Escherichia coli* |
| pdxB | AAC75380.1 | 1788660 | *Escherichia coli* |
| pdxB | AAG04764.1 | 9947319 | *Pseudomonas aeruginosa* |

A wide variety of alcohol dehydrogenase enzymes catalyze the reduction of a ketone to an alcohol functional group. Two such enzymes from *E. coli* are encoded by malate dehydrogenase (mdh) and lactate dehydrogenase (ldhA). The lactate dehydrogenase from *Ralstonia eutropha* has been shown to demonstrate high activities on 2-ketoacids of various chain lengths including lactate, 2-oxobutyrate, 2-oxopentanoate and 2-oxoglutarate (Steinbuchel et al., *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). An additional oxidoreductase is the mitochondrial 3-hydroxybutyrate dehydrogenase (bdh) from the human heart which has been cloned and characterized (Marks et al., *J. Biol. Chem.* 267:15459-15463 (1992)). Alcohol dehydrogenase enzymes of *C. beijerinckii* (Ismaiel et al., *J. Bacteriol.* 175:5097-5105 (1993)) and *T. brockii* (Lamed et al., *Biochem. J.* 195:183-190 (1981); Peretz et al., *Biochemistry.* 28:6549-6555 (1989)) convert acetone to isopropanol. Methyl ethyl ketone reductase, or alternatively, 2-butanol dehydrogenase, catalyzes the reduction of MEK to form 2-butanol. Exemplary enzymes can be found in *Rhodococcus ruber* (Kosjek et al., *Biotechnol Bioeng.* 86:55-62 (2004)) and *Pyrococcus furiosus* (van der et al., *Eur. J. Biochem.* 268:3062-3068 (2001)).

| Gene | GenBank Accession No. | GI No. | Organism |
|---|---|---|---|
| mdh | AAC76268.1 | 1789632 | *Escherichia coli* |
| ldhA | NP_415898.1 | 16129341 | *Escherichia coli* |
| ldh | YP_725182.1 | 113866693 | *Ralstonia eutropha* |
| bdh | AAA58352.1 | 177198 | *Homo sapiens* |
| adh | AAA23199.2 | 60592974 | *Clostridium beijerinckii* NRRL B593 |
| adh | P14941.1 | 113443 | *Thermoanaerobacter brockii* HTD4 |
| adhA | AAC25556 | 3288810 | *Pyrococcus furiosus* |
| sadh | CAD36475 | 21615553 | *Rhodococcus ruber* |

A number of organisms can catalyze the reduction of 4-hydroxy-2-butanone to 1,3-butanediol, including those belonging to the genus *Bacillus, Brevibacterium, Candida,* and *Klebsiella* among others, as described by Matsuyama et al. ((1995)). A mutated *Rhodococcus* phenylacetaldehyde reductase (Sar268) and a *Leifonia* alcohol dehydrogenase have also been shown to catalyze this transformation at high yields (Itoh et al., *Appl. Microbiol Biotechnol.* 75:1249-1256 (2007)).

Homoserine dehydrogenase (EC 1.1.1.13) catalyzes the NAD(P)H-dependent reduction of aspartate semialdehyde to homoserine. In many organisms, including *E. coli*, homoserine dehydrogenase is a bifunctional enzyme that also catalyzes the ATP-dependent conversion of aspartate to aspartyl-4-phosphate (Starnes et al., *Biochemistry* 11:677-687 (1972)). The functional domains are catalytically independent and connected by a linker region (Sibilli et al., *J Biol. Chem.* 256:10228-10230 (1981)) and both domains are subject to allosteric inhibition by threonine. The homoserine dehydrogenase domain of the *E. coli* enzyme, encoded by thrA, was separated from the aspartate kinase domain, characterized, and found to exhibit high catalytic activity and reduced inhibition by threonine (James et al., *Biochemistry* 41:3720-3725 (2002)). This can be applied to other bifunctional threonine kinases including, for example, hom1 of *Lactobacillus plantarum* (Cahyanto et al., *Microbiology* 152:105-112 (2006)) and *Arabidopsis thaliana*. The monofunctional homoserine dehydrogenases encoded by hom6 in *S. cerevisiae* (Jacques et al., *Biochim. Biophys. Acta* 1544: 28-41 (2001)) and hom2 in *Lactobacillus plantarum* (Cahyanto et al., *Microbiology* 152:105-112 (2006)) have been functionally expressed and characterized in *E. coli*.

| Gene | GenBank Accession No. | GI No. | Organism |
|---|---|---|---|
| thrA | AAC73113.1 | 1786183 | *Escherichia coli* K12 |
| akthr2 | O81852 | 75100442 | *Arabidopsis thaliana* |
| hom6 | CAA89671 | 1015880 | *Saccharomyces cerevisiae* |
| hom1 | CAD64819 | 28271914 | *Lactobacillus plantarum* |
| hom2 | CAD63186 | 28270285 | *Lactobacillus plantarum* |

Example VII

Pathways to Benzene and Toluene

This Example shows pathways from benzoate and benzoyl-CoA to benzene, and p-toluate and p-methylbenzoyl-CoA to toluene.

Pathways for enzymatic production of benzene from benzoate or benzoyl-CoA are shoen in FIG. 10. Benzoate and benzoyl-CoA are naturally occurring metabolic intermediates common to diverse aromatic degradation pathways. Benzoate can also be produced by the alternate shikimate pathway route described herein. Several routes from benzoate and/or benzoyl-CoA to benzene are shown in FIG. 10. First, benzene can be produced directly from benzoate via decarboxylation (FIG. 10, path E). Alternately, the acid moiety can be reduced to an aldehyde either directly by a benzoic acid reductase (FIG. 10, path B) or indirectly via benzoyl-CoA and/or (benzoyloxy)phosphonate intermediates (FIG. 10, paths A and D, path B, path H and G, or path A. F, and G). Benzaldehyde can be subsequently decarbonylated to form benzene (FIG. 10, path C).

Figure 11:
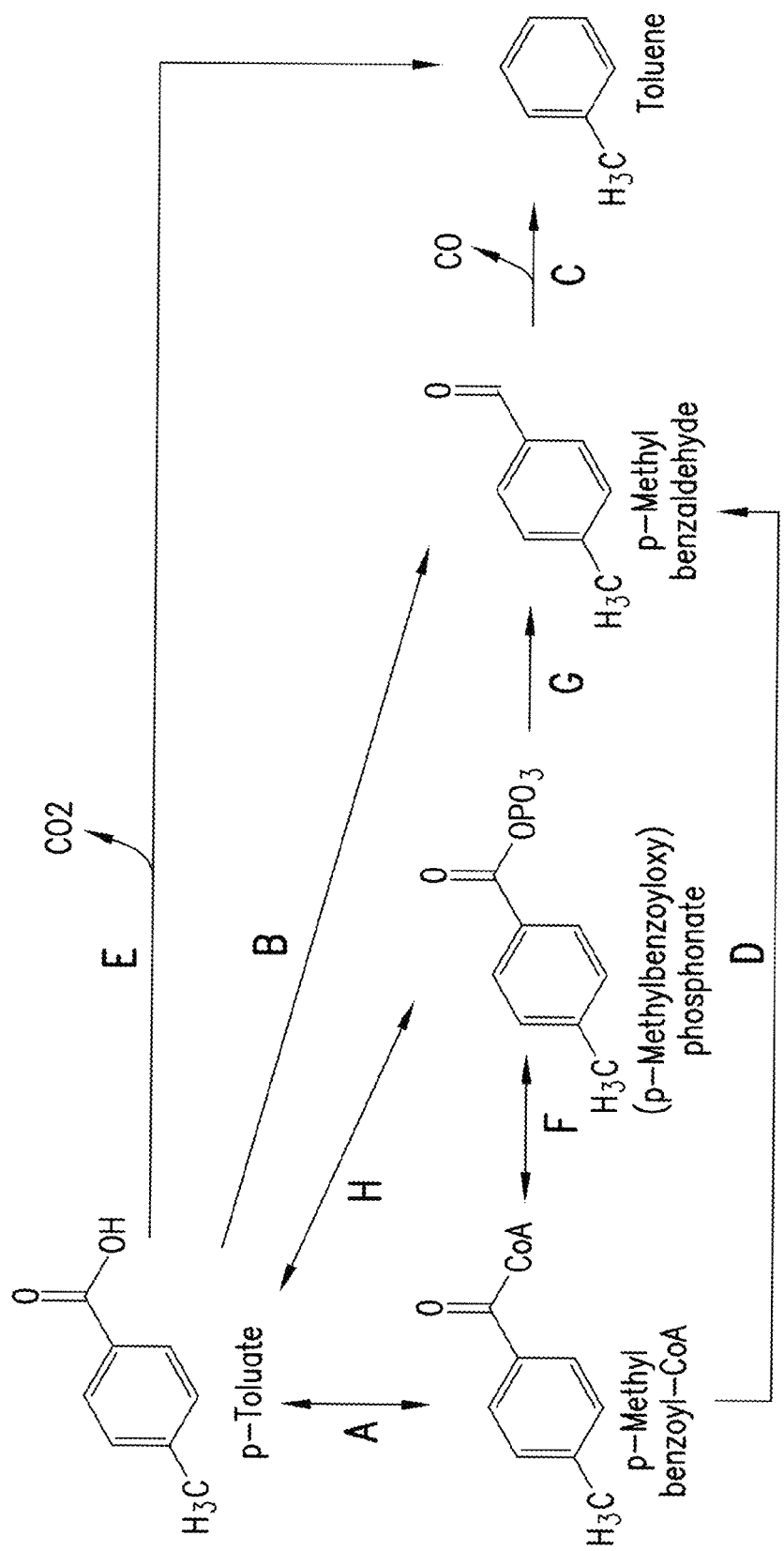
FIG. 11 shows pathways from p-toluate (also called p-toluic acid) and p-methylbenzoyl-CoA to toluene. Enzymes are A. p-methylbenzoyl-CoA synthetase, transferase and/or hydrolase, B. p-toluate reductase, C. p-methylbenzaldehyde decarbonylase, D. p-methylbenzoyl-CoA reductase, E. p-toluate decarboxylase, F. phosphotrans-p-methylbenzoylase, G. (p-methylbenzoyloxy)phosphonate reductase (dephosphorylating), H. p-toluate kinase.

Similar pathways for enzymatic production of toluene from p-toluate and/or p-methylbenzoyl-CoA are shown in FIG. 11. p-Toluate can be produced by the alternate shikimate pathway as described herein. Routes for converting p-toluate (also known as p-methylbenzoate) and/or p-methylbenzoyl-CoA to toluene are analogous to the transformation of benzoate or benzoyl-CoA to benzene, described above. Enzymes for catalyzing the transformations shown in FIGS. 10 and 11 are categorized by EC number and described further below.

| Label | Function | FIG.-Path |
|---|---|---|
| 1.2.1.b | Oxidoreductase (acyl-CoA to aldehyde) | 6/7-D |
| 1.2.1.d | Oxidoreductase (phosphorylating/dephosphorylating) | 6/7-G |
| 1.2.1.e | Oxidoreductase (acid to aldehyde) | 6/7-B |
| 2.3.1.a | Acyltransferase (transferring phosphate group to CoA; phosphotransacylase) | 6/7-F |
| 2.7.2.a | Phosphotransferase, carboxyl group acceptor (kinase) | 6/7-H |
| 2.8.3.a | Coenzyme-A transferase | 6/7-A |
| 3.1.2.a | Thiolester hydrolase (CoA specific) | 6/7-A |
| 4.1.1.a | Carboxy-lyase | 6/7-E |
| 4.1.99.a | Decarbonylase | 6/7-C |
| 6.2.1.a | Acid-thiol ligase | 6/7-A |

1.2.1.b Oxidoreductase (acyl-CoA to aldehyde): An enzyme with benzoyl-CoA reductase activity is used to convert benzoyl-CoA into benzaldehyde (Path D of FIG. 10). Similarly, the reduction of p-methylbenzoyl-CoA to p-methylbenzaldehyde (also called p-tolualdehyde) is catalyzed by an enzyme with p-methylbenzoyl-CoA reductase activity (Path D of FIG. 11). Although enzymes with these activities have not been characterized, an enzyme catalyzing a similar reaction is cinnamoyl-CoA reductase (EC 1.2.1.44). This enzyme catalyzes the NAD(P)H-dependent reduction of cinnamoyl-CoA and substituted aromatic derivatives such as coumaroyl-CoA and feruloyl-CoA. The enzyme has been characterized in organisms including *Arabidopsis thaliana* (Lauvergeat et al., *Phytochemistry* 57:1187-1195 (2001)), *Triticum aestivum* (Ma, *J Exp. Bot.* 58:2011-2021 (2007)) and *Panicum virgatum* (Escamilla-Trevino et al., *New Phytol.* 185:143-155 (2010)). The enzymes from *A. thaliana* and *P. virgatum* were characterized and heterologously expressed in *E. coli*.

| Gene | GenBank Accession No. | GI No. | Organism |
|---|---|---|---|
| TACCR1 | ABE01883.1 | 90902167 | *Triticum aestivum* |
| AtCCR1 | AAU45042.1 | 52355804 | *Arabidopsis thaliana* |
| AtCCR2 | AAG53687.1 | 12407990 | *Arabidopsis thaliana* |
| PvCCR1 | ACZ74580.1 | 270315096 | *Panicum virgatum* |
| PvCCR2 | ACZ74585.1 | 270315106 | *Panicum virgatum* |

Several other well-characterized acyl-CoA reductases reduce an acyl-CoA to its corresponding aldehyde. Exemplary enzymes include fatty acyl-CoA reductase (EC 1.2.1.50), succinyl-CoA reductase (EC 1.2.1.76), acetyl-CoA reductase (EC 1.2.1.10) and butyryl-CoA reductase. Exemplary fatty acyl-CoA reductases enzymes are encoded by acr1 of *Acinetobacter calcoaceticus* (Reiser et al., 179: 2969-2975 (1997)) and *Acinetobacter* sp. M-1 (Ishige et al., *Appl. Environ. Microbiol.* 68:1192-1195 (2002)). Enzymes with succinyl-CoA reductase activity are encoded by sucD of *Clostridium kluyveri* (Sohling et al., *J Bacteriol.* 178: 871-880 (1996a); Sohling et al., 178:871-80 (1996)) and sucD of *P. gingivalis* (Takahashi et al., *J. Bacteriol.* 182: 4704-4710 (2000)). Additional succinyl-CoA reductase enzymes participate in the 3-hydroxypropionate/4-hydroxybutyrate cycle of thermophilic archaea such as *Metallosphaera sedula* (Berg et al., *Science.* 318:1782-1786 (2007)) and *Thermoproteus neutrophilus* (Ramos-Vera et al., *J Bacteriol.* 191:4286-4297 (2009)). The *M. sedula* CoA reductase, encoded by Msed_0709, is NADPH-dependent and also has malonyl-CoA reductase activity. The *T. neutrophilus* enzyme is active with both NADPH and NADH. The acylating acetaldehyde dehydrogenase in *Pseudomonas* sp, encoded by bphG, has been demonstrated to oxidize and acylate acetaldehyde, propionaldehyde, butyraldehyde, isobutyraldehyde and formaldehyde to their corresponding CoA-esters (Powlowski et al., 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol Biochem.* 71:58-68 (2007)). The acyl-CoA reductase encoded by aid in *Clostridium beijerinckii* has been indicated to reduce acetyl-CoA and butyryl-CoA to their corresponding aldehydes (Toth et al., *Appl Environ. Microbiol* 65:4973-4980 (1999)). This enzyme exhibits high sequence homology to the CoA-dependent acetaldehyde dehydrogenase enzymes of *Salmonella typhimurium* and *E. coli* encoded by eutE (Toth et al., *Appl Environ. Microbiol* 65:4973-4980 (1999)).

| Gene | GenBank Accession No. | GI No. | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| MSED_0709 | YP_001190808.1 | 146303492 | *Metallosphaera sedula* |
| Tneu_0421 | ACB39369.1 | 170934108 | *Thermoproteus neutrophilus* |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |
| ald | AAT66436 | 9473535 | *Clostridium beijerinckii* |
| eutE | AAA80209 | 687645 | *Salmonella typhimurium* |
| eutE | P77445 | 2498347 | *Escherichia coli* |

An additional CoA reductase enzyme is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., 318:1782-1786 (2007); Thauer, 318:1732-1733 (2007)). The enzyme utilizes NADPH as a cofactor and has been characterized in *Metallosphaera* and *Sulfolobus* spp (Alber et al., 188:8551-8559 (2006); Hugler et al., 184:2404-2410 (2002)). The enzyme is encoded by Msed_0709 in *Metallosphaera sedula* (Alber et al., 188:8551-8559 (2006); Berg et al., 318:1782-1786 (2007)). A gene encoding a malonyl-CoA reductase from *Sulfolobus tokodaii* was cloned and heterologously expressed in *E. coli* (Alber et al., 188:8551-8559 (2006)). This enzyme has also been indicated to catalyze the conversion of methylmalonyl-CoA to its corresponding aldehyde (WO/2007/141208). Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional genes can be found by sequence homology to proteins in other organisms including *Sulfolobus solfataricus* and *Sulfolobus acidocaldarius*.

| Gene | GenBank Accession No. | GI No. | Organism |
|---|---|---|---|
| MSED_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |

1.2.1.d Oxidoreductase (phosphorylating/dephosphorylating) (10/11 G): The reductions of (benzoyloxy)phosphonate to benzaldehyde (Path G of FIG. 10) and (p-methylbenzoyloxy)phosphonate to p-methylbenzaldehyde (Path G of FIG. 11) are catalyzed by enzymes with phosphonate reductase activities. Although enzymes catalyzing these conversions have not been identified to date, similar transformations catalyzed by glyceraldehyde-3-phosphate dehydrogenase (EC 1.2.1.12), aspartate-semialdehyde dehydrogenase (EC 1.2.1.11) acetylglutamylphosphate reductase (EC 1.2.1.38) and glutamate-5-semialdehyde dehydrogenase (EC 1.2.1.) are well documented. Aspartate semialdehyde dehydrogenase (ASD, EC 1.2.1.11) catalyzes the NADPH-dependent reduction of 4-aspartyl phosphate to aspartate-4-semialdehyde. ASD participates in amino acid biosynthesis and recently has been studied as an antimicrobial target (Hadfield et al., *Biochemistry* 40:14475-14483 (2001)). The *E. coli* ASD structure has been solved (Hadfield et al., *J Mol. Biol.* 289:991-1002 (1999)) and the enzyme has been shown to accept the alternate substrate beta-3-methylaspartyl phosphate (Shames et al., *J. Biol. Chem.* 259:15331-15339 (1984)). The *Haemophilus influenzae* enzyme has been the subject of enzyme engineering studies to alter substrate binding affinities at the active site (Blanco et al., *Acta Crystallogr. D. Biol. Crystallogr.* 60:1388-1395 (2004)). Other ASD genes/enzymes are found in *Mycobacterium tuberculosis* (Shafiani et al., *J Appl Microbiol* 98:832-838 (2005)), *Methanococcus jannaschii* (Faehnle et al., *J Mol. Biol.* 353:1055-1068 (2005)), and the infectious microorganisms *Vibrio cholera* and *Helicobacter pylori* (Moore et al., *Protein Expr. Purif.* 25:189-194 (2002)). A related enzyme is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J Biochem.* 270:1014-1024 (2003)), *B. subtilis* (O'Reilly et al., *Microbiology* 140 (Pt 5):1023-1025 (1994)), *E. coli* (Parsot et al., *Gene*. 68:275-283 (1988)), and other organisms. Additional phosphate reductase enzymes of *E. coli* include glyceraldehyde 3-phosphate dehydrogenase encoded by gapA (Branlant et al., *Eur. J. Biochem.* 150:61-66 (1985)) and glutamate-5-semialdehyde dehydrogenase encoded by proA (Smith et al., *J. Bacteriol.* 157:545-551 (1984b)). Genes encoding glutamate-5-semialdehyde dehydrogenase enzymes from *Salmonella typhimurium* (Mahan et al., *J Bacteriol.* 156:1249-1262 (1983)) and *Campylobacter jejuni* (Louie et al., *Mol. Gen. Genet.* 240:29-35 (1993)) were cloned and expressed in *E. coli*.

| Protein | GenBank ID | GI Number | Organism |
|---|---|---|---|
| asd | NP_417891.1 | 16131307 | *Escherichia coli* |
| asd | YP_248335.1 | 68249223 | *Haemophilus influenzae* |
| asd | AAB49996 | 1899206 | *Mycobacterium tuberculosis* |
| VC2036 | NP_231670 | 15642038 | *Vibrio cholera* |
| asd | YP_002301787.1 | 210135348 | *Helicobacter pylori* |
| ARG5, 6 | NP_010992.1 | 6320913 | *Saccharomyces cerevisiae* |
| argC | NP_389001.1 | 16078184 | *Bacillus subtilis* |
| argC | NP_418393.1 | 16131796 | *Escherichia coli* |
| gapA | P0A9B2.2 | 71159358 | *Escherichia coli* |
| proA | NP_414778.1 | 16128229 | *Escherichia coli* |
| proA | NP_459319.1 | 16763704 | *Salmonella typhimurium* |
| proA | P53000.2 | 9087222 | *Campylobacter jejuni* |

1.2.1.e Oxidoreductase (acid to aldehyde): Direct conversion of benzoate to benzaldehyde or p-toluate to p-methylbenzaldehyde (Path B of FIGS. 10 and 11) is catalyzed by a carboxylic acid reductase. Exemplary enzymes include carboxylic acid reductase, alpha-aminoadipate reductase and retinoic acid reductase. Carboxylic acid reductase (CAR) catalyzes the magnesium, ATP and NADPH-dependent reduction of carboxylic acids to their corresponding aldehydes (Venkitasubramanian et al., *J Biol. Chem.* 282:478-485 (2007)). The natural substrate of this enzyme is benzoate and the enzyme exhibits broad acceptance of aromatic substrates including p-toluate (Venkitasubramanian et al., *Biocatalysis in Pharmaceutical and Biotechnology Industries. CRC press* (2006)). The enzyme from *Nocardia iowensis*, encoded by car, was cloned and functionally expressed in *E. coli* (Venkitasubramanian et al., *J Biol. Chem.* 282:478-485 (2007)). CAR requires post-translational activation by a phosphopantetheine transferase (PPTase) that converts the inactive apo-enzyme to the active holo-enzyme (Hansen et al., *Appl. Environ. Microbiol* 75:2765-2774 (2009)). Expression of the npt gene, encoding a specific PPTase, improved activity of the enzyme. A similar enzyme found in *Streptomyces griseus* is encoded by the griC and griD genes. This enzyme has been indicated to convert 3-amino-4-hydroxybenzoic acid to 3-amino-4-hydroxybenzaldehyde, as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). The *S. griseus* PPTase is likely encoded by SGR_665, as predicted by sequence homology to the *Nocardia* iowensis npt gene.

| Gene | GenBank Accession No. | GI No. | Organism |
|---|---|---|---|
| car | AAR91681.1 | 40796035 | Nocardia iowensis |
| npt | ABI83656.1 | 114848891 | Nocardia iowensis |
| griC | YP_001825755.1 | 182438036 | Streptomyces griseus |
| griD | YP_001825756.1 | 182438037 | Streptomyces griseus |
| SGR_665 | YP_001822177.1 | 182434458 | Streptomyces griseus |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and is activated by a PPTase. Enzymes for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J Biol. Chem.* 278:8250-8256 (2003)). The gene encoding the *P. chrysogenum* PPTase has not been identified to date and no high-confidence hits were identified by sequence comparison homology searching.

| Gene | GenBank Accession No. | GI No. | Organism |
|---|---|---|---|
| LYS2 | AAA34747.1 | 171867 | Saccharomyces cerevisiae |
| LYS5 | P50113.1 | 1708896 | Saccharomyces cerevisiae |
| LYS2 | AAC02241.1 | 2853226 | Candida albicans |
| LYS5 | AAO26020.1 | 28136195 | Candida albicans |
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

2.3.1.a Acyltransferase (phosphotransacylase): An enzyme with phosphotransbenzoylase activity is used to interconvert benzoyl-CoA and (benzoyloxy)phosphonate (Path F of FIG. 10). A similar enzyme with phosphotrans-p-methylbenzoylase activity interconverts p-methylbenzoyl-CoA and (p-methylbenzoyloxy)phosphonate (Path F of FIG. 11). Exemplary phosphate-transferring acyltransferases include phosphotransacetylase (EC 2.3.1.8) and phosphotransbutyrylase (EC 2.3.1.19). The pta gene from *E. coli* encodes a phosphotransacetylase that reversibly converts acetyl-CoA into acetyl-phosphate (Suzuki, *Biochim. Biophys. Acta* 191:559-569 (1969)). This enzyme can also convert propionyl-CoA propionylphosphate (Hesslinger et al., *Mol. Microbiol* 27:477-492 (1998)). Other phosphate acetyltransferases that exhibit activity on propionyl-CoA are found in *Bacillus subtilis* (Rado et al., *Biochim. Biophys. Acta* 321:114-125 (1973)), *Clostridium kluyveri* (Stadtman, 1:596-599 (1955)), and *Thermotoga maritima*(Bock et al., *J Bacteriol.* 181:1861-1867 (1999)). Similarly, the ptb gene from *C. acetobutylicum* encodes phosphotransbutyrylase, an enzyme that reversibly converts butyryl-CoA into butyryl-phosphate (Wiesenborn et al., *Appl Environ. Microbiol* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004)) and *Bacillus megaterium* (Vazquez et al., *Curr. Microbiol* 42:345-349 (2001)).

| Gene | GenBank Accession No. | GI No. | Organism |
|---|---|---|---|
| pta | NP_416800.1 | 71152910 | Escherichia coli |
| pta | P39646 | 730415 | Bacillus subtilis |
| pta | A5N801 | 146346896 | Clostridium kluyveri |
| pta | Q9X0L4 | 6685776 | Thermotoga maritima |
| ptb | NP_349676 | 34540484 | Clostridium acetobutylicum |
| ptb | AAR19757.1 | 38425288 | butyrate-producing bacterium L2-50 |
| ptb | CAC07932.1 | 10046659 | Bacillus megaterium |

2.7.2.a Phosphotransferase, carboxyl group acceptor (kinase): Kinase or phosphotransferase enzymes transform carboxylic acids to phosphonic acids with concurrent hydrolysis of one ATP. Such an enzyme is used to convert benzoate to (benzoyloxy)phosphonate (FIG. 10, Path H) and p-toluate to (p-methyibenzoyloxy)phosphonate (FIG. 11, Path H). These exact transformations have not been demonstrated to date. Exemplary enzymes include butyrate kinase (EC 2.7.2.7), isobutyrate kinase (EC 2.7.2.14), aspartokinase (EC 2.7.2.4), acetate kinase (EC 2.7.2.1) and gamma-glutamyl kinase (EC 2.7.2.11). Butyrate kinase catalyzes the reversible conversion of butyryl-phosphate to butyrate during acidogenesis in *Clostridial* species (Cary et al., *Appl. Environ. Microbiol* 56:1576-1583 (1990)). The *Clostridium acetobutylicum* enzyme is encoded by either of the two buk gene products (Huang et al., *J Mol. Microbiol Biotechnol* 2:33-38 (2000)). Other butyrate kinase enzymes are found in *C. butyricum* and *C. tetanomorphum* (TWAROG et al., *J Bacteriol.* 86:112-117 (1963)). A related enzyme, isobutyrate kinase from *Thermotoga maritima*, was expressed in *E. coli* and crystallized (Diao et al., *J Bacteriol.* 191:2521-2529 (2009); Diao et al., *Acta Crystallogr. D. Biol. Crystallogr.* 59:1100-1102 (2003)). Aspartokinase catalyzes the ATP-dependent phosphorylation of aspartate and participates in the synthesis of several amino acids. The aspartokinase III enzyme in *E. coli*, encoded by lysC, has a broad substrate range and the catalytic residues involved in substrate specificity have been elucidated (Keng et al., *Arch. Biochem. Biophys.* 335:73-81 (1996)). Two additional kinases in *E. coli* are acetate kinase and gamma-glutamyl kinase. The *E. coli* acetate kinase, encoded by ackA (Skarstedt et al., *J. Biol. Chem.* 251:6775-6783 (1976)), phosphorylates propionate in addition to acetate (Hesslinger et al., *Mol. Microbiol* 27:477-492 (1998)). The *E. coli* gamma-glutamyl kinase, encoded by proB (Smith et al., *J. Bacteriol.* 157:545-551 (1984a)), phosphorylates the gamma carbonic acid group of glutamate.

| Gene | GenBank ID | GI Number | Organism |
|---|---|---|---|
| buk1 | NP_349675 | 15896326 | Clostridium acetobutylicum |
| buk2 | Q97II1 | 20137415 | Clostridium acetobutylicum |
| buk2 | Q9X278.1 | 6685256 | Thermotoga maritima |
| lysC | NP_418448.1 | 16131850 | Escherichia coli |
| ackA | NP_416799.1 | 16130231 | Escherichia coli |
| proB | NP_414777.1 | 16128228 | Escherichia coli |

2.8.3.a CoA transferase (10/11 A): CoA transferases catalyze the reversible transfer of a CoA moiety from one molecule to another. Path A of FIG. 10 is catalyzed by an enzyme with benzoyl-CoA transferase activity. In this transformation, benzoyl-CoA is formed from benzoate by the transfer of the CoA group from a CoA donor such as acetyl-CoA, succinyl-CoA or others. p-Methylbenzoyl-CoA transferase catalyzes a similar reaction from p-toluate in Path A of FIG. 11. Exemplary CoA transferase enzymes that react with similar substrates include cinnamoyl-CoA transferase (EC 2.8.3.17) and benzylsuccinyl-CoA transferase. Cinnamoyl-CoA transferase, encoded by fldA in *Clostridium sporogenes*, transfers a CoA moiety from cinnamoyl-CoA to a variety of aromatic acid substrates including phenylacetate, 3-phenylpropionate and 4-phenylbutyrate (Dickert et al., *Eur. J Biochem.* 267:3874-3884 (2000)). Benzylsuccinyl-CoA transferase utilizes succinyl-CoA or maleyl-CoA as the CoA donor, forming benzylsuccinyl-CoA from benzylsuccinate. This enzyme was characterized in the denitrifying bacteria *Thauera aromatica*, where it is encoded by bbsEF (Leutwein et al., *J Bacteriol.* 183:4288-4295 (2001)).

| Gene | GenBank Accession No. | GI No. | Organism |
|---|---|---|---|
| fldA | AAL18808.1 | 16417587 | *Clostridium sporogenes* |
| bbsE | AAF89840.1 | 9622535 | *Thauera aromatica* |
| bbsF | AAF89841.1 | 9622536 | *Thauera aromatica* |

Additional CoA transferase enzymes with diverse substrate ranges include succinyl-CoA transferase, 4-hydroxybutyryl-CoA transferase, butyryl-CoA transferase, glutaconyl-CoA transferase and acetoacetyl-CoA transferase. The gene products of cat1, cat2, and cat3 of *Clostridium kluyveri* have been shown to exhibit succinyl-CoA, 4-hydroxybutyryl-CoA, and butyryl-CoA transferase activity, respectively (Seedorf et al., *Proc. Natl. Acad. Sci U.S.A* 105:2128-2133 (2008); Sohling et al., *J Bacteriol.* 178:871-880 (1996b)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). The glutaconyl-CoA-transferase (EC 2.8.3.12) enzyme from anaerobic bacterium *Acidaminococcus fermentans* reacts with glutaconyl-CoA and 3-butenoyl-CoA (Mack et al., *Eur. J. Biochem.* 226:41-51 (1994)). The genes encoding this enzyme are gctA and gctB. This enzyme has reduced but detectable activity with other CoA derivatives including glutaryl-CoA, 2-hydroxyglutaryl-CoA, adipyl-CoA, crotonyl-CoA and acrylyl-CoA (Bucket et al., *Eur. J Biochem.* 118:315-321 (1981)). The enzyme has been cloned and expressed in *E. coli* (Mack et al., *Eur. J. Biochem.* 226:41-51 (1994)). Glutaconate CoA-transferase activity has also been detected in *Clostridium sporosphaeroides* and *Clostridium symbiosum*. Acetoacetyl-CoA transferase utilizes acetyl-CoA as the CoA donor. This enzyme is encoded by the *E. coli* atoA (alpha subunit) and atoD (beta subunit) genes (Korolev et al., *Acta Crystallogr. D. Biol. Crystallogr.* 58:2116-2121 (2002); Vanderwinkel et al., *Biochem. Biophys. Res. Commun.* 33:902-908 (1968)). This enzyme has a broad substrate range (Sramek et al., *Arch. Biochem. Biophys.* 171:14-26 (1975)) and has been shown to transfer the CoA moiety from acetyl-CoA to a variety of substrates, including isobutyrate (Matthies et al., *Appl Environ. Microbiol* 58:1435-1439 (1992)), valerate (Vanderwinkel et al., *Biochem. Biophys. Res. Commun.* 33:902-908 (1968)) and butanoate (Vanderwinkel et al., *Biochem. Biophys. Res. Commun.* 33:902-908 (1968)). Similar enzymes exist in *Corynebacterium glutamicum* ATCC 13032 (Duncan et al., *Appl. Environ. Microbiol* 68:5186-5190 (2002)), *Clostridium acetobutylicum* (Cary et al., *Appl. Environ. Microbiol* 56:1576-1583 (1990); Wiesenborn et al., *Appl. Environ. Microbiol* 55:323-329 (1989)), and *Clostridium saccharoperbutylacetonicum* (Kosaka et al., *Biosci. Biotechnol Biochem.* 71:58-68 (2007)).

| Gene | GenBank Accession No. | GI No. | Organism |
|---|---|---|---|
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| gctA | CAA57199.1 | 559392 | *Acidaminococcus fermentans* |
| gctB | CAA57200.1 | 559393 | *Acidaminococcus fermentans* |
| gctA | ACJ24333.1 | 212292816 | *Clostridium symbiosum* |
| gctB | ACJ24326.1 | 212292808 | *Clostridium symbiosum* |
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* |
| cg0592 | YP_224801.1 | 62389399 | *Corynebacterium glutamicum* |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

3.1.2.a CoA hydrolase (10/11 A): Benzoyl-CoA and p-methylbenzoyl-CoA can be hydrolyzed to their corresponding acids by CoA hydrolases or thioesterases in the EC class 3.1.2 (Path A of FIGS. 10 and 11). Exemplary CoA thioesters that hydrolyze benzoyl-CoA and/or similar substrates include 4-hydroxybenzoyl-CoA hydrolase (EC 3.1.2.23) and phenylglyoxal-CoA hydrolase (EC 3.1.2.25). The *Azoarcus evansii* gene orf1 encodes an enzyme with benzoyl-CoA hydrolase activity that participates in benzoate metabolism (Ismail, *Arch. Microbiol* 190:451-460 (2008)). This enzyme, when heterologously expressed in *E. coli*, demonstrated activity on a number of alternate substrates. Additional benzoyl-CoA hydrolase enzymes were identified in benzonate degradation gene clusters of *Magnetospirillum magnetotacticum*, *Jannaschia* sp. CCS1 and *Sagittula stellata* E-37 by sequence similarity (Ismail, *Arch. Microbiol* 190:451-460 (2008)). The 4-hydroxybenzoyl-CoA hydrolase of *Pseudomonas* sp. CBS3 accepts benzoyl-CoA and p-methylbenzoyl-CoA as substrates and has been heterologously expressed and characterized in *E. coli* (Song et al., *Bioorg. Chem.* 35:1-10 (2007)). Additional enzymes with demonstrated benzoyl-CoA hydrolase activity include the palmitoyl-CoA hydrolase of *Mycobacterium tuberculosis*

(Wang et al., Chem. Biol. 14:543-551 (2007)) and the acyl-CoA hydrolase of E. coli encoded by entH (Guo et al., Biochemistry 48:1712-1722 (2009)).

| Gene | GenBank Accession No. | GI No. | Organism |
|---|---|---|---|
| orf1 | AAN39365.1 | 23664428 | Azoarcus evansii |
| Magn03011230 | ZP_00207794 | 46200680 | Magnetospirillum magnetotacticum |
| Jann_0674 | YP_508616 | 89053165 | Jannaschia sp. CCS1 |
| SSE37_24444 | ZP_01745221 | 126729407 | Sagittula stellata |
| EF569604.1: 4745 . . . 5170 | ABQ44580.1 | 146761194 | Pseudomonas sp. CBS3 |
| Rv0098 | NP_214612.1 | 15607240 | Mycobacterium tuberculosis |
| entH | AAC73698.1 | 1786813 | Escherichia coli |

Several CoA hydrolases with broad substrate ranges are suitable enzymes for hydrolyzing benzoyl-CoA and/or p-methylbenzoyl-CoA. For example, the enzyme encoded by acot12 from Rattus norvegicus brain (Robinson et al., Biochem. Biophys. Res. Commun. 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., J. Biol. Chem. 280:38125-38132 (2005)). The closest E. coli homolog to this enzyme, tesB, can also hydrolyze a range of CoA thioesters (Naggert et al., J Biol Chem 266:11044-11050 (1991)). A similar enzyme has also been characterized in the rat liver (Deana R., Biochem Int 26:767-773 (1992)).

| Gene name | GI# | GenBank Accession # | Organism |
|---|---|---|---|
| acot12 | 18543355 | NP_570103.1 | Rattus norvegicus |
| tesB | 16128437 | NP_414986 | Escherichia coli |
| acot8 | 3191970 | CAA15502 | Homo sapiens |
| acot8 | 51036669 | NP_570112 | Rattus norvegicus |
| tesA | 16128478 | NP_415027 | Escherichia coli |
| ybgC | 16128711 | NP_415264 | Escherichia coli |
| paaI | 16129357 | NP_415914 | Escherichia coli |
| ybdB | 16128580 | NP_415129 | Escherichia coli |

4.1.1a. Carboxy-lyase (6/7 E): Decarboxylase enzymes in the EC class 4.1.1 are used to convert benzoate to benzene (Path E of FIG. 10) and p-toluate to toluene (Path E of FIG. 11). Exemplary enzymes that react with these or similar substrates include benzene carboxylase, vanillate decarboxylase, cinnamate decarboxylase, aminobenzoate decarboxylase and a variety of hydroxybenzoate decarboxylases. Decarboxylase enzymes can be oxidative or nonoxidative, depending on the cofactors utilized (Lupa et al., Genomics 86:342-351 (2005a)). An enzyme predicted to have benzoate carboxylase activity was identified in a Clostridia bacterium enrichment culture clone BF (Abu et al., Environ. Microbiol (2010)).

| Gene | GenBank Accession No. | GI No. | Organism |
|---|---|---|---|
| abcA | ADJ94002.1 | 300245889 | Clostridia bacterium enrichment culture clone BF |
| abcD | ADJ94001.1 | 300245887 | Clostridia bacterium enrichment culture clone BF |

A number of characterized decarboxylases with demonstrated activity on hydroxylated aromatics such as 4-hydroxybenzoate, 2,3-dihydroxybenzoate, 3,4-dihydroxybenzoate, 2,6-dihydroxybenzoate and 4,5-dihydroxyphthalate can also exhibit activity on alternate substrates such as p-toluate or benzoate. Exemplary hydroxybenzoate decarboxylase enzymes include the 4,5-dihydroxyphthalate decarboxylase of Comamonas testosteroni (Nakazawa et al., Appl. Environ. Microbiol 36:264-269 (1978)), the 2,3-dihydroxybenzoate decarboxylase of Aspergillus niger (Kamath et al., Biochem. Biophys. Res. Commun. 145:586-595 (1987)) and the 3-octaprenyl-4-hydroxybenzoate decarboxylase of E. coli (Zhang et al., J Bacteriol. 182:6243-6246 (2000)). Exemplary 4-hydroxybenzoate decarboxylases are encoded by shdBD and ubiD of Sedimentibacter hydroxyhenzoicus (formerly Clostridium hydroxybenzoicum) and ubiD of Enterobacter cloacae P240 (Matsui et al., Arch. Microbiol 186:21-29 (2006a); He et al., Eur. J Biochem. 229:77-82 (1995)). The 4-hydroxybenzoate decarboxylase from the facultative anaerobe, Enterobacter cloacae, encoded by ubiD, has been tested for activity on multiple substrates and was shown to be induced by both 4-hydroxybenzoic acid and 4-aminobenzoic acid (Matsui et al., Arch. Microbiol 186:21-29 (2006b)). The bsdBCD genes of Bacillus subtilis encode a reversible non-oxidative 4-hydroxybenzoate/vanillate decarboxylase (Lupa et al., Can. J Microbiol 54:75-81 (2008)). This enzyme was heterologously expressed in E. coli. Similar decarboxylases have been indicated in several other organisms (Lupa et al., Genomics 86:342-351 (2005b)) and genes for some of these are listed below.

| Gene | GenBank Accession No. | GI No. | Organism |
|---|---|---|---|
| phtD | Q59727.1 | 3914354 | Comamonas testosteroni |
| dhbD | CAK48106.1 | 134075758 | Aspergillus niger |
| ubiD | NP_418285.1 | 16131689 | Escherichia coli |
| shdD | AAY67851.1 | 67462198 | Sedimentibacter hydroxybenzoicus |
| shdB | AAY67850.1 | 67462197 | Sedimentibacter hydroxybenzoicus |
| ubiD | AAD50377.1 | 5739200 | Sedimentibacter hydroxybenzoicus |
| ubiD | BAE97712.1 | 110331749 | Enterobacter cloacae P240 |
| bsdB | CAB12157.1 | 2632649 | Bacillus subtilis |
| bsdC | CAB12158.1 | 2632650 | Bacillus subtilis |
| bsdD | CAB12159.1 | 2632651 | Bacillus subtilis |
| STM292 | NP_461842.1 | 16766227 | Salmonella typhimurium LT2 |
| STM2922 | NP_461843.1 | 16766228 | Salmonella typhimurium LT2 |
| STM2923 | NP_461844.1 | 16766229 | Salmonella typhimurium LT2 |
| kpdB | YP_002236894.1 | 206580833 | Klebsiella pneumoniae 342 |
| kpdC | YP_002236895.1 | 206576360 | Klebsiella pneumoniae 342 |
| kpdD | YP_002236896.1 | 206579343 | Klebsiella pneumoniae 342 |
| pad1 | NP_311620.1 | 15832847 | Escherichia coli O157 |
| yclC | NP_311619.1 | 15832846 | Escherichia coli O157 |
| yclD | NP_311618.1 | 15832845 | Escherichia coli O157 |

An additional class of decarboxylases has been characterized that catalyze the decarboxylation of cinnamate (phenylacrylate) and substituted cinnamate derivatives. These enzymes are common in a variety of organisms and specific genes encoding these enzymes that have been cloned and expressed in E. coli include pad 1 from Saccharomyces cerevisae (Clausen et al., Gene 142:107-112 (1994)), pdc from Lactobacillus plantarum (Barthelmebs et al., 67:1063-1069 (2001); Qi et al., Metab Eng 9:268-276 (2007); Rodriguez et al., J. Agric. Food Chem. 56:3068-3072 (2008)), pofK (pad) from *Klebsiella oxytoca* (Uchiyama et al., *Biosci. Biotechnol. Biochem.* 72:116-123 (2008); Hashidoko et al., *Biosci. Biotech. Biochem.* 58:217-218 (1994)), *Pediococcus pentosaceus* (Barthelmebs et al., 67:1063-1069 (2001)), and padC from *Bacillus subtilis* and *Bacillus pumilus* (Shingler et al., (74:711-724 (1992)). A ferulic acid decarboxylase from *Pseudomonas fluorescens* also has been purified and characterized (Huang et al., *J. Bacteriol.* 176:5912-5918 (1994)). Enzymes in this class have been shown to be stable and do not require either exogenous or internally bound co-factors, thus making these enzymes suitable for biotransformations (Sariaslani, *Annu. Rev. Microbiol.* 61:51-69 (2007)).

| Protein | GenBank ID | GI Number | Organism |
|---|---|---|---|
| pad1 | AAB64980.1 | 1165293 | *Saccharomyces cerevisae* |
| pdc | AAC45282.1 | 1762616 | *Lactobacillus plantarum* |
| pad | BAF65031.1 | 149941608 | *Klebsiella oxytoca* |
| padC | NP_391320.1 | 16080493 | *Bacillus subtilis* |
| pad | YP_804027.1 | 116492292 | *Pedicoccus pentosaceus* |
| pad | CAC18719.1 | 11691810 | *Bacillus pumilus* |

4.1.99.a Decarbonylase: A decarbonylase enzyme is used to convert benzaldehyde to benzene (Path C of FIG. 10) and p-methylbenzaldehyde to toluene (Path C of FIG. 11). Decarbonylase enzymes catalyze the final step of alkane biosynthesis in plants, mammals, insects and bacteria (Dennis et al., *Arch. Biochem. Biophys.* 287:268-275 (1991)). Non-oxidative decarbonylases transform aldehydes into alkanes with the concurrent release of CO. Exemplary decarbonylase enzymes include octadecanal decarbonylase (EC 4.1.99.5), sterol desaturase and fatty aldehyde decarbonylase. The CER1 gene of *Arabidopsis thaliana* encodes a fatty acid decarbonylase involved in epicuticular wax formation (U.S. Pat. No. 6,437,218). Additional fatty acid decarbonylases are found in *Medicago truncatula, Vitis vinifera* and *Oryza saliva* (US Patent Application 2009/0061493). A cobalt-porphyrin containing decarbonylase was purified and characterized in the algae *Botryococcus braunii*; however, no gene has been associated with this activity to date (Dennis et al., *Proc. Natl. Acad. Sci. U.S.A* 89:5306-5310 (1992)). A copper-containing decarbonylase from *Pisum sativum* was also purified and characterized, but is not yet associated with a gene (Schneider-Belhaddad et al., *Arch. Biochem. Biophys.* 377:341-349 (2000)).

| Gene | GenBank Accession No. | GI No. | Organism |
|---|---|---|---|
| CER1 | NP_850932 | 145361948 | *Arabidopsis thaliana* |
| MtrDRAFT_AC153128g2v2 | ABN07985 | 124359969 | *Medicago truncatula* |
| VITISV_029045 | CAN60676 | 147781102 | *Vitis vinifera* |
| OSJNBa0004N05.14 | CAE03390.2 | 38345317 | *Oryza sativa* |

Alternately, an oxidative decarbonylase can convert an aldehyde into an alkane. Oxidative decarbonylases are cytochrome P450 enzymes that utilize NADPH and $O_2$ as cofactors and release $CO_2$, water and $NADP^+$. This activity was demonstrated in the CYP4G2v1 and CYP4G1 gene products of *Musca domestica* and *Drosophila melanogaster* (US Patent Application 2010/0136595). Additional enzymes with oxidative decarbonylase activity can be identified by sequence homology in other organisms such as *Mamestra brassicae, Helicoverpa zea* and *Acyrthosiphon pisum*.

| Protein | GenBank ID | GI Number | Organism |
|---|---|---|---|
| CYP4G2v1 | ABV48808.1 | 157382740 | *Musca domestica* |
| CYP4G1 | NP_525031.1 | 17933498 | *Drosophila melanogaster* |
| CYP4G25 | BAD81026.1 | 56710314 | *Antheraea yamamai* |
| CYP4M6 | AAM54722.1 | 21552585 | *Helicoverpa zea* |
| LOC100164072 | XP_001944205.1 | 193650239 | *Acyrthosiphon pisum* |

6.2.1.a Acid-thiol ligase (8A, 11B): The ATP-dependent activation of benzoate to benzoyl-CoA or p-toluate to p-methylbenzoyl-CoA (Path A of FIGS. 10 and 11) is catalyzed by a CoA synthetase or acid-thiol ligase. AMP-forming CoA ligases activate the aromatic acids to their corresponding CoA derivatives, whereas ADP-forming CoA ligases are generally reversible. Exemplary AMP-forming benzoyl-CoA ligases from *Thauera aromatica* and *Azoarcus* sp. strain CIB have been characterized (Lopez Barragan et al., *J Bacteriol.* 186:5762-5774 (2004); Schuhle et al., *J. Bacteriol.* 185:4920-4929 (2003)). Alternately, AMP-forming CoA ligases that react with structurally similar substrates can have activity on benzoate or p-toluate. The AMP-forming cyclohexanecarboxylate CoA-ligase from *Rhodopseudomonas palustris*, encoded by aliA, is well-characterized, and alteration of the active site has been shown to impact the substrate specificity of the enzyme (Samanta et al., *Mol. Microbiol* 55:1151-1159 (2005)). This enzyme also functions as a cyclohex-1-ene-1-carboxylate CoA-ligase during anaerobic benzene ring degradation (Egland et al., *Proc. Natl. Acad. Sci U.S.A* 94:6484-6489 (1997)). Additional exemplary CoA ligases include two characterized phenylacetate-CoA ligases from *P. chrysogenum* (Lamas-Maceiras et al., *Biochem. J*395:147-155 (2006); Wang et al., *Biochem. Biophys. Res. Commun.* 360:453-458 (2007)); Wang et al., *Biochem. Biophys. Res. Commun.* 360:453-458 (2007)), the phenylacetate-CoA ligase from *Pseudomonas putida* (Martinez-Blanco et al., *J Biol. Chem.* 265:7084-7090 (1990)), and the 6-carboxyhexanoate-CoA ligase from *Bacillus subtilis* (Bower et al., *J Bacteriol.* 178:4122-4130 (1996)).

| Gene | GenBank Accession No. | GI No. | Organism |
|---|---|---|---|
| bclA | Q8GQN9.1 | 75526585 | *Thauera aromatica* |
| bzdA | AAQ08820.1 | 45649073 | *Azoarcus* sp. strain CIB |
| aliA | AAC23919 | 2190573 | *Rhodopseudomonas palustris* |
| phl | CAJ15517.1 | 77019264 | *Penicillium chrysogenum* |
| phlB | ABS19624.1 | 152002983 | *Penicillium chrysogenum* |
| paaF | AAC24333.2 | 22711873 | *Pseudomonas putida* |
| bioW | NP_390902.2 | 50812281 | *Bacillus subtilis* |

ADP-forming CoA ligases catalyzing these exact transformations have not been characterized to date; however, several enzymes with broad substrate specificities have been described in the literature. The ADP-forming acetyl-CoA synthetase (ACD, EC 6.2.1.13) from *Archaeoglobus fulgidus*, encoded by AF1211, was shown to operate on a variety of linear and branched-chain substrates including isobutyrate, isopentanoate, and fumarate (Musfeldt et al., *J Bacteriol.* 184:636-644 (2002)). A second reversible ACD in *Archaeoglobus fulgidus*, encoded by AF1983, was also indicated to have a broad substrate range with high activity on aromatic compounds phenylacetate and indoleacetate (Musfeldt et al., supra). The enzyme from *Haloarcula marismortui*, annotated as a succinyl-CoA synthetase, accepts propionate, butyrate, and branched-chain acids (isovalerate and isobutyrate) as substrates, and was shown to operate in the forward and reverse directions (Brasen et al., *Arch. Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen and Schonheit, *Arch. Microbiol* 182:277-287 (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, *Arch. Microbiol* 182:277-287 (2004); Musfeldt and Schonheit, *J Bacteriol.* 184:636-644 (2002)). An additional enzyme is encoded by sucCD in *E. coli*, which naturally catalyzes the formation of succinyl-CoA from succinate with the concomitant consumption of one ATP, a reaction which is reversible in vivo (Buck et al., *Biochemistry* 24:6245-6252 (1985)). The acyl CoA ligase from *Pseudomonas putida* has been indicated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Appl. Environ. Microbiol.* 59:1149-1154 (1993)). A related enzyme, malonyl CoA synthetase (6.3.4.9) from *Rhizobium leguminosarum* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)).

| Gene | GenBank Accession No. | GI No. | Organism |
|---|---|---|---|
| AF1211 | NP_070039.1 | 11498810 | *Archaeoglobus fulgidus* |
| AF1983 | NP_070807.1 | 11499565 | *Archaeoglobus fulgidus* |
| scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |
| matB | AAC83455.1 | 3982573 | *Rhizobium leguminosarum* |

Example VIII

Pathways to 2,4-pentadienoate from Pyruvate, Ornithine and Alanine

This example shows pathways from pyruvate, ornithine and alanine to 2,4-pentadienoate.

FIG. 12 shows the conversion of pyruvate to 2,4-pentadienoate. This conversion can be accomplished in four enzymatic steps. Pyruvate and acetaldehyde are first condensed to 4-hydroxy-2-oxovalerate by 4-hydroxy-2-ketovalerate aldolase (Step A of FIG. 12). The 4-hydroxy-2-oxovalerate product is next dehydrated to 2-oxopentenoate (Step B of FIG. 12). Subsequent reduction and dehydration of 2-oxopentenoate yields 2,4-pentadienoate (Steps C/D of FIG. 12).

FIG. 13 shows pathways from alanine or ornithine to 2,4-pentadienoate. In Step A of FIG. 13, alanine and acetyl-CoA are joined by AKP thiolase to form AKP. In one pathway, AKP is deaminated to acetylacrlate (Step B). The 4-oxo group of acetylacrylate is then reduced and dehydrated to 2,4-pentadienoate (Steps C/D). In an alternative pathway, AKP is converted to 2,4-dioxopentanoate by an aminotransferase or dehydrogenase (Step E). Reduction of the 2- or 4-oxo group of 2,4-dioxopentanoate yields 2-hydroxy-4-oxopentanoate (Step H) or 4-hydroxy-2-oxovalerate (Step K), respectively. 4-Hydroxy-2-oxovalerate can alternately be formed by the reduction of AKP to 2-amino-4-hydroxypentanoate (Step J) followed by transamination or oxidative deamination (Step L). Once formed, 4-hydroxy-2-oxovalerate can be converted to 2,4-pentadienoate in three enzymatic steps as shown in FIG. 12 (Steps B/C/D of FIG. 12). The 2-hydroxy-4-oxopentanoate intermediate can undergo dehydration to acetylacrylate (Step F) followed by reduction and dehydration (Steps C/D).

An alternate entry point into the pathways from AKP shown in FIG. 13 is ornithine. An ornithine aminomutase is first required to convert ornithine to 2,4-diaminopentanoate (Step M). The 2,4-diaminopentanoate intermediate is then converted to AKP by transamination or oxidative deamination (Step N).

It is understood that either the D- or L-stereoisomer of alanine or ornithine can serve serve as the precursor or intermediate to a 2,4-pentadienoate pathway shown in FIG. 13. The D- and L-stereoisomers of alanine or ornithine are readily interconverted by alanine racemase or ornithine racemase enzymes.

Enzymes for catalyzing the transformations shown in FIGS. 5 and 6 are categorized by EC number (Table 2) and described further below.

| Label | Function | Step |
|---|---|---|
| 1.1.1.a | Oxidoreductase (oxo to alcohol) | 1C, 2C/H/K/J |
| 1.4.1.a | Oxidoreductase (aminating/deaminating) | 2E/L/N |
| 2.6.1.a | Aminotransferase | 2E/L/N |
| 4.1.3.a | Lyase | 1A |
| 4.2.1.a | Hydro-lyase | 1B/D, 2D/F |
| 4.3.1.a | Ammonia-lyase | 2B |
| 5.1.1.a | D/L Racemase | 2A/M |
| 5.4.3.a | Aminomutase | 2M |
| Other | AKP thiolase | 2A |

1.1.1.a Oxidoreductase (oxo to alcohol): A number of transformations in FIGS. 5 and 6 involve the reduction of a ketone to an alcohol. In Step C of FIG. 12, 2-oxopentenoate is reduced to 2-hyroxypentenoate. A similar transformation is the reduction of the keto-acid 2,4-dioxopentanoate to its corresponding hydroxy-acid, 2-hydroxy-4-oxopentanoate (Step H of FIG. 13). Steps C, J and K of FIG. 13 entail reduction of the 4-oxo groups of AKP, 2,4-dioxopentanoate and acetylacrylate to their corresponding alcohols. These transformations are catalyzed by oxidoreductase enzymes in the EC class 1.1.1.

Several exemplary alcohol dehydrogenases convert a ketone to an alcohol functional group. Two such enzymes from *E. coli* are encoded by malate dehydrogenase (mdh) and lactate dehydrogenase (ldhA). In addition, lactate dehydrogenase from *Ralstonia eutropha* has been shown to demonstrate high activities on 2-ketoacids of various chain lengths includings lactate, 2-oxobutyrate, 2-oxopentanoate and 2-oxoglutarate (Steinbuchel et al., *Eur. J. Biochem.* 130:329-334 (1983)). Conversion of alpha-ketoadipate into alpha-hydroxyadipate is catalyzed by 2-ketoadipate reductase, an enzyme found in rat and in human placenta (Suda et al., *Arch. Biochem. Biophys.* 176:610-620 (1976); Suda et al., *Biochem. Biophys. Res. Commun.* 77:586-591 (1977)). An additional candidate oxidoreductase is the mitochondrial 3-hydroxybutyrate dehydrogenase (bdh) from the human heart which has been cloned and characterized (Marks et al., *J. Biol. Chem.* 267:15459-15463 (1992)). Alcohol dehydrogenase enzymes of *C. beijerinckii* (Ismaiel et al., *J. Bacteriol.* 175:5097-5105 (1993)) and *T. brockii* (Lamed et al., *Biochem. J.* 195:183-190 (1981); Peretz et al., *Biochemistry.* 28:6549-6555 (1989)) convert acetone to isopropanol. Methyl ethyl ketone reductase catalyzes the reduction of MEK to 2-butanol. Exemplary MEK reductase enzymes can be found in *Rhodococcus ruber* (Kosjek et al., *Biotechnol Bioeng.* 86:55-62 (2004)) and *Pyrococcus furiosus* (van der et al., *Eur. J. Biochem.* 268:3062-3068 (2001)).

| Gene | GenBank ID | GI Number | Organism |
| --- | --- | --- | --- |
| mdh | AAC76268.1 | 1789632 | *Escherichia coli* |
| ldhA | NP_415898.1 | 16129341 | *Escherichia coli* |
| ldh | YP_725182.1 | 113866693 | *Ralstonia eutropha* |
| bdh | AAA58352.1 | 177198 | *Homo sapiens* |
| adh | AAA23199.2 | 60592974 | *Clostridium beijerinckii* NRRL B593 |
| adh | P14941.1 | 113443 | *Thermoanaerobacter brockii* HTD4 |
| sadh | CAD36475 | 21615553 | *Rhodococcus ruber* |
| adhA | AAC25556 | 3288810 | *Pyrococcus furiosus* |

1.4.1.a Oxidoreductase (deaminating): Enzymes in the EC class 1.4.1 catalyze the oxidative deamination of amino groups with NAD+, NADP+ or FAD as acceptor. Such an enzyme is required to catalyze the oxidative deamination of AKP to 2,4-dioxopentanoate (FIG. 13, Step E), 2-amino-4-hydroxypentanoate to 4-hydroxy-2-oxovalerate (FIG. 13, Step L) and 2,4-diaminopentanoate to AKP (FIG. 13, Step N). The conversion of 2,4-diaminopentanoate to AKP (Step N of FIG. 13) is catalyzed by 2,4-diaminopentanoate dehydrogenase (EC 1.4.1.12). 2,4-Diaminopentanoate dehydrogenase enzymes have been characterized in organisms that undergo anaerobic fermentation of ornithine, such as the ord gene product of *Clostridium sticklandii* (Fonknechten, *J. Bacteriol.* In Press: (2009)). Additional 2,4-diaminopentanoate dehydrogenase gene candidates can be inferred in other organisms by sequence similarity to the ord gene product. A related enzyme, 3,5-diaminohexanoate dehydrogenase (EC 1.4.1.11), catalyzes the oxidative deamination of 3,5-diaminohexanoate to 5-amino-3-oxohexanoate. The gene encoding this enzyme, kdd, was recently identified in *Fusobacterium nucleatum* (Kreimeyer et al., *J Biol. Chem.* 282:7191-7197 (2007)). The enzyme has been purified and characterized in other organisms that ferment lysine but the genes associated with these enzymes have not been identified to date (Baker et al., *J Biol. Chem.* 247:7724-7734 (1972); Baker et al., *Biochemistry* 13:292-299 (1974)). Candidates in *Myxococcus xanthus, Porphyromonas gingivalis* W83 and other sequenced organisms can be inferred by sequence homology.

| Gene | GenBank ID | GI Number | Organism |
| --- | --- | --- | --- |
| ord | CAQ42978.1 | 226885213 | *Clostridium sticklandii* |
| Hore_21120 | YP_002509852.1 | 220932944 | *Halothermothrix orenii* |
| CD0442 | YP_001086913.1 | 126698016 | *Clostridium difficile* |
| kdd | AAL93966.1 | 19713113 | *Fusobacterium nucleatum* |
| mxan_4391 | ABF87267.1 | 108462082 | *Myxococcus xanthus* |
| pg_1069 | AAQ66183.1 | 34397119 | *Porphyromonas gingivalis* |

The substrates AKP and 2-amino-4-hydroxypentanoate (Steps E and L of FIG. 13), are similar to alpha-amino acids and may serve as alternate substrates for amino acid dehydrogenase enzymes such as glutamate dehydrogenase (EC 1.4.1.2), leucine dehydrogenase (EC 1.4.1.9), and aspartate dehydrogenase (EC 1.4.1.21). Glutamate dehydrogenase catalyzes the reversible NAD(P)+ dependent conversion of glutamate to 2-oxoglutarate. Exemplary enzymes are encoded by gdhA in *Escherichia coli* (McPherson et al., *Nucleic. Acids Res.* 11:5257-5266 (1983); Korber et al., *J. Mol. Biol.* 234:1270-1273 (1993)), gdh in *Thermotoga maritima* (Kort et al., *Extremophiles* 1:52-60 (1997); Lebbink et al., *J. Mol. Biol.* 280:287-296 (1998); Lebbink et al., *J. Mol. Biol.* 289:357-369 (1999)), and gdhA1 in *Halobacterium salinarum* (Ingoldsby et al., *Gene.* 349:237-244 (2005)). Additional glutamate dehydrogenase enzymes have been characterized in *Bacillus subtilis* (Khan et al., *Biosci. Biotechnol Biochem.* 69:1861-1870 (2005)), *Nicotiana tabacum* (Purnell et al., *Planta* 222:167-180 (2005)), *Oryza sativa* (Abiko et al., *Plant Cell Physiol* 46:1724-1734 (2005)), *Haloferax mediterranei* (Diaz et al., *Extremophiles.* 10:105-115 (2006)) and *Halobactreium salinarum* (Hayden et al., *FEMS Microbiol Lett.* 211:37-41 (2002)). The *Nicotiana tabacum* enzyme is composed of alpha and beta subunits encoded by gdh1 and gdh2 (Purnell et al., *Planta* 222:167-180 (2005)). An exemplary leucine dehydrogenase is encoded by ldh of *Bacillus cereus*. This enzyme reacts with a range of substrates including leucine, isoleucine, valine, and 2-aminobutanoate (Stoyan et al., *J. Biotechnol* 54:77-80 (1997); Ansorge et al., *Biotechnol Bioeng.* 68:557-562 (2000)). The aspartate dehydrogenase from *Thermotoga maritime*, encoded by nadX, is involved in the biosynthesis of NAD (Yang et al., *J. Biol. Chem.* 278:8804-8808 (2003)).

| GGene | GenBank ID | GI Number | Organism |
| --- | --- | --- | --- |
| gdhA | P00370 | 118547 | *Escherichia coli* |
| gdh | P96110.4 | 6226595 | *Thermotoga maritima* |
| gdhA1 | NP_279651.1 | 15789827 | *Halobacterium salinarum* |
| rocG | NP_391659.1 | 16080831 | *Bacillus subtilis* |
| gdh1 | AAR11534.1 | 38146335 | *Nicotiana tabacum* |
| gdh2 | AAR11535.1 | 38146337 | *Nicotiana tabacum* |
| GDH | Q852M0 | 75243660 | *Oryza sativa* |
| GDH | Q977U6 | 74499858 | *Haloferax mediterranei* |
| GDH | P29051 | 118549 | *Halobactreium salinarum* |
| GDH2 | NP_010066.1 | 6319986 | *Saccharomyces cerevisiae* |
| ldh | P0A393 | 61222614 | *Bacillus cereus* |
| nadX | NP_229443.1 | 15644391 | *Thermotoga maritima* |

2.6.1.a Aminotransferase: Several transformations in FIG. 13 are catalyzed by aminotransferase or transaminase enzymes, including the conversion of AKP to 2,4-dioxopentanoate (Step E), 2-amino-4-hydroxypentanoate to 4-hydroxy-2-oxovalerate (Step L) and 2,4-diaminopentanoate to AKP (Step N). Several aminotransferases convert amino acids and derivatives to their corresponding 2-oxoacids. Such enzymes are particularly well-suited to catalyze the transformations depicted in Steps E and L of FIG. 13 (i.e. AKP aminotransferase and 2-amino-4-hydroxypentanoate aminotransferase). Selection of an appropriate amino acid aminotransferase for these transformations may depend on the stereochemistry of the substrate. When the substrate is in the D-configuration, a D-amino acid aminotransferase (EC 2.6.1.21) can be utilized, whereas the L-stereoisomer is the preferred substrate of an L-amino acid aminotransferase such as aspartate aminotransferase (EC 2.6.1.1). Aspartate aminotransferase naturally transfers an oxo group from oxaloacetate to glutamate, forming alpha-ketoglutarate and aspartate. Aspartate aminotransferase activity is catalyzed by, for example, the gene products of aspC from *Escherichia coli* (Yagi et al., 100:81-84 (1979); Yagi et al., 113:83-89

(1985)), AAT2 from *Saccharomyces cerevisiae* (Yagi et al., 92:35-43 (1982)) and ASP5 from *Arabidopsis thaliana* (Kwok et al., 55:595-604 (2004); de la et al., 46:414-425 (2006); Wilkie et al., *Protein Expr. Purif* 12:381-389 (1998)). The enzyme from *Rattus norvegicus* has been shown to transaminate alternate substrates such as 2-aminohexanedioic acid and 2,4-diaminobutyric acid (Recasens et al., *Biochemistry* 19:4583-4589 (1980)). Aminotransferases that work on other L-amino-acid substrates may also be able to catalyze these transformation. Valine aminotransferase catalyzes the conversion of valine and pyruvate to 2-ketoisovalerate and alanine. The *E. coli* gene, avtA, encodes a similar enzyme (Whalen et al., J. Bacteriol. 150:739-746 (1982)), which also catalyzes the transamination of α-ketobutyrate to generate α-aminobutyrate, although the amino donor in this reaction has not been identified (Whalen et a)., J. Bacteriol. 158:571-574 (1984)). Another enzyme candidate is alpha-aminoadipate aminotransferase (EC 2.6.1.39), an enzyme that participates in lysine biosynthesis and degradation in some organisms. This enzyme interconverts 2-aminoadipate and 2-oxoadipate, using alpha-ketoglutarate as the amino acceptor. Gene candidates are found in *Homo sapiens* (Okuno et al., *Enzyme Protein* 47:136-148 (1993)) and *Thermus thermophilus* (Miyazaki et al., *Microbiology* 150:2327-2334 (2004)). The *Thermus thermophilus* enzyme, encoded by lysN, is active with several alternate substrates including oxaloacetate, 2-oxoisocaproate, 2-oxoisovalerate, and 2-oxo-3-methylvalerate.

| Gene | GenBank ID | GI Number | Organism |
|---|---|---|---|
| aspC | NP_415448.1 | 16128895 | *Escherichia coli* |
| AAT2 | P23542.3 | 1703040 | *Saccharomyces cerevisiae* |
| ASP5 | P46248.2 | 20532373 | *Arabidopsis thaliana* |
| got2 | P00507 | 112987 | *Rattus norvegicus* |
| avtA | YP_026231.1 | 49176374 | *Escherichia coli* |
| lysN | BAC76939.1 | 31096548 | *Thermus thermophilus* |
| AadAT-II | Q8N5Z0.2 | 46395904 | *Homo sapiens* |

If the substrate is present in the D-stereoisomer, transamination can be catalyzed 6v D-(EC 2.6.1.21), also known as D-amino acid aminotransferase and D-alanine aminotransferase (DAAT). This class of enzyme is noted for its broad substrate specificity, which is species-specific. The D-aminotransferase from *Bacillus* species YM-1, encoded by dat, has been cloned, sequenced (Tanizawa et al., *J Biol. Chem.* 264:2450-2454 (1989)) and the crystal structure has been solved (Peisach et al., *Biochemistry* 37:4958-4967 (1998)). This enzyme has also been engineered to alter the substrate specificity (Gutierrez et al., *Eur. J Biochem.* 267:7218-7223 (2000); Gutierrez et al., *Protein Eng* 11:53-58 (1998)). Additional gene candidates are found in *Bacillus licheniformis* ATCC 10716 (Taylor et al., *Biochim. Biophys. Acta* 1350:38-40 (1997)), *Staphylococcus haemolyticus* (Pucci et al., *J Bacteriol.* 177:336-342 (1995)) and *Bacillus subtilis* (Martinez-Carrion et al., *J Biol. Chem.* 240:3538-3546 (1965)).

| Gene | GenBank ID | GI Number | Organism |
|---|---|---|---|
| dat | P19938 | 118222 | *Bacillus* sp. YM-1 |
| dat | P54692 | 1706292 | *Bacillus licheniformis* ATCC 10716 |
| dat | P54694 | 1706294 | *Staphylococcus haemolyticus* |
| dat | O07597.1 | 3121979 | *Bacillus subtilis* |

The conversion of 2,4-diaminopentanoate to AKP (Step N of FIG. 13) is catalyzed by an enzyme with 2,4-diaminopentanoate aminotransferase activity. Although this activity is has not been characterized in enzymes to date, several enzymes catalyze a similar transformation, the conversion of 2,4-diaminobutanoate to aspartate-4-semialdehyde. Exemplary enzyme candidates include beta-alanine aminotransferase (EC 2.6.1.18), diaminobutyrate aminotransferase (EC 2.6.1.46 and EC 2.6.1.76) and gamma-aminobutyrate (GABA) aminotransferase (EC 2.6.1.19). An exemplary diaminobutyrate aminotransferase enzyme is encoded by the dat gene products in *Acinetobacter baumanii* and *Haemophilus influenza* (Ikai et al., *J Bacteriol.* 179:5118-5125 (1997); Ikai et al., *Biol Pharm. Bull.* 21:170-173 (1998)). In addition to its natural substrate, 2,4-diaminobutyrate, the *A. baumanii* DAT transaminates the terminal amines of lysine, 4-aminobutyrate and ornithine. Additional diaminobutyrate aminotransferase gene candidates include the ectB gene products of *Marinococcus halophilus* and *Halobacillus dabanensis* (Zhao et al., *Curr Microbiol* 53:183-188 (2006): Louis et al., *Microbiology* 143 (Pt 4):1141-1149 (1997)) and the pvdH gene product of *Pseudomonas aeruginosa* (Vandenende et al., *J Bacteriol.* 186:5596-5602 (2004)). Diaminobutyrate aminotransferase enzymes that utilize alpha-ketoglutarate as an amino acceptor are included in the EC class 2.6.1.76. Such enzymes are found in *Acinetobacter baumanii*, The beta-alanine aminotransferase of *Pseudomonas fluorescens* also accepts 2,4-diaminobutyrate as a substrate (Hayaishi et al., *J Biol Chem* 236:781-790 (1961)); however, this activity has not been associated with a gene to date. Gamma-aminobutyrate aminotransferase naturally interconverts succinic semialdehyde and glutamate to 4-aminobutyrate and alpha-ketoglutarate. Generally, GABA aminotransferases react with a broad range of alternate substrates (Schulz et al., 56:1-6 (1990); Liu et al., 43:10896-10905 (2004)). The two GABA transaminases in *E. coli* are encoded by gabT (Bartsch et al., *J Bacteriol.* 172:7035-7042 (1990)) and puuE (Kurihara et al., *J. Biol. Chem.* 280:4602-4608 (2005)). The gabT gene product has been shown to have broad substrate specificity (Schulz et al., 56:1-6 (1990); Liu et al., 43:10896-10905 (2004)). GABA aminotransferases in *Mus musculus* and *Sus scrofa* have been shown to react with a range of alternate substrates (Cooper, *Methods Enzymol.* 113:80-82 (1985)).

| Gene | GenBank ID | GI Number | Organism |
|---|---|---|---|
| dat | P56744.1 | 6685373 | *Acinetobacter baumanii* |
| dat | P44951.1 | 1175339 | *Haemophilus influenzae* |
| ectB | AAB57634.1 | 2098609 | *Marinococcus halophilus* |
| ectB | AAZ57191.1 | 71979940 | *Halobacillus dabanensis* |
| pvdH | AAG05801.1 | 9948457 | *Pseudomonas aeruginosa* |
| gabT | NP_417148.1 | 16130576 | *Escherichia coli* |
| puuE | NP_415818.1 | 16129263 | *Escherichia coli* |
| Abat | NP_766549.2 | 37202121 | *Mus musculus* |
| gabT | YP_257332.1 | 70733692 | *Pseudomonas fluorescens* |
| Abat | NP_999428.1 | 47523600 | *Sus scrofa* |

4.1.3.a Lyase: The condensation of pyruvate and acetaldehyde to 4-hydroxy-2-oxovalerate (Step A of FIG. 12) is catalyzed by 4-hydroxy-2-oxovalerate aldolase (EC 4.1.3.39). This enzyme participates in pathways for the degradation of phenols, cresols and catechols. The *E. coli* enzyme, encoded by mhpE, is highly specific for acetaldehyde as an acceptor but accepts the alternate substrates 2-ketobutyrate or phenylpyruvate as donors (Pollard et al., *Appl Environ Microbiol* 64:4093-4094 (1998)). Similar enzymes are encoded by the cmtG and todH genes of *Pseudomonas putida* (Lau et al., *Gene* 146:7-13 (1994); Eaton, *J Bacteriol.* 178:1351-1362 (1996)). In *Pseudomonas*

CF600, this enzyme is part of a bifunctional aldolase-dehydrogenase heterodimer encoded by dmpFG (Manjasetty et al., *Acta Crystallogr. D. Biol Crystallogr.* 57:582-585 (2001)). The dehydrogenase functionality interconverts acetaldehyde and acetyl-CoA, providing the advantage of reduced cellular concentrations of acetaldehyde, toxic to some cells.

| Gene | GenBank ID | GI Number | Organism |
|---|---|---|---|
| mhpE | AAC73455.1 | 1786548 | *Escherichia coli* |
| cmtG | AAB62295.1 | 1263190 | *Pseudomonas putida* |
| todH | AAA61944.1 | 485740 | *Pseudomonas putida* |
| dmpG | CAA43227.1 | 45684 | *Pseudomonas* sp. CF600 |
| dmpF | CAA43226.1 | 45683 | *Pseudomonas* sp. CF600 |

4.2.1.a Dehydratase: Dehydration of 4-hydroxy-2-oxovalerate to 2-oxopentenoate (Step B of FIG. 12) is catalyzed by 4-hydroxy-2-oxovalerate hydratase (EC 4.2.1.80). A similar enzyme is required to catalyze the dehydration of 4-hydroxypent-2-enoate to 2,4-pentadienoate (Step D of FIG. 13). 4-Hydroxy-2-oxovalerate hydratase participates in aromatic degradation pathways and is typically co-transcribed with a gene encoding an enzyme with 4-hydroxy-2-oxovalerate aldolase activity. Exemplary gene products are encoded by mhpD of *E. coli* (Ferrandez et al., *J Bacteria* 179:2573-2581 (1997); Pollard et al., *Eur J Biochem.* 251: 98-106 (1998)), todG and cmtF of *Pseudomonas putida* (Lau et a)., *Gene* 146:7-13 (1994); Eaton, *J Bacteriol.* 178:1351-1362 (1996)), cnbE of *Comamonas* sp. CNB-1 (Ma et al., *Appl Environ Microbiol* 73:4477-4483 (2007)) and mhpD of *Burkholderia xenovorans* (Wang et al., *FEBS J* 272:966-974 (2005)). A closely related enzyme, 2-oxohepta-4-ene-1,7-dioate hydratase, participates in 4-hydroxyphenylacetic acid degradation, where it converts 2-oxo-hept-4-ene-1,7-dioate (OHED) to 2-oxo-4-hydroxy-hepta-1,7-dioate using magnesium as a cofactor (Burks et al., *J. Am. Chem. Soc.* 120: (1998)). OHED hydratase enzyme candidates have been identified and characterized in *E. coli* C (Roper et al., *Gene* 156:47-51 (1995); Izumi et al., *J Mol. Biol.* 370:899-911 (2007)) and *E. coli* W (Prieto et al., *J Bacteriol.* 178:111-120 (1996)). Sequence comparison reveals homologs in a wide range of bacteria, plants and animals. Enzymes with highly similar sequences are contained in *Klebsiella pneumonia* (91% identity, eval=2e-138) and *Salmonella enterica* (91% identity, eval=4e-138), among others.

| Gene | GenBank ID | GI Number | Organism |
|---|---|---|---|
| mhpD | AAC73453.2 | 87081722 | *Escherichia coli* |
| cmtF | AAB62293.1 | 1263188 | *Pseudomonas putida* |
| todG | AAA61942.1 | 485738 | *Pseudomonas putida* |
| cnbE | YP_001967714.1 | 190572008 | *Comamonas* sp. CNB-1 |
| mhpD | Q13VU0 | 123358582 | *Burkholderia xenovorans* |
| hpcG | CAA57202.1 | 556840 | *Escherichia coli* C |
| hpaH | CAA86044.1 | 757830 | *Escherichia coli* W |
| hpaH | ABR80130.1 | 150958100 | *Klebsiella pneumoniae* |
| Sari_01896 | ABX21779.1 | 160865156 | *Salmonella enterica* |

Enzyme candidates for catalyzing the dehydration of 2-hydroxypentenoate (FIG. 12, Step D) or 2-hydroxy-4-oxopentanoate (FIG. 13, Step F) include fumarase (EC 4.2.1.2), citramalate hydratase (EC 4.2.1.34) and dimethylmaleate hydratase (EC 4.2.1.85). Fumarase enzymes naturally catalyze the reversible dehydration of malate to fumarate. Although the ability of fumarase to react with 2-hydroxypentenotae 2-hydroxy-4-oxopentanoate as substrates has not been described in the literature, a wealth of structural information is available for this enzyme and other researchers have successfully engineered the enzyme to alter activity, inhibition and localization (Weaver, 61:1395-1401 (2005)). *E. coli* has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Tseng et al., 183:461-467 (2001); Woods et al., 954:14-26 (1988); Guest et al., *J Gen Microbiol* 131:2971-2984 (1985)). Additional enzyme candidates are found in *Campylobacter jejuni* (Smith et al., *Int. J Biochem. Cell Biol* 31:961-975 (1999)), *Thermus thermophilus* (Mizobata et al., *Arch. Biochem. Biophys.* 355:49-55 (1998)) and *Rattus norvegicus* (Kobayashi et al., 89:1923-1931 (1981)). Similar enzymes with high sequence homology include fum1 from *Arabidopsis thaliana* and fumC from *Corynebacterium glutamicum*. The mmcBC fumarase from *Pelotomaculum thermopropionicum* is another class of fumarase with two subunits (Shimoyama et al., 270:207-213 (2007)). Citramalate hydrolyase naturally dehydrates 2-methylmalate to mesaconate. This enzyme has been studied in *Methanocaldococcus jannaschii* in the context of the pyruvate pathway to 2-oxobutanoate, where it has been shown to have a broad substrate specificity (Drevland et al., *J Bacteriol.* 189:4391-4400 (2007)). This enzyme activity was also detected in *Clostridium tetanomorphum*, *Morganella morganii*, *Citrobacter amalonaticus* where it is thought to participate in glutamate degradation (Kato et al., *Arch. Microbiol* 168:457-463 (1997)). The *M. jannaschii* protein sequence does not bear significant homology to genes in these organisms. Dimethylmaleate hydratase is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in *Eubacterium barkeri* (Alhapel et al., supra; Kollmann-Koch et al., *Hoppe Seylers. Z. Physiol Chem.* 365:847-857 (1984)).

| Gene | GenBank ID | GI Number | Organism |
|---|---|---|---|
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| fumC | O69294 | 9789756 | *Campylobacter jejuni* |
| fumC | P84127 | 75427690 | *Thermus thermophilus* |
| fumH | P14408 | 120605 | *Rattus norvegicus* |
| fum1 | P93033 | 39931311 | *Arabidopsis thaliana* |
| fumC | Q8NRN8 | 39931596 | *Corynebacterium glutamicum* |
| mmcB | YP_001211906 | 147677691 | *Pelotomaculum thermopropionicum* |
| mmcC | YP_001211907 | 147677692 | *Pelotomaculum thermopropionicum* |
| leuD | Q58673.1 | 3122345 | *Methanocaldococcus jannaschii* |
| dmdA | ABC88408 | 86278276 | *Eubacterium barkeri* |
| dmdB | ABC88409.1 | 86278277 | *Eubacterium barkeri* |

4.3.1.a Ammonia-lyase: An ammonia lyase enzyme is required to catalyze the deamination of 2-amino-4-oxopentanoate (AKP) to acetylacrylate in Step B of FIG. 13. An enzyme catalyzing this exact transformation has not been identified. However the AKP is structurally similar to aspartate, the native substrate of aspartase (EC 4.3.1.1.). Aspartase is a widespread enzyme in microorganisms, and has been characterized extensively (Viola, 74:295-341 (2000)). The *E. coli* enzyme has been shown to react with a variety of alternate substrates including aspartatephenylmethylester, asparagine, benzyl-aspartate and malate (Ma et al., 672:60-65 (1992)). In addition, directed evolution was been employed on this enzyme to alter substrate specificity (Asano et al., 22:95-101 (2005)). The crystal structure of the E. coli aspartase, encoded by aspA, has been solved (Shi et al., 36:9136-9144 (1997)). Enzymes with aspartase functionality have also been characterized in *Haemophilus influenzae* (Sjostrom et al., *Biochim. Biophys. Acta* 1324:182-190 (1997)), *Pseudomonas fluorescens* (Takagi et al., *J. Biochem.* 96:545-552 (1984)), *Bacillus subtilis* (Sjostrom et al., 1324:182-190 (1997)) and *Serratia marcescens* (Takagi et al., 161:1-6 (1985)).

| Gene | GenBank ID | GI Number | Organism |
| --- | --- | --- | --- |
| aspA | NP_418562 | 90111690 | Escherichia coli K12 subsp. MG1655 |
| aspA | P44324.1 | 1168534 | Haemophilus influenzae |
| aspA | P07346.1 | 114273 | Pseudomonas fluorescens |
| ansB | P26899.1 | 251757243 | Bacillus subtilis |
| aspA | P33109.1 | 416661 | Serratia marcescens |

Another enzyme candidate for catalyzing the deamination of AKP is 3-methylaspartase (EC 4.3.1.2). This enzyme, also known as beta-methylaspartase and 3-methylaspartate ammonia-lyase, naturally catalyzes the deamination of threo-3-methylasparatate to mesaconate. The 3-methylaspartase from *Clostridium tetanomorphum* has been cloned, functionally expressed in *E. coli*, and crystallized (Asuncion et al., 57:731-733 (2001); Asuncion et al., *J Biol Chem.* 277:8306-8311 (2002); Botting et al., 27:2953-2955 (1988); Goda et al., 31:10747-10756 (1992)). In *Citrobacter amalonaticus*, this enzyme is encoded by BAA28709 (Kato and Asano, *Arch. Microbiol* 168:457-463 (1997)). 3-Methylaspartase has also been crystallized from *E. coli* YG1002 (Asano et al., *FEMS Microbiol Lett.* 118:255-258 (1994)) although the protein sequence is not listed in public databases such as GenBank. Sequence homology can be used to identify additional candidate genes, including CTC_02563 in *C. tetani* and ECs0761 in *Escherichia coli* O157:H7.

| Gene | GenBank ID | GI Number | Organism |
| --- | --- | --- | --- |
| mal | AAB24070.1 | 259429 | Clostridium tetanomorphum |
| BAA28709 | BAA28709.1 | 3184397 | Citrobacter amalonaticus |
| CTC_02563 | NP_783085.1 | 28212141 | Clostridium tetani |
| ECs0761 | BAB34184.1 | 13360220 | Escherichia coli O157:H7 |

5.1.1.a Racemase: Racemase enzymes in the EC class 5.1.1 isomerize D- and L-amino acids. Such an enzyme may be required to increase the bioavailability of D-alanine and/or D-ornithine and thus enhance the conversion of alanine to AKP (Step A of FIG. 13) or ornithine to 2,4-diaminopentanoate (Step M of FIG. 13). Enzymes with alanine racemase (EC 5.1.1.1) and ornithine racemase (EC 5.1.1.12) activity have been characterized. Alanine racemase interconverts the L and D stereoisomers of alanine. *Escherichia coli* has two alanine aminomutase enzymes, encoded alr and dadX (Lilley et al., *Gene* 129:9-16 (1993); Wild et al., *Mol Gen Genet.* 198:315-322 (1985)). The vanT gene of *Enterococcus gallinarum* also exhibited alanine racemase activity when expressed in *E. coli* (Arias et al., *Microbiology* 146 (Pt 7):1727-1734 (2000)). Additional alanine racemase enzyme candidates have been characterized in *Bacillus subtilis* and *Mycobacterium tuberculosis* (Pierce et al., *FEMS Microbiol Lett.* 283:69-74 (2008); Strych et al., *FEMS Microbiol Lett.* 196:93-98 (2001)). Interconversion of D-ornithine and L-ornithine is catalyzed by ornithine racemase. The enzyme encoded by the orr gene product of *C. sticklandii* was purified and characterized (Fonknechten, *J. Bacteriol.* In Press: (2009)). Additional ornithine racemase gene candidates can be identified by sequence similarity in organisms such as *Clostridium difficile* and *Fusobacterium periodonticum*.

| Gene | GenBank ID | GI Number | Organism |
| --- | --- | --- | --- |
| alr | NP_418477.1 | 16131879 | Escherichia coli |
| dadX | AAC74274.1 | 1787439 | Escherichia coli |
| vanT | Q9X3P3.1 | 20140922 | Enterococcus gallinarum |
| yncD | NP_389646.1 | 16078827 | Bacillus subtilis |
| alr | NP_338056.1 | 15843019 | Mycobacterium tuberculosis CDC1551 |
| alr | NP_217940.1 | 15610559 | Mycobacterium tuberculosis H37Rv |
| orr | CAQ42981.1 | 226885219 | Clostridium sticklandii |
| CdifA_020200002638 | ZP_05349631.1 | 255305459 | Clostridium difficile |
| FUSPEROL_00295 | ZP_06025693.1 | 262066081 | Fusobacterium periodonticum |

5.4.3.a Aminomutase: Ornithine aminomutase (EC 5.4.3.5) catalyzes the conversion of ornithine to 2,4-diaminopentanoate (Step M of FIG. 13). A B12-dependent enzyme with this activity, encoded by oraSE of *Clostridium sticklandii*, has been cloned, sequenced and expressed in *E. coli* (Chen et al., *J. Biol. Chem.* 276:44744-44750 (2001)). This enzyme preferentially reacts with the D-stereoisomer of ornithine (Fonknechten, *J. Bacteriol.* In Press: (2009)). Ornithine aminomutase enzymes have not been characterized in other organisms to date. Similar enzymes in organisms such as *Alkaliphilus oremlandii* and *Clostridium difficile* can be identified by sequence similarity. Lysine aminomutase catalyzes two similar transformations: the interconversin of lysine with 2,5-diaminohexanoate (EC 5.4.3.4), and 3,6-diaminohexanoate with 3,5-diaminohexanoate (EC 5.4.3.3). This enzyme participates in the fermentation of lysine to acetate and butyrate and has been characterized in *Clostridium sticklandii* (Berkovitch et al., *Proc. Natl. Acad. Sci. U.S.A* 101:15870-15875 (2004)) and *Porphyromonas gingivalis* (Tang et al., *Biochemistry* 41:8767-8776 (2002)).

| Gene | GenBank ID | GI Number | Organism |
| --- | --- | --- | --- |
| oraE | AAK72502.1 | 17223685 | Clostridium sticklandii |
| oraS | AAK72501.1 | 17223684 | Clostridium sticklandii |
| oraE (Clos_1695) | YP_001513231.1 | 158320724 | Alkaliphilus oremlandii |
| oraS (Clos_1696) | YP_001513232.1 | 158320725 | Alkaliphilus oremlandii |
| oraE | ZP_05349629.1 | 255305457 | Clostridium difficile |
| oraS | ZP_05349628.1 | 255305456 | Clostridium difficile |
| kamD | AAC79717.1 | 3928904 | Clostridium sticklandii |
| kamE | AAC79718.1 | 3928905 | Clostridium sticklandii |
| kamD | NP_905288.1 | 34540809 | Porphyromonas gingivalis W83 |
| kamE | NP_905289.1 | 34540810 | Porphyromonas gingivalis W83 |

Other: 2-Amino-4-oxopentanoate (AKP) is formed from alanine and acetyl-CoA by AKP thiolase (Step A in FIG.

13). AKP thiolase (AKPT, no EC number) is a pyridoxal phosphate-dependent enzyme that participates in ornithine degradation in *Clostridium sticklandii* (Jeng et al., *Biochemistry* 13:2898-2903 (1974): Kenklies et al., *Microbiology* 145 (Pt 4):819-826 (1999)). A gene cluster encoding the alpha and beta subunits of AKPT (or-2 (ortA) and or-3 (ortB)) was recently described and the biochemical properties of the enzyme were characterized (Fonknechten, *J. Bacteriol*. In Press: (2009)). The enzyme is capable of operating in both directions and reacts with the D-isomer of alanine. Enzyme engineering or directed evolution can enable the enzyme to function with L-alanine as a substrate providing additional pathway versatility with regards to the primary substrate. Alternately, co-expression of an alanine racemase enzyme may enhance substrate availability. Enzymes with high sequence homology are found in *Clostridium difficile, Alkaliphilus metalliredigenes* QYF, *Thermoanaerobacter* sp. X514, and *Thermoanaerobacter tengcongensis* MB4 (Fonknechten, *J. Bacteriol*. In Press: (2009)).

lyase and alpha-ketoglutarate:ferredoxin oxidoreductase indicates the presence of an active reductive TCA cycle in an organism. Enzymes for each step of the reductive TCA cycle are shown below.

ATP-citrate lyase (ACL, EC 2.3.3.8), also called ATP citrate synthase, catalyzes the ATP-dependent cleavage of citrate to oxaloacetate and acetyl-CoA. ACL is an enzyme of the RICA cycle that has been studied in green sulfur bacteria *Chlorobium limicola* and *Chlorobium tepidum*. The alpha (4)beta(4) heteromeric enzyme from *Chlorobium limicola* was cloned and characterized in *E. coli* (Kanao et al., *Eur. J. Biochem.* 269:3409-3416 (2002). The *C. limicola* enzyme, encoded by aclAB, is irreversible and activity of the enzyme is regulated by the ratio of ADP/ATP. A recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, *J. Bacteriol.* 188: 6544-6552 (2006). ACL enzymes have also been identified in *Balnearium lithotrophicum, Sulfurihydrogenibium sub-*

| Gene | GenBank ID | GI Number | Organism |
|---|---|---|---|
| ortA | CAQ42979.1 | 226885215 | *Clostridium sticklandii* |
| ortB | CAQ42980.1 GI: | 226885217 | *Clostridium sticklandii* |
| ortA | YP_001086914.1 | 126698017 | *Clostridium difficile* 630 |
| ortB | YP_001086915.1 | 126698018 | *Clostridium difficile* 630 |
| Amet_2368 | YP_001320181.1 | 150390132 | *Alkaliphilus metalliredigenes* QYF |
| Amet_2369 | YP_001320182.1 | 150390133 | *Alkaliphilus metalliredigenes* QYF |
| Teth514_1478 | YP_001663101.1 | 167040116 | *Thermoanaerobacter* sp. X514 |
| Teth514_1479) | YP_001663102.1 | 167040117 | *Thermoanaerobacter* sp. X514 |
| TTE1235 | NP_622858.1 | 20807687 | *Thermoanaerobacter tengcongensis* MB4 |
| thrC | NP_622859.1 | 20807688 | *Thermoanaerobacter tengcongensis* MB4 |

Example IX

Exemplary Hydrogenase and CO Dehydrogenase Enzymes for Extracting Reducing Equivalents from Syngas and Exemplary Reductive TCA Cycle Enzymes Enzymes of the reductive TCA cycle useful in the non-naturally occurring microbial organisms of the present invention include one or more of ATP-citrate lyase and three $CO_2$-fixing enzymes: isocitrate dehydrogenase, alpha-ketoglutarate:ferredoxin oxidoreductase, pyruvate:ferredoxin oxidoreductase. The presence of ATP-citrate lyase or citrate

*terraneum* and other members of the bacterial phylum Aquificae (Hugler et al., *Environ. Microbiol.* 9:81-92 (2007)). This activity has been reported in some fungi as well. Exemplary organisms include *Sordaria macrospora* (Nowrousian et al., *Curr. Genet.* 37:189-93 (2000), *Aspergillus nidulans, Yarrowia lipolytica* (Hynes and Murray, *Eukaryotic Cell, July:* 1039-1048, (2010) and *Aspergillus niger* (Meijer et al. *J. Ind. Microbiol. Biotechnol.* 36:1275-1280 (2009). Other candidates can be found based on sequence homology. Information related to these enzymes is tabulated below:

| Protein | GenBank ID | GI Number | Organism |
|---|---|---|---|
| aclA | BAB21376.1 | 12407237 | *Chlorobium limicola* |
| aclB | BAB21375.1 | 12407235 | *Chlorobium limicola* |
| aclA | AAM72321.1 | 21647054 | *Chlorobium tepidum* |
| aclB | AAM72322.1 | 21647055 | *Chlorobium tepidum* |
| aclA | ABI50076.1 | 114054981 | *Balnearium lithotrophicum* |
| aclB | ABI50075.1 | 114054980 | *Balnearium lithotrophicum* |
| aclA | ABI50085.1 | 114055040 | *Sulfurihydrogenibium subterraneum* |
| aclB | ABI50084.1 | 114055039 | *Sulfurihydrogenibium subterraneum* |
| aclA | AAX76834.1 | 62199504 | *Sulfurimonas denitrificans* |
| aclB | AAX76835.1 | 62199506 | *Sulfurimonas denitrificans* |
| acl1 | XP_504787.1 | 50554757 | *Yarrowia lipolytica* |
| acl2 | XP_503231.1 | 50551515 | *Yarrowia lipolytica* |
| SPBC1703.07 | NP_596202.1 | 19112994 | *Schizosaccharomyces pombe* |
| SPAC22A12.16 | NP_593246.1 | 19114158 | *Schizosaccharomyces pombe* |
| acl1 | CAB76165.1 | 7160185 | *Sordaria macrospora* |
| acl2 | CAB76164.1 | 7160184 | *Sordaria macrospora* |
| aclA | CBF86850.1 | 259487849 | *Aspergillus nidulans* |
| aclB | CBF86848 | 259487848 | *Aspergillus nidulans* |

In some organisms the conversion of citrate to oxaloacetate and acetyl-CoA proceeds through a citryl-CoA intermediate and is catalyzed by two separate enzymes, citryl-CoA synthetase (EC 6.2.1.18) and citryl-CoA lyase (EC 4.1.3.34) (Aoshima, M., Appl. Microbiol. Biotechnol. 75:249-255 (2007). Citryl-CoA synthetase catalyzes the activation of citrate to citryl-CoA. The *Hydrogenobacter thermophilus* enzyme is composed of large and small subunits encoded by ccsA and ccsB, respectively (Aoshima et al., Mol. Micrbiol. 52:751-761 (2004)). The citryl-CoA synthetase of *Aquifex aeolicus* is composed of alpha and beta subunits encoded by sucC1 and sucD1 (Hugler et al., Environ. Microbiol. 9:81-92 (2007)). Citryl-CoA lyase splits citryl-CoA into oxaloacetate and acetyl-CoA. This enzyme is a homotrimer encoded by ccl in *Hydrogenobacter thermophilus* (Aoshima et al., Mol. Microbiol. 52:763-770 (2004)) and aq_150 in *Aquifex aeolicus* (Hugler et al., supra (2007)). The genes for this mechanism of converting citrate to oxaloacetate and citryl-CoA have also been reported recently in *Chlorobium tepidum* (Eisen et al., PNAS 99(14): 9509-14 (2002).

| Protein | GenBank ID | GI Number | Organism |
|---|---|---|---|
| ccsA | BAD17844.1 | 46849514 | *Hydrogenobacter thermophilus* |
| ccsB | BAD17846.1 | 46849517 | *Hydrogenobacter thermophilus* |
| sucC1 | AAC07285 | 2983723 | *Aquifex aeolicus* |
| sucD1 | AAC07686 | 2984152 | *Aquifex aeolicus* |
| ccl | BAD17841.1 | 46849510 | *Hydrogenobacter thermophilus* |
| aq_150 | AAC06486 | 2982866 | *Aquifex aeolicus* |
| CT0380 | NP_661284 | 21673219 | *Chlorobium tepidum* |
| CT0269 | NP_661173.1 | 21673108 | *Chlorobium tepidum* |
| CT1834 | AAM73055.1 | 21647851 | *Chlorobium tepidum* |

Oxaloacetate is converted into malate by malate dehydrogenase (EC 1.1.1.37), an enzyme which functions in both the forward and reverse direction. *S. cerevisiae* possesses three copies of malate dehydrogenase, MDH1 (McAlister-Henn and Thompson, J. Bacteriol. 169:5157-5166 (1987), MDH2 (Minard and McAlister-Henn, Mol. Cell. Biol. 11:370-380 (1991); Gibson and McAlister-Henn, J. Biol. Chem. 278:25628-25636 (2003)), and MDH3 (Steffan and McAlister-Henn, J. Biol. Chem. 267:24708-24715 (1992)), which localize to the mitochondrion, cytosol, and peroxisome, respectively. *E. coli* is known to have an active malate dehydrogenase encoded by mdh.

| Protein | GenBank ID | GI Number | Organism |
|---|---|---|---|
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| Mdh | NP_417703.1 | 16131126 | *Escherichia coli* |

Fumarate hydratase (EC 4.2.1.2) catalyzes the reversible hydration of fumarate to malate. The three fumarases of *E. coli*, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., J. Bacteriol. 183:461-467 (2001); Woods et al., Biochim. Biophys. Acta 954:14-26 (1988); Guest et al., Gen. Microbiol. 131:2971-2984 (1985)). *S. cerevisiae* contains one copy of a fumarase-encoding gene, FUM1, whose product localizes to both the cytosol and mitochondrion (Sass et al., J. Biol. Chem. 278:45109-45116 (2003)). Additional fumarase enzymes are found in *Campylobacter jejuni* (Smith et al., Int. J. Biochem. Cell. Biol. 31:961-975 (1999)), *Thermus thermophilus* (Mizobata et al., Arch. Biochem. Biophys. 355:49-55 (1998)) and *Rattus norvegicus* (Kobayashi et al., J. Biochem. 89:1923-1931 (1981)). Similar enzymes with high sequence homology include fum1 from *Arabidopsis thaliana* fumC from *Corynebacterium glutamicum*. The MmcBC fumarase from *Pelotomaculum thermopropionicum* is another class of fumarase with two subunits (Shimoyama et al., FEMS Microbiol. Lett. 270:207-213 (2007)).

| Protein | GenBank ID | GI Number | Organism |
|---|---|---|---|
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| FUM1 | NP_015061 | 6324993 | *Saccharomyces cerevisiae* |
| fumC | Q8NRN8.1 | 39931596 | *Corynebacterium glutamicum* |
| fumC | O69294.1 | 9789756 | *Campylobacter jejuni* |
| fumC | P84127 | 75427690 | *Thermus thermophilus* |
| fumH | P14408.1 | 120605 | *Rattus norvegicus* |
| MmcB | YP_001211906 | 147677691 | *Pelotomaculum thermopropionicum* |
| MmcC | YP_001211907 | 147677692 | *Pelotomaculum thermopropionicum* |

Fumarate reductase catalyzes the reduction of fumarate to succinate. The fumarate reductase of *E. coli*, composed of four subunits encoded by frdABCD, is membrane-bound and active under anaerobic conditions. The electron donor for this reaction is menaquinone and the two protons produced in this reaction do not contribute to the proton gradient (Iverson et al., Science 284:1961-1966 (1999)). The yeast genome encodes two soluble fumarate reductase isozymes encoded by FRDS1 (Enomoto et al., DNA Res. 3:263-267 (1996)) and FRDS2 (Muratsubaki et al., Arch. Biochem. Biophys. 352:175-181 (1998)), which localize to the cytosol and promitochondrion, respectively, and are used during anaerobic growth on glucose (Arikawa et al., FEMS Microbiol. Lett. 165:111-116 (1998)).

| Protein | GenBank ID | GI Number | Organism |
|---|---|---|---|
| FRDS1 | P32614 | 418423 | *Saccharomyces cerevisiae* |
| FRDS2 | NP_012585 | 6322511 | *Saccharomyces cerevisiae* |
| frdA | NP_418578.1 | 16131979 | *Escherichia coli* |
| frdB | NP_418577.1 | 16131978 | *Escherichia coli* |
| frdC | NP_418576.1 | 16131977 | *Escherichia coli* |
| frdD | NP_418475.1 | 16131877 | *Escherichia coli* |

The ATP-dependent acylation of succinate to succinyl-CoA is catalyzed by succinyl-CoA synthetase (EC 6.2.1.5). The product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Buck et al., Biochemistry 24:6245-6252 (1985)). These proteins are identified below:

| Protein | GenBank ID | GI Number | Organism |
|---|---|---|---|
| LSC1 | NP_014785 | 6324716 | *Saccharomyces cerevisiae* |
| LSC2 | NP_011760 | 6321683 | *Saccharomyces cerevisiae* |
| sucC | NP_415256.1 | 16128703 | *Escherichia coli* |
| sucD | AAC73823.1 | 1786949 | *Escherichia coli* |

Alpha-ketoglutarate:ferredoxin oxidoreductase (EC 1.2.7.3), also known as 2-oxoglutarate synthase or 2-oxoglutarate:ferredoxin oxidoreductase (OFOR), forms alpha-ketoglutarate from CO2 and succinyl-CoA with concurrent consumption of two reduced ferredoxin equivalents. OFOR and pyruvate:ferredoxin oxidoreductase (PFOR) are members of a diverse family of 2-oxoacid:ferredoxin (flavodoxin) oxidoreductases which utilize thiamine pyrophosphate, CoA and iron-sulfur clusters as cofactors and ferredoxin, flavodoxin and FAD as electron carriers (Adams et al., Archaea. Adv. Protein Chem. 48:101-180 (1996)). Enzymes in this class are reversible and function in the carboxylation direction in organisms that fix carbon by the RTCA cycle such as Hydrogenobacter thermophilus, Desulfobacter hydrogenophilus and Chlorobium species (Shiba et al. 1985; Evans et al., Proc. Natl. Acad. Sci. U.S.A. 55:92934 (1966); Buchanan, 1971). The two-subunit enzyme from H. thermophilus, encoded by korAB, has been cloned and expressed in E. coli (Yun et al., Biochem. Biophys. Res. Commun. 282:589-594 (2001)). A five subunit OFOR from the same organism with strict substrate specificity for succinyl-CoA, encoded by for DABGE, was recently identified and expressed in E. coli (Yun et al. 2002). The kinetics of CO2 fixation of both H. thermophilus OFOR enzymes have been characterized (Yamamoto et al., Extremophiles 14:79-85 (2010)). A CO2-fixing OFOR from Chlorobium thiosulfatophilum has been purified and characterized but the genes encoding this enzyme have not been identified to date. Enzyme candidates in Chlorobium species can be inferred by sequence similarity to the H. thermophilus genes. For example, the Chlorobium limicola genome encodes two similar proteins. Acetogenic bacteria such as Moorella thermoacetica are predicted to encode two OFOR enzymes. The enzyme encoded by Moth_0034 is predicted to function in the CO2-assimilating direction. The genes associated with this enzyme, Moth_0034 have not been experimentally validated to date but can be inferred by sequence similarity to known OFOR enzymes.

OFOR enzymes that function in the decarboxylation direction under physiological conditions can also catalyze the reverse reaction. The OFOR from the thermoacidophilic archaeon Sulfolobus sp. strain 7, encoded by ST2300, has been extensively studied (Zhang et al. 1996. A plasmid-based expression system has been developed for efficiently expressing this protein in E. coli (Fukuda et al., Eur. J. Biochem. 268:5639-5646 (2001)) and residues involved in substrate specificity were determined (Fukuda and Wakagi, Biochim. Biophys. Acta 1597:74-80 (2002)). The OFOR encoded by Ape1472/Ape1473 from Aeropyrum pernix str. K1 was recently cloned into E. coli, characterized, and found to react with 2-oxoglutarate and a broad range of 2-oxoacids (Nishizawa et al., FEBS Lett. 579:2319-2322 (2005)). Another exemplary OFOR is encoded by oorDABC in Helicobacter pylori (Hughes et al. 1998). An enzyme specific to alpha-ketoglutarate has been reported in Thauera aromatica (Dorner and Boll, J, Bacteriol. 184 (14), 3975-83 (2002). A similar enzyme can be found in Rhodospirillum rubrum by sequence homology. A two subunit enzyme has also been identified in Chlorobium tepidum (Eisen et al., PNAS 99(14): 9509-14 (2002)).

| Protein | GenBank ID | GI Number | Organism |
|---|---|---|---|
| korA | BAB21494 | 12583691 | Hydrogenobacter thermophilus |
| korB | BAB21495 | 12583692 | Hydrogenobacter thermophilus |
| forD | BAB62132.1 | 14970994 | Hydrogenobacter thermophilus |
| forA | BAB62133.1 | 14970995 | Hydrogenobacter thermophilus |
| forB | BAB62134.1 | 14970996 | Hydrogenobacter thermophilus |
| forG | BAB62135.1 | 14970997 | Hydrogenobacter thermophilus |
| forE | BAB62136.1 | 14970998 | Hydrogenobacter thermophilus |
| Clim_0204 | ACD89303.1 | 189339900 | Chlorobium limicola |
| Clim_0205 | ACD89302.1 | 189339899 | Chlorobium limicola |
| Clim_1123 | ACD90192.1 | 189340789 | Chlorobium limicola |
| Clim_1124 | ACD90193.1 | 189340790 | Chlorobium limicola |
| Moth_1984 | YP_430825.1 | 83590816 | Moorella thermoacetica |
| Moth_1985 | YP_430826.1 | 83590817 | Moorella thermoacetica |
| Moth_0034 | YP_428917.1 | 83588908 | Moorella thermoacetica |
| ST2300 | NP_378302.1 | 15922633 | Sulfolobus sp. strain 7 |
| Ape1472 | BAA80470.1 | 5105156 | Aeropyrum pernix |
| Ape1473 | BAA80471.2 | 116062794 | Aeropyrum pernix |
| oorD | NP_207383.1 | 15645213 | Helicobacter pylori |
| oorA | NP_207384.1 | 15645214 | Helicobacter pylori |
| oorB | NP_207385.1 | 15645215 | Helicobacter pylori |
| oorC | NP_207386.1 | 15645216 | Helicobacter pylori |
| CT0163 | NP_661069.1 | 21673004 | Chlorobium tepidum |
| CT0162 | NP_661068.1 | 21673003 | Chlorobium tepidum |
| korA | CAA12243.2 | 19571179 | Thauera aromatica |
| korB | CAD27440.1 | 19571178 | Thauera aromatica |
| Rru_A2721 | YP_427805.1 | 83594053 | Rhodospirillum rubrum |
| Rru_A2722 | YP_427806.1 | 83594054 | Rhodospirillum rubrum |

Isocitrate dehydrogenase catalyzes the reversible decarboxylation of isocitrate to 2-oxoglutarate coupled to the reduction of $NAD(P)^+$. IDH enzymes in Saccharomyces cerevisiae and Escherichia coli are encoded by IDP1 and icd, respectively (Haselbeck and McAlister-Henn, J. Biol. Chem. 266:2339-2345 (1991); Nimmo, H. G., Biochem. J. 234:317-2332 (1986)). The reverse reaction in the reductive TCA cycle, the reductive carboxylation of 2-oxoglutarate to isocitrate, is favored by the NADPH-dependent $CO_2$-fixing IDH from Chlorobium limicola and was functionally expressed in E. coli (Kanao et al., Eur. J. Biochem. 269: 1926-1931 (2002)). A similar enzyme with 95% sequence identity is found in the C. tepidum genome in addition to some other candidates listed below.

| Protein | GenBank ID | GI Number | Organism |
|---|---|---|---|
| Icd | ACI84720.1 | 209772816 | Escherichia coli |
| IDP1 | AAA34703.1 | 171749 | Saccharomyces cerevisiae |
| Idh | BAC00856.1 | 21396513 | Chlorobium limicola |
| Icd | AAM71597.1 | 21646271 | Chlorobium tepidum |
| icd | NP_952516.1 | 39996565 | Geobacter sulfurreducens |
| icd | YP_393560. | 78777245 | Sulfurimonas denitrificans |

In H. thermophilus the reductive carboxylation of 2-oxoglutarate to isocitrate is catalyzed by two enzymes: 2-oxoglutarate carboxylase and oxalosuccinate reductase. 2-Oxoglutarate carboxylase (EC 6.4.1.7) catalyzes the ATP-dependent carboxylation of alpha-ketoglutarate to oxalosuccinate (Aoshima and Igarashi, Mol. Microbiol. 62:748-759 (2006)). This enzyme is a large complex composed of two subunits. Biotinylation of the large (A) subunit is required for enzyme function (Aoshima et al., Mol. Microbiol. 51:791-798 (2004)). Oxalosuccinate reductase (EC 1.1.1.-) catalyzes the NAD-dependent conversion of oxalosuccinate to D-threo-isocitrate. The enzyme is a homodimer encoded by icd in H. thermophilus. The kinetic parameters of this enzyme indicate that the enzyme only operates in the reductive carboxylation direction in vivo, in contrast to isocitrate dehydrogenase enzymes in other organisms (Aoshima and Igarashi, *J. Bacteriol.* 190:2050-2055 (2008)). Based on sequence homology, gene candidates have also been found in *Thiobacillus denitrificans* and *Thermocrinis albus*.

| Protein | GenBank ID | GI Number | Organism |
|---|---|---|---|
| cfiA | BAF34932.1 | 116234991 | *Hydrogenobacter thermophilus* |
| cifB | BAF34931.1 | 116234990 | *Hydrogenobacter thermophilus* |
| Icd | BAD02487.1 | 38602676 | *Hydrogenobacter thermophilus* |
| Tbd_1556 | YP_315314 | 74317574 | *Thiobacillus denitrificans* |
| Tbd_1555 | YP_315313 | 74317573 | *Thiobacillus denitrificans* |
| Tbd_0854 | YP_314612 | 74316872 | *Thiobacillus denitrificans* |
| Thal_0268 | YP_003473030 | 289548042 | *Thermocrinis albus* |
| Thal_0267 | YP_003473029 | 289548041 | *Thermocrinis albus* |
| Thal_0646 | YP_003473406 | 289548418 | *Thermocrinis albus* |

Aconitase (EC 4.2.1.3) is an iron-sulfur-containing protein catalyzing the reversible isomerization of citrate and iso-citrate via the intermediate cis-aconitate. Two aconitase enzymes are encoded in the *E. coli* genome by acnA and acnB. AcnB is the main catabolic enzyme, while AcnA is more stable and appears to be active under conditions of oxidative or acid stress (Cunningham et al., *Microbiology* 143 (Pt 12):3795-3805 (1997)). Two isozymes of aconitase in *Salmonella typhimurium* are encoded by acnA and acnB (Horswill and Escalante-Semerena, *Biochemistry* 40:4703-4713 (2001)). The *S. cerevisiae* aconitase, encoded by ACO1, is localized to the mitochondria where it participates in the TCA cycle (Gangloff et al., *Mol. Cell. Biol.* 10:3551-3561 (1990)) and the cytosol where it participates in the glyoxylate shunt (Regev-Rudzki et al., *Mol. Biol. Cell.* 16:4163-4171 (2005)).

expressed in *E. coli* resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. Two cysteine residues in this enzyme form a disulfide bond that protects it against inactivation in the form of oxygen. This disulfide bond and the stability in the presence of oxygen has been found in other *Desulfovibrio* species also (Vita et al., *Biochemistry*, 47: 957-64 (2008)). The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J Biol. Chem.* 275: 28494-28499 (2000)). Further, *E. coli* possesses an uncharacterized open reading frame, ydbK, encoding a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). PFORs have also been described in other organisms, including *Rhodobacter capsulatas* (Yakunin and Hallenbeck, Biochimica et Biophysica Acta 1409 (1998) 39-49 (1998)) and *Choloboum tepidum* (Eisen et al., PNAS 99(14): 9509-14 (2002)). The five subunit PFOR from *H. thermophilus*, encoded by porEDABG, was cloned into *E. coli* and shown to function in both the decarboxylating and $CO_2$-assimilating directions (Ikeda et al. 2006; Yamamoto et al., *Extremophiles* 14:79-85 (2010)). Homologs also exist in *C. carboxidivorans* P7. Several additional PFOR enzymes are described in the following review (Ragsdale, S. W., *Chem. Rev.* 103:2333-2346 (2003)). Finally, flavodoxin reductases (e.g., fqrB from *Helicobacter pylori* or *Campylobacter jejuni*) (St Maurice et al., *J. Bacteriol.* 189:4764-4773 (2007)) or Rnf-type proteins (Seedorf et al., *Proc. Natl. Acad. Sci. U.S.A.* 105:2128-2133 (2008); and Herrmann, J.

| Protein | GenBank ID | GI Number | Organism |
|---|---|---|---|
| acnA | AAC7438.1 | 1787531 | *Escherichia coli* |
| acnB | AAC73229.1 | 2367097 | *Escherichia coli* |
| acnA | NP_460671.1 | 16765056 | *Salmonella typhimurium* |
| HP0779 | NP_207572.1 | 15645398 | *Helicobacter pylori* 26695 |
| H16_B0568 | CAJ95365.1 | 113529018 | *Ralstonia eutropha* |
| DesfrDRAFT_3783 | ZP_07335307.1 | 303249064 | *Desulfovibrio fructosovorans* JJ |
| Suden_1040 (acnB) | ABB44318.1 | 78497778 | *Sulfurimonas denitrificans* |
| Hydth_0755 | ADO45152.1 | 308751669 | *Hydrogenobacter thermophilus* |
| CT0543 (acn) | AAM71785.1 | 21646475 | *Chlorobium tepidum* |
| Clim_2436 | YP_001944436.1 | 189347907 | *Chlorobium limicola* |
| Clim_0515 | ACD89607.1 | 189340204 | *Chlorobium limicola* |
| acnB | NP_459163.1 | 16763548 | *Salmonella typhimurium* |
| ACO1 | AAA34389.1 | 170982 | *Saccharomyces cerevisiae* |

Pyruvate:ferredoxin oxidoreductase (PFOR) catalyzes the reversible oxidation of pyruvate to form acetyl-CoA. The PFOR from *Desulfovibrio africanus* has been cloned and *Bacteriol* 190:784-791 (2008)) provide a means to generate NADH or NADPH from the reduced ferredoxin generated by PFOR. These proteins are identified below.

| Protein | GenBank ID | GI Number | Organism |
|---|---|---|---|
| DesfrDRAFT_0121 | ZP_07331646.1 | 303245362 | *Desulfovibrio fructosovorans* JJ |
| Por | CAA70873.1 | 1770208 | *Desulfovibrio africanus* |
| por | YP_012236.1 | 46581428 | *Desulfovibrio vulgaris* str. Hildenborough |
| Dde_3237 | ABB40031.1 | 78220682 | *DesulfoVibrio desulfuricans* G20 |
| Ddes_0298 | YP_002478891.1 | 220903579 | *Desulfovibrio desulfuricans* subsp. *desulfuricans* str. ATCC 27774 |

-continued

| Protein | GenBank ID | GI Number | Organism |
|---|---|---|---|
| Por | YP_428946.1 | 83588937 | *Moorella thermoacetica* |
| YdbK | NP_415896.1 | 16129339 | *Escherichia coli* |
| nifJ (CT1628) | NP_662511.1 | 21674446 | *Chlorobium tepidum* |
| CJE1649 | YP_179630.1 | 57238499 | *Campylobacter jejuni* |
| nifJ | ADE85473.1 | 294476085 | *Rhodobacter capsulatus* |
| porE | BAA95603.1 | 7768912 | *Hydrogenobacter thermophilus* |
| porD | BAA95604.1 | 7768913 | *Hydrogenobacter thermophilus* |
| porA | BAA95605.1 | 7768914 | *Hydrogenobacter thermophilus* |
| porB | BAA95606.1 | 776891 | *Hydrogenobacter thermophilus* |
| porG | BAA95607.1 | 7768916 | *Hydrogenobacter thermophilus* |
| FqrB | YP_001482096.1 | 157414840 | *Campylobacter jejuni* |
| HP1164 | NP_207955.1 | 15645778 | *Helicobacter pylori* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: the pyruvate decarboxylase (E1), dihydrolipoamide acyltransferase (E2) and dihydrolipoamide dehydrogenase (E3). This enzyme is naturally present in several organisms, including *E. coli* and *S. cerevisiae*. In the *E. coli* enzyme, specific residues in the E1 component are responsible for substrate specificity (Bisswanger, H., J. Biol, Chem. 256:815-82 (1981); Bremer, J., Eur. J. Biochem. 8:535-540 (1969); Gong et al., J. Biol. Chem. 275:13645-13653 (2000)). Enzyme engineering efforts have improved the *E. coli* PDH enzyme activity under anaerobic conditions (Kim et al., J. Bacteriol. 190: 3851-3858 (2008); Kim et al., Appl. Environ. Microbiol. 73:1766-1771 (2007); Zhou et al., Biotechnol. Lett. 30:335-342 (2008)). In contrast to the *E. coli* PDH, the *B. subtilis* complex is active and required for growth under anaerobic conditions (Nakano et al., J. Bacteriol. 179:6749-6755 (1997)). The *Klebsiella pneumoniae* PDH, characterized during growth on glycerol, is also active under anaerobic conditions (5). Crystal structures of the enzyme complex from bovine kidney (18) and the E2 catalytic domain from *Azotobacter vinelandii* are available (4). Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in *Escherichia coli* encoded by pflB (Knappe and Sawers, FEMS. Microbiol Rev. 6:383-398 (1990)), *Lactococcus lactis* (Melchiorsen et al., Appl Microbiol Biotechnol 58:338-344 (2002)), and *Streptococcus mutans* (Takahashi-Abbe et al., Oral. Microbiol Immunol. 18:293-297 (2003)). *E. coli* possesses an additional pyruvate formate lyase, encoded by tdcE, that catalyzes the conversion of pyruvate or 2-oxobutanoate to acetyl-CoA or propionyl-CoA, respectively (Hesslinger et al., Mol. Microbiol 27:477-492 (1998)). Both pflB and tdcE from *E. coli* require the presence of pyruvate formate lyase activating enzyme, encoded by pflA. Further, a short protein encoded by yfiD in *E. coli* can associate with and restore activity to oxygen-cleaved pyruvate formate lyase (Vey et al., Proc. Natl. Acad. Sci. U.S.A. 105:16137-16141 (2008). Note that NIA and pflB from *E. coli* were expressed in *S. cerevisiae* as a means to increase cytosolic acetyl-CoA for butanol production as described in WO/2008/080124]. Additional pyruvate formate lyase and activating enzyme candidates, encoded by pfl and act, respectively, are found in *Clostridium pasteurianum* (Weidner et al., J Bacteriol. 178:2440-2444 (1996)).

Further, different enzymes can be used in combination to convert pyruvate into acetyl-CoA. For example, in *S. cerevisiae*, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase. Acetyl-CoA synthetase is a native enzyme in several other organisms including *E. coli* (Kumari et al., J. Bacteriol. 177:2878-2886 (1995)), *Salmonella enterica* (Starai et al., Microbiology 151:3793-3801 (2005); Starai et al., J. Biol. Chem. 280:26200-26205 (2005)), and *Moorella thermoacetica* (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Both acetate kinase and phosphotransacetlyase are well-studied enzymes in several *Clostridia* and *Methanosarcina thermophila*.

Yet another way of converting pyruvate to acetyl-CoA is via pyruvate oxidase. Pyruvate oxidase converts pyruvate into acetate, using ubiquione as the electron acceptor. In *E. coli*, this activity is encoded by poxB. PoxB has similarity to pyruvate decarboxylase of *S. cerevisiae* and *Zymomonas mobilis*. The enzyme has a thiamin pyrophosphate cofactor (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

For enzymes that use reducing equivalents in the form of NADH or NADPH, these reduced carriers can be generated by transferring electrons from reduced ferredoxin. Two enzymes catalyze the reversible transfer of electrons from reduced ferredoxins to $NAD(P)^+$, ferredoxin:$NAD^+$ oxidoreductase (EC 1.18.1.3) and ferredoxin:$NADP^+$ oxidoreductase (FNR, EC 1.18.1.2). Ferredoxin:$NADP^+$ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., *Eur. J. Biochem.* 123:563-569 (1982); Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in *Campylobacter jejuni* (St et al. 2007). A ferredoxin:NADP$^+$ oxidoreductase enzyme is encoded in the *E. coli* genome by fpr (Bianchi et al. 1993). Ferredoxin:NAD$^+$ oxidoreductase utilizes reduced ferredoxin to generate NADH from NAD. In several organisms, including *E. coli*, this enzyme is a component of multifunctional dioxygenase enzyme complexes. The ferredoxin:NAD$^+$ oxidoreductase of *E. coli*, encoded by hcaD. is a component of the 3-phenylproppionate dioxygenase system involved in involved in aromatic acid utilization (Diaz et al. 1998). NADH:ferredoxin reductase activity was detected in cell extracts of *Hydrogenobacter thermophilus* strain TK-6, although a gene with this activity has not yet been indicated (Yoon et al. 2006). Finally, the energy-conserving membrane-associated Rnf-type proteins (Seedorf et al., Proc. Natl. Acad. Sci. U.S.A. 105:2128-2133 (2008); Herrmann et al., *J. Bacteriol.* 190: 784-791 (2008)) provide a means to generate NADH or NADPH from reduced ferredoxin. Additional ferredoxin: NAD(P)+ oxidoreductases have been annotated in *Clostridium carboxydivorans* P7.

doxins donate electrons to Fe-dependent enzymes such as ferredoxin-NADP$^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermo-*

| Protein | GenBank ID | GI Number | Organism |
|---|---|---|---|
| HP1164 | NP_207955.1 | 15645778 | *Helicobacter pylori* |
| RPA3954 | CAE29395.1 | 39650872 | *Rhodopseudomonas palustris* |
| fpr | BAH29712.1 | 225320633 | *Hydrogenobacter thermophilus* |
| yumC | NP_391091.2 | 255767736 | *Bacillus subtilis* |
| CJE0663 | AAW35824.1 | 57167045 | *Campylobacter jejuni* |
| fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |
| CcarbDRAFT_2639 | ZP_05392639.1 | 255525707 | *Clostridium carboxidivorans* P7 |
| CcarbDRAFT_2638 | ZP_05392638.1 | 255525706 | *Clostridium carboxidivorans* P7 |
| CcarbDRAFT_2636 | ZP_05392636.1 | 255525704 | *Clostridium carboxidivorans* P7 |
| CcarbDRAFT_5060 | ZP_05395060.1 | 255528241 | *Clostridium carboxidivorans* P7 |
| CcarbDRAFT_2450 | ZP_05392450.1 | 255525514 | *Clostridium carboxidivorans* P7 |
| CcarbDRAFT_1084 | ZP_05391084.1 | 255524124 | *Clostridium carboxidivorans* P7 |

Ferredoxins are small acidic proteins containing one or more iron-sulfur clusters that function as intracellular electron carriers with a low reduction potential. Reduced ferre-

*acetica*, *Clostridium carboxidivorans* P7 and *Rhodospirillum rubrum* are predicted to encode several ferredoxins, listed in the table below.

| Protein | GenBank ID | GI Number | Organism |
|---|---|---|---|
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |

-continued

| Protein | GenBank ID | GI Number | Organism |
| --- | --- | --- | --- |
| Moth_2112 | ABC20404.1 | 83573852 | Moorella thermoacetica |
| Moth_1037 | ABC19351.1 | 83572799 | Moorella thermoacetica |
| CcarbDRAFT_4383 | ZP_05394383.1 | 255527515 | Clostridium carboxidivorans P7 |
| CcarbDRAFT_2958 | ZP_05392958.1 | 255526034 | Clostridium carboxidivorans P7 |
| CcarbDRAFT_2281 | ZP_05392281.1 | 255525342 | Clostridium carboxidivorans P7 |
| CcarbDRAFT_5296 | ZP_05395295.1 | 255528511 | Clostridium carboxidivorans P7 |
| CcarbDRAFT_1615 | ZP_05391615.1 | 255524662 | Clostridium carboxidivorans P7 |
| CcarbDRAFT_1304 | ZP_05391304.1 | 255524347 | Clostridium carboxidivorans P7 |
| cooF | AAG29808.1 | 11095245 | Carboxydothermus hydrogenoformans |
| fdxN | CAA35699.1 | 46143 | Rhodobacter capsulatus |
| Rru_A2264 | ABC23064.1 | 83576513 | Rhodospirillum rubrum |
| Rru_A1916 | ABC22716.1 | 83576165 | Rhodospirillum rubrum |
| Rru_A2026 | ABC22826.1 | 83576275 | Rhodospirillum rubrum |
| cooF | AAC45122.1 | 1498747 | Rhodospirillum rubrum |
| fdxN | AAA26460.1 | 152605 | Rhodospirillum rubrum |
| Alvin_2884 | ADC63789.1 | 288897953 | Allochromatium vinosum DSM 180 |
| fdx | YP_002801146.1 | 226946073 | Azotobacter vinelandii DJ |
| CKL_3790 | YP_001397146.1 | 153956381 | Clostridium kluyveri DSM 555 |
| fer1 | NP_949965.1 | 39937689 | Rhodopseudomonas palustris CGA009 |
| fdx | CAA12251.1 | 3724172 | Thauera aromatica |
| CHY_2405 | YP_361202.1 | 78044690 | Carboxydothermus hydrogenoformans |
| fer | YP_359966.1 | 78045103 | Carboxydothermus hydrogenoformans |
| fer | AAC83945.1 | 1146198 | Bacillus subtilis |
| fdx1 | NP_249053.1 | 15595559 | Pseudomonas aeruginosa PA01 |
| yfhL | AP_003148.1 | 89109368 | Escherichia coli K-12 |

Succinyl-CoA transferase catalyzes the conversion of succinyl-CoA to succinate while transferring the CoA moiety to a CoA acceptor molecule. Many transferases have broad specificity and can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, and butyrate, among others.

The conversion of succinate to succinyl-CoA can be carried by a transferase which does not require the direct consumption of an ATP or GTP. This type of reaction is common in a number of organisms. The conversion of succinate to succinyl-CoA can also be catalyzed by succinyl-CoA:Acetyl-CoA transferase. The gene product of cat1 of Clostridium kluyveri has been shown to exhibit succinyl-CoA: acetyl-CoA transferase activity (Sohling and Gottschalk, J. Bacteriol. 178:871-880 (1996)). In addition, the activity is present in Trichomonas vaginalis (van Grinsven et al. 2008) and Trypanosoma brucei (Riviere et al. 2004). The succinyl-CoA:acetate CoA-transferase from Acetobacter aceti, encoded by aarC, replaces succinyl-CoA synthetase in a variant TCA cycle (Mullins et al. 2008). Similar succinyl-CoA transferase activities are also present in Trichomonas vaginalis (van Grinsven et al. 2008), Trypanosoma brucei (Riviere et al. 2004) and Clostridium kluyveri (Sohling and Gottschalk, 1996c). The beta-ketoadipate:succinyl-CoA transferase encoded by pcaI and pcaI in Pseudomonas putida is yet another candidate (Kaschabek et al. 2002). The aforementioned proteins are identified below.

| Protein | GenBank ID | GI Number | Organism |
| --- | --- | --- | --- |
| cat1 | P38946.1 | 729048 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| pcaI | AAN69545.1 | 24985644 | Pseudomonas putida |
| pcaJ | NP_746082.1 | 26990657 | Pseudomonas putida |
| aarC | ACD85596.1 | 189233555 | Acetobacter aceti |

An additional exemplary transferase that converts succinate to succinyl-CoA while converting a 3-ketoacyl-CoA to a 3-ketoacid is succinyl-CoA:3:ketoacid-CoA transferase (EC 2.8.3.5). Exemplary succinyl-CoA:3:ketoacid-CoA transferases are present in Helicobacter pylori (Corthesy-Theulaz et al. 1997), Bacillus subtilis, and Homo sapiens (Fukao et al. 2000; Tanaka et al. 2002). The aforementioned proteins are identified below.

| Protein | GenBank ID | GI Number | Organism |
| --- | --- | --- | --- |
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |
| OXCT1 | NP_000427 | 4557817 | Homo sapiens |
| OXCT2 | NP_071403 | 11545841 | Homo sapiens |

Converting succinate to succinyl-CoA by succinyl-CoA:3:ketoacid-CoA transferase requires the simultaneous conversion of a 3-ketoacyl-CoA such as acetoacetyl-CoA to a 3-ketoacid such as acetoacetate. Conversion of a 3-ketoacid back to a 3-ketoacyl-CoA can be catalyzed by an acetoacetyl-CoA:acetate:CoA transferase. Acetoacetyl-CoA:acetate:CoA transferase converts acetoacetyl-CoA and acetate to acetoacetate and acetyl-CoA, or vice versa. Exemplary enzymes include the gene products of atoAD from E.

coli (Hanai et al., Appl Environ Microbiol 73:7814-7818 (2007), ctfAB from *C. acetobutylicum* (Jojima et al., Appl Microbiol Biotechnol 77:1219-1224 (2008), and ctfAB from *Clostridium saccharoperbutylacetonicum* (Kosaka et a)., Biosci. Biotechnol Biochem. 71:58-68 (2007)) are shown below.

| Protein | GenBank ID | GI Number | Organism |
|---|---|---|---|
| AtoA | NP_416726.1 | 2492994 | *Escherichia coli* |
| AtoD | NP_416725.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Yet another possible CoA acceptor is benzylsuccinate. Succinyl-CoA:(R)-Benzylsuccinate CoA-Transferase functions as part of an anaerobic degradation pathway for toluene in organisms such as *Thauera aromatica* (Leutwein and Heider, J. Bact. 183(14) 4288-4295 (2001)). Homologs can be found in *Azoarcus* sp. T, *Aromatoleum aromaticum* EbN1, and *Geobacter metallireducens* GS-15. The aforementioned proteins are identified below.

| Protein | GenBank ID | GI Number | Organism |
|---|---|---|---|
| bbsE | AAF89840 | 9622535 | *Thauera aromatic* |
| Bbsf | AAF89841 | 9622536 | *Thauera aromatic* |
| bbsE | AAU45405.1 | 52421824 | *Azoarcus* sp. T |
| bbsF | AAU45406.1 | 52421825 | *Azoarcus* sp. T |
| bbsE | YP_158075.1 | 56476486 | *Aromatoleum aromaticum* EbN1 |
| bbsF | YP_158074.1 | 56476485 | *Aromatoleum aromaticum* EbN1 |
| Gmet_1521 | YP_384480.1 | 78222733 | *Geobacter metallireducens* GS-15 |
| Gmet_1522 | YP_384481.1 | 78222734 | *Geobacter metallireducens* GS-15 |

Additionally, ygfH encodes a propionyl CoA:succinate CoA transferase in *E. coli* (Haller et al., Biochemistry, 39(16) 4622-4629). Close homologs can be found in, for example, *Citrobacter youngae* ATCC 29220, *Salmonella enterica* subsp. *arizonae* serovar, and *Yersinia intermedia* ATCC 29909. The aforementioned proteins are identified below.

| Protein | GenBank ID | GI Number | Organism |
|---|---|---|---|
| ygfH | NP_417395.1 | 16130821 | *Escherichia coli* str. K-12 substr. MG1655 |
| CIT292_04485 | ZP_03838384.1 | 227334728 | *Citrobacter youngae* ATCC 29220 |
| SARI_04582 | YP_001573497.1 | 161506385 | *Salmonella enterica* subsp. *arizonae* serovar |
| yinte0001_14430 | ZP_04635364.1 | 238791727 | *Yersinia intermedia* ATCC 29909 |

Citrate lyase (EC 4.1.3.6) catalyzes a series of reactions resulting in the cleavage of citrate to acetate and oxaloacetate. The enzyme is active under anaerobic conditions and is composed of three subunits: an acyl-carrier protein (ACP, gamma), an ACP transferase (alpha), and a acyl lyase (beta). Enzyme activation uses covalent binding and acetylation of an unusual prosthetic group, 2'-(5"-phosphoribosyl)-3-'-dephospho-CoA, which is similar in structure to acetyl-CoA. Acylation is catalyzed by CitC, a citrate lyase synthetase. Two additional proteins, CitG and CitX, are used to convert the apo enzyme into the active holo enzyme (Schneider et al., Biochemistry 39:9438-9450 (2000)). Wild type *E. coli* does not have citrate lyase activity; however, mutants deficient in molybdenum cofactor synthesis have an active citrate lyase (Clark, FEMS Microbiol. Lett. 55:245-249 (1990)). The *E. coli* enzyme is encoded by citEFD and the citrate lyase synthetase is encoded by citC (Nilekani and SivaRaman, Biochemistry 22:4657-4663 (1983)). The *Leuconostoc mesenteroides* citrate lyase has been cloned, characterized and expressed in *E. coli* (Bekal et al., J. Bacteriol. 180:647-654 (1998)). Citrate lyase enzymes have also been identified in enterobacteria that utilize citrate as a carbon and energy source, including *Salmonella typhimurium* and *Klebsiella pneumoniae* (Bott, Arch. Microbiol. 167: 78-88 (1997); Bott and Dimroth, Mol. Microbiol. 14:347-356 (1994)). The aforementioned proteins are tabulated below.

| Protein | GenBank ID | GI Number | Organism |
|---|---|---|---|
| citF | AAC73716.1 | 1786832 | *Escherichia coli* |
| Cite | AAC73717.2 | 87081764 | *Escherichia coli* |
| citD | AAC73718.1 | 1786834 | *Escherichia coli* |
| citC | AAC73719.2 | 87081765 | *Escherichia coli* |
| citG | AAC73714.1 | 1786830 | *Escherichia coli* |
| citX | AAC73715.1 | 1786831 | *Escherichia coli* |
| citF | CAA71633.1 | 2842397 | *Leuconostoc mesenteroides* |

-continued

| Protein | GenBank ID | GI Number | Organism |
|---|---|---|---|
| Cite | CAA71632.1 | 2842396 | *Leuconostoc mesenteroides* |
| citD | CAA71635.1 | 2842395 | *Leuconostoc mesenteroides* |

-continued

| Protein | GenBank ID | GI Number | Organism |
|---|---|---|---|
| citC | CAA71636.1 | 3413797 | *Leuconostoc mesenteroides* |
| citG | CAA71634.1 | 2842398 | *Leuconostoc mesenteroides* |
| citX | CAA71634.1 | 2842398 | *Leuconostoc mesenteroides* |
| citF | NP_459613.1 | 16763998 | *Salmonella typhimurium* |
| cite | AAL19573.1 | 16419133 | *Salmonella typhimurium* |
| citD | NP_459064.1 | 16763449 | *Salmonella typhimurium* |
| citC | NP_459616.1 | 16764001 | *Salmonella typhimurium* |

| Protein | GenBank ID | GI Number | Organism |
|---|---|---|---|
| citG | NP_459611.1 | 16763996 | Salmonella typhimurium |
| citX | NP_459612.1 | 16763997 | Salmonella typhimurium |
| citF | CAA56217.1 | 565619 | Klebsiella pneumoniae |
| cite | CAA56216.1 | 565618 | Klebsiella pneumoniae |
| citD | CAA56215.1 | 565617 | Klebsiella pneumoniae |
| citC | BAH66541.1 | 238774045 | Klebsiella pneumoniae |
| citG | CAA56218.1 | 565620 | Klebsiella pneumoniae |
| citX | AAL60463.1 | 18140907 | Klebsiella pneumoniae |

Acetate kinase (EC 2.7.2.1) catalyzes the reversible ATP-dependent phosphorylation of acetate to acetylphosphate. Exemplary acetate kinase enzymes have been characterized in many organisms including *E. coli, Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)).

| Protein | GenBank ID | GI Number | Organism |
|---|---|---|---|
| ackA | NP_416799.1 | 16130231 | Escherichia coli |
| Ack | AAB18301.1 | 1491790 | Clostridium acetobutylicum |
| Ack | AAA72042.1 | 349834 | Methanosarcina thermophila |
| purT | AAC74919.1 | 1788155 | Escherichia coli |
| buk1 | NP_349675 | 15896326 | Clostridium acetobutylicum |
| buk2 | Q97II1 | 20137415 | Clostridium acetobutylicum |

The formation of acetyl-CoA from acetylphosphate is catalyzed by phosphotransacetylase (EC 2.3.1.8). The pta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction is also catalyzed by some phosphotranbutyrylase enzymes (EC 2.3.1.19) including the ptb gene products from *Clostridium acetobutylicum* (Wiesenborn et al., *App. Environ. Microbiol.* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001).

| Protein | GenBank ID | GI Number | Organism |
|---|---|---|---|
| Pta | NP_416800.1 | 71152910 | Escherichia coli |
| Pta | P39646 | 730415 | Bacillus subtilis |
| Pta | A5N801 | 146346896 | Clostridium kluyveri |
| Pta | Q9X0L4 | 6685776 | Thermotoga maritima |
| Ptb | NP_349676 | 34540484 | Clostridium acetobutylicum |
| Ptb | AAR19757.1 | 38425288 | butyrate-producing bacterium L2-50 |
| Ptb | CAC07932.1 | 10046659 | Bacillus megaterium |

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (2004)). ADP-forming acetyl-CoA synthetases are reversible enzymes with a generally broad substrate range (Musfeldt and Schonheit, *J. Bacteriol.* 184:636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are tabulated below.

| Protein | GenBank ID | GI Number | Organism |
|---|---|---|---|
| acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |
| AF1211 | NP_070039.1 | 11498810 | Archaeoglobus fulgidus |
| AF1983 | NP_070807.1 | 11499565 | Archaeoglobus fulgidus |
| scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| paaF | AAC24333.2 | 22711873 | Pseudomonas putida |

Conversion of acetyl-CoA to malonyl-CoA can be carried out by an acetyl-CoA carboxylase enzyme. These enzymes contain multiple subunits. Three of such enzymes are provided below.

| Gene | Organism | Accession number | GI Number |
|---|---|---|---|
| accA | Escherichia coli K-12 | AAC73296.1 | 1786382 |
| accB | Escherichia coli K-12 | AAC76287.1 | 1789653 |
| accC | Escherichia coli K-12 | AAC76288.1 | 1789654 |

| Gene | Organism | Accession number | GI Number |
|---|---|---|---|
| accD | Escherichia coli K-12 | AAC75376.1 | 1788655 |
| accA | Salmonella enterica | CAD08690.1 | 16501513 |
| accB | Salmonella enterica | CAD07894.1 | 16504441 |
| accC | Salmonella enterica | CAD07895.1 | 16504442 |
| accD | Salmonella enterica | CAD07598.1 | 16503590 |
| YMR207C | Saccharomyces cerevisiae | NP_013934.1 | 6323863 |
| YNR016C | Saccharomyces cerevisiae | NP_014413.1 | 6324343 |
| YGR037C | Saccharomyces cerevisiae | NP_011551.1 | 6321474 |
| YKL182W | Saccharomyces cerevisiae | NP_012739.1 | 6322666 |
| YPL231W | Saccharomyces cerevisiae | NP_015093.1 | 6325025 |

The product yields per C-mol of substrate of microbial cells synthesizing reduced fermentation products such as 2,4-pentadienoate, 3-butene-1-ol, or 1,3-butadiene, are limited by insufficient reducing equivalents in the carbohydrate feedstock. Reducing equivalents, or electrons, can be extracted from synthesis gas components such as CO and $H_2$ using carbon monoxide dehydrogenase (CODH) and hydrogenase enzymes, respectively. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, $H_2$, or water, respectively. Reduced ferredoxin and NAD(P)H are particularly useful as they can serve as redox carriers for various Wood-Ljungdahl pathway and reductive TCA cycle enzymes.

Herein below the enzymes and the corresponding genes used for extracting redox from synags components are described. CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica*, *C. hydrogenoformans*, *C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicotinamide adenine dinucleotide phosphate (NAD(P)H) carriers or ferredoxin-dependent cellular processes (Ragsdale, *Annals of the New York Academy of Sciences* 1125: 129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desulfuricans* subsp. *desulfuricans* str. ATCC 27774, *Pelobacter carbinolicus* DSM 2380, and *Campylobacter curvus* 525.92.

| Protein | GenBank ID | GI Number | Organism |
|---|---|---|---|
| CODH (putative) | YP_430813 | 83590804 | Moorella thermoacetica |
| CODH-II (CooS-II) | YP_358957 | 78044574 | Carboxydothermus hydrogenoformans |
| CooF | YP_358958 | 78045112 | Carboxydothermus hydrogenoformans |
| CODH (putative) | ZP_05390164.1 | 255523193 | Clostridium carboxidivorans P7 |
| CcarbDRAFT_0341 | ZP_05390341.1 | 255523371 | Clostridium carboxidivorans P7 |
| CcarbDRAFT_1756 | ZP_05391756.1 | 255524806 | Clostridium carboxidivorans P7 |
| CcarbDRAFT_2944 | ZP_05392944.1 | 255526020 | Clostridium carboxidivorans P7 |
| CODH | YP_384856.1 | 78223109 | Geobacter metallireducens GS-15 |
| Cpha266_0148 (cytochrome c) | YP_910642.1 | 119355998 | Chlorobium phaeobacteroides DSM 266 |
| Cpha266_0149 (CODH) | YP_910643.1 | 119355999 | Chlorobium phaeobacteroides DSM 266 |
| Ccel_0438 | YP_002504800.1 | 220927891 | Clostridium cellulolyticum H10 |
| Ddes_0382 (CODH) | YP_002478973.1 | 220903661 | Desulfovibrio desulfuricans subsp. desulfuricans str. ATCC 27774 |
| Ddes_0381 (CooC) | YP_002478972.1 | 220903660 | Desulfovibrio desulfuricans subsp. desulfuricans str. ATCC 27774 |
| Pcar_0057 (CODH) | YP_355490.1 | 7791767 | Pelobacter carbinolicus DSM 2380 |
| Pcar_0058 (CooC) | YP_355491.1 | 7791766 | Pelobacter carbinolicus DSM 2380 |
| Pcar_0058 (HypA) | YP_355492.1 | 7791765 | Pelobacter carbinolicus DSM 2380 |
| CooS (CODH) | YP_001407343.1 | 154175407 | Campylobacter curvus 525.92 |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., PLoS Genet. 1:e65 (2005)). The C. hydrogenoformans CODH-I was also shown to exhibit intense CO oxidation and $CO_2$ reduction activities when linked to an electrode (Parkin et al., J Am. Chem. Soc. 129:10328-10329 (2007)). The protein sequences of exemplary CODH and hydrogenase genes can be identified by the following GenBank accession numbers.

| Protein | GenBank ID | GI Number | Organism |
|---|---|---|---|
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |

Native to E. coli and other enteric bacteria are multiple genes encoding up to four hydrogenases (Sawers, G., Antonie Van Leeuwenhoek 66:57-88 (1994); Sawers et al., J Bacteriol. 164:1324-1331 (1985); Sawers and Boxer, Eur. J Biochem. 156:265-275 (1986); Sawers et al., J Bacteriol. 168:398-404 (1986)). Given the multiplicity of enzyme activities, E. coli or another host organism can provide sufficient hydrogenase activity to split incoming molecular hydrogen and reduce the corresponding acceptor. E. coli possesses two uptake hydrogenases, Hyd-1 and Hyd-2, encoded by the hyaABCDEF and hybOABCDEFG gene clusters, respectively (Lukey et al., How E. coli is equipped to oxidize hydrogen under different redox conditions, J Biol Chem published online Nov. 16, 2009). Hyd-1 is oxygen-tolerant, irreversible, and is coupled to quinone reduction via the hyaC cytochrome. Hyd-2 is sensitive to $O_2$, reversible, and transfers electrons to the periplasmic ferredoxin hybA which, in turn, reduces a quinone via the hybB integral membrane protein. Reduced quinones can serve as the source of electrons for fumarate reductase in the reductive branch of the TCA cycle. Reduced ferredoxins can be used by enzymes such as NAD(P)H:ferredoxin oxidoreductases to generate NADPH or NADH. They can alternatively be used as the electron donor for reactions such as pyruvate ferredoxin oxidoreductase, AKG ferredoxin oxidoreductase, and 5,10-methylene-H4folate reductase.

| Protein | GenBank ID | GI Number | Organism |
|---|---|---|---|
| HyaA | AAC74057.1 | 1787206 | Escherichia coli |
| HyaB | AAC74058.1 | 1787207 | Escherichia coli |
| HyaC | AAC74059.1 | 1787208 | Escherichia coli |
| HyaD | AAC74060.1 | 1787209 | Escherichia coli |
| HyaE | AAC74061.1 | 1787210 | Escherichia coli |
| HyaF | AAC74062.1 | 1787211 | Escherichia coli |
| HybO | AAC76033.1 | 1789371 | Escherichia coli |
| HybA | AAC76032.1 | 1789370 | Escherichia coli |
| HybB | AAC76031.1 | 2367183 | Escherichia coli |
| HybC | AAC76030.1 | 1789368 | Escherichia coli |
| HybD | AAC76029.1 | 1789367 | Escherichia coli |
| HybE | AAC76028.1 | 1789366 | Escherichia coli |
| HybF | AAC76027.1 | 1789365 | Escherichia coli |
| HybG | AAC76026.1 | 1789364 | Escherichia coli |

The hydrogen-lyase systems of E. coli include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase 3 has been shown to be a reversible enzyme (Maeda et al., Appl Microbiol Biotechnol 76(5):1035-42 (2007)). Hydrogenase activity in E. coli is also dependent upon the expression of the hyp genes whose corresponding proteins are involved in the assembly of the hydrogenase complexes (Jacobi et al., Arch. Microbiol 158:444-451 (1992); Rangarajan et al., J. Bacteriol. 190:1447-1458 (2008)).

| Protein | GenBank ID | GI Number | Organism |
|---|---|---|---|
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |

The M. thermoacetica hydrogenases are suitable for a host that lacks sufficient endogenous hydrogenase activity. M. thermoacetica can grow with $CO_2$ as the exclusive carbon source indicating that reducing equivalents are extracted from $H_2$ to enable acetyl-CoA synthesis via the Wood-Ljungdahl pathway (Drake, H. L., J. Bacteriol. 150: 702-709 (1982); Drake and Daniel, Res. Microbiol. 155: 869-883 (2004); Kellum and Drake, J. Bacteriol. 160:466-469 (1984)) (see FIG. 22). M. thermoacetica has homologs to several hyp, hyc, and hyf genes from E. coli. The protein sequences encoded for by these genes are identified by the following GenBank accession numbers.

Proteins in M. thermoacetica whose genes are homologous to the E. coli hyp genes are shown below.

| Protein | GenBank ID | GI Number | Organism |
|---|---|---|---|
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |

Proteins in *M. thermoacetica* that are homologous to the *E. coli* Hydrogenase 3 and/or 4 proteins are listed in the following table.

| Protein | GenBank ID | GI Number | Organism |
|---|---|---|---|
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |
| Moth_2192 | YP_431024 | 83591015 | *Moorella thermoacetica* |

In addition, several gene clusters encoding hydrogenase functionality are present in *M. thermoacetica* and their corresponding protein sequences are provided below.

| Protein | GenBank ID | GI Number | Organism |
|---|---|---|---|
| Moth_0439 | YP_429313 | 83589304 | *Moorella thermoacetica* |
| Moth_0440 | YP_429314 | 83589305 | *Moorella thermoacetica* |
| Moth_0441 | YP_429315 | 83589306 | *Moorella thermoacetica* |
| Moth_0442 | YP_429316 | 83589307 | *Moorella thermoacetica* |
| Moth_0809 | YP_429670 | 83589661 | *Moorella thermoacetica* |
| Moth_0810 | YP_429671 | 83589662 | *Moorella thermoacetica* |
| Moth_0811 | YP_429672 | 83589663 | *Moorella thermoacetica* |
| Moth_0812 | YP_429673 | 83589664 | *Moorella thermoacetica* |
| Moth_0814 | YP_429674 | 83589665 | *Moorella thermoacetica* |
| Moth_0815 | YP_429675 | 83589666 | *Moorella thermoacetica* |
| Moth_0816 | YP_429676 | 83589667 | *Moorella thermoacetica* |
| Moth_1193 | YP_430050 | 83590041 | *Moorella thermoacetica* |
| Moth_1194 | YP_430051 | 83590042 | *Moorella thermoacetica* |
| Moth_1195 | YP_430052 | 83590043 | *Moorella thermoacetica* |
| Moth_1196 | YP_430053 | 83590044 | *Moorella thermoacetica* |
| Moth_1717 | YP_430562 | 83590553 | *Moorella thermoacetica* |
| Moth_1718 | YP_430563 | 83590554 | *Moorella thermoacetica* |
| Moth_1719 | YP_430564 | 83590555 | *Moorella thermoacetica* |
| Moth_1883 | YP_430726 | 83590717 | *Moorella thermoacetica* |
| Moth_1884 | YP_430727 | 83590718 | *Moorella thermoacetica* |
| Moth_1885 | YP_430728 | 83590719 | *Moorella thermoacetica* |
| Moth_1886 | YP_430729 | 83590720 | *Moorella thermoacetica* |
| Moth_1887 | YP_430730 | 83590721 | *Moorella thermoacetica* |
| Moth_1888 | YP_430731 | 83590722 | *Moorella thermoacetica* |
| Moth_1452 | YP_430305 | 83590296 | *Moorella thermoacetica* |
| Moth_1453 | YP_430306 | 83590297 | *Moorella thermoacetica* |
| Moth_1454 | YP_430307 | 83590298 | *Moorella thermoacetica* |

*Ralstonia eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta*, 567, 315-324 (1979); Bernhard et al., *Eur. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.*, 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

| Protein | GenBank ID | GI Number | Organism |
|---|---|---|---|
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |
| Hox1E | AAP50519.1 | 37787351 | *Thiocapsa roseopersicina* |
| Hox1F | AAP50520.1 | 37787352 | *Thiocapsa roseopersicina* |
| Hox1U | AAP50521.1 | 37787353 | *Thiocapsa roseopersicina* |
| Hox1Y | AAP50522.1 | 37787354 | *Thiocapsa roseopersicina* |
| Hox1H | AAP50523.1 | 37787355 | *Thiocapsa roseopersicina* |

Several enzymes and the corresponding genes used for fixing carbon dioxide to either pyruvate or phosphoenolpyruvate to form the TCA cycle intermediates, oxaloacetate or malate are described below.

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
|---|---|---|---|
| Ppc | NP_418391 | 16131794 | Escherichia coli |
| ppcA | AAB58883 | 28572162 | Methylobacterium extorquens |
| Ppc | ABB53270 | 80973080 | Corynebacterium glutamicum |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. S. cerevisiae is one such organism whose native PEP carboxykinase, PCK1, serves a gluconeogenic role (Valdes-Hevia et al., FEBS Lett. 258:313-316 (1989). E. coli is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., Appl. Environ. Microbiol. 70:1238-1241 (2004)). Nevertheless, activity of the native E. coli PEP carboxykinase from PEP towards oxaloacetate has been recently demonstrated in ppc mutants of E. coli K-12 (Kwon et al., J. Microbiol. Biotechnol. 16:1448-1452 (2006)). These strains exhibited no growth defects and had increased succinate production at high $NaHCO_3$ concentrations. Mutant strains of E. coli can adopt Pck as the dominant CO2-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into E. coli include those from Mannheimia succiniciproducens (Lee et al., Biotechnol. Bioprocess Eng. 7:95-99 (2002)), Anaerobiospirillum succiniciproducens (Laivenieks et al., Appl. Environ. Microbiol. 63:2273-2280 (1997), and Actinobacillus succinogenes (Kim et al. supra). The PEP carboxykinase enzyme encoded by Haemophilus influenza is effective at forming oxaloacetate from PEP.

| Protein | GenBank ID | GI Number | Organism |
|---|---|---|---|
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |
| pckA | O09460.1 | 3122621 | Anaerobiospirillum succiniciproducens |
| pckA | Q6W6X5 | 75440571 | Actinobacillus succinogenes |
| pckA | P43923.1 | 1172573 | Haemophilus influenza |

Pyruvate carboxylase (EC 6.4.1.1) directly converts pyruvate to oxaloacetate at the cost of one ATP. Pyruvate carboxylase enzymes are encoded by PYC1 (Walker et al., Biochem. Biophys. Res. Commun. 176:1210-1217 (1991) and PYC2 (Walker et al., supra) in Saccharomyces cerevisiae, and pyc in Mycobacterium smegmatis (Mukhopadhyay and Purwantini, Biochim. Biophys. Acta 1475:191-206 (2000)).

| Protein | GenBank ID | GI Number | Organism |
|---|---|---|---|
| PYC1 | NP_011453 | 6321376 | Saccharomyces cerevisiae |
| PYC2 | NP_009777 | 6319695 | Saccharomyces cerevisiae |
| Pyc | YP_890857.1 | 118470447 | Mycobacterium smegmatis |

Malic enzyme can be applied to convert $CO_2$ and pyruvate to malate at the expense of one reducing equivalent. Malic enzymes for this purpose can include, without limitation, malic enzyme (NAD-dependent) and malic enzyme (NADP-dependent). For example, one of the E. coli malic enzymes (Takeo, J. Biochem. 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in E. coli while restoring the lethal Δpfl-ΔldhA phenotype under anaerobic conditions by operating in the carbon-fixing direction (Stols and Donnelly, Appl. Environ. Microbiol. 63(7) 2695-2701 (1997)). A similar observation was made upon overexpressing the malic enzyme from Ascaris suum in E. coli (Stols et al., Appl. Biochem. Biotechnol. 63-65(1), 153-158 (1997)). The second E. coli malic enzyme, encoded by maeB, is NADP-dependent and also decarboxylates oxaloacetate and other alpha-keto acids (Iwakura et al., J. Biochem. 85(5):1355-65 (1979)).

| Protein | GenBank ID | GI Number | Organism |
|---|---|---|---|
| maeA | NP_415996 | 90111281 | Escherichia coli |
| maeB | NP_416958 | 16130388 | Escherichia coli |
| NAD-ME | P27443 | 126732 | Ascaris suum |

The enzymes used for converting oxaloacetate (formed from, for example, PEP carboxylase, PEP carboxykinase, or pyruvate carboxylase) or malate (formed from, for example, malic enzyme or malate dehydrogenase) to succinyl-CoA via the reductive branch of the TCA cycle are malate dehydrogenase, fumarate dehydratase (fumarase), fumarate reductase, and succinyl-CoA transferase. The genes for each of the enzymes are described herein above.

Enzymes, genes and methods for engineering pathways from succinyl-CoA to various products into a microorganism are now known in the art. The additional reducing equivalents obtained from CO and/or $H_2$, as disclosed herein, improve the yields of 2,4-pentadienoate, 3-butene-1-ol, or 1,3-butadiene when utilizing carbohydrate-based feedstock. For example, 2,4-pentadienoate, 3-butene-1-ol, or 1,3-butadiene can be produced from succinyl-CoA via pathways exemplified in FIG. 20. Exemplary enzymes for the conversion succinyl-CoA to 2,4-pentadienoate, 3-butene-1-ol, or 1,3-butadiene include succinyl-CoA: acetyl-CoA acyltransferase, 3-oxoadipyl-CoA transferase, synthetase or hydrolase, 3-oxoadipate dehydrogenase, 2-fumarylacetate decarboxylase, 3-oxopent-4-enoate reductase, 3-hydroxypent-4-enoate dehydratase, 3-oxoadipyl-CoA reductase, 3-hydroxyadipyl-CoA transferase, synthetase or hydrolase, 3-hydroxyadipate dehydrogenase, 3-hydroxyhex-4-enedioate decarboxylase, 3-oxoadipate reductase, 2-fumarylacetate reductase, 3-hydroxypent-4-enoate decarboxylase, 2,4-pentadienoate decarboxylase.

Enzymes, genes and methods for engineering pathways from glycolysis intermediates to various products into a microorganism are known in the art. The additional reducing equivalents obtained from CO and $H_2$, as described herein, improve the yields of all these products on carbohydrates.

Example X

Methods for Handling CO and Anaerobic Cultures

This example describes methods used in handling CO and anaerobic cultures.

A. Handling of CO in Small Quantities for Assays and Small Cultures. CO is an odorless, colorless and tasteless gas that is a poison. Therefore, cultures and assays that utilized CO required special handling. Several assays, including CO oxidation, acetyl-CoA synthesis, CO concentration using myoglobin, and CO tolerance/utilization in small batch cultures, called for small quantities of the CO gas that were dispensed and handled within a fume hood. Biochemical assays called for saturating very small quantities (<2 mL) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO were dispensed to each of several possible cuvettes or vials. The Schlenk line was set up containing an oxygen scrubber on the input side and an oil pressure release bubbler and vent on the other side. Assay cuvettes were both anaerobic and CO-containing. Therefore, the assay cuvettes were tightly sealed with a rubber stopper and reagents were added or removed using gas-tight needles and syringes. Secondly, small (~50 mL) cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes were pierced with 19 or 20 gage disposable syringe needles and were vented with the same. An oil bubbler was used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

B. Handling of CO in Larger Quantities Fed to Large-Scale Cultures. Fermentation cultures are fed either CO or a mixture of CO and $H_2$ to simulate syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas are added to the cultures. At different points, the cultures are harvested or samples removed. Alternatively, cells are harvested with an integrated continuous flow centrifuge that is part of the fermenter.

The fermentative processes are carried out under anaerobic conditions. In some cases, it is uneconomical to pump oxygen or air into fermenters to ensure adequate oxygen saturation to provide a respiratory environment. In addition, the reducing power generated during anaerobic fermentation may be needed in product formation rather than respiration. Furthermore, many of the enzymes for various pathways are oxygen-sensitive to varying degrees. Classic acetogens such as M. thermoacetica are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway might be incompatible in the presence of oxygen because most are metallo-enzymes, key components are ferredoxins, and regulation can divert metabolism away from the Wood-Ljungdahl pathway to maximize energy acquisition. At the same time, cells in culture act as oxygen scavengers that moderate the need for extreme measures in the presence of large cell growth.

C. Anaerobic Chamber and Conditions. Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry CA). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

D. Anaerobic Microbiology. Small cultures were handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12

(10 μM cyanocobalamin), nickel chloride (NiCl$_2$, 20 microM final concentration from a 40 mM stock made in anaerobic water in the chamber and sterilized by autoclaving or by using a syringe filter upon injection into the culture), and ferrous ammonium sulfate (final concentration needed is 100 μM made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

Example XI

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. These clones were assayed for CO oxidation, using an assay that quantitatively measures CODH activity. Antisera to the *M. thermoacetica* gene products was used for Western blots to estimate specific activity. *M. thermoacetica* is Gram positive, and ribosome binding site elements are expected to work well in *E. coli*. This activity, described below in more detail, was estimated to be ~1/50th of the *M. thermoacetica* specific activity. It is possible that CODH activity of recombinant *E. coli* cells could be limited by the fact that *M. thermoacetica* enzymes have temperature optima around 55° C. Therefore, a mesophilic CODH/ACS pathway could be advantageous such as the close relative of *Moorella* that is mesophilic and does have an apparently intact CODH/ACS operon and a Wood-Ljungdahl pathway, *Desulfitobacterium hafniense*. Acetogens as potential host organisms include, but are not limited to, *Rhodospirillum rubrum*, *Moorella thermoacetica* and *Desulfitobacterium hafniense*.

CO oxidation is both the most sensitive and most robust of the CODH/ACS assays. It is likely that an *E. coli*-based syngas using system will ultimately need to be about as anaerobic as *Clostridial* (i.e., *Moorella*) systems, especially for maximal activity. Improvement in CODH should be possible but will ultimately be limited by the solubility of CO gas in water.

Initially, each of the genes was cloned individually into expression vectors. Combined expression units for multiple subunits/1 complex were generated. Expression in *E. coli* at the protein level was determined. Both combined *M. thermoacetica* CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., *Biochemistry* 43:3944-3955 (2004)). A typical activity of *M. thermoacetica* CODH specific activity is 500 U at 55° C. or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette four times in deionized water and one time with acetone. A small amount of vacuum grease was smeared on the top of the rubber gasket. The cuvette was gassed with CO, dried 10 min with a 22 Ga. needle plus an exhaust needle. A volume of 0.98 mlL of reaction buffer (50 mM Hepes, pH 8.5, 2 mM dithiothreitol (DTT) was added using a 22 Ga. needle, with exhaust needled, and 100% CO. Methyl viologen (CH$_3$ viologen) stock was 1 M in water. Each assay used 20 microliters for 20 mM final concentration. When methyl viologen was added, an 18 Ga needle (partial) was used as a jacket to facilitate use of a Hamilton syringe to withdraw the CH$_3$ viologen. 4-5 aliquots were drawn up and discarded to wash and gas equilibrate the syringe. A small amount of sodium dithionite (0.1 M stock) was added when making up the CH$_3$ viologen stock to slightly reduce the CH$_3$ viologen. The temperature was equilibrated to 55° C. in a heated Olis spectrophotometer (Bogart Ga.). A blank reaction (CH$_3$ viologen+buffer) was run first to measure the base rate of CH$_3$ viologen reduction. Crude *E. coli* cell extracts of ACS90 and ACS91 (CODH-ACS operon of *M. thermoacetica* with and without, respectively, the first cooC). 10 microliters of extract were added at a time, mixed and assayed. Reduced CH$_3$ viologen turns purple. The results of an assay are shown in Table I.

TABLE I

Crude extract CO Oxidation Activities.

| ACS90 | 7.7 mg/ml | ACS91 | 11.8 mg/ml |
| Mta98 | 9.8 mg/ml | Mta99 | 11.2 mg/ml |

| Extract | Vol | OD/ | U/ml | U/mg |
| --- | --- | --- | --- | --- |
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

Averages

| ACS90 | 0.057 U/mg |
| ACS91 | 0.045 U/mg |
| Mta99 | 0.0018 U/mg |

Mta98/Mta99 are *E. coli* MG1655 strains that express methanol methyltransferase genes from *M. thermoacetia* and, therefore, are negative controls for the ACS90 ACS91 *E. coli* strains that contain *M. thermoacetica* CODH operons.

If ~1% of the cellular protein is CODH, then these figures would be approximately 100× less than the 500 U/mg activity of pure *M. thermoacetica* CODH. Actual estimates based on Western blots are 0.5% of the cellular protein, so the activity is about 50× less than for *M. thermoacetica* CODH. Nevertheless, this experiment demonstrates CO oxidation activity in recombinant *E. coli* with a much smaller amount in the negative controls. The small amount of CO oxidation ($CH_3$ viologen reduction) seen in the negative controls indicates that *E. coli* may have a limited ability to reduce $CH_3$ viologen.

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified *M. thermoacetica* CODH-ACS and Mtr proteins and were visualized using an alkaline phosphatase-linked goat-anti-rabbit secondary antibody. The Westerns were performed and results are shown in FIG. 24. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant *E. coli* cells express multiple components of a 7 gene operon. In addition, both the methyltransferase and corrinoid iron sulfur protein were active in the same recombinant *E. coli* cells. These proteins are part of the same operon cloned into the same cells.

The CO oxidation assays were repeated using extracts of *Moorella thermoacetica* cells for the positive controls. Though CODH activity in *E. coli* ACS90 and ACS91 was measurable, it was at about 130-150× lower than the *M. thermoacetica* control. The results of the assay are shown in FIG. 25. Briefly, cells (*M. thermoacetica* or *E. coli* with the CODH/ACS operon; ACS90 or ACS91 or empty vector: pZA33S) were grown and extracts prepared as described above. Assays were performed as described above at 55° C. at various times on the day the extracts were prepared. Reduction of methylviologen was followed at 578 nm over a 120 sec time course.

These results describe the CO oxidation (CODH) assay and results. Recombinant *E. coli* cells expressed CO oxidation activity as measured by the methyl viologen reduction assay.

Example XII

E. coli CO Tolerance Experiment and CO Concentration Assay (Myoglobin Assay)

This example describes the tolerance of *E. coli* for high concentrations of CO.

To test whether or not *E. coli* can grow anaerobically in the presence of saturating amounts of CO, cultures were set up in 120 ml serum bottles with 50 ml of Terrific Broth medium (plus reducing solution, $NiCl_2$, $Fe(II)NH_4SO_4$, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both $N_2$ and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. $N_2$ was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. Each of these was added in 1 microliter increments to the same cuvette. Midway through the experiment a second cuvette was set up and used. The results are shown in Table II.

TABLE II

Carbon Monoxide Concentrations, 36 hrs.

| Strain and Growth Conditions | Final CO concentration (micromolar) |
|---|---|
| pZA33-CO | 930 |
| ACS90-CO | 638 |
|  | 494 |
|  | 734 |
|  | 883 |
| ave | 687 |
| SD | 164 |
| ACS91-CO | 728 |
|  | 812 |
|  | 760 |
|  | 611 |
| ave. | 728 |
| SD | 85 |

The results shown in Table II indicate that the cultures grew whether or not a strain was cultured in the presence of CO or not. These results indicate that *E. coli* can tolerate exposure to CO under anaerobic conditions and that *E. coli* cells expressing the CODH-ACS operon can metabolize some of the CO.

These results demonstrate that *E. coli* cells, whether expressing CODH/ACS or not, were able to grow in the presence of saturating amounts of CO. Furthermore, these grew equally well as the controls in nitrogen in place of CO. This experiment demonstrated that laboratory strains of *E. coli* are insensitive to CO at the levels achievable in a syngas project performed at normal atmospheric pressure. In addition, preliminary experiments indicated that the recombinant *E. coli* cells expressing CODH/ACS actually consumed some CO, probably by oxidation to carbon dioxide.

Example XIII

3-Hydroxyacid Decarboxylase Enzymes for Formation of 1,3-butadiene and 3-butene-1-ol 3-Hydroxyacid decarboxylase enzymes catalyze the ATP-driven decarboxylation of 3-hydroxyacids to alkene derivatives. 3-Hyroxyacid decarboxylase enzymes have recently been described that catalyze the formation of isobutylene, propylene and ethylene (WO 2010/001078 and Gogerty and Bobik, Appl. Environ. Microbiol., p. 8004-8010. Vol. 76, No. 24 (2010)). We propose here a the application of similar enzymes to catalyze the conversion of 3-hydroxypent-4-enoate (3HP4) to 1,3-butadiene, shown in FIG. 16 and 3,5-dihydroxypentanoate to 3-butene-1-ol, shown in FIG. 17. The 3-butene-1-ol product can then be converted to butadiene via chemical dehydration or biological dehydration via a 3-butene-1-ol dehydratase enzyme.

Conversion of 3-hydroxypent-4-enoate to butadiene is carried out by a 3-hydroxypent-4-enoate decarboxylase. Similarly, conversion of 3,5-dihydroxypentanoate to 3-butene-1-ol is carried out by a 3,5-dihydroxypentanoate decarboxylase. Such enzymes may share similarity to mevalonate pyrophosphate decarboxylase or diphosphomevalonate decarboxylase enzymes. One potential 3-hydroxypent-4-enoate decarboxylase is the *Saccharomyces cerevisiae* mevalonate diphosphate decarboxylase (ScMDD or ERG19) which was shown to convert 3-hydroxy-3-methylbutyrate (3-HMB) to isobutene (Gogerty and Bobik, 2010, Appl. Environ. Microbiol., p. 8004-8010, Vol. 76, No. 24). Two improved variants of the enzyme, ScMDD1 (1145F) and ScMDD2 (R74H), were demonstrated to achieve 19-fold and 38-fold increases compared to the wild-type His-tagged enzyme. ERG19 and additional enzymes candidates are provided below.

oxides (e.g., zirconium oxide or titanium dioxide) and metal chlorides (e.g., Latshaw B E, Dehydration of Isobutanol to Isobutylene in a Slurry Reactor, Department of Energy Topical Report, February 1994).

Dehydration reactions can be carried out in both gas and liquid phases with both heterogeneous and homogeneous catalyst systems in many different reactor configurations. Typically, the catalysts used are stable to the water that is generated by the reaction. The water is usually removed from the reaction zone with the product. The resulting alkene(s) either exit the reactor in the gas or liquid phase (e.g., depending upon the reactor conditions) and are captured by a downstream purification process or are further converted in the reactor to other compounds (such as butadiene or isoprene) as described herein. The water generated by the dehydration reaction exits the reactor with unreacted alcohol and alkene product(s) and is separated by distillation or phase separation. Because water is generated in large quantities in the dehydration step, the dehydration catalysts used are generally tolerant to water and a process for removing the water from substrate and product may be part of any process that contains a dehydration step. For this reason, it is possible to use wet (i.e., up to about 95% or 98% water by weight) alcohol as a substrate for a dehydration reaction and remove this water with the water generated by the dehydration reaction (e.g., using a zeolite catalyst as described U.S. Pat. Nos. 4,698,452 and 4,873,392). Addi-

| Enzyme | GI | Accession Number | Organism |
| --- | --- | --- | --- |
| ERG19 | 6324371 | NP_014441.1 | *Saccharomyces cerevisiae* S288C |
| CAWG_01359 | 238879484 | EEQ43122.1 | *Candida albicans* WO-1 |
| ANI_1_332184 | 145256805 | XP_001401521.1 | *Aspergillus niger* CBS 513.88 |
| MVD | 4505289 | NP_002452.1 | *Homo sapiens* |
| Ahos_1490 | 332797171 | YP_004458671.1 | *Acidianus hospitalis* W1 |
| SSO2989 | 15899699 | NP_344304.1 | *Sulfolobus solfataricus* P2 |
| UNLARM2_0386 | 255513677 | EET89942.1 | *Candidatus Micrarchaeum acidiphilum* ARMAN-2 |
| mvaD | 146329706 | YP_001209416.1 | *Dichelobacter nodosus* VCS1703A |
| MPTP_0700 | 332686202 | YP_004455976.1 | *Melissococcus plutonius* ATCC 35311 |
| RKLH11_3963 | 254513287 | ZP_05125352.1 | *Rhodobacteraceae bacterium* KLH11 |

Example XIV

Chemical Dehydration of 3-butene-1-ol to Butadiene

Alcohols can be converted to olefins by reaction with a suitable dehydration catalyst under appropriate conditions. Typical dehydration catalysts that convert alcohols such as butanols and pentanols into olefins include various acid treated and untreated alumina (e.g., γ-alumina) and silica catalysts and clays including zeolites (e.g., β-type zeolites, ZSM-5 or Y-type zeolites, fluoride-treated β-zeolite catalysts, fluoride-treated clay catalysts, etc.), sulfonic acid resins (e.g., sulfonated styrenic resins such as Amberlyst® 15), strong acids such as phosphoric acid and sulfuric acid, Lewis acids such boron trifluoride and aluminum trichloride, and many different types of metal salts including metal tionally, neutral alumina and zeolites will dehydrate alcohols to alkenes but generally at higher temperatures and pressures than the acidic versions of these catalysts.

Dehydration of 3-buten-1-ol to butadiene is well known in the art (Gustay. Egloff and George. Hulla, Chem. Rev., 1945, 36 (1), pp 63-141). For example, 3-buten-1-ol is formed as an intermediate in the dehydration of 1,4-butanediol to 1,3-butadiene (Sato, et al, Catalysis Communications, 5 (8), 2004, p. 397-400).

Example XV

Pathways to 2,4-pentadienoate, 3-butene-1-ol and 1,3-butadiene

This example describes pathways to 2,4-pentadienoate, 3-butene-1-ol and 1,3-butadiene. Novel pathways to the intermediates 3HP4, 3,5-dihydroxypentanoate and 3-butene-1-ol are shown in FIGS. 18-21. Pathways to 3HP4 are shown in FIGS. 18, 19 and 20 (new). Pathways to 3,5-dihydroxypentanoate and 3-butene-1-ol are shown in FIGS. 19 and 21 (new). Additional pathways to the butadiene precursor 2,4-pentadienoate are shown in FIGS. 19, 20 and 21 (new).

Several pathways to 2,4-pentadienoate are disclosed in earlier examples (see for example, FIGS. 4, 12, 13 14 and 15. Hydration of 2,4-pentadienoate yields 3-hydroxypent-4-enoate as shown in FIG. 18 (new). 3-Hydroxypent-4-enoate can be subsequently decarboxylated to butadiene by a 3-hydroxyacid decarboxylase, also described above.

Additional pathways from acrylyl-CoA and 3-HP-CoA to 2,4-pentadienoate are shown in FIG. 19. Also shown here are pathways to 3HP4,3-butene-1-ol and butadiene.

Pathways to 3HP4 from acrylyl-CoA include: steps M/O/P, steps M/N/T

Pathways to 3HP4 from 3-HP-CoA include: steps A/L/O/P, steps A/L/N/T

Pathways to 3HP4 and 24PD from succinyl-CoA are shown in FIG. 20. Succinyl-CoA and acetyl-CoA are first joined by 3-oxoadipyl-CoA thiolase to form 3-oxoadipyl-CoA (Step A). In one pathway the 3-oxo group of 3-oxoadipyl-CoA is reduced to form 3-hydroxyadipyl-CoA (Step G). The CoA moiety is then converted to an acid group by a CoA hydrolase, synthetase or transferase. 3-Hydroxyadipate is then oxidized to form 3-hydroxyhex-4-enedioate (Step I). This product is then decarboxylated to form 3HP4. In an alternate route, 3-oxoadipyl-CoA is converted to 3-oxoadipate by a CoA transferase, synthetase or hydrolase in Step B. 3-Oxoadipate is then reduced to 3-hydroxyadipate (Step K), which is converted to 3HP4 as previously described. Alternately, 3-oxoadipate is converted to 2-fumarylacetate in Step C. The 3-oxo group of 2-fumarylacetate is then reduced to 3-hydroxyhex-4-enedioate, which is decarboxylated to 3HP4. In yet another embodiment, the 2-fumarylacetate is decarboxylated to form 3-oxopent-4-enoate (Step D), which is subsequently reduced to 3HP4 (Step E). 3HP4 can then be converted to butadiene in one step by decarboxylation by a 3HP4 decarboxylase (Step M), or in two steps by dehydration to 2,4-pentadiene followed by decarboxylation (Steps F, N).

Pathways to 3-butene-1-ol, butadiene and 2,4-pentadienoate from malonyl-CoA and acetyl-CoA are shown in FIG. 21. In these pathways, malonyl-CoA and acetyl-CoA are joined by a thiolase to form 3-oxoglutaryl-CoA. This intermediate can then be converted to 3,5-dihydroxypentanoate by several alternate routes (Steps B/C/D, Steps B/G, Steps H/I/J, Steps H/L/D, 10). Once formed, 3,5-dihydroxypentanoate can be decarboxylated by a 3-hydroxyacid decarboxylase to form 3-butene-1-ol (Step M). Subsequent dehydration by a 3-butene-1-ol dehydrogenase or a chemical catalyst yields butadiene (Step O). Alternately, 3,5-dihydroxypentanoate can be dehydrated to 5-hydroxypent-2-enoate as shown in Step E. This intermediate can then be decarboxylated to 3-butene-1-ol (Step N) or further dehydrated to 2,4-pentadienoate (Step F).

Enzymes for catalyzing the transformations shown in FIGS. 18-21 are categorized by EC number (Table 1) and described further below.

| Label | Function | Step |
|---|---|---|
| 1.1.1.a | Oxidoreductase (oxo to alcohol) | 19 I, B, N, P<br>20 G, K, L, E<br>21 B, D, J, I, L |
| 1.1.1.c | Oxidoreductase (2 step, acyl-CoA to alcohol) | 21 G, K |
| 1.2.1.b | Oxidoreductase (acyl-CoA to aldehyde) | 21 C, H |
| 1.3.1.a | Oxidoreductase (alkene to alkane) | 20 I, C |
| 2.3.1.b | Beta-ketothiolase | 19A, M<br>20A, 21A |
| 2.8.3.a | Coenzyme-A transferase | 19F, O, G, T, E, H<br>20 B, H |
| 3.1.2.a | Thiolester hydrolase (CoA specific) | 19F, O, G, T, E, H<br>20 B, H |
| 4.1.1.a | Carboxy-lyase | 19 U, Y, V, X<br>20 D, J, M, N<br>21 M, N, P |
| 4.2.1.a | Hydro-lyase | 19 S, K, L, R, D, C, J, Q, W<br>20 F<br>21 E, F, O |
| 6.2.1.a | Acid-thiol ligase | 19F, O, G, T, E, H<br>20 B, H |

Several reactions shown in FIGS. 19-21 are catalyzed by alcohol dehydrogenase enzymes. These reactions include Steps B, I, N and P of FIG. 19, Steps E, G, K and L of FIG. 20 and Steps B, D, I, J and L of FIG. 21.

Exemplary genes encoding enzymes that catalyze the reduction of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.* 66:5231-5235 (2000)), yqhD and fucO from *E. coli* (Sulzenbacher et al., 342:489-502 (2004)), and bdh I and bdh II from *C. acetobutylicum* which converts butyryaldehyde into butanol (Walter et al., 174:7149-7158 (1992)). YqhD catalyzes the reduction of a wide range of aldehydes using NADPH as the cofactor, with a preference for chain lengths longer than C(3) (Sulzenbacher et al., 342:489-502 (2004); Perez et al., *J Biol. Chem.* 283:7346-7353 (2008)). The adhA gene product from *Zymomonas mobilisE* has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)). Additional aldehyde reductase candidates are encoded by bdh in *C. saccharoperbutylacetonicum* and Cbei_1722, Cbei_2181 and Cbei_2421 in *C. Beijerinckii*. Additional aldehyde reductase gene candidates in *Saccharomyces cerevisiae* include the aldehyde reductases GRE3, ALD2-6 and HFD1, glyoxylate reductases GOR1 and YPL113C and glycerol dehydrogenase GCY1 (WO 2011/022651A1; Atsumi et al., *Nature* 451:86-89 (2008)). The enzyme candidates described previously for catalyzing the reduction of methylglyoxal to acetol or lactaldehyde are also suitable lactaldehyde reductase enzyme candidates.

| Protein | GENBANK ID | GI NUMBER | ORGANISM |
| --- | --- | --- | --- |
| alrA | BAB12273.1 | 9967138 | Acinetobacter sp. strain M-1 |
| ADH2 | NP_014032.1 | 6323961 | VSaccharomyces cerevisiae |
| yqhD | NP_417484.1 | 16130909 | Escherichia coli |
| fucO | NP_417279.1 | 16130706 | Escherichia coli |
| bdh I | NP_349892.1 | 15896543 | Clostridium acetobutylicum |
| bdh II | NP_349891.1 | 15896542 | Clostridium acetobutylicum |
| adhA | YP_162971.1 | 56552132 | Zymomonas mobilis |
| bdh | BAF45463.1 | 124221917 | Clostridium saccharoperbutylacetonicum |
| Cbei_1722 | YP_001308850 | 150016596 | Clostridium beijerinckii |
| Cbei_2181 | YP_001309304 | 150017050 | Clostridium beijerinckii |
| Cbei_2421 | YP_001309535 | 150017281 | Clostridium beijerinckii |
| GRE3 | P38715.1 | 731691 | Saccharomyces cerevisiae |
| ALD2 | CAA89806.1 | 825575 | Saccharomyces cerevisiae |
| ALD3 | NP_013892.1 | 6323821 | Saccharomyces cerevisiae |
| ALD4 | NP_015019.1 | 6324950 | Saccharomyces cerevisiae |
| ALD5 | NP_010996.2 | 330443526 | Saccharomyces cerevisiae |
| ALD6 | ABX39192.1 | 160415767 | Saccharomyces cerevisiae |
| HFD1 | Q04458.1 | 2494079 | Saccharomyces cerevisiae |
| GOR1 | NP_014125.1 | 6324055 | Saccharomyces cerevisiae |
| YPL113C | AAB68248.1 | 1163100 | Saccharomyces cerevisiae |
| GCY1 | CAA99318.1 | 1420317 | Saccharomyces cerevisiae |

Enzymes exhibiting 4-hydroxybutyrate dehydrogenase activity (EC 1.1.1.61) also fall into this category. Such enzymes have been characterized in *Ralstonia eutropha* (Bravo et al., *J Forens Sci*, 49:379-387 (2004)), *Clostridium kluyveri* (Wolff et al., *Protein Expr. Purif* 6:206-212 (1995)) and *Arabidopsis thaliana* (Breitkreuz et al., *J Biol Chem*, 278:41552-41556 (2003)). The *A. thaliana* enzyme was cloned and characterized in yeast (Breitkreuz et al., *J. Biol. Chem.* 278:41552-41556 (2003)). Yet another gene is the alcohol dehydrogenase adhI from *Geobacillus thermoglucosidasius* (Jeon et al., *J Biotechnol* 135:127-133 (2008)).

| PROTEIN | GENBANK ID | GI NUMBER | ORGANISM |
| --- | --- | --- | --- |
| 4hbd | YP_726053.1 | 113867564 | Ralstonia eutropha H16 |
| 4hbd | L21902.1 | 146348486 | Clostridium kluyveri DSM 555 |
| 4hbd | Q94B07 | 75249805 | Arabidopsis thaliana |
| adhI | AAR91477.1 | 40795502 | Geobacillus thermoglucosidasius |

Another exemplary aldehyde reductase is methylmalonate semialdehyde reductase, also known as 3-hydroxyisobutyrate dehydrogenase (EC 1.1.1.31). This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J Mol Biol*, 352:905-17 (2005)). The reversibility of the human 3-hydroxyisobutyrate dehydrogenase was demonstrated using isotopically-labeled substrate (Manning et al., *Biochem J*, 231:481-4 (1985)). Additional genes encoding this enzyme include 3hidh in *Homo sapiens* (Hawes et al., *Methods Enzymol*, 324:218-228 (2000)) and *Oryctolagus cuniculus* (Hawes et al., supra; Chowdhury et al., *Biosci. Biotechnol Biochem.* 60:2043-2047 (1996)), mmsB in *Pseudomonas aeruginosa* and *Pseudomonas putida*, and dhat in *Pseudomonas putida* (Aberhart et al., *J Chem. Soc. [Perkin 1]* 6:1404-1406 (1979); Chowdhury et al., *Biosci. Biotechnol Biochem.* 60:2043-2047 (1996); Chowdhury et al., *Biosci. Biotechnol Biochem.* 67:438-441 (2003)). Several 3-hydroxyisobutyrate dehydrogenase enzymes have been characterized in the reductive direction, including mmsB from *Pseudomonas aeruginosa* (Gokarn et al., U.S. Pat. No. 739,676, (2008)) and mmsB from *Pseudomonas putida*.

| PROTEIN | GENBANK ID | GI NUMBER | ORGANISM |
| --- | --- | --- | --- |
| P84067 | P84067 | 75345323 | Thermus thermophilus |
| 3hidh | P31937.2 | 12643395 | Homo sapiens |
| 3hidh | P32185.1 | 416872 | Oryctolagus cuniculus |
| mmsB | NP_746775.1 | 26991350 | Pseudomonas putida |
| mmsB | P28811.1 | 127211 | Pseudomonas aeruginosa |
| dhat | Q59477.1 | 2842618 | Pseudomonas putida |

There exist several exemplary alcohol dehydrogenases that reduce a ketone to a hydroxyl functional group. Two such enzymes from *E. coli* are encoded by malate dehydrogenase (mdh) and lactate dehydrogenase (ldhA). In addition, lactate dehydrogenase from *Ralstonia eutropha*, has been shown to demonstrate high activities on 2-ketoacids of various chain lengths includings lactate, 2-oxobutyrate, 2-oxopentanoate and 2-oxoglutarate (Steinbuchel et al., *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). An additional oxidoreductase is the mitochondrial 3-hydroxybutyrate dehydrogenase (bdh) from the human heart which has been cloned and characterized (Marks et al., *J. Biol. Chem.* 267:15459-15463 (1992)). Alcohol dehydrogenase enzymes of *C. beijerinckii* (Ismaiel et al., *J. Bacteriol.* 175:5097-5105 (1993)) and *T. brockii* (Lamed et al., *Biochem. J.* 195:183-190 (1981); Peretz et al., *Biochemistry.* 28:6549-6555 (1989)) convert acetone to isopropanol. Methyl ethyl ketone reductase catalyzes the reduction of MEK to 2-butanol. Exemplary MEK reductase enzymes can be found in *Rhodococcus ruber* (Kosjek et al., *Biotechnol Bioeng.* 86:55-62 (2004)) and *Pyrococcus furiosus* (van der et al., *Eur. J. Biochem.* 268:3062-3068 (2001)).

| Protein | GenBank Accession No. | GI No. | Organism |
| --- | --- | --- | --- |
| mdh | AAC76268.1 | 1789632 | Escherichia coli |
| ldhA | NP_415898.1 | 16129341 | Escherichia coli |
| ldh | YP_725182.1 | 113866693 | Ralstonia eutropha |
| bdh | AAA58352.1 | 177198 | Homo sapiens |

| Protein | GenBank Accession No. | GI No. | Organism |
|---------|----------------------|--------|----------|
| adh | AAA23199.2 | 60592974 | Clostridium beijerinckii NRRL B593 |
| adh | P14941.1 | 113443 | Thermoanaerobacter brockii HTD4 |
| sadh | CAD36475 | 21615553 | Rhodococcus ruber |
| adhA | AAC25556 | 3288810 | Pyrococcus furiosus |

A number of organisms can catalyze the reduction of 4-hydroxy-2-butanone to 1,3-butanediol, including those belonging to the genus *Bacillus*, *Brevibacterium*, *Candida*, and *Klebsiella* among others, as described by Matsuyama et al. ((1995)). A mutated *Rhodococcus* phenylacetaldehyde reductase (Sar268) and a *Leifonia* alcohol dehydrogenase have also been shown to catalyze this transformation at high yields (Itoh et al., *Appl. Microbiol Biotechnol.* 75:1249-1256 (2007)).

Alcohol dehydrogenase enzymes that reduce 3-oxoacyl-CoA substrates to their corresponding 3-hyroxyacyl-CoA product are also relevant to the pathways depicted in FIGS. 19-21. 3-Oxoacyl-CoA dehydrogenase enzymes (EC 1.1.1.35) convert 3-oxoacyl-CoA molecules into 3-hydroxyacyl-CoA molecules and are often involved in fatty acid beta-oxidation or phenylacetate catabolism. For example, subunits of two fatty acid oxidation complexes in *E. coli*, encoded by fadB and fadJ, function as 3-hydroxyacyl-CoA dehydrogenases (Binstock et al., *Methods Enzymol.* 71 Pt C:403-411 (1981)). Given the proximity in *E. coli* of paaH to other genes in the phenylacetate degradation operon (Nogales et al., 153:357-365 (2007)) and the fact that paaH mutants cannot grow on phenylacetate (Ismail et al., *Eur. J Biochem.* 270:3047-3054 (2003)), it is expected that the *E. coli* paaH gene also encodes a 3-hydroxyacyl-CoA dehydrogenase. Acetoacetyl-CoA reductase participates in the acetyl-CoA fermentation pathway to butyrate in several species of *Clostridia* and has been studied in detail (Jones et al., *Microbiol Rev.* 50:484-524 (1986)). The enzyme from *Clostridium acetobutylicum*, encoded by hbd, has been cloned and functionally expressed in *E. coli* (Youngleson et al., *J Bacteriol.* 171:6800-6807 (1989)). Yet other genes demonstrated to reduce acetoacetyl-CoA to 3-hydroxybutyryl-CoA are phbB from *Zoogloea ramigera* (Ploux et al., *Eur. J Biochem.* 174:177-182 (1988)) and phaB from *Rhodobacter sphaeroides* (Alber et al., *Mol. Microbiol* 61:297-309 (2006)). The former gene is NADPH-dependent, its nucleotide sequence has been determined (Peoples et al., *Mol. Microbiol* 3:349-357 (1989)) and the gene has been expressed in *E. coli*. Substrate specificity studies on the gene led to the conclusion that it could accept 3-oxopropionyl-CoA as a substrate besides acetoacetyl-CoA (Ploux et al., *Eur. J Biochem.* 174:177-182 (1988)). Additional genes include phaB in *Paracoccus denitrificans*, Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos taurus* (Wakil et al., *J Biol. Chem.* 207:631-638 (1954)). The enzyme from *Paracoccus denitrificans* has been functionally expressed and characterized in *E. coli* (Yabutani et al., *FEMS Microbiol Lett.* 133:85-90 (1995)). A number of similar enzymes have been found in other species of *Clostridia* and in *Metallosphaera sedula* (Berg et al., *Science.* 318:1782-1786 (2007)). The enzyme from *Candida tropicalis* is a component of the peroxisomal fatty acid beta-oxidation multifunctional enzyme type 2 (MFE-2). The dehydrogenase B domain of this protein is catalytically active on acetoacetyl-CoA. The domain has been functionally expressed in *E. coli*, a crystal structure is available, and the catalytic mechanism is well-understood (Ylianttila et al., *Biochem Biophys Res Commun* 324:25-30 (2004); Ylianttila et al., *J Mol Biol* 358:1286-1295 (2006)).

| Protein | GENBANK ID | GI NUMBER | ORGANISM |
|---------|-----------|-----------|----------|
| fadB | P21177.2 | 119811 | Escherichia coli |
| fadJ | P77399.1 | 3334437 | Escherichia coli |
| paaH | NP_415913.1 | 16129356 | Escherichia coli |
| Hbd2 | EDK34807.1 | 146348271 | Clostridium kluyveri |
| Hbd1 | EDK32512.1 | 146345976 | Clostridium kluyveri |
| HSD17B10 | O02691.3 | 3183024 | Bos taurus |
| phbB | P23238.1 | 130017 | Zoogloea ramigera |
| phaB | YP_353825.1 | 77464321 | Rhodobacter sphaeroides |
| phaB | BAA08358 | 675524 | Paracoccus denitrificans |
| Hbd | NP_349314.1 | 15895965 | Clostridium acetobutylicum |
| Hbd | AAM14586.1 | 20162442 | Clostridium beijerinckii |
| Msed_1423 | YP_001191505 | 146304189 | Metallosphaera sedula |
| Msed_0399 | YP_001190500 | 146303184 | Metallosphaera sedula |
| Msed_0389 | YP_001190490 | 146303174 | Metallosphaera sedula |
| Msed_1993 | YP_001192057 | 146304741 | Metallosphaera sedula |
| Fox2 | Q02207 | 399508 | Candida tropicalis |

Bifunctional oxidoreductases convert an acyl-CoA to its corresponding alcohol. Enzymes with this activity are required to convert 3-hydroxyglutaryl-CoA to 3,5-dihydroxypentanoate (FIG. 21, Step G) and 3-oxoglutaryl-CoA to 5-hydroxy-3-oxopentanoate (FIG. 21, Step K).

Exemplary bifunctional oxidoreductases that convert an acyl-CoA to alcohol include those that transform substrates such as acetyl-CoA to ethanol (e.g., adhE from *E. coli* (Kessler et al., *FEBS. Lett.* 281:59-63 (1991))) and butyryl-CoA to butanol (e.g. adhE2 from *C. acetobutylicum* (Fontaine et al., *J. Bacteriol.* 184:821-830 (2002))). The *C. acetobutylicum* enzymes encoded by bdh I and bdh II (Walter, et al., *J. Bacteriol.* 174:7149-7158 (1992)), reduce acetyl-CoA and butyryl-CoA to ethanol and butanol, respectively. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol Lett,* 27:505-510 (2005)). Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J Bacteriol,* 184:2404-2410 (2002); Strauss et al., *Eur J Biochem,* 215:633-643 (1993)). This enzyme, with a mass of 300 kDa, is highly substrate-specific and shows little sequence similarity to other known oxidoreductases (Hugler et al., supra). No enzymes in other organisms have been shown to catalyze this specific reaction; however there is bioinformatic evidence that other organisms may have similar pathways (Klatt et al., *Env Microbiol,* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| Protein | GenBank ID | GI Number | Organism |
|---|---|---|---|
| adhE | NP_415757.1 | 16129202 | Escherichia coli |
| adhE2 | AAK09379.1 | 12958626 | Clostridium acetobutylicum |
| bdh I | NP_349892.1 | 15896543 | Clostridium acetobutylicum |
| bdh II | NP_349891.1 | 15896542 | Clostridium acetobutylicum |
| adhE | AAV66076.1 | 55818563 | Leuconostoc mesenteroides |
| mcr | AAS20429.1 | 42561982 | Chloroflexus aurantiacus |
| Rcas_2929 | YP_001433009.1 | 156742880 | Roseiflexus castenholzii |
| NAP1_02720 | ZP_01039179.1 | 85708113 | Erythrobacter sp. NAP1 |
| MGP2080_00535 | ZP_01626393.1 | 119504313 | marine gamma proteobacterium HTCC2080 |

Longer chain acyl-CoA molecules can be reduced to their corresponding alcohols by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al., *Plant Physiol*, 122:635-644 (2000)).

| Protein | GenBank ID | GI Number | Organism |
|---|---|---|---|
| FAR | AAD38039.1 | 5020215 | Simmondsia chinensis |

Another candidate for catalyzing these steps is 3-hydroxy-3-methylglutaryl-CoA reductase (or HMG-CoA reductase). This enzyme naturally reduces the CoA group in 3-hydroxy-3-methylglutaryl-CoA to an alcohol forming mevalonate. The hmgA gene of *Sulfolobus solfataricus*, encoding 3-hydroxy-3-methylglutaryl-CoA reductase, has been cloned, sequenced, and expressed in *E. coli* (Bochar et al., *J Bacteriol*. 179:3632-3638 (1997)). *S. cerevisiae* also has two HMG-CoA reductases in it (Basson et al., *Proc. Natl. Acad. Sci. U.S.A* 83:5563-5567 (1986)). The gene has also been isolated from *Arabidopsis thaliana* and has been shown to complement the HMG-COA reductase activity in *S. cerevisiae* (Learned et al., *Proc. Natl. Acad. Sci. U.S.A* 86:2779-2783 (1989)).

| Protein | GenBank ID | GI Number | Organism |
|---|---|---|---|
| HMG1 | CAA86503.1 | 587536 | Saccharomyces cerevisiae |
| HMG2 | NP_013555 | 6323483 | Saccharomyces cerevisiae |
| HMG1 | CAA70691.1 | 1694976 | Arabidopsis thaliana |
| hmgA | AAC45370.1 | 2130564 | Sulfolobus solfataricus |

Acyl-CoA reductases in the 1.2.1 family reduce an acyl-CoA to its corresponding aldehyde. Such a conversion is required in steps C and H of FIG. 21. Several acyl-CoA dehydrogenase enzymes have been described in the open literature and represent suitable candidates for these steps. These are described below.

Exemplary acyl-CoA reductase enzymes include fatty acyl-CoA reductase, succinyl-CoA reductase (EC 1.2.1.76), acetyl-CoA reductase and butyryl-CoA reductase. Exemplary fatty acyl-CoA reductase enzymes are encoded by acr1 of *Acinetobacter calcoaceticus* (Reiser, *Journal of Bacteriology* 179:2969-2975 (1997)) and *Acinetobacter* sp. M-1 (Ishige et al., *Appl. Environ. Microbiol.* 68:1192-1195 (2002)). Enzymes with succinyl-CoA reductase activity are encoded by sucD of *Clostridium kluyveri* (Sohling, *J. Bacteriol.* 178:871-880 (1996)) and sucD of *P. gingivalis* (Takahashi, *J Bacteriol* 182:4704-4710 (2000)). Additional succinyl-CoA reductase enzymes participate in the 3-hydroxypropionate/4-hydroxybutyrate cycle of thermophilic archaea including *Metallosphaera sedula* (Berg et al., *Science* 318:1782-1786 (2007)) and *Thermoproteus neutrophilus* (Ramos-Vera et al., *J Bacteriol.*, 191:4286-4297 (2009)). The *M. sedula* enzyme, encoded by Msed_0709, is strictly NADPH-dependent and also has malonyl-CoA reductase activity. The *T. neutrophilus* enzyme is active with both NADPH and NADH. The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski, *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *J. Gen. Appl. Microbiol.* 18:43-55 (1972); and Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci Biotechnol Biochem.*, 71:58-68 (2007)).

| Protein | GenBank ID | GI Number | Organism |
|---|---|---|---|
| acr1 | YP_047869.1 | 50086359 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| MSED_0709 | YP_001190808.1 | 146303492 | Metallosphaera sedula |
| Tneu_0421 | ACB39369.1 | 170934108 | Thermoproteus neutrophilus |
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |
| adhE | AAV66076.1 | 55818563 | Leuconostoc mesenteroides |
| Bld | AAP42563.1 | 31075383 | Clostridium saccharoperbutylacetonicum |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, Science 318:1782-1786 (2007); and Thauer, Science 318:1732-1733 (2007)). The enzyme utilizes NADPH as a cofactor and has been characterized in Metallosphaera and Sulfolobus sp. (Alber et al., J. Bacteriol. 188:8551-8559 (2006); and Hugler, J. Bacteriol. 184:2404-2410 (2002)). The enzyme is encoded by Msed_0709 in Metallosphaera sedula (Alber et al., J. Bacteriol. 188:8551-8559 (2006); and Berg, Science 318:1782-1786 (2007)). A gene encoding a malonyl-CoA reductase from Sulfolobus tokodaii was cloned and heterologously expressed in E. coli (Alber et al., J. Bacteriol 188:8551-8559 (2006). This enzyme has also been shown to catalyze the conversion of methylmalonyl-CoA to its corresponding aldehyde (WO2007141208 (2007)). Although the aldehyde dehydrogenase functionality of these enzymes is similar to the bifunctional dehydrogenase from Chloroflexus aurantiacus, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including Sulfolobus solfataricus and Sulfolobus acidocaldarius and have been listed below. Yet another candidate for CoA-acylating aldehyde dehydrogenase is the aid gene from Clostridium beijerinckii (Toth, Appl. Environ. Microbiol. 65:4973-4980 (1999). This enzyme has been reported to reduce acetyl-CoA and butyryl-CoA to their corresponding aldehydes. This gene is very similar to eutE that encodes acetaldehyde dehydrogenase of Salmonella typhimurium and E. coli (Toth, Appl. Environ. Microbiol. 65:4973-4980 (1999).

enr gene has also been expressed in a catalytically active form in E. coli (Rohdich et al., J Biol. Chem. 276:5779-5787 (2001)). This enzyme exhibits activity on a broad range of alpha, beta-unsaturated carbonyl compounds.

| Protein | GenBank ID | GI Number | Organism |
|---|---|---|---|
| enr | ACA54153.1 | 169405742 | Clostridium botulinum A3 str |
| enr | CAA71086.1 | 2765041 | Clostridium tyrobutyricum |
| enr | CAA76083.1 | 3402834 | Clostridium kluyveri |
| enr | YP_430895.1 | 83590886 | Moorella thermoacetica |
| fadH | NP_417552.1 | 16130976 | Escherichia coli |

Another candidate 2-enoate reductase is maleylacetate reductase (MAR, EC 1.3.1.32), an enzyme catalyzing the reduction of 2-maleylacetate (4-oxohex-2-enedioate) to 3-oxoadipate. MAR enzymes naturally participate in aromatic degradation pathways (Kaschabek et al., J Bacteriol. 175:6075-6081 (1993); Kaschabek et al., J Bacteriol. 177: 320-325 (1995); Camara et al., J Bacteria (2009); Huang et al., Appl Environ. Microbiol 72:7238-7245 (2006)). The enzyme activity was identified and characterized in Pseudomonas sp. strain B13 (Kaschabek et al., 175:6075-6081 (1993); Kaschabek et al., 177:320-325 (1995)), and the coding gene was cloned and sequenced (Kasberg et al., J Bacteriol. 179:3801-3803 (1997)). Additional MAR gene candidates include cicE gene from Pseudomonas sp. strain B13 (Kasberg et al., J Bacteriol. 179:3801-3803 (1997)), macA gene from Rhodococcus opacus (Seibert et al., 180: 3503-3508 (1998)), the macA gene from Ralstonia eutropha (also known as Cupriavidus necator) (Seibert et al., Microbiology 150:463-472 (2004)), tfdFII from Ralstonia eutropha (Seibert et al., J Bacteriol. 175:6745-6754 (1993)) and NCgl1112 in Corynebacterium glutamicum (Huang et al., Appl Environ. Microbiol 72:7238-7245 (2006)). A MAR in Pseudomonas reinekei MT1, encoded by ccaD, was recently identified (Camara et al., J Bacteriol. (2009)).

| Protein | GenBank ID | GI Number | Organism |
|---|---|---|---|
| Msed_0709 | YP_001190808.1 | 146303492 | Metallosphaera sedula |
| Mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 49473535 | Clostridium beijerinckii |
| eutE | AAA80209 | 687645 | Salmonella typhimurium |
| eutE | P77445 | 2498347 | Escherichia coli |

2-Enoate reductase enzymes, some of which are reversible, are known to catalyze the NAD(P)H-dependent reduction of a wide variety of α,β-unsaturated carboxylic acids and aldehydes (Rohdich et al., 276:5779-5787 (2001)). These enzymes represent suitable candidates to carry out the transformations depicted by steps I and C of FIG. 20. Several examples are provided below.

In the recently published genome sequence of C. kluyveri, 9 coding sequences for enoate reductases were reported, out of which one has been characterized (Seedorf et al., Proc. Natl. Acad. Sci U.S.A 105:2128-2133 (2008)). The enr genes from both C. tyrobutyricum and M. thermoaceticum have been cloned and sequenced and show 59% identity to each other. The former gene is also found to have approximately 75% similarity to the characterized gene in C. kluyveri (Giesel et al., 135:51-57 (1983)). It has been reported based on these sequence results that enr is very similar to the dienoyl CoA reductase in E. coli (fadH) (Rohdich et al., J Biol. Chem. 276:5779-5787 (2001)). The C. thermoaceticum

| Protein | GenBank ID | GI Number | Organism |
|---|---|---|---|
| clcE | 3913241 | O30847.1 | Pseudomonas sp. strain B13 |
| macA | 7387876 | O84992.1 | Rhodococcus opacus |
| macA | 5916089 | AAD55886 | Cupriavidus necator |
| tfdFII | 1747424 | AAC44727.1 | Ralstonia eutropha JMP134 |
| NCgl1112 | 19552383 | NP_600385 | Corynebacterium glutamicum |
| ccaD | 134133940 | ABO61029.1 | Pseudomonas reinekei MT1 |

Step A of FIGS. 19-21 and Step M of FIG. 19 require condensation of either 3-hydroxypropionyl-CoA, acrylyl-CoA, succinyl-CoA or malonyl-CoA with acetyl-CoA. Several □-ketothiolase enzymes have been described in the open literature and represent suitable candidates for these steps. These are described below.

For example, 3-Oxoadipyl-CoA thiolase represents one type of beta-ketothiolase enzyme that is suitable for the aforementioned steps. 3-Oxoadipyl-CoA thiolase (EC 2.3.1.174) naturally converts beta-ketoadipyl-CoA to succinyl-CoA and acetyl-CoA and is a key enzyme of the beta-ketoadipate pathway for aromatic compound degradation. The enzyme is widespread in soil bacteria and fungi including *Pseudomonas putida* (Harwood et al., *J Bacteriol*. 176: 6479-6488 (1994)) and *Acinetobacter calcoaceticus* (Doten et al., *J Bacteriol*. 169:3168-3174 (1987)). The gene products encoded by pcaF in *Pseudomonas* strain B13 (Kaschabek et al., *J Bacteriol*. 184:207-215 (2002)), phaD in *Pseudomonas putida* U (Olivera et al., *Proc. Natl. Acad. Sci U.S.A* 95:6419-6424 (1998)), paaE in *Pseudomonas fluorescens* ST (Di et al., *Arch. Microbiol* 188:117-125 (2007)), and paaJ from *E. coli* (Nogales et al., *Microbiology* 153: 357-365 (2007)) also catalyze this transformation. Several beta-ketothiolases exhibit significant and selective activities in the oxoadipyl-CoA forming direction including bkt from *Pseudomonas putida*, pcaF and bkt from *Pseudomonas aeruginosa* PAM, bkt from *Burkholderia ambifaria* AMMD, paaJ from *E. coli*, and phaD from *P. putida*.

| Protein | GI# | GenBank Accession # | Organism |
|---|---|---|---|
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| pcaF | 506695 | AAA85138.1 | *Pseudomonas putida* |
| pcaF | 141777 | AAC37148.1 | *Acinetobacter calcoaceticus* |
| paaE | 106636097 | ABF82237.1 | *Pseudomonas fluorescens* |
| bkt | 115360515 | YP_777652.1 | *Burkholderia ambifaria* AMMD |
| bkt | 9949744 | AAG06977.1 | *Pseudomonas aeruginosa* PAO1 |
| pcaF | 9946065 | AAG03617.1 | *Pseudomonas aeruginosa* PAO1 |

Glutaryl-CoA and acetyl-CoA are condensed to form 3-oxopimeloyl-CoA by oxopimeloyl-CoA:glutaryl-CoA acyltransferase, a beta-ketothiolase (EC 2.3.1.16). An enzyme catalyzing this transformation is found *Ralstonia eutropha* (formerly known as *Alcaligenes eutrophus*), encoded by genes bktB and bktC (Slater et al., *J. Bacteriol*. 180:1979-1987 (1998); Haywood et al., 52:91-96 (1988)). The sequence of the BktB protein is known; however, the sequence of the BktC protein has not been reported. The pim operon of *Rhodopseudomonas palustris* also encodes a beta-ketothiolase, encoded by pimB, predicted to catalyze this transformation in the degradative direction during benzoyl-CoA degradation (Harrison et al., 151:727-736 (2005)). A beta-ketothiolase enzyme candidate in *S. aciditrophicus* was identified by sequence homology to bktB (43% identity, evalue=1e-93).

| Protein | GenBank ID | GI Number | Organism |
|---|---|---|---|
| bktB | YP_725948 | 11386745 | *Ralstonia eutropha* |
| pimB | CAE29156 | 39650633 | *Rhodopseudomonas palustris* |
| syn_02642 | YP_462685.1 | 85860483 | *Syntrophus aciditrophicus* |

Beta-ketothiolase enzymes catalyzing the formation of beta-ketovalerate from acetyl-CoA and propionyl-CoA may also be able to catalyze the condensation of acetyl-CoA with 3-hydroxypropionyl-CoA, acrylyl-CoA, succinyl-CoA, or malonyl-CoA. *Zoogloea ramigera* possesses two ketothiolases that can form □-ketovaleryl-CoA from propionyl-CoA and acetyl-CoA and *R. eutropha* has a □-oxidation ketothiolase that is also capable of catalyzing this transformation (Gruys et al., U.S. Pat. No. 5,958,745 (1999)). The sequences of these genes or their translated proteins have not been reported, but several candidates in *R. eutropha, Z. ramigera*, or other organisms can be identified based on sequence homology to bktB from *R. eutropha*. These include:

| Protein | GenBank ID | GI Number | Organism |
|---|---|---|---|
| phaA | YP_725941.1 | 113867452 | *Ralstonia eutropha* |
| h16_A1713 | YP_726205.1 | 113867716 | *Ralstonia eutropha* |
| pcaF | YP_728366.1 | 116694155 | *Ralstonia eutropha* |
| h16_B1369 | YP_40888.1 | 116695312 | *Ralstonia eutropha* |
| h16_A0170 | YP_724690.1 | 113866201 | *Ralstonia eutropha* |
| h16_A0462 | YP_724980.1 | 113866491 | *Ralstonia eutropha* |
| h16_A1528 | YP_726028.1 | 113867539 | *Ralstonia eutropha* |
| h16_B0381 | YP_728545.1 | 116694334 | *Ralstonia eutropha* |
| h16_B0662 | YP_728824.1 | 116694613 | *Ralstonia eutropha* |
| h16_B0759 | YP_728921.1 | 116694710 | *Ralstonia eutropha* |
| h16_B0668 | YP_728830.1 | 116694619 | *Ralstonia eutropha* |
| h16_A1720 | YP_726212.1 | 113867723 | *Ralstonia eutropha* |
| h16_A1887 | YP_726356.1 | 113867867 | *Ralstonia eutropha* |
| phbA | P07097.4 | 135759 | *Zoogloea ramigera* |
| bktB | YP_002005382.1 | 194289475 | *Cupriavidus taiwanensis* |
| Rmet_1362 | YP_583514.1 | 94310304 | *Ralstonia metallidurans* |
| Bphy_0975 | YP_001857210.1 | 186475740 | *Burkholderia phymatum* |

Additional candidates include beta-ketothiolases that are known to convert two molecules of acetyl-CoA into acetoacetyl-CoA (EC 2.1.3.9). Exemplary acetoacetyl-CoA thiolase enzymes include the gene products of atoB from *E. coli* (Martin et al. *Nat. Biotechnol* 21:796-802 (2003)), thlA and thlB from *C. acetobutylicum* (Hanai et al., *Appl Environ Microbiol* 73:7814-7818 (2007); Winzer et al., *J. Mol. Microbiol Biotechnol* 2:531-541 (2000)), and ERG10 from *S. cerevisiae* (Hiser et al., *J. Biol. Chem*. 269:31383-31389 (1994)).

| Protein | GenBank ID | GI Number | Organism |
|---|---|---|---|
| atoB | NP_416728 | 16130161 | *Escherichia coli* |
| thlA | NP_349476.1 | 15896127 | *Clostridium acetobutylicum* |
| thlB | NP_149242.1 | 15004782 | *Clostridium acetobutylicum* |
| ERG10 | NP_015297 | 6325229 | *Saccharomyces cerevisiae* |

Enzymes in the 2.8.3 family catalyze the reversible transfer of a CoA moiety from one molecule to another. Such a transformation is required by steps F, O, G, T, H, and E of FIG. 19 and steps B and H of FIG. 20. Several CoA transferase enzymes have been described in the open literature and represent suitable candidates for these steps. These are described below.

Many transferases have broad specificity and thus can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. For example, an enzyme from *Roseburia* sp. A2-183 was shown to have butyryl-CoA:acetate:CoA transferase and propionyl-CoA:acetate:CoA transferase activity (Charrier et al., *Microbiology* 152, 179-185 (2006)). Close homologs can be found in, for example, *Roseburia intestinalis* L1-82, *Roseburia inulinivorans* DSM 16841, *Eubacterium rectale* ATCC 33656. Another enzyme with propionyl-CoA transferase activity can be found in *Clostridium propionicum* (Selmer et al., *Eur J Biochem* 269, 372-380 (2002)). This enzyme can use acetate, (R)-lactate, (S)-lactate, acrylate, and butyrate as the CoA acceptor (Selmer et al., *Eur J Biochem* 269, 372-380 (2002); Schweiger and Buckel, *FEBS Letters,* 171 (1) 79-84 (1984)). Close homologs can be found in, for example, *Clostridium novyi* NT, *Clostridium beijerinckii* NCIMB 8052, and *Clostridium botulinum* C str. Eklund. YgfH encodes a propionyl CoA:succinate CoA transferase in *E. coli* (Haller et al., *Biochemistry,* 39(16) 4622-4629). Close homologs can be found in, for example, *Citrobacter youngae* ATCC 29220, *Salmonella enterica* subsp. *arizonae serovar*, and *Yersinia intermedia* ATCC 29909. These proteins are identified below.

33:902-908 (1968); Korolev et al., *Acta Crystallogr. D Biol Crystallogr.* 58:2116-2121 (2002)). This enzyme has also been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., supra) and butanoate (Vanderwinkel et al., supra). Similar enzymes exist in *Corynebacterium glutamicum* ATCC 13032 (Duncan et al., *Appl Environ Microbiol* 68:5186-5190 (2002)), *Clostridium acetobutylicum* (Cary et al., *Appl Environ Microbiol* 56:1576-1583 (1990)), and *Clostridium saccharoperbutylacetonicum* (Kosaka et al., *Biosci. Biotechnol Biochem.* 71:58-68 (2007)). These proteins are identified below.

| Protein | GenBank ID | GI Number | Organism |
| --- | --- | --- | --- |
| Ach1 | AAX19660.1 | 60396828 | *Roseburia* sp. A2-183 |
| ROSINTL182_07121 | ZP_04743841.2 | 257413684 | *Roseburia intestinalis* L1-82 |
| ROSEINA2194_03642 | ZP_03755203.1 | 225377982 | *Roseburia inulinivorans* |
| EUBREC_3075 | YP_002938937.1 | 238925420 | *Eubacterium rectale* ATCC 33656 |
| Pct | CAB77207.1 | 7242549 | *Clostridium propionicum* |
| NT01CX_2372 | YP_878445.1 | 118444712 | *Clostridium novyi* NT |
| Cbei_4543 | YP_001311608.1 | 150019354 | *Clostridium beijerinckii* |
| CBC_A0889 | ZP_02621218.1 | 168186583 | *Clostridium botulinum* C str. Eklund |
| ygfH | NP_417395.1 | 16130821 | *Escherichia coli* |
| CIT292_04485 | ZP_03838384.1 | 227334728 | *Citrobacter youngae* ATCC 29220 |
| SARI_04582 | YP_001573497.1 | 161506385 | *Salmonella enterica* subsp. *arizonae* serovar |
| yinte0001_14430 | ZP_04635364.1 | 238791727 | *Yersinia intermedia* ATCC 29909 |

An additional candidate enzyme is the two-unit enzyme encoded by pcaI and pcaJ in *Pseudomonas*, which has been shown to have 3-oxoadipyl-CoA/succinate transferase activity (Kaschabek et al., supra). Similar enzymes based on homology exist in *Acinetobacter* sp. ADP1 (Kowalchuk et al., *Gene* 146:23-30 (1994)) and *Streptomyces coelicolor*. Additional exemplary succinyl-CoA:3:oxoacid-CoA transferases are present in *Helicobacter pylori* (Corthesy-Theulaz et al., *J. Biol. Chem.* 272:25659-25667 (1997)) and *Bacillus subtilis* (Stols et al., *Protein. Expr. Purif.* 53:396-403 (2007)). These proteins are identified below.

| Protein | GenBank ID | GI Number | Organism |
| --- | --- | --- | --- |
| pcaI | AAN69545.1 | 24985644 | *Pseudomonas putida* |
| pcaJ | NP_746082.1 | 26990657 | *Pseudomonas putida* |
| pcaI | YP_046368.1 | 50084858 | *Acinetobacter* sp. ADP1 |
| pcaJ | AAC37147.1 | 141776 | *Acinetobacter* sp. ADP1 |
| pcaI | NP_630776.1 | 21224997 | *Streptomyces coelicolor* |
| pcaJ | NP_630775.1 | 21224996 | *Streptomyces coelicolor* |
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |

A CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res Commun.*

| Protein | GenBank ID | GI Number | Organism |
| --- | --- | --- | --- |
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* ATCC 13032 |
| cg0592 | YP_224801.1 | 62389399 | *Corynebacterium glutamicum* ATCC 13032 |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

Additional exemplary transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., supra; Sohling et al., *Eur. J Biochem.* 212:121-127 (1993); Sohling et al., *J Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). These proteins are identified below.

| Protein | GenBank ID | GI Number | Organism |
| --- | --- | --- | --- |
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack et al., *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Bucket et al., *Eur. J. Biochem.* 118:315-321 (1981)). The enzyme has been cloned and expressed in *E. coli* (Mack et al., *Eur. J. Biochem.* 226:41-51 (1994)). These proteins are identified below.

| Protein | GenBank ID | GI Number | Organism |
| --- | --- | --- | --- |
| gctA | CAA57199.1 | 559392 | Acidaminococcus fermentans |
| gctB | CAA57200.1 | 559393 | Acidaminococcus fermentans |

Enzymes in the 3.1.2 family hydrolyze acyl-CoA molecules to their corresponding acids. Such a transformation is required by steps F, O, G, T, H, and E of FIG. 19 and steps B and H of FIG. 20. Several such enzymes have been described in the literature and represent suitable candidates for these steps.

For example, the enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280: 38125-38132 (2005)). The closest *E. coli* homolog to this enzyme, tesB, can also hydrolyze a range of CoA thioesters (Naggert et al., *J Biol Chem* 266:11044-11050 (1991)). A similar enzyme has also been characterized in the rat liver (Deana R., *Biochem Int* 26:767-773 (1992)). Additional enzymes with hydrolase activity in *E. coli* include ybgC, paaI, and ybdB (Kuznetsova, et al., *FEMS Microbiol Rev*, 2005, 29(2):263-279; Song et al., *J Biol Chem*, 2006, 281(16):11028-38). Though its sequence has not been reported, the enzyme from the mitochondrion of the pea leaf has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)) The acetyl-CoA hydrolase, ACH1, from *S. cerevisiae* represents another candidate hydrolase (Buu et al., *J. Biol. Chem.* 278:17203-17209 (2003)).

| Protein | GenBank Accession # | GI# | Organism |
| --- | --- | --- | --- |
| acot12 | NP_570103.1 | 18543355 | Rattus norvegicus |
| tesB | NP_414986 | 16128437 | Escherichia coli |
| acot8 | CAA15502 | 3191970 | Homo sapiens |
| acot8 | NP_570112 | 51036669 | Rattus norvegicus |
| tesA | NP_415027 | 16128478 | Escherichia coli |
| ybgC | NP_415264 | 16128711 | Escherichia coli |
| paaI | NP_415914 | 16129357 | Escherichia coli |
| ybdB | NP_415129 | 16128580 | Escherichia coli |
| ACH1 | NP_009538 | 6319456 | Saccharomyces cerevisiae |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). This suggests that the enzymes encoding succinyl-CoA:3-ketoacid-CoA transferases and acetoacetyl-CoA: acetyl-CoA transferases may also serve as candidates for this reaction step but would require certain mutations to change their function.

| Protein | GenBank Accession # | GI# | Organism |
| --- | --- | --- | --- |
| gctA | CAA57199 | 559392 | Acidaminococcus fermentans |
| gctB | CAA57200 | 559393 | Acidaminococcus fermentans |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J Biol Chem.* 269:14248-14253 (1994)). Genes encoding this enzyme include hibch of *Rattus norvegicus* (Shimomura et al., *Methods Enzymol.* 324:229-240 (2000)) and *Homo sapiens* (Shimomura et al., supra). Similar gene candidates can also be identified by sequence homology, including hibch of *Saccharomyces cerevisiae* and BC_2292 of *Bacillus cereus*.

| Protein | GenBank Accession # | GI# | Organism |
| --- | --- | --- | --- |
| hibch | Q5XIE6.2 | 146324906 | Rattus norvegicus |
| hibch | Q6NVY1.2 | 146324905 | Homo sapiens |
| hibch | P28817.2 | 2506374 | Saccharomyces cerevisiae |
| BC_2292 | AP09256 | 29895975 | Bacillus cereus |

Decarboxylase enzymes in the EC class 4.1.1 are required to catalyze steps U, Y, V, and X of FIG. 19, steps D, J, M, and N of FIG. 20, and steps M, N, and P of FIG. 21. Candidate decarboxylase enzymes have been described earlier in this application.

The hydration of a double bond can be catalyzed by hydratase enzymes in the 4.2.1 family of enzymes. The removal of water to form a double bond is catalyzed by dehydratase enzymes in the 4.2.1 family of enzymes. Hydratase enzymes are sometimes reversible and also catalyze dehydration. Dehydratase enzymes are sometimes reversible and also catalyze hydration. The addition or removal of water from a given substrate is required by steps S, K, L, R, D, C, J, Q, and Win FIG. 19, by step F in FIG. 20, and by steps E, F, and O in FIG. 21. Several hydratase and dehydratase enzymes have been described in the literature and represent suitable candidates for these steps.

For example, many dehydratase enzymes catalyze the alpha, beta-elimination of water which involves activation of the alpha-hydrogen by an electron-withdrawing carbonyl, carboxylate, or CoA-thiol ester group and removal of the hydroxyl group from the beta-position (Bucket et al, *J Bacteriol*, 117:1248-60 (1974); Martins et al, *PNAS* 101: 15645-9 (2004)). Exemplary enzymes include 2-(hydroxymethyl)glutarate dehydratase (EC 4.2.1.-), fumarase (EC 4.2.1.2), 3-dehydroquinate dehydratase (EC 4.2.1.10), cyclohexanone hydratase (EC 4.2.1.-) and 2-keto-4-pentenoate dehydratase (EC 4.2.1.80), citramalate hydrolyase and dimethylmaleate hydratase.

2-(Hydroxymethyl)glutarate dehydratase is a [4Fe-4S]-containing enzyme that dehydrates 2-(hydroxymethyl)glutarate to 2-methylene-glutarate, studied for its role in nicontinate catabolism in *Eubacterium barkeri* (formerly *Clostridium barkeri*) (Alhapel et al., *Proc Natl Acad Sci* 103:12341-6 (2006)). Similar enzymes with high sequence homology are found in *Bacteroides capillosus, Anaerotruncus colihominis*, and *Natranaerobius thermophilius*. These enzymes are homologous to the alpha and beta subunits of [4Fe-4S]-containing bacterial serine dehydratases (e.g., *E. coli* enzymes encoded by tdcG, sdhB, and sdaA). An enzyme with similar functionality in *E. barkeri* is dimethylmaleate hydratase, a reversible Fe$^{2+}$-dependent and oxygen-sensitive enzyme in the aconitase family that hydrates dimethylmaeate to form (2R,3S)-2,3-dimethylmalate. This enzyme is encoded by dmdAB (Alhapel et al., *Proc Natl Acad Sci US A* 103:12341-6 (2006); Kollmann-Koch et al., *Hoppe Seylers. Z. Physiol Chem.* 365:847-857 (1984)).

tion (Weaver, 61:1395-1401 (2005)). *E. coli* has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Tseng et al., *J Bacteriol*, 183: 461-467 (2001); Woods et al., 954:14-26 (1988); Guest et al., *J Gen Microbiol* 131:2971-2984 (1985)). Additional enzyme candidates are found in *Campylobacter jejuni* (Smith et al., *Int. J Biochem. Cell Biol* 31:961-975 (1999)), *Thermus thermophilus* (Mizobata et al., *Arch. Biochem. Biophys.* 355:49-55 (1998)) and *Rattus norvegicus* (Kobayashi et al., *J. Biochem*, 89:1923-1931 (1981)). Similar enzymes with high sequence homology include fum1 from *Arabidopsis thaliana* and fumC from *Corynebacterium glutamicum*. The MmcBC fumarase from *Pelotomaculum thermopropionicum* is another class of fumarase with two subunits (Shimoyama et al., *FEMS Microbiol Lett*, 270:207-213 (2007)).

| Protein | GenBank ID | GI Number | Organism |
|---|---|---|---|
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| fumC | O69294 | 9789756 | *Campylobacter jejuni* |
| fumC | P84127 | 75427690 | *Thermus thermophilus* |
| fumH | P14408 | 120605 | *Rattus norvegicus* |
| fum1 | P93033 | 39931311 | *Arabidopsis thaliana* |
| fumC | Q8NRN8 | 39931596 | *Corynebacterium glutamicum* |
| MmcB | YP_001211906 | 147677691 | *Pelotomaculum thermopropionicum* |
| MmcC | YP_001211907 | 147677692 | *Pelotomaculum thermopropionicum* |

Dehydration of 4-hydroxy-2-oxovalerate to 2-oxopentenoate is catalyzed by 4-hydroxy-2-oxovalerate hydratase (EC 4.2.1.80). This enzyme participates in aromatic degradation pathways and is typically co-transcribed with a gene encoding an enzyme with 4-hydroxy-2-oxovalerate aldolase activity. Exemplary gene products are encoded by mhpD of *E. coli* (Ferrandez et al., *J Bacteriol*. 179:2573-2581 (1997); Pollard et al., *Eur J Biochem*. 251:98-106 (1998)), todG and cmtF of *Pseudomonas putida* (Lau et al., *Gene* 146:7-13 (1994); Eaton, *J Bacteriol*. 178:1351-1362 (1996)), cnbE of *Comamonas* sp. CNB-1 (Ma et al., *Appl Environ Microbiol* 73:4477-4483 (2007)) and mhpD of *Burkholderia xenovorans* (Wang et al., *FEBS J* 272:966-974 (2005)). A closely related enzyme, 2-oxohepta-4-ene-1,7-dioate hydratase, participates in 4-hydroxyphenylacetic acid degradation, where it converts 2-oxo-hept-4-ene-1,7-dioate (OHED) to 2-oxo-

| Protein | GenBank ID | GI Number | Organism |
|---|---|---|---|
| hmd | ABC88407.1 | 86278275 | *Eubacterium barkeri* |
| BACCAP_02294 | ZP_02036683.1 | 154498305 | *Bacteroides capillosus* |
| ANACOL_02527 | ZP_02443222.1 | 167771169 | *Anaerotruncus colihominis* |
| NtherDRAFT_2368 | ZP_02852366.1 | 169192667 | *Natranaerobius thermophilus* |
| dmdA | ABC88408 | 86278276 | *Eubacterium barkeri* |
| dmdB | ABC88409 | 86278277 | *Eubacterium barkeri* |

Fumarate hydratase (EC 4.2.1.2) enzymes naturally catalyze the reversible hydration of fumarate to malate. Although the ability of fumarate hydratase to react with 3-oxobutanol as a substrate has not been described in the literature, a wealth of structural information is available for this enzyme and other researchers have successfully engineered the enzyme to alter activity, inhibition and localiza- 4-hydroxy-hepta-1,7-dioate using magnesium as a cofactor (Burks et al., *J. Am. Chem. Soc.* 120: (1998)). OHED hydratase enzyme candidates have been identified and characterized in *E. coli* C (Roper et al., *Gene* 156:47-51 (1995); Izumi et al., *J Mol. Biol.* 370:899-911 (2007)) and *E. coli* W (Prieto et al., *J Bacteriol*. 178:111-120 (1996)). Sequence comparison reveals homologs in a wide range of bacteria, plants and animals. Enzymes with highly similar sequences are contained in *Klebsiella pneumonia* (91% identity, eval=2e-138) and *Salmonella enterica* (91% identity, eval=4e-138), among others.

| Protein | GenBank Accession No. | GI No. | Organism |
|---|---|---|---|
| mhpD | AAC73453.2 | 87081722 | *Escherichia coli* |
| cmtF | AAB62293.1 | 1263188 | *Pseudomonas putida* |
| todG | AAA61942.1 | 485738 | *Pseudomonas putida* |
| cnbE | YP_001967714.1 | 190572008 | *Comamonas* sp. CNB-1 |
| mhpD | Q13VU0 | 123358582 | *Burkholderia xenovorans* |
| hpcG | CAA57202.1 | 556840 | *Escherichia coli* C |
| hpaH | CAA86044.1 | 757830 | *Escherichia coli* W |
| hpaH | ABR80130.1 | 150958100 | *Klebsiella pneumoniae* |
| Sari_01896 | ABX21779.1 | 160865156 | *Salmonella enterica* |

Another enzyme candidate is citramalate hydrolyase (EC 4.2.1.34), an enzyme that naturally dehydrates 2-methylmalate to mesaconate. This enzyme has been studied in *Methanocaldococcus jannaschii* in the context of the pyruvate pathway to 2-oxobutanoate, where it has been shown to have a broad substrate specificity (Drevland et al., *J Bacteriol.* 189:4391-4400 (2007)). This enzyme activity was also detected in *Clostridium tetanomorphum, Morganella morganii, Citrobacter amalonaticus* where it is thought to participate in glutamate degradation (Kato et al., *Arch. Microbiol* 168:457-463 (1997)). The *M. jannaschii* protein sequence does not bear significant homology to genes in these organisms.

| Protein | GenBank ID | GI Number | Organism |
|---|---|---|---|
| leuD | Q58673.1 | 3122345 | *Methanocaldococcus jannaschii* |

Dimethylmaleate hydratase (EC 4.2.1.85) is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in *Eubacterium barkeri* (Alhapel et al., supra; Kollmann-Koch et al., *Hoppe Seylers. Z. Physiol Chem.* 365:847-857 (1984)).

| Protein | GenBank ID | GI Number | Organism |
|---|---|---|---|
| dmdA | ABC88408 | 86278276 | *Eubacterium barkeri* |
| dmdB | ABC88409.1 | 86278277 | *Eubacterium barkeri* |

Oleate hydratases represent additional suitable candidates as suggested in WO2011076691. These are particularly useful for step W of FIG. 19 and step O of FIG. 21. Examples include the following proteins.

| Protein | GenBank ID | GI Number | Organism |
|---|---|---|---|
| OhyA | ACT54545.1 | 254031735 | *Elizabethkingia meningoseptica* |
| HMPREF0841_1446 | ZP_07461147.1 | 306827879 | *Streptococcus pyogenes* ATCC 10782 |
| P700755_13397 | ZP_01252267.1 | 91215295 | *Psychroflexus torquis* ATCC 700755 |
| RPB_2430 | YP_486046.1 | 86749550 | *Rhodopseudomonas palustris* |

Enoyl-CoA hydratases (EC 4.2.1.17) catalyze the dehydration of a range of 3-hydroxyacyl-CoA substrates (Roberts et al., *Arch. Microbiol* 117:99-108 (1978); Agnihotri et al., *Bioorg. Med. Chem.* 11:9-20 (2003); Conrad et al., *J Bacteriol.* 118:103-111 (1974)). The enoyl-CoA hydratase of *Pseudomonas putida*, encoded by ech, catalyzes the conversion of 3-hydroxybutyryl-CoA to crotonyl-CoA (Roberts et al., *Arch. Microbiol* 117:99-108 (1978)). This transformation is also catalyzed by the crt gene product of *Clostridium acetobutylicum*, the crt1 gene product of *C. kluyveri*, and other *clostridial* organisms Atsumi et al., *Metab Eng* 10:305-311 (2008); Boynton et al., *J Bacteriol.* 178:3015-3024 (1996); Hillmer et al., *FEBS Lett.* 21:351-354 (1972)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). The gene product of pimF in *Rhodopseudomonas palustris* is predicted to encode an enoyl-CoA hydratase that participates in pimeloyl-CoA degradation (Harrison et al., *Microbiology* 151:727-736 (2005)). Lastly, a number of *Escherichia coli* genes have been shown to demonstrate enoyl-CoA hydratase functionality including maoC (Park et al., *J Bacteriol.* 185:5391-5397 (2003)), paaF (Ismail et al., *Eur. J Biochem.* 270:3047-3054 (2003); Park et al., *Appl. Biochem. Biotechnol* 113-116:335-346 (2004); Park et al., *Biotechnol Bioeng* 86:681-686 (2004)) and paaG (Ismail et al., *Eur. J Biochem.* 270:3047-3054 (2003); Park and Lee, *Appl. Biochem. Biotechnol* 113-116:335-346 (2004); Park and Yup, *Biotechnol Bioeng* 86:681-686 (2004)).

| Protein | GenBank Accession No. | GI No. | Organism |
|---|---|---|---|
| ech | NP_745498.1 | 26990073 | *Pseudomonas putida* |
| crt | NP_349318.1 | 15895969 | *Clostridium acetobutylicum* |
| crt1 | YP_001393856 | 153953091 | *Clostridium kluyveri* |
| phaA | ABF82233.1 | 26990002 | *Pseudomonas putida* |
| phaB | ABF82234.1 | 26990001 | *Pseudomonas putida* |
| paaA | NP_745427.1 | 106636093 | *Pseudomonas fluorescens* |
| paaB | NP_745426.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Alternatively, the *E. coli* gene products of fadA and fadB encode a multienzyme complex involved in fatty acid oxidation that exhibits enoyl-CoA hydratase activity (Yang et al., *Biochemistry* 30:6788-6795 (1991); Yang, *J Bacteriol.* 173:7405-7406 (1991); Nakahigashi et al., *Nucleic Acids Res.* 18:4937 (1990)). Knocking out a negative regulator encoded by fadR can be utilized to activate the fadB gene product (Sato et al., *J Biosci. Bioeng* 103:38-44 (2007)). The fadI and fadJ genes encode similar functions and are naturally expressed under anaerobic conditions (Campbell et al., *Mol. Microbiol* 47:793-805 (2003)).

| Protein | GenBank ID | GI Number | Organism |
|---|---|---|---|
| fadA | YP_026272.1 | 49176430 | Escherichia coli |
| fadB | NP_418288.1 | 16131692 | Escherichia coli |
| fadI | NP_416844.1 | 16130275 | Escherichia coli |
| fadJ | NP_416843.1 | 16130274 | Escherichia coli |
| fadR | NP_415705.1 | 16129150 | Escherichia coli |

The conversion of acyl-CoA substrates to their acid products can be catalyzed by a CoA acid-thiol ligase or CoA synthetase in the 6.2.1 family of enzymes, several of which are reversible. Several reactions shown in FIGS. 19-20 are catalyzed by acid-thiol ligase enzymes. These reactions include Steps F, O, G, T, H, and E of FIG. 19 and Steps B and H of FIG. 20. Several enzymes catalyzing CoA acid-thiol ligase or CoA synthetase activities have been described in the literature and represent suitable candidates for these steps.

For example, ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF1211, was shown to operate on a variety of linear and branched-chain substrates including isobutyrate, isopentanoate, and fumarate (Musfeldt et al., *J Bacteriol.* 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt and Schonheit, *J Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et a)., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al, supra). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra; Musfeldt and Schonheit, *J Bacteriol.* 184:636-644 (2002)). An additional candidate is succinyl-CoA synthetase, encoded by sucCD of *E. coli* and LSC1 and LSC2 genes of *Saccharomyces cerevisiae*. These enzymes catalyze the formation of succinyl-CoA from succinate with the concomitant consumption of one ATP in a reaction which is reversible in viva (Buck et al., *Biochemistry* 24:6245-6252 (1985)). The acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Appl. Environ. Microbiol.* 59:1149-1154 (1993)). A related enzyme, malonyl CoA synthetase (6.3.4.9) from *Rhizobium leguminosarum* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)).

| Protein | GenBank ID | GI Number | Organism |
|---|---|---|---|
| AF1211 | NP_070039.1 | 11498810 | Archaeoglobus fulgidus |
| AF1983 | NP_070807.1 | 11499565 | Archaeoglobus fulgidus |
| Scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| LSC1 | NP_014785 | 6324716 | Saccharomyces cerevisiae |
| LSC2 | NP_011760 | 6321683 | Saccharomyces cerevisiae |
| paaF | AAC24333.2 | 22711873 | Pseudomonas putida |
| matB | AAC83455.1 | 3982573 | Rhizobium leguminosarum |

Another candidate enzyme for these steps is 6-carboxyhexanoate-CoA ligase, also known as pimeloyl-CoA ligase (EC 6.2.1.14), which naturally activates pimelate to pimeloyl-CoA during biotin biosynthesis in gram-positive bacteria. The enzyme from *Pseudomonas mendocina*, cloned into *E. coli*, was shown to accept the alternate substrates hexanedioate and nonanedioate (Binieda et al., *Biochem. J* 340 (Pt 3):793-801 (1999)). Other candidates are found in *Bacillus subtilis* (Bower et al., *J Bacteriol.* 178: 4122-4130 (1996)) and *Lysinibacillus sphaericus* (formerly *Bacillus sphaericus*) (Ploux et al., *Biochem. J* 287 (Pt 3):685-690 (1992)).

| Protein | GenBank ID | GI Number | Organism |
|---|---|---|---|
| bioW | NP_390902.2 | 50812281 | Bacillus subtilis |
| bioW | CAA10043.1 | 3850837 | Pseudomonas mendocina |
| bioW | P22822.1 | 115012 | Bacillus sphaericus |

Additional CoA-ligases include the rat dicarboxylate-CoA ligase for which the sequence is yet uncharacterized (Vamecq et al., *Biochem. J* 230:683-693 (1985)), either of the two characterized phenylacetate-CoA ligases from *P. chrysogenum* (Lamas-Maceiras et al., *Biochem. J* 395:147-155 (2006); Wang et al., 360:453-458 (2007)), the phenylacetate-CoA ligase from *Pseudomonas putida* (Martinez-Blanco et al., *J Biol Chem* 265:7084-7090 (1990)) and the 6-carboxyhexanoate-CoA ligase from *Bacillus subtilis* (Bower et al. *J Bacteriol* 178(14):4122-4130 (1996)). Acetoacetyl-CoA synthetases from *Mus musculus* (Hasegawa et al., *Biochim Biophys Acta* 1779:414-419 (2008)) and *Homo sapiens* (Ohgami et al., *Biochem. Pharmacol.* 65:989-994 (2003)) naturally catalyze the ATP-dependent conversion of acetoacetate into acetoacetyl-CoA.

| Protein | Accession No. | GI No. | Organism |
|---|---|---|---|
| phl | CAJ15517.1 | 77019264 | *Penicillium chrysogenum* |
| phlB | ABS19624.1 | 152002983 | *Penicillium chrysogenum* |
| paaF | AAC24333.2 | 22711873 | *Pseudomonas putida* |
| bioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |

Like enzymes in other classes, certain enzymes in the EC class 6.2.1 have been determined to have broad substrate specificity. The acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Applied and Environmental Microbiology* 59:1149-1154 (1993)). A related enzyme, malonyl CoA synthetase (6.3.4.9) from *Rhizobium trifolii* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)).

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism comprising exogenous nucleic acids encoding enzymes to produce 2,4-pentadienoate, wherein said enzymes comprise: a malonyl-CoA:acetyl-CoA acyltransferase; a 3-oxoglutaryl-CoA reductase (ketone-reducing); a 3-hydroxyglutaryl-CoA reductase (aldehyde forming); a 3-hydroxy-5-oxopentanoate reductase; a 3,5-dihydroxypentanoate dehydratase; and a 5-hydroxypent-2-enoate dehydratase.

2. The non-naturally occurring microbial organism of claim 1, wherein at least one of the exogenous nucleic acids is a heterologous nucleic acid.

3. The non-naturally occurring microbial organism of claim 1, wherein said non-naturally occurring microbial organism is in a substantially anaerobic culture medium.

4. A method for producing 2,4-pentadienoate, comprising culturing the non-naturally occurring microbial organism of claim 1 under conditions and for a sufficient period of time to produce 2,4-pentadienoate.

5. The method of claim 4, wherein at least one of the exogenous nucleic acids is a heterologous nucleic acid.

6. The method of claim 4, wherein said non-naturally occurring microbial organism is in a substantially anaerobic culture medium.

\* \* \* \* \*